(12) United States Patent
Masternak et al.

(10) Patent No.: US 11,840,553 B2
(45) Date of Patent: *Dec. 12, 2023

(54) ANTI-CD47 ANTIBODIES AND METHODS OF USE THEREOF

(71) Applicant: NovImmune S.A., Geneva (CH)

(72) Inventors: Krzysztof Masternak, Mollens (CH); Nicolas Fischer, Geneva (CH); Francois Rousseau, Collonges sous Saleve (FR); Elie Dheilly, Geneva (CH); Marie Kosco-Vilbois, Minzier (FR)

(73) Assignee: Novimmune SA, Geneva (CH)

( * ) Notice: Subject to any disclaimer, the term of this patent is extended or adjusted under 35 U.S.C. 154(b) by 303 days.

This patent is subject to a terminal disclaimer.

(21) Appl. No.: 16/015,601

(22) Filed: Jun. 22, 2018

(65) Prior Publication Data

US 2018/0291115 A1 Oct. 11, 2018

Related U.S. Application Data

(63) Continuation of application No. 14/095,395, filed on Dec. 3, 2013, now Pat. No. 11,059,910.

(60) Provisional application No. 61/898,710, filed on Nov. 1, 2013, provisional application No. 61/881,523, filed on Sep. 24, 2013, provisional application No. 61/863,106, filed on Aug. 7, 2013, provisional application No. 61/816,788, filed on Apr. 28, 2013, provisional application No. 61/732,452, filed on Dec. 3, 2012.

(51) Int. Cl.
| | | |
|---|---|---|
| C07K 16/30 | (2006.01) | |
| C07K 16/28 | (2006.01) | |
| C07K 16/46 | (2006.01) | |
| A61K 39/00 | (2006.01) | |

(52) U.S. Cl.
CPC ........ *C07K 16/468* (2013.01); *C07K 16/2803* (2013.01); *C07K 16/2896* (2013.01); *C07K 16/461* (2013.01); *A61K 2039/505* (2013.01); *C07K 2317/30* (2013.01); *C07K 2317/31* (2013.01); *C07K 2317/565* (2013.01); *C07K 2317/622* (2013.01); *C07K 2317/76* (2013.01); *C07K 2317/92* (2013.01)

(58) Field of Classification Search
CPC ............. C07K 16/468; C07K 16/2896; C07K 16/461; C07K 16/2803; C07K 2317/30; C07K 2317/31; C07K 2317/565; C07K 2317/622; C07K 2317/76; C07K 2317/92; A61K 2039/505; A61P 35/00
See application file for complete search history.

(56) References Cited

U.S. PATENT DOCUMENTS

| | | |
|---|---|---|
| 3,773,919 A | 11/1973 | Boswell et al. |
| 4,485,045 A | 11/1984 | Regen |
| 4,522,811 A | 6/1985 | Eppstein et al. |
| 4,544,545 A | 10/1985 | Ryan et al. |
| 4,676,980 A | 6/1987 | Segal et al. |
| 4,816,567 A | 3/1989 | Cabilly et al. |
| 5,013,556 A | 5/1991 | Woodle et al. |
| 5,030,719 A | 7/1991 | Umemoto et al. |
| 5,225,539 A | 7/1993 | Winter |
| 5,545,806 A | 8/1996 | Lonberg et al. |
| 5,545,807 A | 8/1996 | Surani et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,916,771 A | 6/1999 | Hori et al. |
| 5,939,598 A | 8/1999 | Kucherlapati et al. |
| 6,075,181 A | 6/2000 | Kucherlapati et al. |
| 6,150,584 A | 11/2000 | Kucherlapati et al. |
| 6,528,624 B1 | 3/2003 | Idusogie et al. |
| 7,531,643 B2 | 5/2009 | Fukushima et al. |
| 7,696,325 B2 | 4/2010 | Fukushima et al. |
| 7,776,330 B2 | 8/2010 | Yazaki et al. |
| 8,101,719 B2 | 1/2012 | Kikuchi et al. |
| 8,236,313 B2 | 8/2012 | Isenberg et al. |
| 8,287,865 B2 | 10/2012 | Hansen et al. |
| 8,642,742 B2 | 2/2014 | Hofer et al. |
| 2006/0241067 A1 | 10/2006 | Varner et al. |

(Continued)

FOREIGN PATENT DOCUMENTS

| | | |
|---|---|---|
| EP | 0 546 073 A1 | 6/1993 |
| EP | 2573567 A1 | 3/2013 |

(Continued)

OTHER PUBLICATIONS

Bendig M. M. (Methods: A Companion to Methods in Enzymology, 1995; 8:83-93) (Year: 1995).*

(Continued)

*Primary Examiner* — Michael Allen

(74) *Attorney, Agent, or Firm* — COOLEY LLP; Ivor R. Elrifi; Cynthia A. Kozakiewicz

(57) ABSTRACT

The invention relates to monoclonal and/or monovalent antibodies that bind CD47. The invention relates to monoclonal and/or monovalent antibodies that bind CD19. The invention also relates to novel bispecific monoclonal antibodies carrying a different specificity for each binding site of the immunoglobulin molecule, where one of the binding sites is specific for CD47. The invention also relates to novel bispecific monoclonal antibodies carrying a different specificity for each binding site of the immunoglobulin molecule, where one of the binding sites is specific for CD19.

2 Claims, 29 Drawing Sheets

Specification includes a Sequence Listing.

(56) References Cited

U.S. PATENT DOCUMENTS

| | | |
|---|---|---|
| 2009/0142349 A1 | 6/2009 | Rao-Naik et al. |
| 2009/0191199 A1 | 7/2009 | Kanda et al. |
| 2009/0191202 A1 | 7/2009 | Jamieson |
| 2010/0104509 A1 | 4/2010 | King et al. |
| 2010/0239578 A1 | 9/2010 | Danska et al. |
| 2011/0038870 A1 | 2/2011 | van den Berg |
| 2012/0184716 A1 | 7/2012 | Fischer et al. |
| 2012/0225073 A1 | 9/2012 | Weissman et al. |
| 2012/0282174 A1 | 11/2012 | Weissman et al. |
| 2013/0011401 A1 | 1/2013 | Huber et al. |
| 2013/0142786 A1 | 6/2013 | Liu et al. |
| 2013/0224188 A1 | 8/2013 | Eckelman et al. |
| 2014/0271683 A1 | 9/2014 | Chao et al. |
| 2018/0142018 A1 | 5/2018 | Fischer |

FOREIGN PATENT DOCUMENTS

| | | |
|---|---|---|
| JP | 2003/247999 | 5/2003 |
| JP | 2009-526823 A | 7/2009 |
| WO | WO 91/00360 | 1/1991 |
| WO | WO 92/00373 | 1/1992 |
| WO | WO 92/03918 | 3/1992 |
| WO | WO 93/08829 | 5/1993 |
| WO | WO 94/02602 | 2/1994 |
| WO | WO 94/011026 | 5/1994 |
| WO | WO 95/02140 | 1/1995 |
| WO | WO 95/22618 | 8/1995 |
| WO | WO 96/27011 | 9/1996 |
| WO | WO 96/33735 | 10/1996 |
| WO | WO 96/34096 | 10/1996 |
| WO | WO 99/53049 | 10/1999 |
| WO | WO 2004/003019 | 1/2004 |
| WO | WO-2005044857 A1 | 5/2005 |
| WO | WO 2007/093630 A1 | 8/2007 |
| WO | WO 2009/054863 A2 | 4/2009 |
| WO | WO 2009/091601 | 7/2009 |
| WO | WO 2010/135558 | 11/2010 |
| WO | WO 2011/034969 A1 | 3/2011 |
| WO | WO 2011/041453 A1 | 4/2011 |
| WO | WO 2011/084255 | 7/2011 |
| WO | WO 2011/143624 A2 | 11/2011 |
| WO | WO 2012/023053 | 2/2012 |
| WO | WO 2012/088309 A1 | 6/2012 |
| WO | WO 2013/088259 | 6/2013 |
| WO | WO 2014/087248 A2 | 6/2014 |
| WO | WO 2015/197582 A1 | 12/2015 |
| WO | WO 2016/033570 A1 | 3/2016 |

OTHER PUBLICATIONS

Johnson and Wu (Methods in Molecular Biology, Antibody Engineering: Methods and Protocols, vol. 248, p. 11-25, 2004) (Year: 2004).*
Baldrick P. "Pharmaceutical excipient development: the need for preclinical guidance" Regul. Toxicol Pharmacol. 32(2):210-8 (2000).
Bobo et al., "Convection-enhanced delivery of macromolecules in the brain", Proc. Natl. Acad. Sci. USA 91:2076-2080 (1994).
Bowie et al. "A Method to Identify Protein Sequences That Fold Into a Known Three-Dimensional Stucture", 1991, Science, vol. 253, p. 164-171.
Brodeur et al., "Monoclonal Antibody Production Techniques and Applications", pp. 51-63 (1987).
Brown, E.J. and Frazier, W A., "Integrin-associated protein (CD47) and its ligands", Trends Cell Biol. Mar. 2001;11(3):130-5.
Caron et al., "Engineered Humanized Dimeric Forms of IgG Are More Effective Antibodies", J. Exp Med., 176: 1191-1195 (1992).
Chao, M.P. et al., "Therapeutic antibody targeting of CD47 eliminates human acute lymphoblastic leukemia", Cancer Res. Feb. 15, 2011;71(4):1374-84.
Chappell et al. "A 9-nt segment of a cellular mRNA can function as an internal ribosome entry site (IRES) and when present in linked multiple copies greatly enhances IRES activity", Proc Natl Acad Sci USA 97:4, 1536-1541 (2000).
Charman, W.N., "Lipids, Lipophilic Drugs, and Oral Drug Delivery—Some Emerging Concepts." J Pharm Sci. 89(8):967-78 (2000).
Cole, S. et al., "The EBV-Hybridoma Technique and Its Application to Human Lung Cancer", Monoclonal Antibodies and Cancer Therapy, p. 77-96 (1985).
Cote, R. et al., "Generation of human monoclonal antibodies reactive with cellular antigens", Proc Natl Acad Sci USA, vol. 80, p. 2026-2030 (1983).
Davidson, et al., "A model system for in vivo gene transfer into the central nervous system using an adenoviral vector", Nat. Genet 3:219 (1993).
Davis, J.H. et al., "SEEDbodies: fusion proteins based on strand-exchange engineered domain (SEED) CH3 heterodimers in an Fc analogue platform for asymmetric binders or immunofusions and bispecific antibodies", Protein Engineering, Design & Selection, 23(4):195-202 (2010).
Epstein et al., "Biological activity of liposome-encapsulated murine interferon γ is mediated by a cell membrane receptor", Proc. Natl. Acad. Sci. USA, 82: 3688 (1985).
Fishwild et al., "High-avidity IgGk monoclonal antibodies from a novel strain of minilocus transgenic mice", Nature Biotechnology 14, 845-51 (1996).
Geller, A.I. et al., "An HSV-1 Vector Expressing Tyrosine Hydroxylase Causes Production and Release of L-DOPA from Cultured Rat Striatal Cells", J. Neurochem, 64:487 (1995).
Geller, A.I. et al., "Infection of cultured central nervous system neurons with a defective herpes simplex virus 1 vector results in stable expression of *Escherichia coli* β-galactosidase". Proc Natl. Acad. Sci USA 87:1149 (1990).
Geller, A.I. et al., "Long-term increases in neurotransmitter release from neuronal cells expressing a constitutively active adenylate cyclase from a herpes simplex virus type 1 vector", Proc Natl. Acad. Sci.: U.S.A. 90:7603 (1993).
Goding, "Production of Monoclonal Antibodies", in *Monoclonal Antibodies: Principles and Practice*. Academic Press, pp. 59-103, (1986).
Gramer et al., "Production of stable bispecific IgG1 by controlled Fab-arm exchange scalability from bench to large-scale manufacturing by application of standard approaches", MAbs. 5(6):962-973, (2013).
Gruber et al., "Efficient Tumor Cell Lysis Mediated by a Bispecific Single Chain Antibody Expressed in *Escherichia coli*" Journal of Immunology, 152: 5368-5374 (1994).
Gunasekaran, K et al., "Enhancing Antibody Fc Heterodimer Formation through Electrostatic Steering Effects", Journal of Biological Chemistry, 285(25):19637-19646 (2010).
Harris, R.J. et al. "Assessing Genetic Hetorgeneity in Production Cell Lines: Detection by Peptide Mapping of a Low Level Tyr to Gln Sequence Variant in a Recombinant Antibody" Bio/Technolgy, 11: 1293-1297 (1993).
Hellen C. and Sarnow P. "Internal ribosome entry sites in eukaryotic mRNA molecules", Genes Dev 15: 1593-612 (2001).
Holliger et al., "'Diabodies': Small bivalent and bispecific antibody fragments", Proc. Natl. Acad. Sci. USA 90:6444-6448 (1993).
Hoogenboom et al., "Building Antibodies Fom Their Genes", Immunological Reviews 130:43-68 (1992).
Hwang et al., "Hepatic uptake and degradation of unilamellar sphingomyelin/cholesterol liposomes: A kinetic study", Proc. Natl Acad. Sci. USA, 77: 4030 (1980).
Jaiswal, S. et al., "CD47 is upregulated on circulating hematopoietic stem cells and leukemia cells to avoid phagocytosis", Cell, Jul. 23, 2009;138(2):271-85.
Jansen et al., "Immunotoxins: Hybrid Molecules Combining High Specificity and Potent Cytotoxicity", Immunological Reviews 62: 185-216 (1982).
Johnson, G. and Wu, T.T. "The Kabat Database and a Bioinfomatics Example" in *Methods in Molecular Biology*, vol. 248: *Antibody Engineering: Methods and Protocols*. B.K.C. Lo (Ed.) Totowa, New Jersey: Humana Press Inc., 2004; pp. 11-25.
Jones et al., "Replacing the complementarity-determining regions in a human antibody with those from a mouse", Nature, 321: 522-525 (1986).

(56) References Cited

OTHER PUBLICATIONS

Kaplitt, M. G. et al., "Long-term gene expression and phenotypic correction using adeno-associated virus vectors in the mammalian bran", Nat. Genet. 8:148 (1994).
Killen and Lindstrom, "Specific killing of lymphocytes that cause experimental autoimmune myasthenia gravis by ricin toxin-acetylcholine receptor conjugates", J. Immunol. 133:1335-2549 (1984).
Klein, C et al. "Progress in overcoming the chain association issue in bispecific heterodimeric IgG antibodies", MAbs 4(6):653-663 (2012).
Kohler and Milstein, "Continuous cultures of fused cells secreting antibody of predefined specificity", Nature, 256:495 (1975).
Kontermann R. et al., "Complement recruitment using bispecific diabodies", Nat Biotechnol. 15(7):629-31 (1997).
Kostelny et al., "Formation of a Bispecific Antibody by the Use of Leucine Zippers", Journal of Immunol. 148, 1547-1553 (1992).
Kozbor, et al., "The production of monoclonal antibodies from human lymphocytes", Immunol Today 4: 72 (1983).
Kozbor, T., "A human hybrid myeloma for production of human monoclonal antibodies", J. Immunol., 133:3001 (1984).
Le Gal La Salle et al., "An Adenovirus Vector for Gene Transfer into Neurons and Glia in the Brain", Science, 259:988 (1993).
Lefranc, M-P. et al. "IMGT unique numbering for immunoglobulin and T cell receptor variable domains and Ig superfamily V-like domains" Developmental and Comparative Immunology, 27: 55-77 (2003).
Lonberg and Huszar, "Human Antibodies from Transgenic Mice", Intern. Rev. Immunol. 13 65-93 (1995).
Lonberg et al., "Antigen-specific human antibodies from mice comprising four distinct genetic modifications", Nature 368 856-859 (1994).
Majeti, R. et al., "CD47 is an adverse prognostic factor and therapeutic antibody target on human acute myeloid leukemia stem cells" Cell, Jul. 23, 2009;138(2):286-99.
Malmqvist, M. "Biosepcific interaction analysis using biosensor technology", Nature 361: 186-187 (1993).
Marasco et al., "Design, intracellular expression, and activity of a human anti-human immunodeficiency virus type 1 gp120 single-chain antibody", Proc. Natl. Acad. Sci. USA, 90: 7889-7893 (1993).
Marks et al. "By-passing Immunization: Building High Affinity Human Antibodies by Chain Shuffling", Bio/Technology 10, 779-783 (1992).
Marks et al., "By-passing Immunization. Human Antibodies from V-gene Libraries Displayed on Phage", J. Mol. Biol., 222:581 (1991).
Martin et al., "Irreversible Coupling of Immunoglobulin Fragments to Preformed Vesicles", J. Biol. Chem., 257: 286-288 (1982).
Milstein and Cuello, "Hybrid hybridomas and their use in immunohistochemistry", Nature, 305: 537-539 (1983).
Moore P. et al., "Application of dual affinity retargeting molecules to achieve optimal redirected T-cell killing of B-cell lymphoma", Blood 117(17):4542-51 (2011).
Morrison et al., "High-flow microinfusion: tissue penetration and pharmacodynamics", Am. J. Physiol. 266:292-305 (1994).
Morrison, "Success in specification", Nature 368, 812-13 (1994).
Munson et al. "Ligand: A Versatile Computerized Approach for Characterization of Ligand-Binding Systems", Analytical Biochemistry 107:220-239 (1980).
Neuberger, M. "Generating high-avidity human Mabs in mice" Nature Biotechnology 14, 826 (1996).
Oldenborg, P A., "Role of CD47 in erythroid cells and in autoimmunity" Leuk Lymphoma, Jul. 2004;45(7): 1319-27.
Oldenborg, P.A. "CD47: A Cell Surface Glycoprotein Which Regulates Multiple Functions of Hematopoietic Cells in Health and Disease" ISRN Hematol., 2013; 2013:614619.
Oldenborg, P.A. et al., "Role of CD47 as a Marker of Self on Red Blood Cells" Science. Jun. 16, 2000;288(5473):2051-4.
Oldenborg, P.A., et al., "CD47-Signal Regulatory Protein a (Sirpa) Regulates Fey and Complement Receptor-Mediated Phagocytosis" J Exp Med. Apr. 2, 2001;193(7):855-62.
Olsson, M., "Role of the CD47/SIRPa-interaction in regulation of macrophage phagocytosis" Thesis: Department of Integrative Medical Biology, Section for Histology and CellBiology, Umea University, Umea, Sweden (2008).
Panka, D.J. et al. "Variable region framework differences result in decreased or increased affinity of variant anti-digoxin antibodies" Proc. Natl. Acad. Sci. USA, 85: 3080-3084 (1988).
Paul, W.E. (Ed.), *Fundamental Immunology*, 3rd Edition. New York: Raven Press, 1993; pp. 292-295.
Portner L. et al., "T and NK cells of B cell NHL patients exert cytotoxicity against lymphoma cells following binding of bispecific tetravalent antibody CD19 3 CD3 or CD19 3 CD16", Cancer Immunol Immunother. 61(10):1869-75, (2012).
Powell et al., "Compendium of excipients for parenteral formulations" PDA J Pharm Sci Technol. 52:238-311 (1998).
Presta, "Antibody engineering", Current Opinion in Structural Biology, 2:593-596 (1992).
Ramakrishnan, S. et al., "Comparison of the Selective Cytotoxic Effects of Immunotoxins Containing Ricin A Chain or Pokeweed Antiviral Protein and Anti-Thy 1.1 Monoclonal Antibodies", Cancer Res. 44:201-208 (1984).
Ridgway et al., "Knobs-into-holes engineering of antibody CH3 domains for heavy chain heterodimerization", Protein Eng 7:617-621 (1996).
Riechmann et al., "Reshaping human antibodies for therapy", Nature, 332:323-327 (1988).
Rudikoff, S. et al. "Single amino acid substitution altering antigen-binding specificity" Proc. Natl. Acad. Sci. USA, 79: 1979-1983 (1982).
Shopes, "A genetically engineered human IgG mutant with enhanced cytolytic activity", J. Immunol., 148: 2918-2922 (1992).
Sick, E et al., "CD47 Update: a multifaced actor in the tumor microenvironment of potential therapeutic interest" Br J Pharmacol. Dec. 2012;167(7):1415-30.
Soto-Pantoja, D.R. et al., "Therapeutic opportunities for targeting the ubiquitous cell surface receptor CD47" Expert Opin Ther Targets. Jan. 2013;17(1):89-103.
Stevenson et al., "A chimeric antibody with dual Fe regions (bisFabFc) prepared by manipulations at the IgG hinge", Anti-Cancer Drug Design, 3: 219-230 (1989).
Strohl, W. "Optimization of Fc-mediated effector functions of monoclonal Antibodies", Curr Opin Biotechnol (6):685-91 (2009).
Suresh et al., "Bispecific Monoclonal Antibodies from Hybrid Hybridomas", Methods in Enzymology, 121: 210 (1986).
Thornton et al., "Prediction of progress at last", Nature, 354: 105-106 (1991).
Traunecker et al., "Bispecific single chain molecules (Janusins) target cytotoxic lymphocytes on HIV infected cells" EMBO Journal, 10:3655-3659 (1991).
Tutt et al., "Trispecific F(ab')$_3$ Derivatives that Use Cooperative Signaling via the TCR/CD3 Complex and CD2 to Activate and Redirect Resting Cytotoxic T Cells", Journal of Immunology, 147:60-69 (1991).
Vaughan et al., "Human Antibodies with Sub-nanomolar Affinities Isolated From a Large Non-immunized Phage Display Library", Nat. Biotech. 14:309-314 (1996).
Verhoeyen et al., "Reshaping Human Antibodies: Grafting an Antilysozyme Activity", Science, 239:1534-1536 (1988).
Vitetta et al., "Redesigning Nature's Poisons to Create Anti-Tumor Reagents", Science 238: 1098-1104 (1987).
Von Kreudenstein, T. et al., "Improving biophysical properties of a bispecific antibody scaffold to aid developability", MAbs. 5(5):646-654 (2013).
Wang, W., "Lyophilization and development of solid protein pharmaceuticals." Int. J. Pharm. 203: 1-60 (2000).
Weiskopf, K, et al., "Engineered SIRPa Variants as Immunotherapeutic Adjuvants to Anticancer Antibodies", Science. Jul. 5, 2013;341(6141):88-91.
Wilkinson, D. *The Scientist*, published by The Scientist, Inc., Philadelphia PA, vol. 14, No. 8 (Apr. 17, 2000), p. 25-28.

(56) References Cited

OTHER PUBLICATIONS

Willingham, S.B. et al., "The CD47-signal regulatory protein alpha (SIRPa) interaction is a therapeutic target for human solid tumors", Proc Natl Acad Sci US A. Apr. 24, 2012;109(17):6662-7.

Wolf, E. et al., "BiTEs: bispecific antibody constructs with unique anti-tumor activity", Drug Discov. Today 10(18):1237-1244 (2005).

Yang, et al., "Cellular and Humoral Immune Responses to Viral Antigens Create Barriers to Lung-Directed Gene Therapy with Recombinant Adenoviruses", Journal of Virology 69:2004-2015 (1995).

Hoogenboom, H.R. and Winter, G. "By-passing Immunisation. Human Antibodies from Synthetic Repertoires of Germline VH Gene Segments Rearranged in Vitro" *J. Mol. Biol.*, 227:381-388 (1992).

Kearns, J.D. et al. (2015) "Enhanced Targeting of the EGFR Network with MM-151, an Oligoclonal Anti-EGFR Antibody Therapeutic" *Mol. Cancer Ther.* 14(7):1625-1636.

Lefranc, M-P. (2014) "Immunoglobulins: 25 Years of Immunoinformatics and IMGT-Ontology" *Biomolecules*, 4:1102-1139; doi: 10.3390/biom4041102.

Yu, J. and M.F. Lin (Apr. 2005) "Anti-CD47 monoclonal antibody (B6H12) impairs the maturation and function of human dendritic cells" *J Exp Hematol (Zhongguo Shi Yan Xue Ye Xue Za Zhi)*, 13(2):192-197. Chinese with English Abstract on p. 192.

Beiboer, S. H. W. et al., "Guided Selection of a Pan Carcinoma Specific Antibody Reveals Similar Binding Characteristics yet Structural Divergence Between the Original Murine Antibody and its Human Equivalent," J. Mol. Biol., 296:833-849 (2000).

Dondelinger, M. et al., "Understanding the Significance and Implications of Antibody Numbering and Antigen-Binding Surface/Residue Definition," Front Immunol, 9:2278 (2018); doi: 10.3389/fimmu.2018.02278, 15 pages.

Portolano, S. et al., "Lack of Promiscuity in Autoantigen-Specific H and L Chain Combinations as Revealed by Human H and L Chain 'Roulette'", The Journal of Immunology, 150(3):880-887 (1993).

Cuzick et al., "Overview of the main outcomes in breast-cancer prevention trials", The Lancet, vol. 361, p. 296-300, (Year: 2003).

Evans et al., "Vaccine therapy for cancer—fact or fiction?", Q.J. Med 1999: 92: 299-307, (Year: 1999).

Hernandez-Ledesma et al., "Lunasin, a novel seed peptide for cancer prevention", Peptides, vol. 30, p. 426-430, (Year: 2009).

Komenaka et al., "Immunotherapy for Melanoma", Clinics in Dermatology, 2004, vol. 22, p. 251-265, (Year: 2004).

Sanders et al., "Classification of cea-related positivity in primary and metastatic malignant melanoma", Journal of Pathology, vol. 172, p. 343-348, 1994.

Schiffman et al., "The Promise of Global Cervical-Cancer Prevention", The New England Journal of Medicine, vol. 353, No. 20, p. 2101-2105, (Year: 2005).

Subramanian et al., "Species- and Cell type-specific between CD47 and human SIRPα", Blood, Mar. 15, 2006, vol. 107, No. 6, pp. 2548-2556.

Mariuzza, et al., "The Structural Basis of Antigen-antibody Recognition," Annual Review of Biophysics and Biophysical Chemistry, 1987, vol. 16.1: 139-159.

Li et al., "Research progress of correlation between CD47 and tumor immunity," Guangdong Medical Journal, vol. 32, No. 18, Sep. 30, 2011, pp. 2480-2481 (English Abstract provided).

\* cited by examiner

FIG. 1

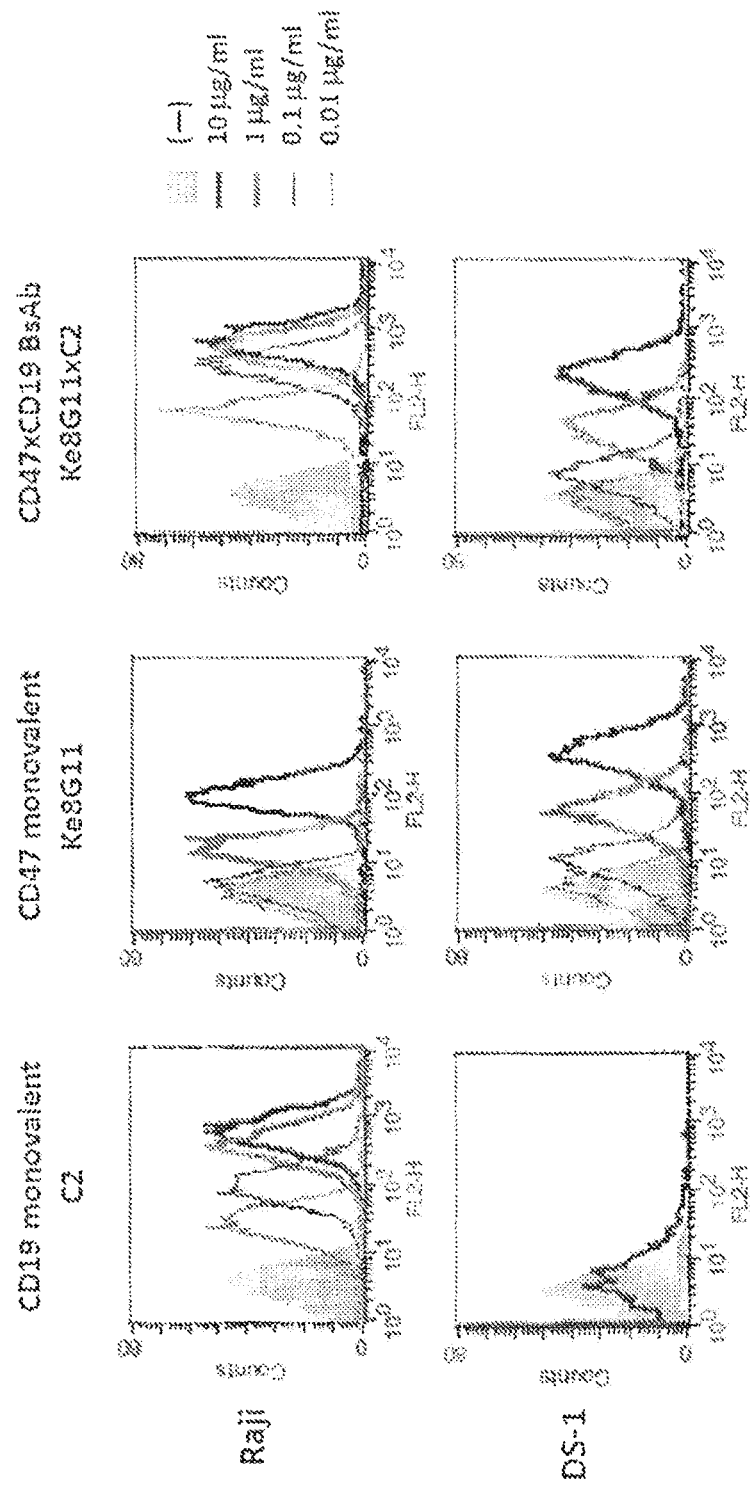

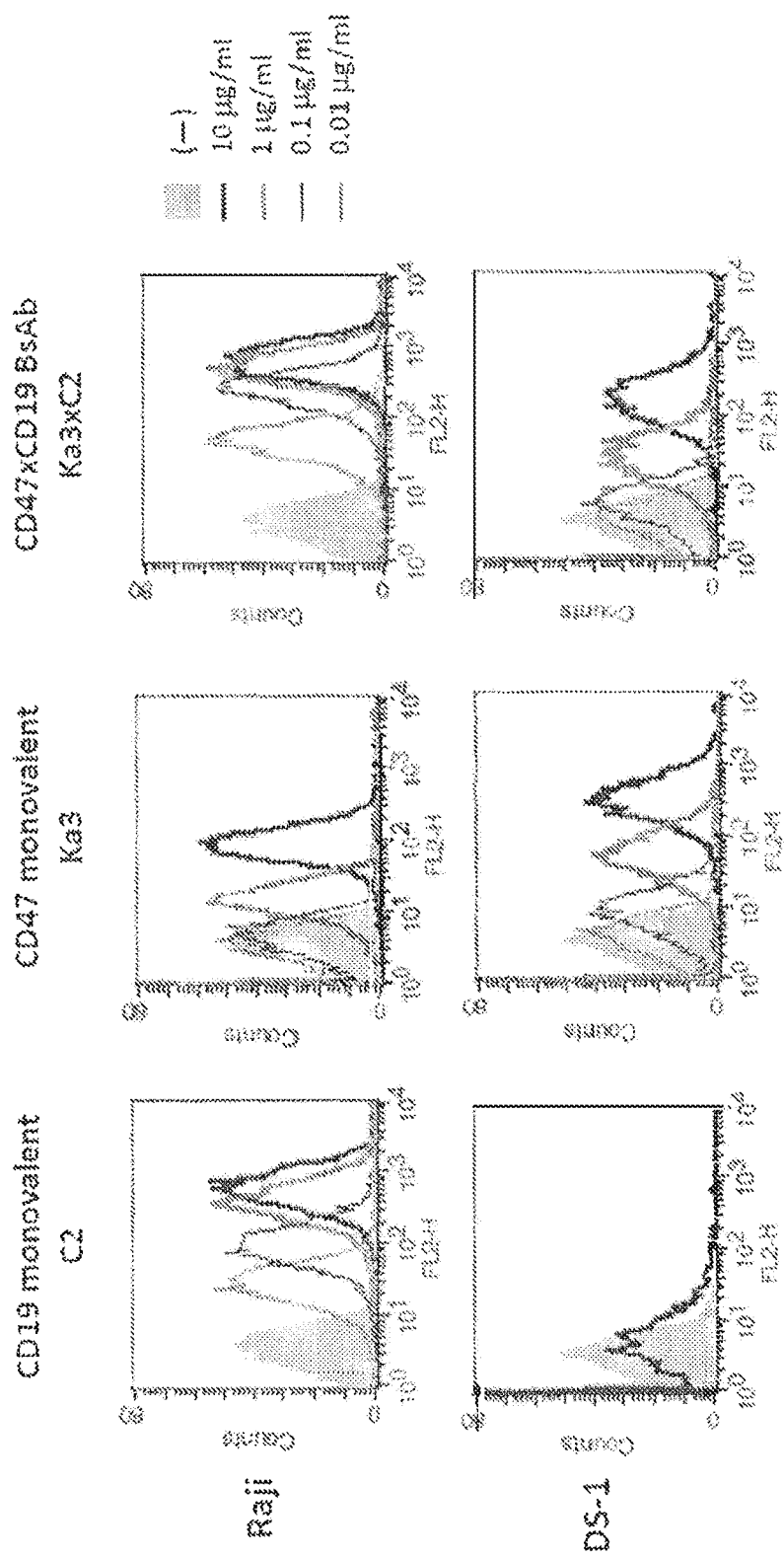

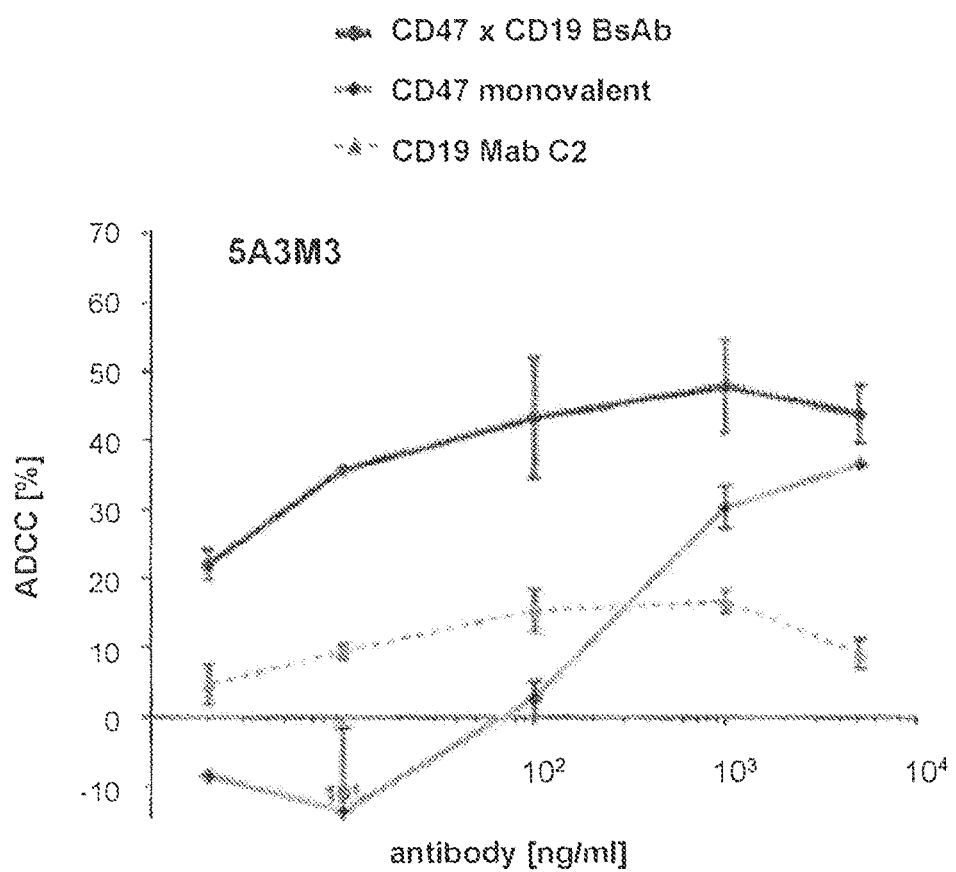

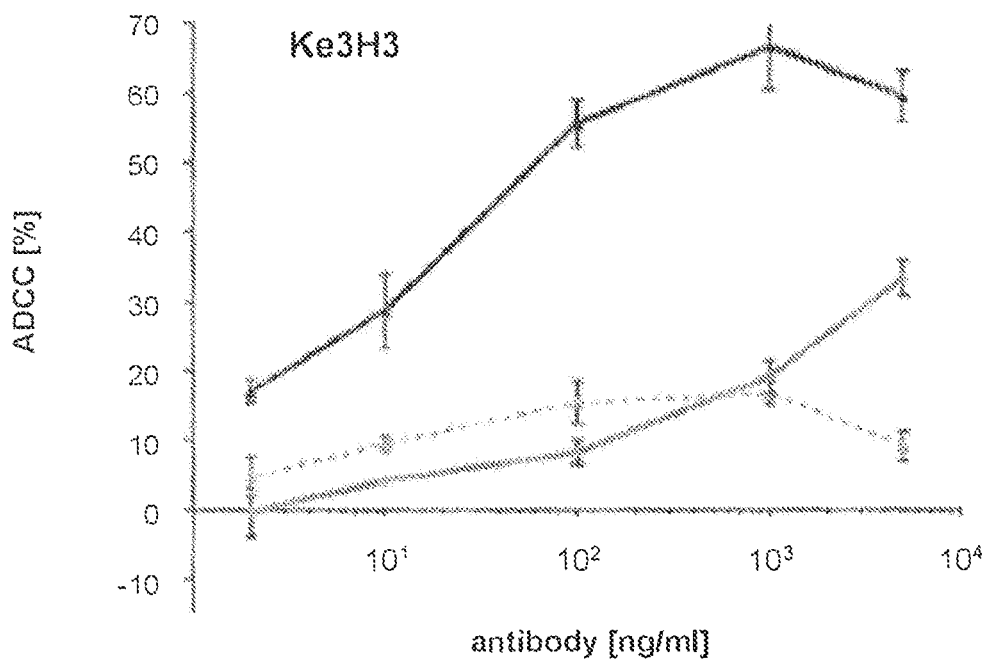

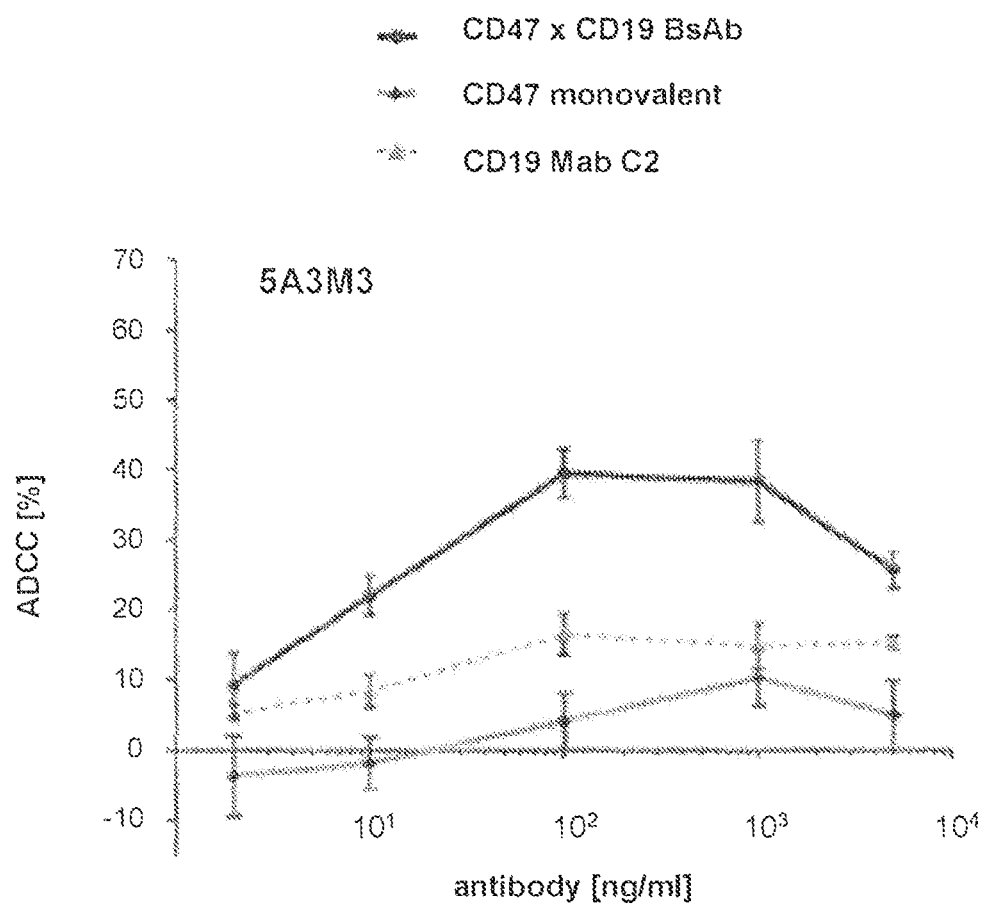

FIG. 11Q
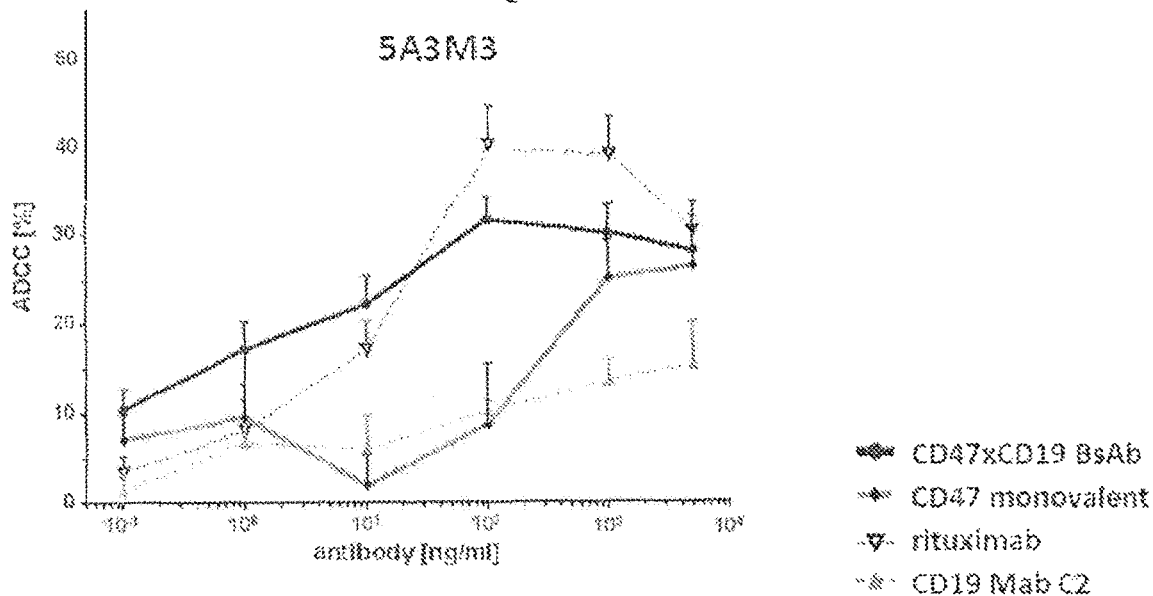
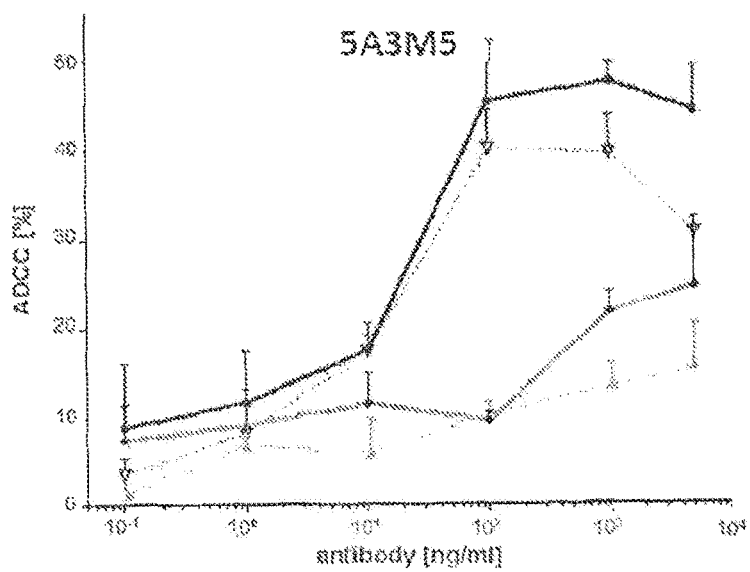

SEQUENCE LISTING

<160> NUMBER OF SEQ ID NOS: 287

<210> SEQ ID NO 1
<211> LENGTH: 1338
<212> TYPE: DNA
<213> ORGANISM: Artificial Sequence
<220> FEATURE:
<223> OTHER INFORMATION: common heavy chain

<400> SEQUENCE: 1

```
gaggtgcagc tgttggagtc tgggggaggc ttggtacagc ctgggggtc cctgagactc      60 tcctgtgcag cctctggatt cacctttagc agctatgcca tgagctgggt ccgccaggct     120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtat attactgtgc gaaaagttat    300
ggtgcttttg actactgggg ccagggaacc ctggtcacag tctcgagcgc ctccaccaag    360
ggcccatcgg tcttccccct ggcaccctcc tccaagagca cctctggggg cacagcggcc    420
ctgggctgcc tggtcaagga ctacttcccc gaaccggtga cagtctcgtg gaactcagga    480
gccctgacca gcggcgtgca caccttcccg gctgtcctac agtcctcagg actctactcc    540
ctcagcagcg tggtgactgt gccctccagc agcttgggca cccagaccta catctgcaac    600
gtgaatcaca agcccagcaa caccaaggtg gacaagagag ttgagcccaa atcttgtgac    660
aaaactcaca catgcccacc gtgcccagca cctgaactcc tggggggacc gtcagtcttc    720
ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagccccc atcgagaaaa ccatctccaa agccaaaggg   1020
cagccccgag aaccacaggt gtatacctg ccccccatctc gggaggagat gaccaagaac  1080
caggtcagcc tgacttgcct ggtcaaaggc ttctatccca gcgacatcgc cgtggagtgg   1140
gagagcaacg ggcagccgga gaacaactac aagaccacgc ctcccgtgct ggactccgac   1200
ggctccttct tcctctatag caagctcacc gtggacaagt ccaggtggca gcagggaac   1260 gtcttctcat gctccgtgat gcatgaggct ctgcacaacc actacacgca gaagagcctc  1320
tccctgtctc cgggttaa                                                1338
```

<210> SEQ ID NO 2
<211> LENGTH: 445
<212> TYPE: PRT
<213> ORGANISM: Artificial Sequence
<220> FEATURE:
<223> OTHER INFORMATION: common heavy chain

<400> SEQUENCE: 2

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Gly Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365
```

```
Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
            435                 440                 445

<210> SEQ ID NO 3
<211> LENGTH: 648
<212> TYPE: DNA
<213> ORGANISM: Artificial Sequence
<220> FEATURE:
<223> OTHER INFORMATION: anti-CD47 5A3 kappa light chain

<400> SEQUENCE: 3
gacatccaga tgacccagtc tccatcctcc ctgtctgcat ctgtaggaga cagagtcacc    60
atcacttgcc aggcgagtca ggacattaat aagtatttaa attggtatca gcagaaacca   120
gggaaagccc ctaagctcct gatctacggt gcatccaggt tggaaacagg gtcccatca    180 aggttcagtg gaagtggatc tgggacagat tttactttca ccatcagcag cctgcagcct   240
gaagatattg caacatatta ctgtcagcag aagcaccccc gggggccgag gaccttcggc   300
caagggacca aggtggaaat caaacgtacg gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca agcagactac gagaaacac aaagtctacg cctgcgaagt cacccatcag   600
ggcctgagct cgcccgtcac aaagagcttc aacaggggag agtgttaa              648

<210> SEQ ID NO 4
<211> LENGTH: 215
<212> TYPE: PRT
<213> ORGANISM: Artificial Sequence
<220> FEATURE:
<223> OTHER INFORMATION: anti-CD47 5A3 kappa light chain

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Lys Tyr
            20                  25                  30

Leu Asn Trp Tyr Gln Gln Lys Pro Gly Lys Ala Pro Lys Leu Leu Ile
        35                  40                  45

Tyr Gly Ala Ser Arg Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Lys His Pro Arg Gly Pro
                85                  90                  95

Arg Thr Phe Gly Gln Gly Thr Lys Val Glu Ile Lys Arg Thr Val Ala
            100                 105                 110
```

Ala Pro Ser Val Phe Ile Phe Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 5
<211> LENGTH: 648
<212> TYPE: DNA
<213> ORGANISM: Artificial Sequence
<220> FEATURE:
<223> OTHER INFORMATION: anti-CD47 5A3-M4 kappa light chain

<400> SEQUENCE: 5
gacatccaga tgacccagtc tccatcctcc ctgtctgcat ctgtaggaga cagagtcacc      60
atcacttgcc aggcgagtca ggacattaat aagtatttaa attggtatca gcagaaacca     120
gggaaagccc ctaagctcct gatctacggt gcatccaggt tggaaacagg ggtcccatca     180
aggttcagtg gaagtggatc tgggacagat tttactttca ccatcagcag cctgcagcct     240
gaagatattg caacatatta ctgtcagcag aagcaccccc ggaacccgag gaccttcggc     300
caagggacca aggtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca aagcagacta cgagaaacac aaagtctacg cctgcgaagt cacccatcag     600
ggcctgagct cgcccgtcac aaagagcttc aacaggggag agtgttaa                  648

<210> SEQ ID NO 6
<211> LENGTH: 215
<212> TYPE: PRT
<213> ORGANISM: Artificial Sequence
<220> FEATURE:
<223> OTHER INFORMATION: anti-CD47 5A3-M4 kappa light chain

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Lys Tyr
            20                  25                  30

Leu Asn Trp Tyr Gln Gln Lys Pro Gly Lys Ala Pro Lys Leu Leu Ile
        35                  40                  45

Tyr Gly Ala Ser Arg Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Lys His Pro Arg Asn Pro

```
                85                  90                  95
Arg Thr Phe Gly Gln Gly Thr Lys Val Glu Ile Lys Arg Thr Val Ala
                    100                 105                 110

Ala Pro Ser Val Phe Ile Phe Pro Pro Ser Asp Glu Gln Leu Lys Ser
                    115                 120                 125

Gly Thr Ala Ser Val Val Cys Leu Leu Asn Asn Phe Tyr Pro Arg Glu
                130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
                210                 215

<210> SEQ ID NO 7
<211> LENGTH: 648
<212> TYPE: DNA
<213> ORGANISM: Artificial Sequence
<220> FEATURE:
<223> OTHER INFORMATION: anti-CD47 5A3-M3 kappa light chain

<400> SEQUENCE: 7
gacatccaga tgacccagtc tccatcctcc ctgtctgcat ctgtaggaga cagagtcacc      60
atcacttgcc aggcgagtca gtccattagt agttatttaa attggtatca gcagaaacca     120
gggaaagccc ctaagctcct gatctacgct gcatcctcgt tggaaacagg ggtcccatca     180
aggttcagtg gaagtggatc tgggacagat tttactttca ccatcagcag cctgcagcct     240
gaagatattg caacatatta ctgtcagcag aagcaccccc gggggccgag gaccttcggc     300
caagggacca aggtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca aagcagacta cgagaaacac aaagtctacg cctgcgaagt cacccatcag     600
ggcctgagct cgcccgtcac aaagagcttc aacaggggag agtgttaa                  648

<210> SEQ ID NO 8
<211> LENGTH: 215
<212> TYPE: PRT
<213> ORGANISM: Artificial Sequence
<220> FEATURE:
<223> OTHER INFORMATION: anti-CD47 5A3-M3 kappa light chain

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Glu Thr Gly Val Pro Ser Arg Phe Ser Gly
    50                  55                  60
```

```
Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Lys His Pro Arg Gly Pro
                 85                  90                  95

Arg Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 9
<211> LENGTH: 648
<212> TYPE: DNA
<213> ORGANISM: Artificial Sequence
<220> FEATURE:
<223> OTHER INFORMATION: anti-CD47 5A3-M5 kappa light chain

<400> SEQUENCE: 9
gacatccaga tgacccagtc tccatcctcc ctgtctgcat ctgtaggaga cagagtcacc      60
atcacttgcc aggcgagtca ggacattaat aagtatttaa attggtatca gcagaaacca     120
gggaaagccc ctaagctcct gatctacggt gcatccaggt tggaaacagg ggtcccatca     180
aggttcagtg gaagtggatc tgggacagat tttactttca ccatcagcag cctgcagcct     240
gaagatattg caacatatta ctgtcagcag aagcaccccc ggtacccgag gaccttcggc     300
caagggacca aggtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag     600
ggcctgagct cgcccgtcac aaagagcttc aacaggggag agtgttaa                  648

<210> SEQ ID NO 10
<211> LENGTH: 215
<212> TYPE: PRT
<213> ORGANISM: Artificial Sequence
<220> FEATURE:
<223> OTHER INFORMATION: anti-CD47 5A3-M5 kappa light chain

<400> SEQUENCE: 10

Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Asn Lys Tyr
             20                  25                  30
```

```
Leu Asn Trp Tyr Gln Gln Lys Pro Gly Lys Ala Pro Lys Leu Leu Ile
         35                  40                  45

Tyr Gly Ala Ser Arg Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Lys His Pro Arg Tyr Pro
                 85                  90                  95

Arg Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 11
<211> LENGTH: 648
<212> TYPE: DNA
<213> ORGANISM: Artificial Sequence
<220> FEATURE:
<223> OTHER INFORMATION: anti-CD47 Ke8 kappa light chain

<400> SEQUENCE: 11
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat tcactctca ccatcagcag tctgcaacct     240
gaagattttg caacttacta ctgtcagcag ttccacaagc ggcggccgca gaccttcggc     300
caagggacca aggtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcccctg     540 acgctgagca agcagactac agaaaacac aaagtctacg cctgcgaagt cacccatcag     600
ggcctgagct cgcccgtcac aaagagcttc aacaggggag agtgttaa                  648

<210> SEQ ID NO 12
<211> LENGTH: 215
<212> TYPE: PRT
<213> ORGANISM: Artificial Sequence
<220> FEATURE:
<223> OTHER INFORMATION: anti-CD47 Ke8 kappa light chain

<400> SEQUENCE: 12

Asp Ile Gln Met Thr Gln Ser Pro Ser Ser Leu Ser Ala Ser Val Gly
```

```
              1               5                  10                 15
Asp Arg Val Thr Ile Thr Cys Arg Ala Ser Gln Ser Ile Ser Ser Tyr
                20                  25                 30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe His Lys Arg Arg Pro
                85                  90                  95

Gln Thr Phe Gly Gln Gly Thr Lys Val Glu Ile Lys Arg Thr Val Ala
                100                 105                110

Ala Pro Ser Val Phe Ile Phe Pro Pro Ser Asp Glu Gln Leu Lys Ser
                115                 120                125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
        210                 215

<210> SEQ ID NO 13
<211> LENGTH: 648
<212> TYPE: DNA
<213> ORGANISM: Artificial Sequence
<220> FEATURE:
<223> OTHER INFORMATION: anti-CD47 Ke8H5 kappa light chain

<400> SEQUENCE: 13
gacatccaga tgacccagtc tccatcctcc ctgtctgcat ctgtaggaga cagagtcacc    60
atcacttgcc gggcaagtca gagcattgcg aggtatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcag ttccataagc gtcgccgcca gaccttcggc   300
caagggacca aggtggaaat caaacgtacg gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca agcagactac gagaaacac aaagtctacg cctgcgaagt cacccatcag   600
ggcctgagct cgcccgtcac aaagagcttc aacaggggag agtgttaa                648

<210> SEQ ID NO 14
<211> LENGTH: 215
<212> TYPE: PRT
<213> ORGANISM: Artificial Sequence
<220> FEATURE:
```

<223> OTHER INFORMATION: anti-CD47 Ke8H5 kappa light chain

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe His Lys Arg Ala Pro
                85                  90                  95

Gln Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 15
<211> LENGTH: 648
<212> TYPE: DNA
<213> ORGANISM: Artificial Sequence
<220> FEATURE:
<223> OTHER INFORMATION: anti-CD47 Ke8B2 kappa light chain

<400> SEQUENCE: 15

```
gacatccaga tgacccagtc tccatcctcc ctgtctgcat ctgtaggaga cagagtcacc      60
atcacttgcc gggcaagtca gagcattggt aagtatttaa attggtatca gcagaaacca     120
gggaaagccc ctaagctcct gatctatgcg catccaggt tgcaaagtgg ggtcccatca      180
aggttcagtg gcagtggatc tgggacagat ttcactctca ccatcagcag tctgcaacct     240
gaagattttg caacttacta ctgtcagcag aagcacccgc gtgccccgcg gaccttcggc     300
caagggacca aggtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag     600
ggcctgagct cgcccgtcac aaagagcttc aacaggggag agtgttaa                  648
```

<210> SEQ ID NO 16
<211> LENGTH: 215
<212> TYPE: PRT
<213> ORGANISM: Artificial Sequence
<220> FEATURE:
<223> OTHER INFORMATION: anti-CD47 Ke8B2 kappa light chain

<400> SEQUENCE: 16

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys His Pro Arg Ala Pro
                85                  90                  95

Arg Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 17
<211> LENGTH: 648
<212> TYPE: DNA
<213> ORGANISM: Artificial Sequence
<220> FEATURE:
<223> OTHER INFORMATION: anti-CD47 Ke8A2 kappa light chain

<400> SEQUENCE: 17

```
gacatccaga tgacccagtc tccatcctcc ctgtctgcat ctgtaggaga cagagtcacc     60
atcacttgcc gggcaagtca gagcattgat aggtatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcag aagcatcccc gtgggccgag gaccttcggc   300
caagggacca aggtggaaat caaacgtacg gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
```

```
acgctgagca aagcagacta cgagaaacac aaagtctacg cctgcgaagt cacccatcag    600
ggcctgagct cgcccgtcac aaagagcttc aacaggggag agtgttaa               648
```

<210> SEQ ID NO 18
<211> LENGTH: 215
<212> TYPE: PRT
<213> ORGANISM: Artificial Sequence
<220> FEATURE:
<223> OTHER INFORMATION: anti-CD47 Ke8A2 kappa light chain

<400> SEQUENCE: 18

```
Asp Ile Gln Met Thr Gln Ser Pro Ser Leu Ser Ala Ser Val Gly
1               5                   10                  15

Asp Arg Val Thr Ile Thr Cys Arg Ala Ser Gln Ser Ile Asp Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys His Pro Arg Gly Pro
                85                  90                  95

Arg Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 19
<211> LENGTH: 648
<212> TYPE: DNA
<213> ORGANISM: Artificial Sequence
<220> FEATURE:
<223> OTHER INFORMATION: anti-CD47 Ke8E8 kappa light chain

<400> SEQUENCE: 19

```
gacatccaga tgacccagtc tccatcctcc ctgtctgcat ctgtaggaga cagagtcacc    60
atcacttgcc aggcgagtca ggacattaat aagtatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcag aagcatcccc gtggcccgcg gaccttcggc   300
caagggacca gtggaaat caaacgtacg gtggctgcac catctgtctt catcttcccg   360
ccatctgatg agcagttgaa atctggaact gcctctgttg tgtgcctgct gaataacttc   420
```

```
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgttaa                 648
```

<210> SEQ ID NO 20
<211> LENGTH: 215
<212> TYPE: PRT
<213> ORGANISM: Artificial Sequence
<220> FEATURE:
<223> OTHER INFORMATION: anti-CD47 Ke8E8 kappa light chain

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys His Pro Arg Gly Pro
                85                  90                  95

Arg Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 21
<211> LENGTH: 648
<212> TYPE: DNA
<213> ORGANISM: Artificial Sequence
<220> FEATURE:
<223> OTHER INFORMATION: anti-CD47 Ke8H3 kappa light chain

<400> SEQUENCE: 21

```
gacatccaga tgacccagtc tccatcctcc ctgtctgcat ctgtaggaga cagagtcacc    60
atcacttgcc gggcaagtca gagcattaat aggtatttaa attggtatca gcagaaacca    120
gggaaagccc ctaagctcct gatctatgct gcatccaggt tgcaaagtgg ggtcccatca    180
aggttcagtg gcagtggatc tgggacagat ttcactctca ccatcagcag tctgcaacct    240
```

```
gaagattttg caacttacta ctgtcagcag aagcatccgc gtgggccgag gaccttcggc    300
caagggacca aggtggaaat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagacta cgagaaacac aaagtctacg cctgcgaagt cacccatcag    600
ggcctgagct cgcccgtcac aaagagcttc aacaggggag agtgttaa                648
```

<210> SEQ ID NO 22
<211> LENGTH: 215
<212> TYPE: PRT
<213> ORGANISM: Artificial Sequence
<220> FEATURE:
<223> OTHER INFORMATION: anti-CD47 Ke8H3 kappa light chain

<400> SEQUENCE: 22

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys His Pro Arg Gly Pro
                85                  90                  95

Arg Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 23
<211> LENGTH: 648
<212> TYPE: DNA
<213> ORGANISM: Artificial Sequence
<220> FEATURE:
<223> OTHER INFORMATION: anti-CD47 Ke8G6 kappa light chain

<400> SEQUENCE: 23

```
gacatccaga tgacccagtc tccatcctcc ctgtctgcat ctgtaggaga cagagtcacc     60
atcacttgcc gggcaagtca gagcattggt aggtatttaa attggtatca gcagaaacca    120
```

```
gggaaagccc ctaagctcct gatctatgct gcatccagtt tgcaaagtgg ggtcccatca      180
aggttcagtg gcagtggatc tgggacagat ttcactctca ccatcagcag tctgcaacct      240
gaagattttg caacttacta ctgtcagcag atgcatccgc gtgcgccgaa gaccttcggc      300
caagggacca aggtggaaat caaacgtacg gtggctgcac catctgtctt catcttcccg      360
ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacagagca ggacagcaag gacagcacct acagcctcag cagcaccctg      540
acgctgagca aagcagacta cgagaaacac aaagtctacg cctgcgaagt cacccatcag      600
ggcctgagct cgcccgtcac aaagagcttc aacaggggag agtgttaa                  648
```

```
<210> SEQ ID NO 24
<211> LENGTH: 215
<212> TYPE: PRT
<213> ORGANISM: Artificial Sequence
<220> FEATURE:
<223> OTHER INFORMATION: anti-CD47 Ke8G6 kappa light chain

<400> SEQUENCE: 24
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

```
<210> SEQ ID NO 25
<211> LENGTH: 648
<212> TYPE: DNA
<213> ORGANISM: Artificial Sequence
<220> FEATURE:
<223> OTHER INFORMATION: anti-CD47 Ke8A3 kappa light chain
```

<400> SEQUENCE: 25

```
gacatccaga tgacccagtc tccatcctcc ctgtctgcat ctgtaggaga cagagtcacc    60
atcacttgcc gggtaagtca gagcattagt aagtatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcag aggcatcccc gtgggccgag caccttcggc   300
caagggacca aggtggaaat caaacgtacg gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca aagcagacta cgagaaacac aaagtctacg cctgcgaagt cacccatcag   600
ggcctgagct cgcccgtcac aaagagcttc aacaggggag agtgttaa                648
```

<210> SEQ ID NO 26
<211> LENGTH: 215
<212> TYPE: PRT
<213> ORGANISM: Artificial Sequence
<220> FEATURE:
<223> OTHER INFORMATION: anti-CD47 Ke8A3 kappa light chain

<400> SEQUENCE: 26

```
Asp Ile Gln Met Thr Gln Ser Pro Ser Ser Leu Ser Ala Ser Val Gly
1               5                   10                  15

Asp Arg Val Thr Ile Thr Cys Arg Val Ser Gln Ser Ile Ser Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg His Pro Arg Gly Pro
                85                  90                  95

Ser Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 27
<211> LENGTH: 648

<212> TYPE: DNA
<213> ORGANISM: Artificial Sequence
<220> FEATURE:
<223> OTHER INFORMATION: anti-CD47 Ke81A3 kappa light chain

<400> SEQUENCE: 27

```
gacatccaga tgacccagtc tccatcctcc ctgtctgcat ctgtaggaga cagagtcacc      60
atcacttgcc aggcgagtca ggacattaat aggtatttaa attggtatca gcagaaacca     120
gggaaagccc ctaagctcct gatctatgct gcatccagtt tgcaaagtgg ggtcccatca     180
aggttcagtg gcagtggatc tgggacagat tcactctca ccatcagcag tctgcaacct     240
gaagattttg caacttacta ctgtcagcag aggcatccgc gtgccccgcg gaccttcggc     300
caagggacca aggtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca aagcagacta cgagaaacac aaagtctacg cctgcgaagt cacccatcag     600
ggcctgagct cgcccgtcac aaagagcttc aacaggggag agtgttaa                  648
```

<210> SEQ ID NO 28
<211> LENGTH: 215
<212> TYPE: PRT
<213> ORGANISM: Artificial Sequence
<220> FEATURE:
<223> OTHER INFORMATION: anti-CD47 Ke81A3 kappa light chain

<400> SEQUENCE: 28

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg His Pro Arg Ala Pro
                85                  90                  95

Arg Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
```

<210> SEQ ID NO 29
<211> LENGTH: 648
<212> TYPE: DNA
<213> ORGANISM: Artificial Sequence
<220> FEATURE:
<223> OTHER INFORMATION: anti-CD47 Ke8A8 kappa light chain

<400> SEQUENCE: 29

```
gacatccaga tgacccagtc tccatcctcc ctgtctgcat ctgtaggaga cagagtcacc      60
atcacttgcc gggcaagtca gagcattagt aagtatttaa attggtatca gcagaaacca     120
gggaaagccc ctaagctcct gatctatgct gcatccactt tgcaaagtgg ggtcccatca     180
aggttcagtg gcagtggatc tgggacagat ttcactctca ccatcagcag tctgcaacct     240
gaagattttg caacttacta ctgtcagcag atgcatccgc gtgcgccgaa gaccttcggc     300
caagggacca aggtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagacta cgagaaacac aaagtctacg cctgcgaagt cacccatcag     600
ggcctgagct cgcccgtcac aaagagcttc aacaggggag agtgttaa                  648
```

<210> SEQ ID NO 30
<211> LENGTH: 215
<212> TYPE: PRT
<213> ORGANISM: Artificial Sequence
<220> FEATURE:
<223> OTHER INFORMATION: anti-CD47 Ke8A8 kappa light chain

<400> SEQUENCE: 30

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Lys Tyr
                20                  25                  30

Leu Asn Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190
```

Tyr Ala Cys Glu Val Thr His Gln Gly Leu Ser Ser Pro Val Thr Lys
            195                 200                 205
Ser Phe Asn Arg Gly Glu Cys
    210                 215

<210> SEQ ID NO 31
<211> LENGTH: 648
<212> TYPE: DNA
<213> ORGANISM: Artificial Sequence
<220> FEATURE:
<223> OTHER INFORMATION: anti-CD47 Ke8C7 kappa light chain

<400> SEQUENCE: 31
gacatccaga tgacccagtc tccatcctcc ctgtctgcat ctgtaggaga cagagtcacc      60
atcacttgcc aggcgagtca ggacattaat aggtatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcagcag cgccatccgc gtggcccgag gaccttcggc    300
caagggacca aggtggaaat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac aaagtctacg cctgcgaagt cacccatcag    600
ggcctgagct cgcccgtcac aaagagcttc aacaggggag agtgttaa               648

<210> SEQ ID NO 32
<211> LENGTH: 215
<212> TYPE: PRT
<213> ORGANISM: Artificial Sequence
<220> FEATURE:
<223> OTHER INFORMATION: anti-CD47 Ke8C7 kappa light chain

<400> SEQUENCE: 32

Asp Ile Gln Met Thr Gln Ser Pro Ser Ser Leu Ser Ala Ser Val Gly
1               5                   10                  15
Asp Arg Val Thr Ile Thr Cys Gln Ala Ser Gln Asp Ile Asn Arg Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Arg His Pro Arg Gly Pro
                85                  90                  95
Arg Thr Phe Gly Gln Gly Thr Lys Val Glu Ile Lys Arg Thr Val Ala
            100                 105                 110
Ala Pro Ser Val Phe Ile Phe Pro Pro Ser Asp Glu Gln Leu Lys Ser
        115                 120                 125
Gly Thr Ala Ser Val Val Cys Leu Leu Asn Asn Phe Tyr Pro Arg Glu
    130                 135                 140
Ala Lys Val Gln Trp Lys Val Asp Asn Ala Leu Gln Ser Gly Asn Ser
145                 150                 155                 160

```
Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 33
<211> LENGTH: 648
<212> TYPE: DNA
<213> ORGANISM: Artificial Sequence
<220> FEATURE:
<223> OTHER INFORMATION: anti-CD47 Ke8G2 kappa light chain

<400> SEQUENCE: 33
gacatccaga tgacccagtc tccatcctcc ctgtctgcat ctgtaggaga cagagtcacc      60
atcacttgcc gggcaagtca gagcattggt aggtatttaa attggtatca gcagaaacca    120
gggaaagccc ctaagctcct gatctatgcg gcatccaggt tgcaaagtgg ggtcccatca    180
aggttcagtg gcagtggatc tgggacagat ttcactctca ccatcaacag tctgcaacct    240
gaagattttg caacttacta ctgtcagcag aagcatcccc gtgcgccgag gaccttcggc    300
caagggacca aggtggaaat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac aaagtctacg cctgcgaagt cacccatcag    600
ggcctgagct cgcccgtcac aaagagcttc aacaggggag agtgttaa                  648

<210> SEQ ID NO 34
<211> LENGTH: 215
<212> TYPE: PRT
<213> ORGANISM: Artificial Sequence
<220> FEATURE:
<223> OTHER INFORMATION: anti-CD47 Ke8G2 kappa light chain

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Lys His Pro Arg Ala Pro
                85                  90                  95

Arg Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
```

```
                    130                 135                 140
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 35
<211> LENGTH: 648
<212> TYPE: DNA
<213> ORGANISM: Artificial Sequence
<220> FEATURE:
<223> OTHER INFORMATION: anti-CD47 Ke81G9 kappa light chain

<400> SEQUENCE: 35
gacatccaga tgacccagtc tccatcctcc ctgtctgcat ctgtaggaga cagagtcacc    60
atcacttgcc gggcaagtca gagcattgat aagtatttaa attggtatca gcagaaacca   120
gggaaagccc ctaagctcct gatctatgcg gcatccaggt tgcaaagtgg ggtcccatca   180
aggttcagtg gcagtggatc tgggacagat ttcactctca ccatcagcag tctgcaacct   240
gaagattttg caacttacta ctgtcagcag cggcataagc gttccccgca gaccttcggc   300
caagggacca aggtggaaat caaacgtacg gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca aagcagacta cgagaaacac aaagtctacg cctgcgaagt cacccatcag   600
ggcctgagct cgcccgtcac aaagagcttc aacaggggag agtgttaa                648

<210> SEQ ID NO 36
<211> LENGTH: 215
<212> TYPE: PRT
<213> ORGANISM: Artificial Sequence
<220> FEATURE:
<223> OTHER INFORMATION: anti-CD47 Ke81G9 kappa light chain

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg His Lys Arg Ser Pro
                85                  90                  95

Gln Thr Phe Gly Gln Gly Thr Lys Val Glu Ile Lys Arg Thr Val Ala
            100                 105                 110
```

```
Ala Pro Ser Val Phe Ile Phe Pro Pro Ser Asp Glu Gln Leu Lys Ser
        115                 120                 125
Gly Thr Ala Ser Val Val Cys Leu Leu Asn Asn Phe Tyr Pro Arg Glu
    130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
            165                 170                 175
Ser Ser Thr Leu Thr Leu Ser Lys Ala Asp Tyr Glu Lys His Lys Val
        180                 185                 190
Tyr Ala Cys Glu Val Thr His Gln Gly Leu Ser Ser Pro Val Thr Lys
        195                 200                 205
Ser Phe Asn Arg Gly Glu Cys
    210                 215

<210> SEQ ID NO 37
<211> LENGTH: 648
<212> TYPE: DNA
<213> ORGANISM: Artificial Sequence
<220> FEATURE:
<223> OTHER INFORMATION: anti-CD47 Ke8F2 kappa light chain

<400> SEQUENCE: 37
gacatccaga tgacccagtc tccatcctcc ctgtctgcat ctgtaggaga cagagtcacc    60
atcacttgcc gggcaagtca gagcattgat aagtatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcag aagcatccgc gtgcgccgcg gaccttcggc   300
caagggacca aggtggaaat caaacgtacg gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca aagcagacta cgagaaacac aaagtctacg cctgcgaagt cacccatcag   600
ggcctgagct cgcccgtcac aaagagcttc aacaggggag agtgttaa                648

<210> SEQ ID NO 38
<211> LENGTH: 215
<212> TYPE: PRT
<213> ORGANISM: Artificial Sequence
<220> FEATURE:
<223> OTHER INFORMATION: anti-CD47 Ke8F2 kappa light chain

<400> SEQUENCE: 38

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Asp Lys Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Lys His Pro Arg Ala Pro
            85                  90                  95

Arg Thr Phe Gly Gln Gly Thr Lys Val Glu Ile Lys Thr Val Ala
        100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 39
<211> LENGTH: 648
<212> TYPE: DNA
<213> ORGANISM: Artificial Sequence
<220> FEATURE:
<223> OTHER INFORMATION: anti-CD47 Ke8B7 kappa light chain

<400> SEQUENCE: 39
gacatccaga tgacccagtc tccatcctcc ctgtctgcat ctgtaggaga cagagtcacc      60
atcacttgcc gggcaagtca gagcattggg aagtatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcag atgcatccgc gtagcccgaa gaccttcggc     300
caagggacca aggtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag     600
ggcctgagct cgcccgtcac aaagagcttc aacaggggag agtgttaa                  648

<210> SEQ ID NO 40
<211> LENGTH: 215
<212> TYPE: PRT
<213> ORGANISM: Artificial Sequence
<220> FEATURE:
<223> OTHER INFORMATION: anti-CD47 Ke8B7 kappa light chain

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly

```
                50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Met His Pro Arg Ser Pro
                 85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 41
<211> LENGTH: 648
<212> TYPE: DNA
<213> ORGANISM: Artificial Sequence
<220> FEATURE:
<223> OTHER INFORMATION: anti-CD47 Ke8C4 kappa light chain

<400> SEQUENCE: 41
gacatccaga tgacccagtc tccatcctcc ctgtctgcat ctgtaggaga cagagtcacc      60
atcacttgcc gggcaagtca gagcattagt aggtatttaa attggtatca gcagaaacca    120
gggaaagccc ctaagctcct gatctatgct gcatccaatt tgcaaagtgg ggtcccatca    180
aggttcagtg gcagtggatc tgggacagat ttcactctca ccatcagcag tctgcaacct    240
gaagattttg caacttacta ctgtcagcag atgcatccgc gtgggccgaa gaccttcggc    300
caagggacca aggtggaaat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgttaa              648

<210> SEQ ID NO 42
<211> LENGTH: 215
<212> TYPE: PRT
<213> ORGANISM: Artificial Sequence
<220> FEATURE:
<223> OTHER INFORMATION: anti-CD47 Ke8C4 kappa light chain

<400> SEQUENCE: 42

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Arg Tyr
             20                  25                  30
```

Leu Asn Trp Tyr Gln Gln Lys Pro Gly Lys Ala Pro Lys Leu Leu Ile
            35                  40                  45

Tyr Ala Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Gly Pro
                85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
210                 215

<210> SEQ ID NO 43
<211> LENGTH: 648
<212> TYPE: DNA
<213> ORGANISM: Artificial Sequence
<220> FEATURE:
<223> OTHER INFORMATION: anti-CD47 Ke8F1 kappa light chain

<400> SEQUENCE: 43
gacatccaga tgacccagtc tccatcctcc ctgtctgcat ctgtaggaga cagagtcacc      60
atcacttgcc gggcaagtca gagcattgct tcttatgtaa attggtatca gcagaaacca     120
gggaaagccc ctaagctcct gatctatgct gcatccggtt tgcaaagtgg ggtcccatca     180
aggttcagtg gcagtggatc tgggacagat ttcactctca ccatcagcag tctgcaacct     240
gaagattttg caacttacta ctgtcagcag ttccataagc gtcggccgca gaccttcggc     300
caagggacca aggtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag     600
ggcctgagct cgcccgtcac aaagagcttc aacaggggag agtgttaa                  648

<210> SEQ ID NO 44
<211> LENGTH: 215
<212> TYPE: PRT
<213> ORGANISM: Artificial Sequence
<220> FEATURE:
<223> OTHER INFORMATION: anti-CD47 Ke8F1 kappa light chain

<400> SEQUENCE: 44

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Ser Tyr
            20                  25                  30

Val Asn Trp Tyr Gln Gln Lys Pro Gly Lys Ala Pro Lys Leu Leu Ile
        35                  40                  45

Tyr Ala Ala Ser Gly Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe His Lys Arg Arg Pro
                85                  90                  95

Gln Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 45
<211> LENGTH: 648
<212> TYPE: DNA
<213> ORGANISM: Artificial Sequence
<220> FEATURE:
<223> OTHER INFORMATION: anti-CD47 Ke8G11 kappa light chain

<400> SEQUENCE: 45
gacatccaga tgacccagtc tccatcctcc ctgtctgcat ctgtaggaga cagagtcacc    60
atcacttgcc gggcaagtca gagcattggg aggtatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcag atgcatccgc gtgggccgaa gaccttcggc   300
caagggacca aggtggaaat caaacgtacg gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca agcagactac gagaaacac aaagtctacg cctgcgaagt cacccatcag   600
ggcctgagct cgcccgtcac aaagagcttc aacagggag agtgttaa                 648

<210> SEQ ID NO 46
<211> LENGTH: 215
<212> TYPE: PRT
<213> ORGANISM: Artificial Sequence
```

<220> FEATURE:
<223> OTHER INFORMATION: anti-CD47 Ke8G11 kappa light chain

<400> SEQUENCE: 46

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Gly Pro
                85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 47
<211> LENGTH: 648
<212> TYPE: DNA
<213> ORGANISM: Artificial Sequence
<220> FEATURE:
<223> OTHER INFORMATION: anti-CD47 Ke8H6 kappa light chain

<400> SEQUENCE: 47

```
gacatccaga tgacccagtc tccatcctcc ctgtctgcat ctgtaggaga cagagtcacc        60
atcacttgcc gggcaagtca gagcattagt aagtatttaa attggtatca gcagaaacca       120
gggaaagccc ctaagctcct gatctataat gcatccactt tgcaaagtgg ggtcccatca       180
aggttcagtg gcagtggatc tgggacagat ttcactctca ccatcagcag tctgcaacct       240
gaagattttg caacttacta ctgtcagcag aggcatccgc gtgggccgcg cacccttcgg       300
caagggacca aggtggaaat caaacgtacg gtggctgcac catctgtctt catcttcccg       360
ccatctgatg agcagttgaa atctggaact gcctctgttg tgtgcctgct gaataacttc       420
tatcccagag aggccaaagt acagtggaag gtggataacg ccctccaatc gggtaactcc       480
caggagagtg tcacagagca ggacagcaag gacagcacct acagcctcag cagcaccctg       540
acgctgagca agcagactac gagaaacac aaagtctacg cctgcgaagt cacccatcag       600
ggcctgagct cgcccgtcac aaagagcttc aacaggggag agtgttaa                    648
```

<210> SEQ ID NO 48
<211> LENGTH: 215
<212> TYPE: PRT
<213> ORGANISM: Artificial Sequence
<220> FEATURE:
<223> OTHER INFORMATION: anti-CD47 Ke8H6 kappa light chain

<400> SEQUENCE: 48

```
Asp Ile Gln Met Thr Gln Ser Pro Ser Leu Ser Ala Ser Val Gly
1               5                   10                  15

Asp Arg Val Thr Ile Thr Cys Arg Ala Ser Gln Ser Ile Ser Lys Tyr
            20                  25                  30

Leu Asn Trp Tyr Gln Gln Lys Pro Gly Lys Ala Pro Lys Leu Leu Ile
        35                  40                  45

Tyr Asn Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Arg His Pro Arg Gly Pro
                85                  90                  95

Arg Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 49
<211> LENGTH: 648
<212> TYPE: DNA
<213> ORGANISM: Artificial Sequence
<220> FEATURE:
<223> OTHER INFORMATION: anti-CD47 Ke84G9 kappa light chain

<400> SEQUENCE: 49

```
gacatccaga tgacccagtc tccatcctcc ctgtctgcat ctgtaggaga cagagtcacc    60
atcacttgcc gggcaagtca gagcattagt aagtatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcag aagcatccgc gtagcccgcg gaccttcggc   300
caagggacca aggtggaaat caaacgtacg gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
```

```
acgctgagca aagcagacta cgagaaacac aaagtctacg cctgcgaagt cacccatcag    600
ggcctgagct cgcccgtcac aaagagcttc aacaggggag agtgttaa                 648
```

<210> SEQ ID NO 50
<211> LENGTH: 215
<212> TYPE: PRT
<213> ORGANISM: Artificial Sequence
<220> FEATURE:
<223> OTHER INFORMATION: anti-CD47 Ke84G9 kappa light chain

<400> SEQUENCE: 50

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys His Pro Arg Ser Pro
                85                  90                  95

Arg Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 51
<211> LENGTH: 648
<212> TYPE: DNA
<213> ORGANISM: Artificial Sequence
<220> FEATURE:
<223> OTHER INFORMATION: anti-CD47 Ke8A4 kappa light chain

<400> SEQUENCE: 51

```
gacatccaga tgacccagtc tccatcctcc ctgtctgcat ctgtaggaga cagagtcacc    60
atcacttgcc gggcaagtca gagcattgct aagtatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcag ttcataagc gtagcccgca gaccttcggc    300
caagggacca aggtggaaat caaacgtacg gtggctgcac catctgtctt catcttcccg   360
```

```
ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacagagca ggacagcaag gacagcacct acagcctcag cagcaccctg      540
acgctgagca aagcagacta cgagaaacac aaagtctacg cctgcgaagt cacccatcag      600
ggcctgagct cgcccgtcac aaagagcttc aacaggggag agtgttaa                   648
```

<210> SEQ ID NO 52
<211> LENGTH: 215
<212> TYPE: PRT
<213> ORGANISM: Artificial Sequence
<220> FEATURE:
<223> OTHER INFORMATION: anti-CD47 Ke8A4 kappa light chain

<400> SEQUENCE: 52

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe His Lys Arg Ser Pro
                85                  90                  95

Gln Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 53
<211> LENGTH: 648
<212> TYPE: DNA
<213> ORGANISM: Artificial Sequence
<220> FEATURE:
<223> OTHER INFORMATION: anti-CD47 Ke86G9 kappa light chain

<400> SEQUENCE: 53

```
gacatccaga tgacccagtc tccatcctcc ctgtctgcat ctgtaggaga cagagtcacc      60
atcacttgcc gggcaagtca gagcattagt aagtatttaa attggtatca gcagaaacca      120
gggaaagccc ctaagctcct gatctataat gcatccaatt tgcaaagtgg ggtcccatca      180
aggttcagtg gcagtggatc tgggacagat ttcactctca ccatcagcag tctgcaacct      240
```

```
gaagattttg caacttacta ctgtcagcag aggcatccgc gtgggccgac caccttcggc      300
caagggacca aggtggaaat caaacgtacg gtggctgcac catctgtctt catcttcccg      360
ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacagagca ggacagcaag gacagcacct acagcctcag cagcaccctg      540
acgctgagca aacagacta cgagaaacac aaagtctacg cctgcgaagt cacccatcag      600
ggcctgagct cgcccgtcac aaagagcttc aacaggggag agtgttaa                   648
```

<210> SEQ ID NO 54
<211> LENGTH: 215
<212> TYPE: PRT
<213> ORGANISM: Artificial Sequence
<220> FEATURE:
<223> OTHER INFORMATION: anti-CD47 Ke86G9 kappa light chain

<400> SEQUENCE: 54

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Lys Tyr
            20                  25                  30

Leu Asn Trp Tyr Gln Gln Lys Pro Gly Lys Ala Pro Lys Leu Leu Ile
        35                  40                  45

Tyr Asn Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg His Pro Arg Gly Pro
                85                  90                  95

Thr Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 55
<211> LENGTH: 648
<212> TYPE: DNA
<213> ORGANISM: Artificial Sequence
<220> FEATURE:
<223> OTHER INFORMATION: anti-CD47 Ka3 kappa light chain

<400> SEQUENCE: 55

```
gacatccaga tgacccagtc tccatcctcc ctgtctgcat ctgtaggaga cagagtcacc      60
```

```
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat tcactctca ccatcagcag tctgcaacct    240
gaagattttg caacttacta ctgtcagcag atgcacccgc gcgccccgaa gaccttcggc    300
caagggacca aggtggaaat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgttaa                 648
```

<210> SEQ ID NO 56  
<211> LENGTH: 215  
<212> TYPE: PRT  
<213> ORGANISM: Artificial Sequence  
<220> FEATURE:  
<223> OTHER INFORMATION: anti-CD47 Ka3 kappa light chain

<400> SEQUENCE: 56

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 57  
<211> LENGTH: 648  
<212> TYPE: DNA  
<213> ORGANISM: Artificial Sequence  
<220> FEATURE:  
<223> OTHER INFORMATION: anti-CD47 Ka3A2 kappa light chain -continued

<400> SEQUENCE: 57

```
gacatccaga tgacccagtc tccatcctcc ctgtctgcat ctgtaggaga cagagtcacc      60
atcacttgcc gggcaagtca gagcattagt aagtatttaa attggtatca gcagaaacca     120
gggaaagccc ctaagctcct gatctatgct gcatccaggt tgcaaagtgg ggtcccatca     180
aggttcagtg gcagtggatc tgggacagat ttcactctca ccatcagcag tctgcaacct     240
gaagattttg caacttacta ctgtcagcag atgcatcctc gctcgccgaa aaccttcggc     300
caagggacca aggtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca aagcagacta cgagaaacac aaagtctacg cctgcgaagt cacccatcag     600
ggcctgagct cgcccgtcac aaagagcttc aacaggggag agtgttaa                  648
```

<210> SEQ ID NO 58
<211> LENGTH: 215
<212> TYPE: PRT
<213> ORGANISM: Artificial Sequence
<220> FEATURE:
<223> OTHER INFORMATION: anti-CD47 Ka3A2 kappa light chain

<400> SEQUENCE: 58

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ser Pro
                85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 59

<211> LENGTH: 648
<212> TYPE: DNA
<213> ORGANISM: Artificial Sequence
<220> FEATURE:
<223> OTHER INFORMATION: anti-CD47 Ka3H3 kappa light chain

<400> SEQUENCE: 59

```
gacatccaga tgacccagtc tccatcctcc ctgtctgcat ctgtaggaga cagagtcacc      60
atcacttgcc aggcgagtca ggacattgct aagtatttaa attggtatca gcagaaacca     120
gggaaagccc ctaagctcct gatctatgct gcatccgctt tgcaaagtgg ggtcccatca     180
aggttcagtg gcagtggatc tgggacagat ttcactctca ccatcagcag tctgcaacct     240
gaagattttg caacttacta ctgtcagcag atgcatcctc gctcgccgaa aaccttcggc     300
caagggacca aggtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag     600
ggcctgagct cgcccgtcac aaagagcttc aacaggggag agtgttaa                 648
```

<210> SEQ ID NO 60
<211> LENGTH: 215
<212> TYPE: PRT
<213> ORGANISM: Artificial Sequence
<220> FEATURE:
<223> OTHER INFORMATION: anti-CD47 Ka3H3 kappa light chain

<400> SEQUENCE: 60

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ala Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Ala Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ser Pro
                85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205
```

Ser Phe Asn Arg Gly Glu Cys
        210                 215

<210> SEQ ID NO 61
<211> LENGTH: 648
<212> TYPE: DNA
<213> ORGANISM: Artificial Sequence
<220> FEATURE:
<223> OTHER INFORMATION: anti-CD47 Ka3A3 kappa light chain

<400> SEQUENCE: 61

```
gacatccaga tgacccagtc tccatcctcc ctgtctgcat ctgtaggaga cagagtcacc    60
atcacttgcc gggcaagtca gagcattgct agttatttaa attggtatca gcagaaacca   120
gggaaagccc ctaagctcct gatctatgcg gcatccaggt tgcaaagtgg ggtcccatca   180
aggttcagtg gcagtggatc tgggacagat ttcactctca ccatcagcag tctgcaacct   240
gaagattttg caacttacta ctgtcagcag atgcatcctc gcgcgccgaa aaccttcggc   300
caagggacca aggtggaaat caaacgtacg gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca agcagactac gagaaacac aaagtctacg cctgcgaagt cacccatcag   600
ggcctgagct cgcccgtcac aaagagcttc aacaggggag agtgttaa                648
```

<210> SEQ ID NO 62
<211> LENGTH: 215
<212> TYPE: PRT
<213> ORGANISM: Artificial Sequence
<220> FEATURE:
<223> OTHER INFORMATION: anti-CD47 Ka3A3 kappa light chain

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val

```
                180               185               190
Tyr Ala Cys Glu Val Thr His Gln Gly Leu Ser Ser Pro Val Thr Lys
        195                 200                 205

Ser Phe Asn Arg Gly Glu Cys
        210                 215

<210> SEQ ID NO 63
<211> LENGTH: 648
<212> TYPE: DNA
<213> ORGANISM: Artificial Sequence
<220> FEATURE:
<223> OTHER INFORMATION: anti-CD47 Ka3H8 kappa light chain

<400> SEQUENCE: 63
gacatccaga tgacccagtc tccatcctcc ctgtctgcat ctgtaggaga cagagtcacc      60
atcacttgcc gggcaagtca gagcattgcg agttatttaa attggtatca gcagaaacca     120
gggaaagccc ctaagctcct gatctatgcg gcatccaggt tgcaaagtgg ggtcccatca     180
aggttcagtg gcagtggatc tgggacagat ttcactctca ccatcagcag tctgcaacct     240
gaagattttg caacttacta ctgtcagcag atgcatcctc gctcgccgaa aaccttcggc     300
caagggacca aggtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag     600
ggcctgagct cgcccgtcac aaagagcttc aacaggggag agtgttaa                  648

<210> SEQ ID NO 64
<211> LENGTH: 215
<212> TYPE: PRT
<213> ORGANISM: Artificial Sequence
<220> FEATURE:
<223> OTHER INFORMATION: anti-CD47 Ka3H8 kappa light chain

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ser Pro
                85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160
```

```
Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 65
<211> LENGTH: 648
<212> TYPE: DNA
<213> ORGANISM: Artificial Sequence
<220> FEATURE:
<223> OTHER INFORMATION: anti-CD47 Ka3B2 kappa light chain

<400> SEQUENCE: 65
gacatccaga tgacccagtc tccatcctcc ctgtctgcat ctgtaggaga cagagtcacc      60
atcacttgcc gggcaagtca gaacattggt aagtatttaa attggtatca gcagaaacca    120
gggaaagccc ctaagctcct gatctatagt gcatccaggt tgcaaagtgg ggtcccatca    180
aggttcagtg gcagtggatc tgggacagat ttcactctca ccatcagcag tctgcaacct    240
gaagattttg caacttacta ctgtcagcag atgcatcctc gcgcgccgaa aaccttcggc    300
caagggacca aggtggaaat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac aaagtctacg cctgcgaagt cacccatcag    600
ggcctgagct cgcccgtcac aaagagcttc aacaggggag agtgttaa                648

<210> SEQ ID NO 66
<211> LENGTH: 215
<212> TYPE: PRT
<213> ORGANISM: Artificial Sequence
<220> FEATURE:
<223> OTHER INFORMATION: anti-CD47 Ka3B2 kappa light chain

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Gly Lys Tyr
            20                  25                  30

Leu Asn Trp Tyr Gln Gln Lys Pro Gly Lys Ala Pro Lys Leu Leu Ile
        35                  40                  45

Tyr Ser Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125
```

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys
210                 215

<210> SEQ ID NO 67
<211> LENGTH: 648
<212> TYPE: DNA
<213> ORGANISM: Artificial Sequence
<220> FEATURE:
<223> OTHER INFORMATION: anti-CD47 Ka3C5 kappa light chain

<400> SEQUENCE: 67
gacatccaga tgacccagtc tccatcctcc ctgtctgcat ctgtaggaga cagagtcacc     60
atcacttgcc gggcaagtca gagcattagt aggtatttaa attggtatca gcagaaacca    120
gggaaagccc ctaagctcct gatctattct gcatcctctt tgcaaagtgg ggtcccatca    180
aggttcagtg gcagtggatc tgggacagat ttcactctca ccatcagcag tctgcaacct    240
gaagattttg caacttacta ctgtcagcag atgcatcctc gcgccccgaa aaccttcggc    300
caagggacca aggtggaaat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacaca aaagtctacg cctgcgaagt cacccatcag    600
ggcctgagct cgcccgtcac aaagagcttc aacaggggag agtgttaa                 648

<210> SEQ ID NO 68
<211> LENGTH: 215
<212> TYPE: PRT
<213> ORGANISM: Artificial Sequence
<220> FEATURE:
<223> OTHER INFORMATION: anti-CD47 Ka3C5 kappa light chain

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
                20                  25                  30

Leu Asn Trp Tyr Gln Gln Lys Pro Gly Lys Ala Pro Lys Leu Leu Ile
            35                  40                  45

Tyr Ser Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys Arg Thr Val Ala

```
                100             105             110
Ala Pro Ser Val Phe Ile Phe Pro Pro Ser Asp Glu Gln Leu Lys Ser
            115                 120                 125
Gly Thr Ala Ser Val Val Cys Leu Leu Asn Asn Phe Tyr Pro Arg Glu
        130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
            180                 185                 190
Tyr Ala Cys Glu Val Thr His Gln Gly Leu Ser Ser Pro Val Thr Lys
        195                 200                 205
Ser Phe Asn Arg Gly Glu Cys
        210                 215

<210> SEQ ID NO 69
<211> LENGTH: 648
<212> TYPE: DNA
<213> ORGANISM: Artificial Sequence
<220> FEATURE:
<223> OTHER INFORMATION: anti-CD47 Ka3G2 kappa light chain

<400> SEQUENCE: 69
gacatccaga tgacccagtc tccatcctcc ctgtctgcat ctgtaggaga cagagtcacc      60
atcacttgcc gggcaagtca gagcattgat aagtatttaa attggtatca gcagaaacca     120
gggaaagccc ctaagctcct gatctatgct gcatccaggt tgcaaagtgg ggtcccatca     180
aggttcagtg gcagtggatc tgggacagat ttcactctca ccatcagcag tctgcaacct     240
gaagattttg caacttacta ctgtcagcag atgcatcctc gcgggccgaa aaccttcggc     300
caagggacca aggtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag     600
ggcctgagct cgcccgtcac aaagagcttc aacaggggag agtgttaa                  648

<210> SEQ ID NO 70
<211> LENGTH: 215
<212> TYPE: PRT
<213> ORGANISM: Artificial Sequence
<220> FEATURE:
<223> OTHER INFORMATION: anti-CD47 Ka3G2 kappa light chain

<400> SEQUENCE: 70

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Asp Lys Tyr
            20                  25                  30
Leu Asn Trp Tyr Gln Gln Lys Pro Gly Lys Ala Pro Lys Leu Leu Ile
        35                  40                  45
Tyr Ala Ala Ser Arg Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Met His Pro Arg Gly Pro
                    85                  90                  95

Lys Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 71
<211> LENGTH: 648
<212> TYPE: DNA
<213> ORGANISM: Artificial Sequence
<220> FEATURE:
<223> OTHER INFORMATION: anti-CD47 Ka3D3 kappa light chain

<400> SEQUENCE: 71
gacatccaga tgacccagtc tccatcctcc ctgtctgcat ctgtaggaga cagagtcacc      60
atcacttgcc gggcaagtca gagcattggt aagtatttaa attggtatca gcagaaacca     120
gggaaagccc ctaagctcct gatctatgct gcatccaggt tgcaaagtgg ggtcccatca     180
aggttcagtg gcagtggatc tgggacagat ttcactctca ccatcagcag tctgcaacct     240
gaagattttg caacttacta ctgtcagcag atgcatcctc gcgcgccgaa aaccttcggc     300
caagggacca aggtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagccctg      540
acgctgagca agcagacta cgagaaacac aaagtctacg cctgcgaagt cacccatcag     600
ggcctgagct cgcccgtcac aaagagcttc aacaggggag agtgttaa                  648

<210> SEQ ID NO 72
<211> LENGTH: 215
<212> TYPE: PRT
<213> ORGANISM: Artificial Sequence
<220> FEATURE:
<223> OTHER INFORMATION: anti-CD47 Ka3D3 kappa light chain

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Met His Pro Arg Ala Pro
                 85                  90                  95

Lys Thr Phe Gly Gln Gly Thr Lys Val Glu Ile Lys Arg Thr Val Ala
             100                 105                 110

Ala Pro Ser Val Phe Ile Phe Pro Pro Ser Asp Glu Gln Leu Lys Ser
         115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
210                 215

<210> SEQ ID NO 73
<211> LENGTH: 654
<212> TYPE: DNA
<213> ORGANISM: Artificial Sequence
<220> FEATURE:
<223> OTHER INFORMATION: anti-CD47 Kc4 kappa light chain

<400> SEQUENCE: 73
cagtctgccc tgactcagcc tgcctccgtg tctgggtctc ctggacagtc gatcaccatc     60
tcctgcactg gaaccagcag tgacgttggt ggttataact atgtctcctg gtaccaacag    120
cacccaggca agcccccaa actcatgatt tatgaggtca gtaatcggcc ctcaggggtt     180
tctaatcgct tctctggctc caagtctggc aacacggcct ccctgaccat ctctgggctc    240
caggctgagg acgaggctga ttattactgc agctcatatg attggtggtt ccgccccaag    300
gtgttcggcg gagggaccaa gctgaccgtc ctaggtcagc ccaaggctgc ccctcggtc    360 actctgttcc cgccctcctc tgaggagctt caagccaaca ggccacact ggtgtgtctc    420 ataagtgact tctacccggg agccgtgaca gtggcttgga agcagatag cagcccgtc    480 aaggcgggag tggagaccac cacaccctcc aaacaaagca acaacaagta cgcggccagc    540
agctatctga gcctgacgcc tgagcagtgg aagtcccaca gaagctacag ctgccaggtc    600
acgcatgaag ggagcaccgt ggagaagaca gtggccccta cagaatgttc ataa           654

<210> SEQ ID NO 74
<211> LENGTH: 217
<212> TYPE: PRT
<213> ORGANISM: Artificial Sequence
<220> FEATURE:
<223> OTHER INFORMATION: anti-CD47 Kc4 kappa light chain

<400> SEQUENCE: 74

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr

```
                    20                  25                  30
Asn Tyr Val Ser Trp Tyr Gln Gln His Pro Gly Lys Ala Pro Lys Leu
                35                  40                  45
Met Ile Tyr Glu Val Ser Asn Arg Pro Ser Gly Val Ser Asn Arg Phe
         50                  55                  60
Ser Gly Ser Lys Ser Gly Asn Thr Ala Ser Leu Thr Ile Ser Gly Leu
 65                  70                  75                  80
Gln Ala Glu Asp Glu Ala Asp Tyr Tyr Cys Ser Ser Tyr Asp Trp Trp
                85                  90                  95
Phe Arg Pro Lys Val Phe Gly Gly Gly Thr Lys Leu Thr Val Leu Gly
               100                 105                 110
Gln Pro Lys Ala Ala Pro Ser Val Thr Leu Phe Pro Pro Ser Ser Glu
           115                 120                 125
Glu Leu Gln Ala Asn Lys Ala Thr Leu Val Cys Leu Ile Ser Asp Phe
           130                 135                 140
Tyr Pro Gly Ala Val Thr Val Ala Trp Lys Ala Asp Ser Ser Pro Val
145                 150                 155                 160
Lys Ala Gly Val Glu Thr Thr Thr Pro Ser Lys Gln Ser Asn Asn Lys
               165                 170                 175
Tyr Ala Ala Ser Ser Tyr Leu Ser Leu Thr Pro Glu Gln Trp Lys Ser
           180                 185                 190
His Arg Ser Tyr Ser Cys Gln Val Thr His Glu Gly Ser Thr Val Glu
           195                 200                 205
Lys Thr Val Ala Pro Thr Glu Cys Ser
       210                 215

<210> SEQ ID NO 75
<211> LENGTH: 654
<212> TYPE: DNA
<213> ORGANISM: Artificial Sequence
<220> FEATURE:
<223> OTHER INFORMATION: anti-CD47 Kc4G11 kappa light chain

<400> SEQUENCE: 75
cagtctgccc tgactcagcc tgcctccgtg tctgggtctc ctggacagtc gatcaccatc      60
tcctgcactg gaaccagcag tgacgttggg aaggcgaact atgtctcctg gtaccaacag     120
cacccaggca agcccccaa actcatgatt tataaggata gtgatcggcc ctcaggggtt      180
tctaatcgct tctctggctc caagtctggc aacacggcct ccctgaccat ctctgggctc     240
caggctgagg acgaggctga ttattactgc agctcatatg attggtggtt ccgcccaag     300 gtgttcggcg gagggaccaa gctgaccgtc ctaggtcagc ccaaggctgc ccctcggtc     360 actctgttcc cgccctcctc tgaggagctt caagccaaca ggccacact ggtgtgtctc    420 ataagtgact tctacccggg agccgtgaca gtggcttgga agcagatag cagccccgtc    480 aaggcgggag tggagaccac cacccctcc aaacaaagca caacaagta cgcggccagc    540 agctatctga gcctgacgcc tgagcagtgg aagtcccaca aagctacag ctgccaggtc    600 acgcatgaag ggagcaccgt ggagaagaca gtggccccta cagaatgttc ataa          654

<210> SEQ ID NO 76
<211> LENGTH: 217
<212> TYPE: PRT
<213> ORGANISM: Artificial Sequence
<220> FEATURE:
<223> OTHER INFORMATION: anti-CD47 Kc4G11 kappa light chain

<400> SEQUENCE: 76
```

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Lys Ala
            20                  25                  30

Asn Tyr Val Ser Trp Tyr Gln Gln His Pro Gly Lys Ala Pro Lys Leu
        35                  40                  45

Met Ile Tyr Lys Asp Ser Asp Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 77
<211> LENGTH: 654
<212> TYPE: DNA
<213> ORGANISM: Artificial Sequence
<220> FEATURE:
<223> OTHER INFORMATION: anti-CD47 Kc4C11 kappa light chain

<400> SEQUENCE: 77
cagtctgccc tgactcagcc tgcctccgtg tctgggtctc ctggacagtc gatcaccatc      60
tcctgcactg gaaccagcag tgacgttagg gggaataact atgtctcctg gtaccaacag     120
cacccaggca aagcccccaa actcatgatt tatgagaata gtaagcggcc ctcaggggtt     180
tctaatcgct tctctggctc caagtctggc aacacggcct ccctgaccat ctctgggctc     240
caggctgagg acgaggctga ttattactgc agctcatatg attggtggtt ccgccccaag     300
gtgttcggcg gagggaccaa gctgaccgtc ctaggtcagc ccaaggctgc cccctcggtc     360
actctgttcc cgccctcctc tgaggagctt caagccaaca ggccacact ggtgtgtctc     420 ataagtgact tctacccggg agccgtgaca gtggcttgga aagcagatag cagccccgtc     480
aaggcgggag tggagaccac cacaccctcc aaacaaagca acaacaagta cgcggccagc     540
agctatctga gcctgacgcc tgagcagtgg aagtcccaca gaagctacag ctgccaggtc     600
acgcatgaag ggagcaccgt ggagaagaca gtggccccta cagaatgttc ataa           654

<210> SEQ ID NO 78
<211> LENGTH: 217
<212> TYPE: PRT

<213> ORGANISM: Artificial Sequence
<220> FEATURE:
<223> OTHER INFORMATION: anti-CD47 Kc4C11 kappa light chain

<400> SEQUENCE: 78

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Arg Gly Asn
            20                  25                  30

Asn Tyr Val Ser Trp Tyr Gln Gln His Pro Gly Lys Ala Pro Lys Leu
        35                  40                  45

Met Ile Tyr Glu Asn Ser Lys Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
210                 215

<210> SEQ ID NO 79
<211> LENGTH: 654
<212> TYPE: DNA
<213> ORGANISM: Artificial Sequence
<220> FEATURE:
<223> OTHER INFORMATION: anti-CD47 Kc4A1 kappa light chain

<400> SEQUENCE: 79
cagtctgccc tgactcagcc tgcctccgtg tctgggtctc ctggacagtc gatcaccatc      60
tcctgcactg gaaccagcag tgacgttagt gcgaggaact atgtctcctg gtaccaacag     120
cacccaggca agccccccaa actcatgatt tatgagagta gtaagcggcc ctcaggggtt     180
tctaatcgct tctctggctc caagtctggc aacacggcct ccctgaccat ctctgggctc     240
caggctgagg acgaggctga ttattactgc agctcatatg attggtggtt ccgccccaag     300
gtgttcggcg gagggaccaa gctgaccgtc ctaggtcagc ccaaggctgc ccctcggtc      360 actctgttcc cgccctcctc tgaggagctt caagccaaca ggccacact ggtgtgtctc      420 ataagtgact tctacccggg agccgtgaca gtggcttgga agcagatag cagccccgtc      480 aaggcgggag tggagaccac cacaccctcc aaacaaagca acaacaagta cgcggccagc     540
agctatctga gcctgacgcc tgagcagtgg aagtcccaca agagctacag ctgccaggtc     600
acgcatgaag ggagcaccgt ggagaagaca gtggccccta cagaatgttc ataa           654

<210> SEQ ID NO 80
<211> LENGTH: 217
<212> TYPE: PRT
<213> ORGANISM: Artificial Sequence
<220> FEATURE:
<223> OTHER INFORMATION: anti-CD47 Kc4A1 kappa light chain

<400> SEQUENCE: 80

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Ser Ala Arg
            20                  25                  30

Asn Tyr Val Ser Trp Tyr Gln Gln His Pro Gly Lys Ala Pro Lys Leu
        35                  40                  45

Met Ile Tyr Glu Ser Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 81
<211> LENGTH: 654
<212> TYPE: DNA
<213> ORGANISM: Artificial Sequence
<220> FEATURE:
<223> OTHER INFORMATION: anti-CD47 Kc4A4 kappa light chain

<400> SEQUENCE: 81
cagtctgccc tgactcagcc tgcctccgtg tctgggtctc ctggacagtc gatcaccatc      60
tcctgcacta gaaccagcag tgacgttaat aatactaact atgtctcctg gtaccaacag     120
cacccaggca agcccccaa actcatgatt tataagacta gtggtcggcc ctcaggggtt      180
tctaatcgct tctctggctc caagtctggc aacacggcct ccctgaccat ctctgggctc     240
caggctgagg acgaggctga ttattactgc agctcatatg attggtggtt ccgccccaag    300
gtgttcggcg gagggaccaa gctgaccgtc ctaggtcagc ccaaggctgc ccctcggtc     360 actctgttcc cgccctcctc tgaggagctt caagccaaca ggccacact ggtgtgtctc      420 ataagtgact tctacccggg agccgtgaca gtggcttgga aagcagatag cagccccgtc    480

-continued

| | | |
|---|---|---|
| aaggcgggag tggagaccac cacaccctcc aaacaaagca acaacaagta cgcggccagc | 540 | |
| agctatctga gcctgacgcc tgagcagtgg aagtcccaca gaagctacag ctgccaggtc | 600 | |
| acgcatgaag ggagcaccgt ggagaagaca gtggcccta cagaatgttc ataa | 654 | |

<210> SEQ ID NO 82
<211> LENGTH: 217
<212> TYPE: PRT
<213> ORGANISM: Artificial Sequence
<220> FEATURE:
<223> OTHER INFORMATION: anti-CD47 Kc4A4 kappa light chain

<400> SEQUENCE: 82

Gln Ser Ala Leu Thr Gln Pro Ala Ser Val Ser Gly Ser Pro Gly Gln
1               5                   10                  15

Ser Ile Thr Ile Ser Cys Thr Arg Thr Ser Ser Asp Val Asn Asn Thr
            20                  25                  30

Asn Tyr Val Ser Trp Tyr Gln Gln His Pro Gly Lys Ala Pro Lys Leu
        35                  40                  45

Met Ile Tyr Lys Thr Ser Gly Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 83
<211> LENGTH: 654
<212> TYPE: DNA
<213> ORGANISM: Artificial Sequence
<220> FEATURE:
<223> OTHER INFORMATION: anti-CD47 Kc4E10 kappa light chain

<400> SEQUENCE: 83

| | | |
|---|---|---|
| cagtctgccc tgactcagcc tgcctccgtg tctgggtctc ctggacagtc gatcaccatc | 60 | |
| tcctgcactg gaaccagcag tgacgttaat tctgctaact atgtctcctg gtaccaacag | 120 | |
| cacccaggca agcccccaa actcatgatt tataagagta gtagtcggcc ctcaggggtt | 180 | |
| tctaatcgct tctctggctc caagtctggc aacacggcct ccctgaccat ctctgggctc | 240 | |
| caggctgagg acgaggctga ttattactgc agctcatatg attggtggtt ccgcccaag | 300 | |
| gtgttcggcg gagggaccaa gctgaccgtc ctaggtcagc ccaaggctgc ccctcggtc | 360 | |

```
actctgttcc cgccctcctc tgaggagctt caagccaaca aggccacact ggtgtgtctc    420
ataagtgact tctacccggg agccgtgaca gtggcttgga aagcagatag cagccccgtc    480
aaggcgggag tggagaccac cacaccctcc aaacaaagca acaacaagta cgcggccagc    540
agctatctga gcctgacgcc tgagcagtgg aagtcccaca aagctacag ctgccaggtc     600 acgcatgaag ggagcaccgt ggagaagaca gtggccccta cagaatgttc ataa          654
```

<210> SEQ ID NO 84
<211> LENGTH: 217
<212> TYPE: PRT
<213> ORGANISM: Artificial Sequence
<220> FEATURE:
<223> OTHER INFORMATION: anti-CD47 Kc4E10 kappa light chain

<400> SEQUENCE: 84

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Asn Ser Ala
                20                  25                  30

Asn Tyr Val Ser Trp Tyr Gln Gln His Pro Gly Lys Ala Pro Lys Leu
            35                  40                  45

Met Ile Tyr Lys Ser Ser Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 85
<211> LENGTH: 654
<212> TYPE: DNA
<213> ORGANISM: Artificial Sequence
<220> FEATURE:
<223> OTHER INFORMATION: anti-CD47 Kc4G9 kappa light chain

<400> SEQUENCE: 85

```
cagtctgccc tgactcagcc tgcctccgtg tccgggtctc ctggacagtc gatcaccatc    60
tcctgcactg gaaccagcag tgacgttgag aggaagaact atgtctcctg gtaccaacag   120
cacccaggca aagcccccaa actcatgatt tataagaata gtactcggcc ctcagggggtt  180
```

```
tctaatcgct tctctggctc caagtctggc aacacggcct ccctgaccat ctctgggctc      240
caggctgagg acgaggctga ttattactgc agctcatatg attggtggtt ccgccccaag      300
gtgttcggcg agggaccaa gctgaccgtc ctaggtcagc ccaaggctgc ccctcggtc        360 actctgttcc cgccctcctc tgaggagctt caagccaaca aggccacact ggtgtgtctc      420
ataagtgact tctacccggg agccgtgaca gtggcttgga agcagatag cagccccgtc       480 aaggcgggag tggagaccac cacaccctcc aaacaaagca acaacaagta cgcggccagc      540
agctatctga gcctgacgcc tgagcagtgg aagtcccaca gaagctacag ctgccaggtc      600
acgcatgaag ggagcaccgt ggagaagaca gtggccccta cagaatgttc ataa            654
```

<210> SEQ ID NO 86
<211> LENGTH: 217
<212> TYPE: PRT
<213> ORGANISM: Artificial Sequence
<220> FEATURE:
<223> OTHER INFORMATION: anti-CD47 Kc4G9 kappa light chain

<400> SEQUENCE: 86

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Glu Arg Lys
            20                  25                  30

Asn Tyr Val Ser Trp Tyr Gln Gln His Pro Gly Lys Ala Pro Lys Leu
        35                  40                  45

Met Ile Tyr Lys Asn Ser Thr Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 87
<211> LENGTH: 654
<212> TYPE: DNA
<213> ORGANISM: Artificial Sequence
<220> FEATURE:
<223> OTHER INFORMATION: anti-CD47 Kc4C3 kappa light chain

<400> SEQUENCE: 87

```
cagtctgccc tgactcagcc tgcctccgtg tctgggtctc ctggacagtc gatcaccatc      60
```

```
tcctgcactg gaaccagcag tgacgttagg gcggctaact atgtctcctg gtaccaacag      120
cacccaggca agccccccaa actcatgatt tataagaata gtactcggcc ctcagggggtt    180 tctaatcgct ctctggctc caagtctggc aacacggcct ccctgaccat ctctgggctc      240
caggctgagg acgaggctga ttattactgc agctcatatg attggtggtt ccgcccccaag   300 gtgttcggcg agggaccaa gctgaccgtc ctaggtcagc ccaaggctgc ccctcggtc      360 actctgttcc cgccctcctc tgaggagctt caagccaaca aggccacact ggtgtgtctc    420
ataagtgact tctacccggg agccgtgaca gtggcttgga aagcagatag cagccccgtc    480
aaggcgggag tggagaccac cacacccctcc aaacaaagca acaacaagta cgcggccagc   540
agctatctga gcctgacgcc tgagcagtgg aagtcccaca aagctacag ctgccaggtc     600 acgcatgaag ggagcaccgt ggagaagaca gtggccccta cagaatgttc ataa           654
```

<210> SEQ ID NO 88
<211> LENGTH: 217
<212> TYPE: PRT
<213> ORGANISM: Artificial Sequence
<220> FEATURE:
<223> OTHER INFORMATION: anti-CD47 Kc4C3 kappa light chain

<400> SEQUENCE: 88

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Arg Ala Ala
            20                  25                  30

Asn Tyr Val Ser Trp Tyr Gln Gln His Pro Gly Lys Ala Pro Lys Leu
        35                  40                  45

Met Ile Tyr Lys Asn Ser Thr Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 89
<211> LENGTH: 654
<212> TYPE: DNA
<213> ORGANISM: Artificial Sequence
<220> FEATURE:

<223> OTHER INFORMATION: anti-CD47 Kc4F4 kappa light chain

<400> SEQUENCE: 89

```
cagtctgccc tgactcagcc tgcctccgtg tctgggtctc ctggacagtc gatcaccatc      60
tcctgcactg gaaccagcag tgacgttagg agggctaact atgtctcctg gtaccaacag     120
cacccaggca aagcccccaa actcatgatt tatcaggata gtagtcggcc ctcaggggtt     180
tctaatcgct tctctggctc caagtctggc aacacggcct ccctgaccat ctctgggctc     240
caggctgagg acgaggctga ttattactgc agctcatatg attggtggtt ccgccccaag     300
gtgttcggcg agggaccaa gctgaccgtc ctaggtcagc ccaaggctgc ccctcggtc       360
actctgttcc cgccctcctc tgaggagctt caagccaaca ggccacact ggtgtgtctc      420
ataagtgact ctacccgggg agccgtgaca gtggcttgga agcagatag cagccccgtc      480
aaggcgggag tggagaccac cacaccctcc aaacaaagca acaacaagta cgcggccagc     540
agctatctga gcctgacgcc tgagcagtgg aagtcccaca agctacag ctgccaggtc      600
acgcatgaag ggagcaccgt ggagaagaca gtggcccta cagaatgttc ataa            654
```

<210> SEQ ID NO 90
<211> LENGTH: 217
<212> TYPE: PRT
<213> ORGANISM: Artificial Sequence
<220> FEATURE:
<223> OTHER INFORMATION: anti-CD47 Kc4F4 kappa light chain

<400> SEQUENCE: 90

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Arg Arg Ala
            20                  25                  30

Asn Tyr Val Ser Trp Tyr Gln Gln His Pro Gly Lys Ala Pro Lys Leu
        35                  40                  45

Met Ile Tyr Gln Asp Ser Ser Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 91
<211> LENGTH: 654
<212> TYPE: DNA
<213> ORGANISM: Artificial Sequence
<220> FEATURE:
<223> OTHER INFORMATION: anti-CD47 Kc4B1 kappa light chain

<400> SEQUENCE: 91

```
cagtctgccc tgactcagcc tgcctccgtg tctgggtctc ctggacagtc gatcaccatc      60
tcctgcactg gaaccagcag tgacgttagg gctaataact atgtctcctg gtaccaacag     120
cacccaggca agcccccaaa actcatgatt tatgagagta gtgcgcggcc ctcaggggtt     180
tctaatcgct tctctggctc caagtctggc aacacggcct ccctgaccat ctctgggctc     240
caggctgagg acgaggctga ttattactgc agctcatatg attggtggtt ccgccccaag     300
gtgttcggcg agggaccaa gctgaccgtc ctaggtcagc ccaaggctgc ccctcggtc       360
actctgttcc cgccctcctc tgaggagctt caagccaaca ggccacact ggtgtgtctc      420
ataagtgact tctacccggg agccgtgaca gtggcttgga agcagatag cagcccgtc       480
aaggcgggag tggagaccac cacaccctcc aaacaaagca caacaagta cgcggccagc     540
agctatctga gcctgacgcc tgagcagtgg aagtcccaca agctacag ctgccaggtc       600
acgcatgaag ggagcaccgt ggagaagaca gtggccccta cagaatgttc ataa           654
```

<210> SEQ ID NO 92
<211> LENGTH: 217
<212> TYPE: PRT
<213> ORGANISM: Artificial Sequence
<220> FEATURE:
<223> OTHER INFORMATION: anti-CD47 Kc4B1 kappa light chain

<400> SEQUENCE: 92

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Arg Ala Asn
            20                  25                  30

Asn Tyr Val Ser Trp Tyr Gln Gln His Pro Gly Lys Ala Pro Lys Leu
        35                  40                  45

Met Ile Tyr Glu Ser Ser Ala Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205
```

Lys Thr Val Ala Pro Thr Glu Cys Ser
        210                 215

<210> SEQ ID NO 93
<211> LENGTH: 654
<212> TYPE: DNA
<213> ORGANISM: Artificial Sequence
<220> FEATURE:
<223> OTHER INFORMATION: anti-CD47 Kc4E2 kappa light chain

<400> SEQUENCE: 93
cagtctgccc tgactcagcc tgcctccgtg tctgggtctc ctggacagtc gatcaccatc      60
tcctgcactg gaaccagcag tgacgtttat tataataagt atgtctcctg gtaccaacag     120
cacccaggca agcccccaa actcatgatt tatgagagta gtaagcggcc ctcagggggtt     180 tctaatcgct tctctggctc caagtctggc aacacggcct ccctgaccat ctctgggctc     240
caggctgagg acgaggctga ttattactgc agctcatatg attggtggtt ccgccccaag     300
gtgttcggcg gagggaccaa gctgaccgtc ctaggtcagc ccaaggctgc ccctcggtc      360 actctgttcc cgccctcctc tgaggagctt caagccaaca ggccacact ggtgtgtctc      420 ataagtgact tctacccggg agccgtgaca gtggcttgga agcagatag cagccccgtc      480 aaggcgggag tggagaccac cacaccctcc aaacaaagca acaacaagta cgcggccagc     540
agctatctga gcctgacgcc tgagcagtgg aagtcccaca aagctacag ctgccaggtc      600 acgcatgaag ggagcaccgt ggagaagaca gtggccccta cagaatgttc ataa            654

<210> SEQ ID NO 94
<211> LENGTH: 217
<212> TYPE: PRT
<213> ORGANISM: Artificial Sequence
<220> FEATURE:
<223> OTHER INFORMATION: anti-CD47 Kc4E2 kappa light chain

<400> SEQUENCE: 94

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Tyr Tyr Asn
            20                  25                  30

Lys Tyr Val Ser Trp Tyr Gln Gln His Pro Gly Lys Ala Pro Lys Leu
        35                  40                  45

Met Ile Tyr Glu Ser Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 95
<211> LENGTH: 657
<212> TYPE: DNA
<213> ORGANISM: Artificial Sequence
<220> FEATURE:
<223> OTHER INFORMATION: anti-CD19 C2 lambda light chain

<400> SEQUENCE: 95
aattttatgc tgactcagcc ccactctgtg tcggagtctc cggggaagac ggtaaccatc     60
tcctgcaccc gcagcagtgg ctctatcgaa gataagtatg tgcagtggta ccagcagcgc    120
ccgggcagtt cccccaccat tgtgatctat tatgataacg aaagaccctc tggggtccct    180
gatcggttct ctggctccat cgacagctcc tccaactctg cctccctcac catctctgga    240
ctgaagactg aggacgaggc tgactactac tgtcagacct acgaccagag cctgtatggt    300
tgggtgttcg gcggagggac caagctgacc gtcctaggtc agcccaaggc tgccccctcg    360
gtcactctgt tcccgccctc ctctgaggag cttcaagcca acaaggccac actggtgtgt    420
ctcataagtg acttctaccc gggagccgtg acagtggctt ggaaagcaga tagcagcccc    480
gtcaaggcgg gagtggagac caccacaccc tccaaacaaa gcaacaacaa gtacgcggcc    540
agcagctatc tgagcctgac gcctgagcag tggaagtccc acagaagcta cagctgccag    600
gtcacgcatg aagggagcac cgtggagaag acagtggccc ctacagaatg ttcataa       657

<210> SEQ ID NO 96
<211> LENGTH: 218
<212> TYPE: PRT
<213> ORGANISM: Artificial Sequence
<220> FEATURE:
<223> OTHER INFORMATION: anti-CD19 C2 lambda light chain

<400> SEQUENCE: 96

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Glu Asp Lys
            20                  25                  30

Tyr Val Gln Trp Tyr Gln Gln Arg Pro Gly Ser Ser Pro Thr Ile Val
        35                  40                  45

Ile Tyr Tyr Asp Asn Glu Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Thr Tyr Asp Gln
                85                  90                  95

Ser Leu Tyr Gly Trp Val Phe Gly Gly Gly Thr Lys Leu Thr Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro

```
                145                 150                 155                 160
Val Lys Ala Gly Val Glu Thr Thr Thr Pro Ser Lys Gln Ser Asn Asn
                    165                 170                 175

Lys Tyr Ala Ala Ser Ser Tyr Leu Ser Leu Thr Pro Glu Gln Trp Lys
                    180                 185                 190

Ser His Arg Ser Tyr Ser Cys Gln Val Thr His Glu Gly Ser Thr Val
                    195                 200                 205

Glu Lys Thr Val Ala Pro Thr Glu Cys Ser
                    210                 215
```

<210> SEQ ID NO 97
<211> LENGTH: 657
<212> TYPE: DNA
<213> ORGANISM: Artificial Sequence
<220> FEATURE:
<223> OTHER INFORMATION: anti-CD19 A6 lambda light chain

<400> SEQUENCE: 97

```
aattttatgc tgactcagcc ccactctgtg tcggagtctc cggggaagac ggtaaccatc      60
tcctgcaccc gcagcagtgg ctctatcggt gataagtatg tgcagtggta ccagcagcgc     120
ccgggcagtt cccccaccat tgtgatctat tatgataacg aaagaccctc tggggtccct     180
gatcggttct ctggctccat cgacagctcc tccaactctg cctccctcac catctctgga     240
ctgaagactg aggacgaggc tgactactac tgtcagacgt acgacgagag cctgtatggt     300
tgggtgttcg gcggagggac caagctgacc gtcctaggtc agcccaaggc tgccccctcg     360
gtcactctgt tcccgccctc ctctgaggag cttcaagcca acaaggccac actggtgtgt     420
ctcataagtg acttctaccc gggagccgtg acagtggctt ggaaagcaga tagcagcccc     480
gtcaaggcgg gagtggagac caccacaccc tccaaacaaa gcaacaacaa gtacgcggcc     540
agcagctatc tgagcctgac gcctgagcag tggaagtccc acagaagcta cagctgccag     600
gtcacgcatg aagggagcac cgtggagaag acagtggccc ctacagaatg ttcataa       657
```

<210> SEQ ID NO 98
<211> LENGTH: 218
<212> TYPE: PRT
<213> ORGANISM: Artificial Sequence
<220> FEATURE:
<223> OTHER INFORMATION: anti-CD19 A6 lambda light chain

<400> SEQUENCE: 98

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Gly Asp Lys
                20                  25                  30

Tyr Val Gln Trp Tyr Gln Gln Arg Pro Gly Ser Ser Pro Thr Ile Val
            35                  40                  45

Ile Tyr Tyr Asp Asn Glu Arg Pro Ser Gly Val Pro Asp Arg Phe Ser
        50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Thr Tyr Asp Glu
                85                  90                  95

Ser Leu Tyr Gly Trp Val Phe Gly Gly Gly Thr Lys Leu Thr Val Leu
            100                 105                 110

Gly Gln Pro Lys Ala Ala Pro Ser Val Thr Leu Phe Pro Pro Ser Ser
        115                 120                 125
```

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215

<210> SEQ ID NO 99
<211> LENGTH: 657
<212> TYPE: DNA
<213> ORGANISM: Artificial Sequence
<220> FEATURE:
<223> OTHER INFORMATION: anti-CD19 C6 lambda light chain

<400> SEQUENCE: 99
aattttatgc tgactcagcc ccactctgtg tcggagtctc cggggaagac ggtaaccatc      60
tcctgcaccc gcagcagtgg ctctatcaat gataagtatg tgcagtggta ccagcagcgc     120
ccgggcagtt cccccaccat tgtgatctat tttgataacg aaagaccctc tggggtccct     180
gatcggttct ctggctccat cgacagctcc tccaactctg cctccctcac catctctgga     240
ctgaagactg aggacgaggc tgactactac tgtcagacct acgacaccag cctgtatggt     300
tgggtgttcg gcggagggac caagctgacc gtcctaggtc agcccaaggc tgccccctcg     360
gtcactctgt tcccgccctc ctctgaggag cttcaagcca acaaggccac actggtgtgt     420
ctcataagtg acttctaccc gggagccgtg acagtggctt ggaaagcaga tagcagcccc     480
gtcaaggcgg gagtggagac caccacaccc tccaaacaaa gcaacaacaa gtacgcggcc     540
agcagctatc tgagcctgac gcctgagcag tggaagtccc acagaagcta cagctgccag     600
gtcacgcatg aagggagcac cgtggagaag acagtggccc ctacagaatg ttcataa       657

<210> SEQ ID NO 100
<211> LENGTH: 218
<212> TYPE: PRT
<213> ORGANISM: Artificial Sequence
<220> FEATURE:
<223> OTHER INFORMATION: anti-CD19 C6 lambda light chain

<400> SEQUENCE: 100

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Asn Asp Lys
            20                  25                  30

Tyr Val Gln Trp Tyr Gln Gln Arg Pro Gly Ser Ser Pro Thr Ile Val
        35                  40                  45

Ile Tyr Phe Asp Asn Glu Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Thr Tyr Asp Thr
                85                  90                  95

```
Ser Leu Tyr Gly Trp Val Phe Gly Gly Thr Lys Leu Thr Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215
```

<210> SEQ ID NO 101
<211> LENGTH: 657
<212> TYPE: DNA
<213> ORGANISM: Artificial Sequence
<220> FEATURE:
<223> OTHER INFORMATION: anti-CD19 C9 lambda light chain

<400> SEQUENCE: 101

```
aattttatgc tgactcagcc ccactctgtg tcggagtctc cggggaagac ggtaaccatc    60
tcctgcaccc gcagcagtgg ctctatcgct gataagtatg tgcagtggta ccagcagcgc   120
ccgggcagtt cccccaccat tgtgatctat tatgataacg aaagacccte tggggtccct   180
gatcggttct ctggctccat cgacagctcc tccaactctg cctccctcac catctctgga   240
ctgaagactg aggacgaggc tgactactac tgtcagacct acgacgagag cctgtatggt   300
tgggtgttcg gcggagggac caagctgacc gtcctaggtc agcccaaggc tgccccctcg   360
gtcactctgt tcccgccctc ctctgaggag cttcaagcca acaaggccac actggtgtgt   420
ctcataagtg acttctaccc gggagccgtg acagtggctt ggaaagcaga tagcagcccc   480
gtcaaggcgg gagtggagac caccacaccc tccaaacaaa gcaacaacaa gtacgcggcc   540
agcagctatc tgagcctgac gcctgagcag tggaagtccc acagaagcta cagctgccag   600
gtcacgcatg aagggagcac cgtggagaag acagtggccc ctacagaatg ttcataa     657
```

<210> SEQ ID NO 102
<211> LENGTH: 218
<212> TYPE: PRT
<213> ORGANISM: Artificial Sequence
<220> FEATURE:
<223> OTHER INFORMATION: anti-CD19 C9 lambda light chain

<400> SEQUENCE: 102

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Asp Lys
            20                  25                  30

Tyr Val Gln Trp Tyr Gln Gln Arg Pro Gly Ser Ser Pro Thr Ile Val
        35                  40                  45

Ile Tyr Tyr Asp Asn Glu Arg Pro Ser Gly Val Pro Asp Arg Phe Ser
    50                  55                  60

Gly Ser Ile Asp Ser Ser Ser Asn Ser Ala Ser Leu Thr Ile Ser Gly
```

```
                65                  70                  75                  80
Leu Lys Thr Glu Asp Glu Ala Asp Tyr Tyr Cys Gln Thr Tyr Asp Glu
                    85                  90                  95

Ser Leu Tyr Gly Trp Val Phe Gly Gly Gly Thr Lys Leu Thr Val Leu
                100                 105                 110

Gly Gln Pro Lys Ala Ala Pro Ser Val Thr Leu Phe Pro Pro Ser Ser
                115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
                180                 185                 190

Ser His Arg Ser Tyr Ser Cys Gln Val Thr His Glu Gly Ser Thr Val
                195                 200                 205

Glu Lys Thr Val Ala Pro Thr Glu Cys Ser
    210                 215

<210> SEQ ID NO 103
<211> LENGTH: 657
<212> TYPE: DNA
<213> ORGANISM: Artificial Sequence
<220> FEATURE:
<223> OTHER INFORMATION: anti-CD19 B11 lambda light chain

<400> SEQUENCE: 103
aattttatgc tgactcagcc ccactctgtg tcggagtctc cggggaagac ggtaaccatc      60
tcctgcaccc gcagcagtgg ctctatcgaa gataagtatg tgcagtggta ccagcagcgc     120
ccgggcagtt cccccaccat tgtgatctat tatgataacg aaagaccctc tggggtccct     180
gatcggttct ctggctccat cgacagctcc tccaactctg cctccctcac catctctgga     240
ctgaagactg aggacgaggc tgactactac tgtcagacct acgacaacag cctgtatggt     300
tgggtgttcg gcggagggac caagctgacc gtcctaggtc agcccaaggc tgccccctcg     360
gtcactctgt tcccgccctc ctctgaggag cttcaagcca acaaggccac actggtgtgt     420
ctcataagtg acttctaccc gggagccgtg acagtggctt ggaaagcaga tagcagcccc     480
gtcaaggcgg gagtggagac caccacaccc tccaaacaaa gcaacaacaa gtacgcggcc     540
agcagctatc tgagcctgac gcctgagcag tggaagtccc acagaagcta cagctgccag     600
gtcacgcatg aagggagcac cgtggagaag acagtggccc ctacagaatg ttcataa      657

<210> SEQ ID NO 104
<211> LENGTH: 218
<212> TYPE: PRT
<213> ORGANISM: Artificial Sequence
<220> FEATURE:
<223> OTHER INFORMATION: anti-CD19 B11 lambda light chain

<400> SEQUENCE: 104

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Glu Asp Lys
                20                  25                  30

Tyr Val Gln Trp Tyr Gln Gln Arg Pro Gly Ser Ser Pro Thr Ile Val
            35                  40                  45
```

Ile Tyr Tyr Asp Asn Glu Arg Pro Ser Gly Val Pro Asp Arg Phe Ser
            50                  55                  60

Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Thr Tyr Asp Asn
                85                  90                  95

Ser Leu Tyr Gly Trp Val Phe Gly Gly Gly Thr Lys Leu Thr Val Leu
            100                 105                 110

Gly Gln Pro Lys Ala Ala Pro Ser Val Thr Leu Phe Pro Pro Ser Ser
            115                 120                 125

Glu Glu Leu Gln Ala Asn Lys Ala Thr Leu Val Cys Leu Ile Ser Asp
        130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215

<210> SEQ ID NO 105
<211> LENGTH: 657
<212> TYPE: DNA
<213> ORGANISM: Artificial Sequence
<220> FEATURE:
<223> OTHER INFORMATION: anti-CD19 D11 lambda light chain

<400> SEQUENCE: 105
aattttatgc tgactcagcc ccactctgtg tcggagtctc cggggaagac ggtaaccatc      60
tcctgcaccc gcagcagtgg cagcatcgat gataagtttg tgcagtggta ccagcagcgc     120
ccgggcagtt cccccaccac tgtgatctat tatgataaca ttagaccctc tggggtccct     180
gatcggttct ctggctccat cgacagctcc tccaactctg cctccctcac catctctgga     240
ctgaagactg aggacgaggc tgactactac tgtcagtcct atgacgcgag cctgtatggt     300
tgggtgttcg gcggagggac caagctgacc gtcctaggtc agcccaaggc tgccccctcg     360
gtcactctgt tcccgccctc ctctgaggag cttcaagcca acaaggccac actggtgtgt     420
ctcataagtg acttctaccc gggagccgtg acagtggctt ggaaagcaga tagcagcccc     480
gtcaaggcgg gagtggagac caccacaccc tccaaacaaa gcaacaacaa gtacgcggcc     540
agcagctatc tgagcctgac gcctgagcag tggaagtccc acagaagcta cagctgccag     600
gtcacgcatg aagggagcac cgtggagaag acagtggccc ctacagaatg ttcataa        657

<210> SEQ ID NO 106
<211> LENGTH: 218
<212> TYPE: PRT
<213> ORGANISM: Artificial Sequence
<220> FEATURE:
<223> OTHER INFORMATION: anti-CD19 D11 lambda light chain

<400> SEQUENCE: 106

Asn Phe Met Leu Thr Gln Pro His Ser Val Ser Glu Ser Pro Gly Lys
 1               5                  10                  15

```
Thr Val Thr Ile Ser Cys Thr Arg Ser Ser Gly Ser Ile Asp Asp Lys
         20                  25                  30

Phe Val Gln Trp Tyr Gln Gln Arg Pro Gly Ser Ser Pro Thr Thr Val
         35                  40                  45

Ile Tyr Tyr Asp Asn Ile Arg Pro Ser Gly Val Pro Asp Arg Phe Ser
         50                  55                  60

Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ala
                 85                  90                  95

Ser Leu Tyr Gly Trp Val Phe Gly Gly Gly Thr Lys Leu Thr Val Leu
                100                 105                 110

Gly Gln Pro Lys Ala Ala Pro Ser Val Thr Leu Phe Pro Pro Ser Ser
            115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
                180                 185                 190

Ser His Arg Ser Tyr Ser Cys Gln Val Thr His Glu Gly Ser Thr Val
            195                 200                 205

Glu Lys Thr Val Ala Pro Thr Glu Cys Ser
210                 215

<210> SEQ ID NO 107
<211> LENGTH: 657
<212> TYPE: DNA
<213> ORGANISM: Artificial Sequence
<220> FEATURE:
<223> OTHER INFORMATION: anti-CD19 B7 lambda light chain

<400> SEQUENCE: 107
aattttatgc tgactcagcc ccactctgtg tcggagtctc cggggaagac ggtaaccatc      60
tcctgcaccc gcagcagtgg ctctatcgcg gataagtatg tgcagtggta ccagcagcgc     120
ccgggcagtt cccccaccac tgtgatctat gaggataacc aaagaccctc tggggtccct     180
gatcggttct ctggctccat cgacagctcc tccaactctg cctccctcac catctctgga     240
ctgaagactg aggacgaggc tgactactac tgtcagtcct atgacagcag cctgtatggt     300
tgggtgttcg gcggagggac caagctgacc gtcctaggtc agcccaaggc tgccccctcg     360
gtcactctgt tcccgccctc tctgaggag cttcaagcca acaaggccac actggtgtgt     420
ctcataagtg acttctaccc gggagccgtg acagtggctt ggaaagcaga tagcagcccc     480
gtcaaggcgg gagtggagac caccacaccc tccaaacaaa gcaacaacaa gtacgcggcc     540
agcagctatc tgagcctgac gcctgagcag tggaagtccc acagaagcta cagctgccag     600
gtcacgcatg aagggagcac cgtggagaag acagtggccc ctacagaatg ttcataa       657

<210> SEQ ID NO 108
<211> LENGTH: 218
<212> TYPE: PRT
<213> ORGANISM: Artificial Sequence
<220> FEATURE:
<223> OTHER INFORMATION: anti-CD19 B7 lambda light chain
```

<400> SEQUENCE: 108

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Asp Lys
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Leu Tyr Gly Trp Val Phe Gly Gly Gly Thr Lys Leu Thr Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215
```

<210> SEQ ID NO 109
<211> LENGTH: 651
<212> TYPE: DNA
<213> ORGANISM: Artificial Sequence
<220> FEATURE:
<223> OTHER INFORMATION: dummy light chain 1

<400> SEQUENCE: 109

```
cagtctgtgt tgacgcagcc gccctcagtg tctgcggccc caggacagaa ggtcaccatc    60
tcctgctctg gaagcagctc caatattgag actggttctg tatccagcag ctc          120
ccaggaacag cccccaaact cctcatttat gacaataata gcgaccctc agggattcct    180
gaccgattct ctggctccaa gtctggcacg tcagccaccc tgggcatcac cggactccag    240
actggggacg aggccgatta ttactgcgga acatgggatg acagcctgcc tggatgggtg    300
ttcggcggag gaccaagct gaccgtccta ggtcagccca ggctgcccc ctcggtcact    360
ctgttcccgc cctcctctga ggagcttcaa gccaacaagg ccacactggt gtgtctcata    420
agtgacttct acccgggagc cgtgacagtg gcttggaaag cagatagcag ccccgtcaag    480
gcgggagtgg agaccaccac accctccaaa caaagcaaca acaagtacgc ggccagcagc    540
tatctgagcc tgacgcctga gcagtggaag tcccacagaa gctacagctg ccaggtcacg    600
catgaaggga gcaccgtgga agacagtgtg cccctacag aatgttcata a             651
```

<210> SEQ ID NO 110
<211> LENGTH: 216

```
<212> TYPE: PRT
<213> ORGANISM: Artificial Sequence
<220> FEATURE:
<223> OTHER INFORMATION: dummy light chain 1

<400> SEQUENCE: 110

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Glu Thr Gly
            20                  25                  30

Ser Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Asp Ser Leu
                85                  90                  95

Pro Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 111
<211> LENGTH: 657
<212> TYPE: DNA
<213> ORGANISM: Artificial Sequence
<220> FEATURE:
<223> OTHER INFORMATION: dummy light chain 2

<400> SEQUENCE: 111
gaaatagtga tgacgcagtc tccagccacc ctgtctgtgt ctccagggga aagagccacc      60
ctctcctgca gggccagtca gacggttaag aataatttag cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatta ctgtcagcag tataacaact ggttgcccat caacccctat    300
accttcggcc aagggaccaa ggtggaaatc aaacgtacgg tggctgcacc atctgtcttc    360
atcttcccgc catctgatga gcagttgaaa tctggaactg cctctgttgt gtgcctgctg    420
aataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgagcaa agcagactac gagaaacaca agtctacgc ctgcgaagtc    600
```
acccatcagg gcctgagctc gcccgtcaca aagagcttca acagggagag gtgttaa    657

```
<210> SEQ ID NO 112
<211> LENGTH: 218
<212> TYPE: PRT
<213> ORGANISM: Artificial Sequence
<220> FEATURE:
<223> OTHER INFORMATION: dummy light chain 2

<400> SEQUENCE: 112
```

| Glu | Ile | Val | Met | Thr | Gln | Ser | Pro | Ala | Thr | Leu | Ser | Val | Ser | Pro | Gly |
|---|---|---|---|---|---|---|---|---|---|---|---|---|---|---|---|
| 1 | | | | 5 | | | | | 10 | | | | | 15 | |

| Glu | Arg | Ala | Thr | Leu | Ser | Cys | Arg | Ala | Ser | Gln | Thr | Val | Lys | Asn | Asn |
|---|---|---|---|---|---|---|---|---|---|---|---|---|---|---|---|
| | | | 20 | | | | | 25 | | | | | 30 | | |

| Leu | Ala | Trp | Tyr | Gln | Gln | Lys | Pro | Gly | Gln | Ala | Pro | Arg | Leu | Leu | Ile |
|---|---|---|---|---|---|---|---|---|---|---|---|---|---|---|---|
| | | | 35 | | | | | 40 | | | | | 45 | | |

| Tyr | Gly | Ala | Ser | Thr | Arg | Ala | Thr | Gly | Ile | Pro | Ala | Arg | Phe | Ser | Gly |
|---|---|---|---|---|---|---|---|---|---|---|---|---|---|---|---|
| 50 | | | | | 55 | | | | | 60 | | | | | |

| Ser | Gly | Ser | Gly | Thr | Glu | Phe | Thr | Leu | Thr | Ile | Ser | Ser | Leu | Gln | Ser |
|---|---|---|---|---|---|---|---|---|---|---|---|---|---|---|---|
| 65 | | | | | 70 | | | | | 75 | | | | | 80 |

| Glu | Asp | Phe | Ala | Val | Tyr | Tyr | Cys | Gln | Gln | Tyr | Asn | Asn | Trp | Leu | Pro |
|---|---|---|---|---|---|---|---|---|---|---|---|---|---|---|---|
| | | | 85 | | | | | 90 | | | | | 95 | | |

| Ile | Asn | Pro | Tyr | Thr | Phe | Gly | Gln | Gly | Thr | Lys | Val | Glu | Ile | Lys | Arg |
|---|---|---|---|---|---|---|---|---|---|---|---|---|---|---|---|
| | | | 100 | | | | | 105 | | | | | 110 | | |

| Thr | Val | Ala | Ala | Pro | Ser | Val | Phe | Ile | Phe | Pro | Pro | Ser | Asp | Glu | Gln |
|---|---|---|---|---|---|---|---|---|---|---|---|---|---|---|---|
| | | | 115 | | | | | 120 | | | | | 125 | | |

| Leu | Lys | Ser | Gly | Thr | Ala | Ser | Val | Val | Cys | Leu | Leu | Asn | Asn | Phe | Tyr |
|---|---|---|---|---|---|---|---|---|---|---|---|---|---|---|---|
| 130 | | | | | 135 | | | | | 140 | | | | | |

| Pro | Arg | Glu | Ala | Lys | Val | Gln | Trp | Lys | Val | Asp | Asn | Ala | Leu | Gln | Ser |
|---|---|---|---|---|---|---|---|---|---|---|---|---|---|---|---|
| 145 | | | | | 150 | | | | | 155 | | | | | 160 |

| Gly | Asn | Ser | Gln | Glu | Ser | Val | Thr | Glu | Gln | Asp | Ser | Lys | Asp | Ser | Thr |
|---|---|---|---|---|---|---|---|---|---|---|---|---|---|---|---|
| | | | 165 | | | | | 170 | | | | | 175 | | |

| Tyr | Ser | Leu | Ser | Ser | Thr | Leu | Thr | Leu | Ser | Lys | Ala | Asp | Tyr | Glu | Lys |
|---|---|---|---|---|---|---|---|---|---|---|---|---|---|---|---|
| | | | 180 | | | | | 185 | | | | | 190 | | |

| His | Lys | Val | Tyr | Ala | Cys | Glu | Val | Thr | His | Gln | Gly | Leu | Ser | Ser | Pro |
|---|---|---|---|---|---|---|---|---|---|---|---|---|---|---|---|
| | | | 195 | | | | | 200 | | | | | 205 | | |

| Val | Thr | Lys | Ser | Phe | Asn | Arg | Gly | Glu | Cys |
|---|---|---|---|---|---|---|---|---|---|
| 210 | | | | | 215 | | | | |

```
<210> SEQ ID NO 113
<211> LENGTH: 348
<212> TYPE: DNA
<213> ORGANISM: Artificial Sequence
<220> FEATURE:
<223> OTHER INFORMATION: common variable heavy domain

<400> SEQUENCE: 113
```
gaggtgcagc tgttggagtc tgggggaggc ttggtacagc ctggggggtc cctgagactc    60
tcctgtgcag cctctggatt cacctttagc agctatgcca tgagctgggt ccgccaggct   120
ccagggaagg gctggagtg gtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtat attactgtgc gaaaagttat   300
ggtgcttttg actactgggg ccagggaacc ctggtcacag tctcgagc    348

```
<210> SEQ ID NO 114
<211> LENGTH: 116
```

```
<212> TYPE: PRT
<213> ORGANISM: Artificial Sequence
<220> FEATURE:
<223> OTHER INFORMATION: common variable heavy domain

<400> SEQUENCE: 114

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Gly Ala Phe Asp Tyr Trp Gly Gln Gly Thr Leu Val
            100                 105                 110

Thr Val Ser Ser
        115

<210> SEQ ID NO 115
<211> LENGTH: 324
<212> TYPE: DNA
<213> ORGANISM: Artificial Sequence
<220> FEATURE:
<223> OTHER INFORMATION: anti-CD47 5A3 kappa variable light domain

<400> SEQUENCE: 115
gacatccaga tgacccagtc tccatcctcc ctgtctgcat ctgtaggaga cagagtcacc      60
atcacttgcc aggcgagtca ggacattaat aagtatttaa attggtatca gcagaaacca     120
gggaaagccc ctaagctcct gatctacggt gcatccaggt tggaaacagg ggtcccatca     180
aggttcagtg gaagtggatc tgggacagat tttactttca ccatcagcag cctgcagcct     240
gaagatattg caacatatta ctgtcagcag aagcaccccc gggggccgag gaccttcggc     300
caagggacca aggtggaaat caaa                                            324

<210> SEQ ID NO 116
<211> LENGTH: 108
<212> TYPE: PRT
<213> ORGANISM: Artificial Sequence
<220> FEATURE:
<223> OTHER INFORMATION: anti-CD47 5A3 kappa variable light domain

<400> SEQUENCE: 116

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Lys Tyr
            20                  25                  30

Leu Asn Trp Tyr Gln Gln Lys Pro Gly Lys Ala Pro Lys Leu Leu Ile
        35                  40                  45

Tyr Gly Ala Ser Arg Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Lys His Pro Arg Gly Pro
```

```
                    85                  90                  95
Arg Thr Phe Gly Gln Gly Thr Lys Val Glu Ile Lys
                100                 105
```

<210> SEQ ID NO 117
<211> LENGTH: 324
<212> TYPE: DNA
<213> ORGANISM: Artificial Sequence
<220> FEATURE:
<223> OTHER INFORMATION: anti-CD47 5A3-M4  kappa variable light domain

<400> SEQUENCE: 117

```
gacatccaga tgacccagtc tccatcctcc ctgtctgcat ctgtaggaga cagagtcacc    60
atcacttgcc aggcgagtca ggacattaat aagtatttaa attggtatca gcagaaacca   120
gggaaagccc ctaagctcct gatctacggt gcatccaggt tggaaacagg ggtcccatca   180
aggttcagtg gaagtggatc tgggacagat tttactttca ccatcagcag cctgcagcct   240
gaagatattg caacatatta ctgtcagcag aagcaccccc ggaacccgag gaccttcggc   300
caagggacca aggtggaaat caaa                                          324
```

<210> SEQ ID NO 118
<211> LENGTH: 108
<212> TYPE: PRT
<213> ORGANISM: Artificial Sequence
<220> FEATURE:
<223> OTHER INFORMATION: anti-CD47 5A3-M4  kappa variable light domain

<400> SEQUENCE: 118

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Lys Tyr
            20                  25                  30

Leu Asn Trp Tyr Gln Gln Lys Pro Gly Lys Ala Pro Lys Leu Leu Ile
        35                  40                  45

Tyr Gly Ala Ser Arg Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Lys His Pro Arg Asn Pro
                85                  90                  95

Arg Thr Phe Gly Gln Gly Thr Lys Val Glu Ile Lys
                100                 105
```

<210> SEQ ID NO 119
<211> LENGTH: 324
<212> TYPE: DNA
<213> ORGANISM: Artificial Sequence
<220> FEATURE:
<223> OTHER INFORMATION: anti-CD47 5A3-M3  kappa variable light domain

<400> SEQUENCE: 119

```
gacatccaga tgacccagtc tccatcctcc ctgtctgcat ctgtaggaga cagagtcacc    60
atcacttgcc aggcgagtca gtccattagt agtatttaa attggtatca gcagaaacca   120
gggaaagccc ctaagctcct gatctacgct gcatcctcgt tggaaacagg ggtcccatca   180
aggttcagtg gaagtggatc tgggacagat tttactttca ccatcagcag cctgcagcct   240
gaagatattg caacatatta ctgtcagcag aagcaccccc ggggccgag gaccttcggc   300 caagggacca aggtggaaat caaa                                          324
```

<210> SEQ ID NO 120
<211> LENGTH: 108
<212> TYPE: PRT
<213> ORGANISM: Artificial Sequence
<220> FEATURE:
<223> OTHER INFORMATION: anti-CD47 5A3-M3 kappa variable light domain

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Lys His Pro Arg Gly Pro
                85                  90                  95

Arg Thr Phe Gly Gln Gly Thr Lys Val Glu Ile Lys
            100                 105

<210> SEQ ID NO 121
<211> LENGTH: 324
<212> TYPE: DNA
<213> ORGANISM: Artificial Sequence
<220> FEATURE:
<223> OTHER INFORMATION: anti-CD47 5A3-M5 kappa variable light domain

<400> SEQUENCE: 121
gacatccaga tgacccagtc tccatcctcc ctgtctgcat ctgtaggaga cagagtcacc      60
atcacttgcc aggcgagtca ggacattaat aagtatttaa attggtatca gcagaaacca     120
gggaaagccc ctaagctcct gatctacggt gcatccaggt tggaaacagg ggtcccatca     180
aggttcagtg gaagtggatc tgggacagat tttactttca ccatcagcag cctgcagcct     240
gaagatattg caacatatta ctgtcagcag aagcaccccc ggtacccgag gaccttcggc     300
caagggacca aggtggaaat caaa                                            324

<210> SEQ ID NO 122
<211> LENGTH: 108
<212> TYPE: PRT
<213> ORGANISM: Artificial Sequence
<220> FEATURE:
<223> OTHER INFORMATION: anti-CD47 5A3-M5 kappa variable light domain

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Lys Tyr
            20                  25                  30

Leu Asn Trp Tyr Gln Gln Lys Pro Gly Lys Ala Pro Lys Leu Leu Ile
        35                  40                  45

Tyr Gly Ala Ser Arg Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Lys His Pro Arg Tyr Pro
            85                  90                  95

Arg Thr Phe Gly Gln Gly Thr Lys Val Glu Ile Lys
        100                 105

<210> SEQ ID NO 123
<211> LENGTH: 324
<212> TYPE: DNA
<213> ORGANISM: Artificial Sequence
<220> FEATURE:
<223> OTHER INFORMATION: anti-CD47 Ke8 kappa variable light domain

<400> SEQUENCE: 123
gacatccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcagcag ttccacaagc ggcggccgca gaccttcggc    300
caagggacca aggtggaaat caaa                                           324

<210> SEQ ID NO 124
<211> LENGTH: 108
<212> TYPE: PRT
<213> ORGANISM: Artificial Sequence
<220> FEATURE:
<223> OTHER INFORMATION: anti-CD47 Ke8 kappa variable light domain

<400> SEQUENCE: 124

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe His Lys Arg Arg Pro
            85                  90                  95

Gln Thr Phe Gly Gln Gly Thr Lys Val Glu Ile Lys
        100                 105

<210> SEQ ID NO 125
<211> LENGTH: 324
<212> TYPE: DNA
<213> ORGANISM: Artificial Sequence
<220> FEATURE:
<223> OTHER INFORMATION: anti-CD47 Ke8H5 kappa variable light domain

<400> SEQUENCE: 125
gacatccaga tgacccagtc tccatcctcc ctgtctgcat ctgtaggaga cagagtcacc     60
atcacttgcc gggcaagtca gagcattgcg agtatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcagcag ttccataagc gtgcgccgca gaccttcggc    300

```
caagggacca aggtggaaat caaa                                          324
```

<210> SEQ ID NO 126
<211> LENGTH: 108
<212> TYPE: PRT
<213> ORGANISM: Artificial Sequence
<220> FEATURE:
<223> OTHER INFORMATION: anti-CD47 Ke8H5 kappa variable light domain

<400> SEQUENCE: 126

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe His Lys Arg Ala Pro
                85                  90                  95

Gln Thr Phe Gly Gln Gly Thr Lys Val Glu Ile Lys
            100                 105
```

<210> SEQ ID NO 127
<211> LENGTH: 324
<212> TYPE: DNA
<213> ORGANISM: Artificial Sequence
<220> FEATURE:
<223> OTHER INFORMATION: anti-CD47 Ke8B2 kappa variable light domain

<400> SEQUENCE: 127

```
gacatccaga tgacccagtc tccatcctcc ctgtctgcat ctgtaggaga cagagtcacc       60
atcacttgcc gggcaagtca gagcattggt aagtatttaa attggtatca gcagaaacca      120
gggaaagccc ctaagctcct gatctatgcg gcatccaggt tgcaaagtgg ggtcccatca      180
aggttcagtg gcagtggatc tgggacagat ttcactctca ccatcagcag tctgcaacct      240
gaagattttg caacttacta ctgtcagcag aagcacccgc gtgccccgcg gaccttcggc      300
caagggacca aggtggaaat caaa                                             324
```

<210> SEQ ID NO 128
<211> LENGTH: 108
<212> TYPE: PRT
<213> ORGANISM: Artificial Sequence
<220> FEATURE:
<223> OTHER INFORMATION: anti-CD47 Ke8B2 kappa variable light domain

<400> SEQUENCE: 128

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Lys His Pro Arg Ala Pro
                85                  90                  95

Arg Thr Phe Gly Gln Gly Thr Lys Val Glu Ile Lys
            100                 105

<210> SEQ ID NO 129
<211> LENGTH: 324
<212> TYPE: DNA
<213> ORGANISM: Artificial Sequence
<220> FEATURE:
<223> OTHER INFORMATION: anti-CD47 Ke8A2 kappa variable light domain

<400> SEQUENCE: 129
gacatccaga tgacccagtc tccatcctcc ctgtctgcat ctgtaggaga cagagtcacc    60
atcacttgcc gggcaagtca gagcattgat aggtatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcag aagcatcccc gtgggccgag gaccttcggc   300
caagggacca aggtggaaat caaa                                          324

<210> SEQ ID NO 130
<211> LENGTH: 108
<212> TYPE: PRT
<213> ORGANISM: Artificial Sequence
<220> FEATURE:
<223> OTHER INFORMATION: anti-CD47 Ke8A2 kappa variable light domain

<400> SEQUENCE: 130

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys His Pro Arg Gly Pro
                85                  90                  95

Arg Thr Phe Gly Gln Gly Thr Lys Val Glu Ile Lys
            100                 105

<210> SEQ ID NO 131
<211> LENGTH: 324
<212> TYPE: DNA
<213> ORGANISM: Artificial Sequence
<220> FEATURE:
<223> OTHER INFORMATION: anti-CD47 Ke8E8 kappa variable light domain

<400> SEQUENCE: 131
gacatccaga tgacccagtc tccatcctcc ctgtctgcat ctgtaggaga cagagtcacc    60
atcacttgcc aggcgagtca ggacattaat aagtatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcag aagcatcccc gtggcccgcg gaccttcggc   300
caagggacca aggtggaaat caaa                                             324

<210> SEQ ID NO 132
<211> LENGTH: 108
<212> TYPE: PRT
<213> ORGANISM: Artificial Sequence
<220> FEATURE:
<223> OTHER INFORMATION: anti-CD47 Ke8E8 kappa variable light domain

<400> SEQUENCE: 132

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys His Pro Arg Gly Pro
                85                  90                  95

Arg Thr Phe Gly Gln Gly Thr Lys Val Glu Ile Lys
            100                 105

<210> SEQ ID NO 133
<211> LENGTH: 324
<212> TYPE: DNA
<213> ORGANISM: Artificial Sequence
<220> FEATURE:
<223> OTHER INFORMATION: anti-CD47 Ke8H3 kappa variable light domain

<400> SEQUENCE: 133
gacatccaga tgacccagtc tccatcctcc ctgtctgcat ctgtaggaga cagagtcacc      60
atcacttgcc gggcaagtca gagcattaat aggtatttaa attggtatca gcagaaacca     120
gggaaagccc ctaagctcct gatctatgct gcatccaggt tgcaaagtgg ggtcccatca     180
aggttcagtg gcagtggatc tgggacagat ttcactctca ccatcagcag tctgcaacct    240
gaagattttg caacttacta ctgtcagcag aagcatccgc gtgggccgag gaccttcggc    300
caagggacca aggtggaaat caaa                                             324

<210> SEQ ID NO 134
<211> LENGTH: 108
<212> TYPE: PRT
<213> ORGANISM: Artificial Sequence
<220> FEATURE:
<223> OTHER INFORMATION: anti-CD47 Ke8H3 kappa variable light domain

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro

```
                65                  70                  75                  80
Glu Asp Phe Ala Thr Tyr Tyr Cys Gln Gln Lys His Pro Arg Gly Pro
                        85                  90                  95

Arg Thr Phe Gly Gln Gly Thr Lys Val Glu Ile Lys
                100                 105

<210> SEQ ID NO 135
<211> LENGTH: 324
<212> TYPE: DNA
<213> ORGANISM: Artificial Sequence
<220> FEATURE:
<223> OTHER INFORMATION: anti-CD47 Ke8G6 kappa variable light domain

<400> SEQUENCE: 135
gacatccaga tgacccagtc tccatcctcc ctgtctgcat ctgtaggaga cagagtcacc      60
atcacttgcc gggcaagtca gagcattggt aggtatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcag atgcatccgc gtgcgccgaa gaccttcggc     300
caagggacca aggtggaaat caaa                                            324

<210> SEQ ID NO 136
<211> LENGTH: 108
<212> TYPE: PRT
<213> ORGANISM: Artificial Sequence
<220> FEATURE:
<223> OTHER INFORMATION: anti-CD47 Ke8G6 kappa variable light domain

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys
                100                 105

<210> SEQ ID NO 137
<211> LENGTH: 324
<212> TYPE: DNA
<213> ORGANISM: Artificial Sequence
<220> FEATURE:
<223> OTHER INFORMATION: anti-CD47 Ke8A3 kappa variable light domain

<400> SEQUENCE: 137
gacatccaga tgacccagtc tccatcctcc ctgtctgcat ctgtaggaga cagagtcacc      60
atcacttgcc gggtaagtca gagcattagt aagtatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
```
gaagattttg caacttacta ctgtcagcag aggcatcccc gtgggccgag caccttcggc    300
caagggacca aggtggaaat caaa                                           324

<210> SEQ ID NO 138
<211> LENGTH: 108
<212> TYPE: PRT
<213> ORGANISM: Artificial Sequence
<220> FEATURE:
<223> OTHER INFORMATION: anti-CD47 Ke8A3 kappa variable light domain

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Arg Val Ser Gln Ser Ile Ser Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg His Pro Arg Gly Pro
                85                  90                  95

Ser Thr Phe Gly Gln Gly Thr Lys Val Glu Ile Lys
            100                 105

<210> SEQ ID NO 139
<211> LENGTH: 324
<212> TYPE: DNA
<213> ORGANISM: Artificial Sequence
<220> FEATURE:
<223> OTHER INFORMATION: anti-CD47 Ke81A3 kappa variable light domain

<400> SEQUENCE: 139
gacatccaga tgacccagtc tccatcctcc ctgtctgcat ctgtaggaga cagagtcacc    60
atcacttgcc aggcgagtca ggacattaat aggtatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcagcag aggcatccgc gtgccccgcg gaccttcggc    300
caagggacca aggtggaaat caaa                                           324

<210> SEQ ID NO 140
<211> LENGTH: 108
<212> TYPE: PRT
<213> ORGANISM: Artificial Sequence
<220> FEATURE:
<223> OTHER INFORMATION: anti-CD47 Ke81A3 kappa variable light domain

<400> SEQUENCE: 140

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Arg His Pro Arg Ala Pro
                 85                  90                  95

Arg Thr Phe Gly Gln Gly Thr Lys Val Glu Ile Lys
            100                 105

<210> SEQ ID NO 141
<211> LENGTH: 324
<212> TYPE: DNA
<213> ORGANISM: Artificial Sequence
<220> FEATURE:
<223> OTHER INFORMATION: anti-CD47 Ke8A8 kappa variable light domain

<400> SEQUENCE: 141
gacatccaga tgacccagtc tccatcctcc ctgtctgcat ctgtaggaga cagagtcacc      60
atcacttgcc gggcaagtca gagcattagt aagtatttaa attggtatca gcagaaacca     120
gggaaagccc ctaagctcct gatctatgct gcatccactt tgcaaagtgg ggtcccatca     180
aggttcagtg gcagtggatc tgggacagat ttcactctca ccatcagcag tctgcaacct     240
gaagattttg caacttacta ctgtcagcag atgcatccgc gtgcgccgaa gaccttcggc     300
caagggacca aggtggaaat caaa                                            324

<210> SEQ ID NO 142
<211> LENGTH: 108
<212> TYPE: PRT
<213> ORGANISM: Artificial Sequence
<220> FEATURE:
<223> OTHER INFORMATION: anti-CD47 Ke8A8 kappa variable light domain

<400> SEQUENCE: 142

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Lys Tyr
                20                  25                  30

Leu Asn Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Met His Pro Arg Ala Pro
                 85                  90                  95

Lys Thr Phe Gly Gln Gly Thr Lys Val Glu Ile Lys
            100                 105

<210> SEQ ID NO 143
<211> LENGTH: 324
<212> TYPE: DNA
<213> ORGANISM: Artificial Sequence
<220> FEATURE:
<223> OTHER INFORMATION: anti-CD47 Ke8C7 kappa variable light domain

<400> SEQUENCE: 143
gacatccaga tgacccagtc tccatcctcc ctgtctgcat ctgtaggaga cagagtcacc      60
atcacttgcc aggcgagtca ggacattaat aggtatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240

```
gaagattttg caacttacta ctgtcagcag cgccatccgc gtggcccgag gaccttcggc    300
caagggacca aggtggaaat caaa                                           324
```

<210> SEQ ID NO 144
<211> LENGTH: 108
<212> TYPE: PRT
<213> ORGANISM: Artificial Sequence
<220> FEATURE:
<223> OTHER INFORMATION: anti-CD47 Ke8C7 kappa variable light domain

<400> SEQUENCE: 144

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg His Pro Arg Gly Pro
                85                  90                  95

Arg Thr Phe Gly Gln Gly Thr Lys Val Glu Ile Lys
            100                 105

<210> SEQ ID NO 145
<211> LENGTH: 324
<212> TYPE: DNA
<213> ORGANISM: Artificial Sequence
<220> FEATURE:
<223> OTHER INFORMATION: anti-CD47 Ke8G2 kappa variable light domain

<400> SEQUENCE: 145

```
gacatccaga tgacccagtc tccatcctcc ctgtctgcat ctgtaggaga cagagtcacc    60
atcacttgcc gggcaagtca gagcattggt aggtatttaa attggtatca gcagaaacca   120
gggaaagccc ctaagctcct gatctatgcg gcatccaggt tgcaaagtgg ggtcccatca   180
aggttcagtg gcagtggatc tgggacagat ttcactctca ccatcaacag tctgcaacct   240
gaagattttg caacttacta ctgtcagcag aagcatcccc gtgcgccgag gaccttcggc   300
caagggacca aggtggaaat caaa                                          324
```

<210> SEQ ID NO 146
<211> LENGTH: 108
<212> TYPE: PRT
<213> ORGANISM: Artificial Sequence
<220> FEATURE:
<223> OTHER INFORMATION: anti-CD47 Ke8G2 kappa variable light domain

<400> SEQUENCE: 146

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

```
Ser Gly Ser Gly Thr Asp Phe Thr Leu Thr Ile Asn Ser Leu Gln Pro
 65                  70                  75                  80

Glu Asp Phe Ala Thr Tyr Tyr Cys Gln Gln Lys His Pro Arg Ala Pro
                 85                  90                  95

Arg Thr Phe Gly Gln Gly Thr Lys Val Glu Ile Lys
            100                 105

<210> SEQ ID NO 147
<211> LENGTH: 324
<212> TYPE: DNA
<213> ORGANISM: Artificial Sequence
<220> FEATURE:
<223> OTHER INFORMATION: anti-CD47 Ke81G9 kappa variable light domain

<400> SEQUENCE: 147
gacatccaga tgacccagtc tccatcctcc ctgtctgcat ctgtaggaga cagagtcacc      60
atcacttgcc gggcaagtca gagcattgat aagtatttaa attggtatca gcagaaacca     120
gggaaagccc ctaagctcct gatctatgcg gcatccaggt tgcaaagtgg ggtcccatca     180
aggttcagtg gcagtggatc tgggacagat ttcactctca ccatcagcag tctgcaacct     240
gaagattttg caacttacta ctgtcagcag cggcataagc gttccccgca gaccttcggc     300
caagggacca aggtggaaat caaa                                            324

<210> SEQ ID NO 148
<211> LENGTH: 108
<212> TYPE: PRT
<213> ORGANISM: Artificial Sequence
<220> FEATURE:
<223> OTHER INFORMATION: anti-CD47 Ke81G9 kappa variable light domain

<400> SEQUENCE: 148

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Asp Lys Tyr
             20                  25                  30

Leu Asn Trp Tyr Gln Gln Lys Pro Gly Lys Ala Pro Lys Leu Leu Ile
         35                  40                  45

Tyr Ala Ala Ser Arg Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Arg His Lys Arg Ser Pro
                 85                  90                  95

Gln Thr Phe Gly Gln Gly Thr Lys Val Glu Ile Lys
            100                 105

<210> SEQ ID NO 149
<211> LENGTH: 324
<212> TYPE: DNA
<213> ORGANISM: Artificial Sequence
<220> FEATURE:
<223> OTHER INFORMATION: anti-CD47 Ke8F2 kappa variable light domain

<400> SEQUENCE: 149
gacatccaga tgacccagtc tccatcctcc ctgtctgcat ctgtaggaga cagagtcacc      60
atcacttgcc gggcaagtca gagcattgat aagtatttaa attggtatca gcagaaacca    120
gggaaagccc ctaagctcct gatctatgct gcatccagtt tgcaaagtgg ggtcccatca    180
```

-continued

```
aggttcagtg gcagtggatc tgggacagat ttcactctca ccatcagcag tctgcaacct    240
gaagattttg caacttacta ctgtcagcag aagcatccgc gtgcgccgcg gaccttcggc    300
caagggacca aggtggaaat caaa                                          324
```

<210> SEQ ID NO 150
<211> LENGTH: 108
<212> TYPE: PRT
<213> ORGANISM: Artificial Sequence
<220> FEATURE:
<223> OTHER INFORMATION: anti-CD47 Ke8F2 kappa variable light domain

<400> SEQUENCE: 150

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys His Pro Arg Ala Pro
                85                  90                  95

Arg Thr Phe Gly Gln Gly Thr Lys Val Glu Ile Lys
            100                 105
```

<210> SEQ ID NO 151
<211> LENGTH: 324
<212> TYPE: DNA
<213> ORGANISM: Artificial Sequence
<220> FEATURE:
<223> OTHER INFORMATION: anti-CD47 Ke8B7 kappa variable light domain

<400> SEQUENCE: 151

```
gacatccaga tgacccagtc tccatcctcc ctgtctgcat ctgtaggaga cagagtcacc    60
atcacttgcc gggcaagtca gagcattggg aagtatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcagcag atgcatccgc gtagcccgaa gaccttcggc    300
caagggacca aggtggaaat caaa                                          324
```

<210> SEQ ID NO 152
<211> LENGTH: 108
<212> TYPE: PRT
<213> ORGANISM: Artificial Sequence
<220> FEATURE:
<223> OTHER INFORMATION: anti-CD47 Ke8B7 kappa variable light domain

<400> SEQUENCE: 152

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
```

```
                50                55                60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Met His Pro Arg Ser Pro
                 85                  90                  95

Lys Thr Phe Gly Gln Gly Thr Lys Val Glu Ile Lys
            100                 105
```

<210> SEQ ID NO 153
<211> LENGTH: 324
<212> TYPE: DNA
<213> ORGANISM: Artificial Sequence
<220> FEATURE:
<223> OTHER INFORMATION: anti-CD47 Ke8C4 kappa variable light domain

<400> SEQUENCE: 153

```
gacatccaga tgacccagtc tccatcctcc ctgtctgcat ctgtaggaga cagagtcacc      60
atcacttgcc gggcaagtca gagcattagt aggtatttaa attggtatca gcagaaacca    120
gggaaagccc ctaagctcct gatctatgct gcatccaatt tgcaaagtgg ggtcccatca    180
aggttcagtg gcagtggatc tgggacagat ttcactctca ccatcagcag tctgcaacct    240
gaagattttg caacttacta ctgtcagcag atgcatccgc gtgggccgaa gaccttcggc    300
caagggacca aggtggaaat caaa                                            324
```

<210> SEQ ID NO 154
<211> LENGTH: 108
<212> TYPE: PRT
<213> ORGANISM: Artificial Sequence
<220> FEATURE:
<223> OTHER INFORMATION: anti-CD47 Ke8C4 kappa variable light domain

<400> SEQUENCE: 154

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Arg Tyr
             20                  25                  30

Leu Asn Trp Tyr Gln Gln Lys Pro Gly Lys Ala Pro Lys Leu Leu Ile
         35                  40                  45

Tyr Ala Ala Ser Asn Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Met His Pro Arg Gly Pro
                 85                  90                  95

Lys Thr Phe Gly Gln Gly Thr Lys Val Glu Ile Lys
            100                 105
```

<210> SEQ ID NO 155
<211> LENGTH: 324
<212> TYPE: DNA
<213> ORGANISM: Artificial Sequence
<220> FEATURE:
<223> OTHER INFORMATION: anti-CD47 Ke8F1 kappa variable light domain

<400> SEQUENCE: 155

```
gacatccaga tgacccagtc tccatcctcc ctgtctgcat ctgtaggaga cagagtcacc      60
atcacttgcc gggcaagtca gagcattgct tcttatgtaa attggtatca gcagaaacca    120
gggaaagccc ctaagctcct gatctatgct gcatccggtt tgcaaagtgg ggtcccatca    180
```

```
aggttcagtg gcagtggatc tgggacagat ttcactctca ccatcagcag tctgcaacct    240
gaagattttg caacttacta ctgtcagcag ttccataagc gtcggccgca gaccttcggc    300
caagggacca aggtggaaat caaa                                           324
```

<210> SEQ ID NO 156
<211> LENGTH: 108
<212> TYPE: PRT
<213> ORGANISM: Artificial Sequence
<220> FEATURE:
<223> OTHER INFORMATION: anti-CD47 Ke8F1 kappa variable light domain

<400> SEQUENCE: 156

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Ser Tyr
            20                  25                  30

Val Asn Trp Tyr Gln Gln Lys Pro Gly Lys Ala Pro Lys Leu Leu Ile
        35                  40                  45

Tyr Ala Ala Ser Gly Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe His Lys Arg Arg Pro
                85                  90                  95

Gln Thr Phe Gly Gln Gly Thr Lys Val Glu Ile Lys
            100                 105
```

<210> SEQ ID NO 157
<211> LENGTH: 324
<212> TYPE: DNA
<213> ORGANISM: Artificial Sequence
<220> FEATURE:
<223> OTHER INFORMATION: anti-CD47 Ke8G11 kappa variable light domain

<400> SEQUENCE: 157

```
gacatccaga tgacccagtc tccatcctcc ctgtctgcat ctgtaggaga cagagtcacc    60
atcacttgcc gggcaagtca gagcattggg aggtatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcagcag atgcatccgc gtgggccgaa gaccttcggc    300
caagggacca aggtggaaat caaa                                           324
```

<210> SEQ ID NO 158
<211> LENGTH: 108
<212> TYPE: PRT
<213> ORGANISM: Artificial Sequence
<220> FEATURE:
<223> OTHER INFORMATION: anti-CD47 Ke8G11 kappa variable light domain

<400> SEQUENCE: 158

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Arg Tyr
            20                  25                  30

Leu Asn Trp Tyr Gln Gln Lys Pro Gly Lys Ala Pro Lys Leu Leu Ile
        35                  40                  45
```

```
Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Gly Pro
                 85                  90                  95

Lys Thr Phe Gly Gln Gly Thr Lys Val Glu Ile Lys
                100                 105
```

```
<210> SEQ ID NO 159
<211> LENGTH: 324
<212> TYPE: DNA
<213> ORGANISM: Artificial Sequence
<220> FEATURE:
<223> OTHER INFORMATION: anti-CD47 Ke8H6 kappa variable light domain

<400> SEQUENCE: 159
gacatccaga tgacccagtc tccatcctcc ctgtctgcat ctgtaggaga cagagtcacc    60
atcacttgcc gggcaagtca gagcattagt aagtatttaa attggtatca gcagaaacca   120
gggaaagccc ctaagctcct gatctataat gcatccactt tgcaaagtgg ggtcccatca   180
aggttcagtg gcagtggatc tgggacagat ttcactctca ccatcagcag tctgcaacct   240
gaagattttg caacttacta ctgtcagcag aggcatccgc gtgggccgcg caccttcggc   300
caagggacca aggtggaaat caaa                                           324
```

```
<210> SEQ ID NO 160
<211> LENGTH: 108
<212> TYPE: PRT
<213> ORGANISM: Artificial Sequence
<220> FEATURE:
<223> OTHER INFORMATION: anti-CD47 Ke8H6 kappa variable light domain

<400> SEQUENCE: 160

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Lys Tyr
                20                  25                  30

Leu Asn Trp Tyr Gln Gln Lys Pro Gly Lys Ala Pro Lys Leu Leu Ile
            35                  40                  45

Tyr Asn Ala Ser Thr Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg His Pro Arg Gly Pro
                 85                  90                  95

Arg Thr Phe Gly Gln Gly Thr Lys Val Glu Ile Lys
                100                 105
```

```
<210> SEQ ID NO 161
<211> LENGTH: 324
<212> TYPE: DNA
<213> ORGANISM: Artificial Sequence
<220> FEATURE:
<223> OTHER INFORMATION: anti-CD47 Ke84G9 kappa variable light domain

<400> SEQUENCE: 161
gacatccaga tgacccagtc tccatcctcc ctgtctgcat ctgtaggaga cagagtcacc    60
atcacttgcc gggcaagtca gagcattagt aagtatttaa attggtatca gcagaaacca   120
```

```
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcagcag aagcatccgc gtagcccgcg gaccttcggc    300
caagggacca aggtggaaat caaa                                           324
```

<210> SEQ ID NO 162
<211> LENGTH: 108
<212> TYPE: PRT
<213> ORGANISM: Artificial Sequence
<220> FEATURE:
<223> OTHER INFORMATION: anti-CD47 Ke84G9 kappa variable light domain

<400> SEQUENCE: 162

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys His Pro Arg Ser Pro
                85                  90                  95

Arg Thr Phe Gly Gln Gly Thr Lys Val Glu Ile Lys
            100                 105
```

<210> SEQ ID NO 163
<211> LENGTH: 324
<212> TYPE: DNA
<213> ORGANISM: Artificial Sequence
<220> FEATURE:
<223> OTHER INFORMATION: anti-CD47 Ke8A4 kappa variable light domain

<400> SEQUENCE: 163

```
gacatccaga tgacccagtc tccatcctcc ctgtctgcat ctgtaggaga cagagtcacc    60
atcacttgcc gggcaagtca gagcattgct aagtatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcagcag ttccataagc gtagcccgca gaccttcggc    300
caagggacca aggtggaaat caaa                                           324
```

<210> SEQ ID NO 164
<211> LENGTH: 108
<212> TYPE: PRT
<213> ORGANISM: Artificial Sequence
<220> FEATURE:
<223> OTHER INFORMATION: anti-CD47 Ke8A4 kappa variable light domain

<400> SEQUENCE: 164

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Lys Tyr
            20                  25                  30

Leu Asn Trp Tyr Gln Gln Lys Pro Gly Lys Ala Pro Lys Leu Leu Ile
        35                  40                  45
```

```
Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Lys Arg Ser Pro
                85                  90                  95

Gln Thr Phe Gly Gln Gly Thr Lys Val Glu Ile Lys
            100                 105
```

<210> SEQ ID NO 165
<211> LENGTH: 324
<212> TYPE: DNA
<213> ORGANISM: Artificial Sequence
<220> FEATURE:
<223> OTHER INFORMATION: anti-CD47 Ke86G9 kappa variable light domain

<400> SEQUENCE: 165

```
gacatccaga tgacccagtc tccatcctcc ctgtctgcat ctgtaggaga cagagtcacc    60
atcacttgcc gggcaagtca gagcattagt aagtatttaa attggtatca gcagaaacca   120
gggaaagccc ctaagctcct gatctataat gcatccaatt tgcaaagtgg ggtcccatca   180
aggttcagtg gcagtggatc tgggacagat ttcactctca ccatcagcag tctgcaacct   240
gaagattttg caacttacta ctgtcagcag aggcatccgc gtgggccgac caccttcggc   300
caagggacca aggtggaaat caaa                                          324
```

<210> SEQ ID NO 166
<211> LENGTH: 108
<212> TYPE: PRT
<213> ORGANISM: Artificial Sequence
<220> FEATURE:
<223> OTHER INFORMATION: anti-CD47 Ke86G9 kappa variable light domain

<400> SEQUENCE: 166

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Lys Tyr
            20                  25                  30

Leu Asn Trp Tyr Gln Gln Lys Pro Gly Lys Ala Pro Lys Leu Leu Ile
        35                  40                  45

Tyr Asn Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg His Pro Arg Gly Pro
                85                  90                  95

Thr Thr Phe Gly Gln Gly Thr Lys Val Glu Ile Lys
            100                 105
```

<210> SEQ ID NO 167
<211> LENGTH: 324
<212> TYPE: DNA
<213> ORGANISM: Artificial Sequence
<220> FEATURE:
<223> OTHER INFORMATION: anti-CD47 Ka3 kappa variable light domain

<400> SEQUENCE: 167

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
```

```
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcagcag atgcacccgc gcgccccgaa gaccttcggc    300
caagggacca aggtggaaat caaa                                           324
```

<210> SEQ ID NO 168
<211> LENGTH: 108
<212> TYPE: PRT
<213> ORGANISM: Artificial Sequence
<220> FEATURE:
<223> OTHER INFORMATION: anti-CD47 Ka3 kappa variable light domain

<400> SEQUENCE: 168

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys
            100                 105

<210> SEQ ID NO 169
<211> LENGTH: 324
<212> TYPE: DNA
<213> ORGANISM: Artificial Sequence
<220> FEATURE:
<223> OTHER INFORMATION: anti-CD47 Ka3A2 kappa variable light domain

<400> SEQUENCE: 169

```
gacatccaga tgacccagtc tccatcctcc ctgtctgcat ctgtaggaga cagagtcacc    60
atcacttgcc gggcaagtca gagcattagt aagtatttaa attggtatca gcagaaacca    120
gggaaagccc ctaagctcct gatctatgct gcatccaggt tgcaaagtgg ggtcccatca    180
aggttcagtg gcagtggatc tgggacagat ttcactctca ccatcagcag tctgcaacct    240
gaagattttg caacttacta ctgtcagcag atgcatcctc gctcgccgaa aaccttcggc    300
caagggacca aggtggaaat caaa                                           324
```

<210> SEQ ID NO 170
<211> LENGTH: 108
<212> TYPE: PRT
<213> ORGANISM: Artificial Sequence
<220> FEATURE:
<223> OTHER INFORMATION: anti-CD47 Ka3A2 kappa variable light domain

<400> SEQUENCE: 170

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Lys Tyr
            20                  25                  30

Leu Asn Trp Tyr Gln Gln Lys Pro Gly Lys Ala Pro Lys Leu Leu Ile

```
                35                  40                  45
Tyr Ala Ala Ser Arg Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ser Pro
                85                  90                  95

Lys Thr Phe Gly Gln Gly Thr Lys Val Glu Ile Lys
            100                 105
```

<210> SEQ ID NO 171
<211> LENGTH: 324
<212> TYPE: DNA
<213> ORGANISM: Artificial Sequence
<220> FEATURE:
<223> OTHER INFORMATION: anti-CD47 Ka3H3 kappa variable light domain

<400> SEQUENCE: 171

```
gacatccaga tgacccagtc tccatcctcc ctgtctgcat ctgtaggaga cagagtcacc    60
atcacttgcc aggcgagtca ggacattgct aagtatttaa attggtatca gcagaaacca   120
gggaaagccc ctaagctcct gatctatgct gcatccgctt tgcaaagtgg ggtcccatca   180
aggttcagtg gcagtggatc tgggacagat ttcactctca ccatcagcag tctgcaacct   240
gaagattttg caacttacta ctgtcagcag atgcatcctc gctcgccgaa aaccttcggc   300
caagggacca aggtggaaat caaa                                          324
```

<210> SEQ ID NO 172
<211> LENGTH: 108
<212> TYPE: PRT
<213> ORGANISM: Artificial Sequence
<220> FEATURE:
<223> OTHER INFORMATION: anti-CD47 Ka3H3 kappa variable light domain

<400> SEQUENCE: 172

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ala Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Ala Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ser Pro
                85                  90                  95

Lys Thr Phe Gly Gln Gly Thr Lys Val Glu Ile Lys
            100                 105
```

<210> SEQ ID NO 173
<211> LENGTH: 324
<212> TYPE: DNA
<213> ORGANISM: Artificial Sequence
<220> FEATURE:
<223> OTHER INFORMATION: anti-CD47 Ka3A3 kappa variable light domain

<400> SEQUENCE: 173

```
gacatccaga tgacccagtc tccatcctcc ctgtctgcat ctgtaggaga cagagtcacc    60
```

```
atcacttgcc gggcaagtca gagcattgct agttatttaa attggtatca gcagaaacca    120
gggaaagccc ctaagctcct gatctatgcg catccaggt tgcaaagtgg ggtcccatca     180
aggttcagtg gcagtggatc tgggacagat tcactctca ccatcagcag tctgcaacct     240
gaagattttg caacttacta ctgtcagcag atgcatcctc gcgcgccgaa aaccttcggc    300
caagggacca aggtggaaat caaa                                          324
```

<210> SEQ ID NO 174
<211> LENGTH: 108
<212> TYPE: PRT
<213> ORGANISM: Artificial Sequence
<220> FEATURE:
<223> OTHER INFORMATION: anti-CD47 Ka3A3 kappa variable light domain

<400> SEQUENCE: 174

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys
            100                 105
```

<210> SEQ ID NO 175
<211> LENGTH: 324
<212> TYPE: DNA
<213> ORGANISM: Artificial Sequence
<220> FEATURE:
<223> OTHER INFORMATION: anti-CD47 Ka3H8 kappa variable light domain

<400> SEQUENCE: 175

```
gacatccaga tgacccagtc tccatcctcc ctgtctgcat ctgtaggaga cagagtcacc    60
atcacttgcc gggcaagtca gagcattgcg agttatttaa attggtatca gcagaaacca    120
gggaaagccc ctaagctcct gatctatgcg gcatccaggt tgcaaagtgg ggtcccatca    180
aggttcagtg gcagtggatc tgggacagat tcactctca ccatcagcag tctgcaacct     240
gaagattttg caacttacta ctgtcagcag atgcatcctc gctcgccgaa aaccttcggc    300
caagggacca aggtggaaat caaa                                          324
```

<210> SEQ ID NO 176
<211> LENGTH: 108
<212> TYPE: PRT
<213> ORGANISM: Artificial Sequence
<220> FEATURE:
<223> OTHER INFORMATION: anti-CD47 Ka3H8 kappa variable light domain

<400> SEQUENCE: 176

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Ser Tyr
            20                  25                  30
```

```
Leu Asn Trp Tyr Gln Gln Lys Pro Gly Lys Ala Pro Lys Leu Leu Ile
            35                  40                  45

Tyr Ala Ala Ser Arg Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Met His Pro Arg Ser Pro
                 85                  90                  95

Lys Thr Phe Gly Gln Gly Thr Lys Val Glu Ile Lys
            100                 105
```

<210> SEQ ID NO 177
<211> LENGTH: 324
<212> TYPE: DNA
<213> ORGANISM: Artificial Sequence
<220> FEATURE:
<223> OTHER INFORMATION: anti-CD47 Ka3B2 kappa variable light domain

<400> SEQUENCE: 177

```
gacatccaga tgacccagtc tccatcctcc ctgtctgcat ctgtaggaga cagagtcacc      60
atcacttgcc gggcaagtca gaacattggt aagtatttaa attggtatca gcagaaacca     120
gggaaagccc ctaagctcct gatctatagt gcatccaggt tgcaaagtgg ggtcccatca     180
aggttcagtg gcagtggatc tgggacagat ttcactctca ccatcagcag tctgcaacct     240
gaagattttg caacttacta ctgtcagcag atgcatcctc gcgcgccgaa aaccttcggc     300
caagggacca aggtggaaat caaa                                            324
```

<210> SEQ ID NO 178
<211> LENGTH: 108
<212> TYPE: PRT
<213> ORGANISM: Artificial Sequence
<220> FEATURE:
<223> OTHER INFORMATION: anti-CD47 Ka3B2 kappa variable light domain

<400> SEQUENCE: 178

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asn Ile Gly Lys Tyr
                 20                  25                  30

Leu Asn Trp Tyr Gln Gln Lys Pro Gly Lys Ala Pro Lys Leu Leu Ile
            35                  40                  45

Tyr Ser Ala Ser Arg Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Met His Pro Arg Ala Pro
                 85                  90                  95

Lys Thr Phe Gly Gln Gly Thr Lys Val Glu Ile Lys
            100                 105
```

<210> SEQ ID NO 179
<211> LENGTH: 324
<212> TYPE: DNA
<213> ORGANISM: Artificial Sequence
<220> FEATURE:
<223> OTHER INFORMATION: anti-CD47 Ka3C5 kappa variable light domain

<400> SEQUENCE: 179

```
gacatccaga tgacccagtc tccatcctcc ctgtctgcat ctgtaggaga cagagtcacc      60
```

```
atcacttgcc gggcaagtca gagcattagt aggtatttaa attggtatca gcagaaacca    120
gggaaagccc ctaagctcct gatctattct gcatcctctt tgcaaagtgg ggtcccatca    180
aggttcagtg gcagtggatc tgggacagat ttcactctca ccatcagcag tctgcaacct    240
gaagattttg caacttacta ctgtcagcag atgcatcctc gcgccccgaa aaccttcggc    300
caagggacca aggtggaaat caaa                                           324
```

```
<210> SEQ ID NO 180
<211> LENGTH: 108
<212> TYPE: PRT
<213> ORGANISM: Artificial Sequence
<220> FEATURE:
<223> OTHER INFORMATION: anti-CD47 Ka3C5 kappa variable light domain

<400> SEQUENCE: 180

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Asn Trp Tyr Gln Gln Lys Pro Gly Lys Ala Pro Lys Leu Leu Ile
        35                  40                  45

Tyr Ser Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys
            100                 105
```

```
<210> SEQ ID NO 181
<211> LENGTH: 324
<212> TYPE: DNA
<213> ORGANISM: Artificial Sequence
<220> FEATURE:
<223> OTHER INFORMATION: anti-CD47 Ka3G2 kappa variable light domain

<400> SEQUENCE: 181
gacatccaga tgacccagtc tccatcctcc ctgtctgcat ctgtaggaga cagagtcacc     60
atcacttgcc gggcaagtca gagcattgat aagtatttaa attggtatca gcagaaacca    120
gggaaagccc ctaagctcct gatctatgct gcatccaggt tgcaaagtgg ggtcccatca    180
aggttcagtg gcagtggatc tgggacagat ttcactctca ccatcagcag tctgcaacct    240
gaagattttg caacttacta ctgtcagcag atgcatcctc gcgggccgaa aaccttcggc    300
caagggacca aggtggaaat caaa                                           324
```

```
<210> SEQ ID NO 182
<211> LENGTH: 108
<212> TYPE: PRT
<213> ORGANISM: Artificial Sequence
<220> FEATURE:
<223> OTHER INFORMATION: anti-CD47 Ka3G2 kappa variable light domain

<400> SEQUENCE: 182

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Lys Tyr
            20                  25                  30
```

```
Leu Asn Trp Tyr Gln Gln Lys Pro Gly Lys Ala Pro Lys Leu Leu Ile
            35                  40                  45

Tyr Ala Ala Ser Arg Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Met His Pro Arg Gly Pro
                 85                  90                  95

Lys Thr Phe Gly Gln Gly Thr Lys Val Glu Ile Lys
            100                 105
```

<210> SEQ ID NO 183
<211> LENGTH: 324
<212> TYPE: DNA
<213> ORGANISM: Artificial Sequence
<220> FEATURE:
<223> OTHER INFORMATION: anti-CD47 Ka3D3 kappa variable light domain

<400> SEQUENCE: 183

```
gacatccaga tgacccagtc tccatcctcc ctgtctgcat ctgtaggaga cagagtcacc    60
atcacttgcc gggcaagtca gagcattggt aagtattaa attggtatca gcagaaacca   120
gggaaagccc ctaagctcct gatctatgct gcatccaggt tgcaaagtgg ggtcccatca   180
aggttcagtg gcagtggatc tgggacagat ttcactctca ccatcagcag tctgcaacct   240
gaagattttg caacttacta ctgtcagcag atgcatcctc gcgcgccgaa aaccttcggc   300
caagggacca aggtggaaat caaa                                          324
```

<210> SEQ ID NO 184
<211> LENGTH: 108
<212> TYPE: PRT
<213> ORGANISM: Artificial Sequence
<220> FEATURE:
<223> OTHER INFORMATION: anti-CD47 Ka3D3 kappa variable light domain

<400> SEQUENCE: 184

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Gly Lys Tyr
             20                  25                  30

Leu Asn Trp Tyr Gln Gln Lys Pro Gly Lys Ala Pro Lys Leu Leu Ile
            35                  40                  45

Tyr Ala Ala Ser Arg Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Met His Pro Arg Ala Pro
                 85                  90                  95

Lys Thr Phe Gly Gln Gly Thr Lys Val Glu Ile Lys
            100                 105
```

<210> SEQ ID NO 185
<211> LENGTH: 333
<212> TYPE: DNA
<213> ORGANISM: Artificial Sequence
<220> FEATURE:
<223> OTHER INFORMATION: anti-CD47 Kc4 kappa variable light domain

<400> SEQUENCE: 185

```
cagtctgccc tgactcagcc tgcctccgtg tctgggtctc ctggacagtc gatcaccatc    60
tcctgcactg gaaccagcag tgacgttggt ggttataact atgtctcctg gtaccaacag   120
cacccaggca aagcccccaa actcatgatt tatgaggtca gtaatcggcc ctcaggggtt   180
tctaatcgct tctctggctc caagtctggc aacacggcct ccctgaccat ctctgggctc   240
caggctgagg acgaggctga ttattactgc agctcatatg attggtggtt ccgccccaag   300
gtgttcggcg agggaccaa gctgaccgtc cta                                 333
```

```
<210> SEQ ID NO 186
<211> LENGTH: 111
<212> TYPE: PRT
<213> ORGANISM: Artificial Sequence
<220> FEATURE:
<223> OTHER INFORMATION: anti-CD47 Kc4 kappa variable light domain

<400> SEQUENCE: 186
```

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu
            100                 105                 110

```
<210> SEQ ID NO 187
<211> LENGTH: 333
<212> TYPE: DNA
<213> ORGANISM: Artificial Sequence
<220> FEATURE:
<223> OTHER INFORMATION: anti-CD47 Kc4G11 kappa variable light domain

<400> SEQUENCE: 187
```

```
cagtctgccc tgactcagcc tgcctccgtg tctgggtctc ctggacagtc gatcaccatc    60
tcctgcactg gaaccagcag tgacgttggg aaggcgaact atgtctcctg gtaccaacag   120
cacccaggca aagcccccaa actcatgatt tataaggata gtgatcggcc ctcaggggtt   180
tctaatcgct tctctggctc caagtctggc aacacggcct ccctgaccat ctctgggctc   240
caggctgagg acgaggctga ttattactgc agctcatatg attggtggtt ccgccccaag   300
gtgttcggcg agggaccaa gctgaccgtc cta                                 333
```

```
<210> SEQ ID NO 188
<211> LENGTH: 111
<212> TYPE: PRT
<213> ORGANISM: Artificial Sequence
<220> FEATURE:
<223> OTHER INFORMATION: anti-CD47 Kc4G11 kappa variable light domain

<400> SEQUENCE: 188
```

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Lys Ala
            20                  25                  30

```
            20                  25                  30

Asn Tyr Val Ser Trp Tyr Gln Gln His Pro Gly Lys Ala Pro Lys Leu
            35                  40                  45

Met Ile Tyr Lys Asp Ser Asp Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Asp Trp Trp
                 85                  90                  95

Phe Arg Pro Lys Val Phe Gly Gly Gly Thr Lys Leu Thr Val Leu
             100                 105                 110
```

```
<210> SEQ ID NO 189
<211> LENGTH: 333
<212> TYPE: DNA
<213> ORGANISM: Artificial Sequence
<220> FEATURE:
<223> OTHER INFORMATION: anti-CD47 Kc4C11 kappa variable light domain

<400> SEQUENCE: 189
cagtctgccc tgactcagcc tgcctccgtg tctgggtctc ctggacagtc gatcaccatc      60
tcctgcactg gaaccagcag tgacgttagg gggaataact atgtctcctg gtaccaacag     120
cacccaggca agcccccaa actcatgatt tatgagaata gtaagcggcc ctcaggggtt      180
tctaatcgct tctctggctc caagtctggc aacacggcct ccctgaccat ctctgggctc     240
caggctgagg acgaggctga ttattactgc agctcatatg attggtggtt ccgccccaag     300
gtgttcggcg gagggaccaa gctgaccgtc cta                                  333
```

```
<210> SEQ ID NO 190
<211> LENGTH: 111
<212> TYPE: PRT
<213> ORGANISM: Artificial Sequence
<220> FEATURE:
<223> OTHER INFORMATION: anti-CD47 Kc4C11 kappa variable light domain

<400> SEQUENCE: 190

Gln Ser Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Arg Gly Asn
             20                  25                  30

Asn Tyr Val Ser Trp Tyr Gln Gln His Pro Gly Lys Ala Pro Lys Leu
            35                  40                  45

Met Ile Tyr Glu Asn Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Asp Trp Trp
                 85                  90                  95

Phe Arg Pro Lys Val Phe Gly Gly Gly Thr Lys Leu Thr Val Leu
             100                 105                 110
```

```
<210> SEQ ID NO 191
<211> LENGTH: 333
<212> TYPE: DNA
<213> ORGANISM: Artificial Sequence
<220> FEATURE:
<223> OTHER INFORMATION: anti-CD47 Kc4A1 kappa variable light domain

<400> SEQUENCE: 191
```

```
cagtctgccc tgactcagcc tgcctccgtg tctgggtctc ctggacagtc gatcaccatc    60
tcctgcactg gaaccagcag tgacgttagt gcgaggaact atgtctcctg gtaccaacag   120
cacccaggca agccccccaa actcatgatt tatgagagta gtaagcggcc ctcaggggtt   180
tctaatcgct tctctggctc caagtctggc aacacggcct ccctgaccat ctctgggctc   240
caggctgagg acgaggctga ttattactgc agctcatatg attggtggtt ccgccccaag   300
gtgttcggcg agggaccaa gctgaccgtc cta                                 333
```

<210> SEQ ID NO 192
<211> LENGTH: 111
<212> TYPE: PRT
<213> ORGANISM: Artificial Sequence
<220> FEATURE:
<223> OTHER INFORMATION: anti-CD47 Kc4A1 kappa variable light domain

<400> SEQUENCE: 192

```
Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Ser Ala Arg
            20                  25                  30

Asn Tyr Val Ser Trp Tyr Gln Gln His Pro Gly Lys Ala Pro Lys Leu
        35                  40                  45

Met Ile Tyr Glu Ser Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu
            100                 105                 110
```

<210> SEQ ID NO 193
<211> LENGTH: 333
<212> TYPE: DNA
<213> ORGANISM: Artificial Sequence
<220> FEATURE:
<223> OTHER INFORMATION: anti-CD47 Kc4A4 kappa variable light domain

<400> SEQUENCE: 193

```
cagtctgccc tgactcagcc tgcctccgtg tctgggtctc ctggacagtc gatcaccatc    60
tcctgcacta gaaccagcag tgacgttaat aatactaact atgtctcctg gtaccaacag   120
cacccaggca agccccccaa actcatgatt tataagacta gtggtcggcc ctcaggggtt   180
tctaatcgct tctctggctc caagtctggc aacacggcct ccctgaccat ctctgggctc   240
caggctgagg acgaggctga ttattactgc agctcatatg attggtggtt ccgccccaag   300
gtgttcggcg agggaccaa gctgaccgtc cta                                 333
```

<210> SEQ ID NO 194
<211> LENGTH: 111
<212> TYPE: PRT
<213> ORGANISM: Artificial Sequence
<220> FEATURE:
<223> OTHER INFORMATION: anti-CD47 Kc4A4 kappa variable light domain

<400> SEQUENCE: 194

```
Gln Ser Ala Leu Thr Gln Pro Ala Ser Val Ser Gly Ser Pro Gly Gln
 1               5                  10                  15
```

```
Ser Ile Thr Ile Ser Cys Thr Arg Thr Ser Ser Asp Val Asn Asn Thr
                20                  25                  30

Asn Tyr Val Ser Trp Tyr Gln Gln His Pro Gly Lys Ala Pro Lys Leu
            35                  40                  45

Met Ile Tyr Lys Thr Ser Gly Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu
                100                 105                 110
```

<210> SEQ ID NO 195
<211> LENGTH: 333
<212> TYPE: DNA
<213> ORGANISM: Artificial Sequence
<220> FEATURE:
<223> OTHER INFORMATION: anti-CD47 Kc4E10 kappa variable light domain

<400> SEQUENCE: 195

```
cagtctgccc tgactcagcc tgcctccgtg tctgggtctc ctggacagtc gatcaccatc      60
tcctgcactg gaaccagcag tgacgttaat tctgctaact atgtctcctg gtaccaacag     120
cacccaggca aagcccccaa actcatgatt tataagagta gtagtcggcc ctcaggggtt     180
tctaatcgct tctctggctc caagtctggc aacacggcct ccctgaccat ctctgggctc     240
caggctgagg acgaggctga ttattactgc agctcatatg attggtggtt ccgccccaag     300
gtgttcggcg gagggaccaa gctgaccgtc cta                                  333
```

<210> SEQ ID NO 196
<211> LENGTH: 111
<212> TYPE: PRT
<213> ORGANISM: Artificial Sequence
<220> FEATURE:
<223> OTHER INFORMATION: anti-CD47 Kc4E10 kappa variable light domain

<400> SEQUENCE: 196

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Asn Ser Ala
                20                  25                  30

Asn Tyr Val Ser Trp Tyr Gln Gln His Pro Gly Lys Ala Pro Lys Leu
            35                  40                  45

Met Ile Tyr Lys Ser Ser Ser Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu
                100                 105                 110
```

<210> SEQ ID NO 197
<211> LENGTH: 333
<212> TYPE: DNA
<213> ORGANISM: Artificial Sequence
<220> FEATURE:
<223> OTHER INFORMATION: anti-CD47 Kc4G9 kappa variable light domain

```
<400> SEQUENCE: 197
cagtctgccc tgactcagcc tgcctccgtg tccgggtctc ctggacagtc gatcaccatc    60
tcctgcactg gaaccagcag tgacgttgag aggaagaact atgtctcctg gtaccaacag   120
cacccaggca agccccaa actcatgatt tataagaata gtactcggcc ctcagggggtt    180 tctaatcgct ctctggctc caagtctggc aacacggcct ccctgaccat ctctgggctc    240
caggctgagg acgaggctga ttattactgc agctcatatg attggtggtt ccgccccaag   300
gtgttcggcg agggaccaa gctgaccgtc cta                                 333

<210> SEQ ID NO 198
<211> LENGTH: 111
<212> TYPE: PRT
<213> ORGANISM: Artificial Sequence
<220> FEATURE:
<223> OTHER INFORMATION: anti-CD47 Kc4G9 kappa variable light domain

<400> SEQUENCE: 198

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Glu Arg Lys
            20                  25                  30

Asn Tyr Val Ser Trp Tyr Gln Gln His Pro Gly Lys Ala Pro Lys Leu
        35                  40                  45

Met Ile Tyr Lys Asn Ser Thr Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu
            100                 105                 110

<210> SEQ ID NO 199
<211> LENGTH: 333
<212> TYPE: DNA
<213> ORGANISM: Artificial Sequence
<220> FEATURE:
<223> OTHER INFORMATION: anti-CD47 Kc4C3 kappa variable light domain

<400> SEQUENCE: 199
cagtctgccc tgactcagcc tgcctccgtg tctgggtctc ctggacagtc gatcaccatc    60
tcctgcactg gaaccagcag tgacgttagg gcggctaact atgtctcctg gtaccaacag   120
cacccaggca agccccaa actcatgatt tataagaata gtactcggcc ctcaggggtt     180
tctaatcgct ctctggctc caagtctggc aacacggcct ccctgaccat ctctgggctc    240
caggctgagg acgaggctga ttattactgc agctcatatg attggtggtt ccgccccaag   300
gtgttcggcg agggaccaa gctgaccgtc cta                                 333

<210> SEQ ID NO 200
<211> LENGTH: 111
<212> TYPE: PRT
<213> ORGANISM: Artificial Sequence
<220> FEATURE:
<223> OTHER INFORMATION: anti-CD47 Kc4C3 kappa variable light domain

<400> SEQUENCE: 200

Gln Ser Ala Leu Thr Gln Pro Ala Ser Val Ser Gly Ser Pro Gly Gln
1               5                   10                  15
```

```
Ser Ile Thr Ile Ser Cys Thr Gly Thr Ser Ser Asp Val Arg Ala Ala
            20                  25                  30

Asn Tyr Val Ser Trp Tyr Gln Gln His Pro Gly Lys Ala Pro Lys Leu
            35                  40                  45

Met Ile Tyr Lys Asn Ser Thr Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu
                100                 105                 110

<210> SEQ ID NO 201
<211> LENGTH: 333
<212> TYPE: DNA
<213> ORGANISM: Artificial Sequence
<220> FEATURE:
<223> OTHER INFORMATION: anti-CD47 Kc4F4 kappa variable light domain

<400> SEQUENCE: 201
cagtctgccc tgactcagcc tgcctccgtg tctgggtctc ctggacagtc gatcaccatc      60
tcctgcactg gaaccagcag tgacgttagg agggctaact atgtctcctg gtaccaacag     120
cacccaggca aagcccccaa actcatgatt tatcaggata gtagtcggcc ctcaggggtt     180
tctaatcgct tctctggctc caagtctggc aacacggcct ccctgaccat ctctgggctc     240
caggctgagg acgaggctga ttattactgc agctcatatg attggtggtt ccgccccaag     300
gtgttcggcg gagggaccaa gctgaccgtc cta                                   333

<210> SEQ ID NO 202
<211> LENGTH: 111
<212> TYPE: PRT
<213> ORGANISM: Artificial Sequence
<220> FEATURE:
<223> OTHER INFORMATION: anti-CD47 Kc4F4 kappa variable light domain

<400> SEQUENCE: 202

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Arg Arg Ala
            20                  25                  30

Asn Tyr Val Ser Trp Tyr Gln Gln His Pro Gly Lys Ala Pro Lys Leu
            35                  40                  45

Met Ile Tyr Gln Asp Ser Ser Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu
                100                 105                 110

<210> SEQ ID NO 203
<211> LENGTH: 333
<212> TYPE: DNA
<213> ORGANISM: Artificial Sequence
<220> FEATURE:
<223> OTHER INFORMATION: anti-CD47 Kc4B1 kappa variable light domain
```

<400> SEQUENCE: 203

```
cagtctgccc tgactcagcc tgcctccgtg tctgggtctc ctggacagtc gatcaccatc    60
tcctgcactg gaaccagcag tgacgttagg gctaataact atgtctcctg gtaccaacag   120
cacccaggca agcccccaa actcatgatt tatgagagta gtgcgcggcc ctcagggggtt    180 tctaatcgct ctctctggctc caagtctggc aacacggcct ccctgaccat ctctgggctc   240
caggctgagg acgaggctga ttattactgc agctcatatg attggtggtt ccgccccaag   300
gtgttcggcg agggaccaa gctgaccgtc cta                                  333
```

<210> SEQ ID NO 204
<211> LENGTH: 111
<212> TYPE: PRT
<213> ORGANISM: Artificial Sequence
<220> FEATURE:
<223> OTHER INFORMATION: anti-CD47 Kc4B1 kappa variable light domain

<400> SEQUENCE: 204

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Arg Ala Asn
            20                  25                  30

Asn Tyr Val Ser Trp Tyr Gln Gln His Pro Gly Lys Ala Pro Lys Leu
        35                  40                  45

Met Ile Tyr Glu Ser Ser Ala Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Trp Trp
                85                  90                  95

Phe Arg Pro Lys Val Phe Gly Gly Gly Thr Lys Leu Thr Val Leu
                100                 105                 110
```

<210> SEQ ID NO 205
<211> LENGTH: 333
<212> TYPE: DNA
<213> ORGANISM: Artificial Sequence
<220> FEATURE:
<223> OTHER INFORMATION: anti-CD47 Kc4E2 kappa variable light domain

<400> SEQUENCE: 205

```
cagtctgccc tgactcagcc tgcctccgtg tctgggtctc ctggacagtc gatcaccatc    60
tcctgcactg gaaccagcag tgacgtttat tataataagt atgtctcctg gtaccaacag   120
cacccaggca agcccccaa actcatgatt tatgagagta gtaagcggcc ctcagggggtt    180 tctaatcgct ctctctggctc caagtctggc aacacggcct ccctgaccat ctctgggctc   240
caggctgagg acgaggctga ttattactgc agctcatatg attggtggtt ccgccccaag   300
gtgttcggcg agggaccaa gctgaccgtc cta                                  333
```

<210> SEQ ID NO 206
<211> LENGTH: 111
<212> TYPE: PRT
<213> ORGANISM: Artificial Sequence
<220> FEATURE:
<223> OTHER INFORMATION: anti-CD47 Kc4E2 kappa variable light domain

<400> SEQUENCE: 206

```
Gln Ser Ala Leu Thr Gln Pro Ala Ser Val Ser Gly Ser Pro Gly Gln
```

```
              1               5                  10                 15
Ser Ile Thr Ile Ser Cys Thr Gly Thr Ser Ser Asp Val Tyr Tyr Asn
                      20                 25                 30

Lys Tyr Val Ser Trp Tyr Gln Gln His Pro Gly Lys Ala Pro Lys Leu
                35                 40                 45

Met Ile Tyr Glu Ser Ser Lys Arg Pro Ser Gly Val Ser Asn Arg Phe
            50                 55                 60

Ser Gly Ser Lys Ser Gly Asn Thr Ala Ser Leu Thr Ile Ser Gly Leu
65                 70                 75                 80

Gln Ala Glu Asp Glu Ala Asp Tyr Tyr Cys Ser Ser Tyr Asp Trp Trp
                     85                 90                 95

Phe Arg Pro Lys Val Phe Gly Gly Gly Thr Lys Leu Thr Val Leu
                100                 105                110
```

<210> SEQ ID NO 207
<211> LENGTH: 336
<212> TYPE: DNA
<213> ORGANISM: Artificial Sequence
<220> FEATURE:
<223> OTHER INFORMATION: anti-CD19 C2 lambda variable light domain

<400> SEQUENCE: 207

```
aattttatgc tgactcagcc ccactctgtg tcggagtctc cggggaagac ggtaaccatc    60
tcctgcaccc gcagcagtgg ctctatcgaa gataagtatg tgcagtggta ccagcagcgc   120
ccgggcagtt cccccaccat tgtgatctat tatgataacg aaagaccctc tggggtccct   180
gatcggttct ctggctccat cgacagctcc tccaactctg cctccctcac catctctgga   240
ctgaagactg aggacgaggc tgactactac tgtcagacct acgaccagag cctgtatggt   300
tgggtgttcg gcggagggac caagctgacc gtccta                             336
```

<210> SEQ ID NO 208
<211> LENGTH: 112
<212> TYPE: PRT
<213> ORGANISM: Artificial Sequence
<220> FEATURE:
<223> OTHER INFORMATION: anti-CD19 C2 lambda variable light domain

<400> SEQUENCE: 208

```
Asn Phe Met Leu Thr Gln Pro His Ser Val Ser Glu Ser Pro Gly Lys
1               5                  10                 15

Thr Val Thr Ile Ser Cys Thr Arg Ser Ser Gly Ser Ile Glu Asp Lys
                20                 25                 30

Tyr Val Gln Trp Tyr Gln Gln Arg Pro Gly Ser Ser Pro Thr Ile Val
                35                 40                 45

Ile Tyr Tyr Asp Asn Glu Arg Pro Ser Gly Val Pro Asp Arg Phe Ser
            50                 55                 60

Gly Ser Ile Asp Ser Ser Ser Asn Ser Ala Ser Leu Thr Ile Ser Gly
65                 70                 75                 80

Leu Lys Thr Glu Asp Glu Ala Asp Tyr Tyr Cys Gln Thr Tyr Asp Gln
                     85                 90                 95

Ser Leu Tyr Gly Trp Val Phe Gly Gly Gly Thr Lys Leu Thr Val Leu
                100                 105                110
```

<210> SEQ ID NO 209
<211> LENGTH: 336
<212> TYPE: DNA
<213> ORGANISM: Artificial Sequence
<220> FEATURE:

<223> OTHER INFORMATION: anti-CD19 A6 lambda variable light domain

<400> SEQUENCE: 209

```
aattttatgc tgactcagcc ccactctgtg tcggagtctc cggggaagac ggtaaccatc    60
tcctgcaccc gcagcagtgg ctctatcggt gataagtatg tgcagtggta ccagcagcgc   120
ccgggcagtt cccccaccat tgtgatctat tatgataacg aaagaccctc tggggtccct   180
gatcggttct ctggctccat cgacagctcc tccaactctg cctccctcac catctctgga   240
ctgaagactg aggacgaggc tgactactac tgtcagacgt acgacgagag cctgtatggt   300
tgggtgttcg gcggagggac caagctgacc gtccta                             336
```

<210> SEQ ID NO 210
<211> LENGTH: 112
<212> TYPE: PRT
<213> ORGANISM: Artificial Sequence
<220> FEATURE:
<223> OTHER INFORMATION: anti-CD19 A6 lambda variable light domain

<400> SEQUENCE: 210

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Gly Asp Lys
            20                  25                  30

Tyr Val Gln Trp Tyr Gln Gln Arg Pro Gly Ser Ser Pro Thr Ile Val
        35                  40                  45

Ile Tyr Tyr Asp Asn Glu Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Thr Tyr Asp Glu
                85                  90                  95

Ser Leu Tyr Gly Trp Val Phe Gly Gly Gly Thr Lys Leu Thr Val Leu
            100                 105                 110
```

<210> SEQ ID NO 211
<211> LENGTH: 336
<212> TYPE: DNA
<213> ORGANISM: Artificial Sequence
<220> FEATURE:
<223> OTHER INFORMATION: anti-CD19 C6 lambda variable light domain

<400> SEQUENCE: 211

```
aattttatgc tgactcagcc ccactctgtg tcggagtctc cggggaagac ggtaaccatc    60
tcctgcaccc gcagcagtgg ctctatcaat gataagtatg tgcagtggta ccagcagcgc   120
ccgggcagtt cccccaccat tgtgatctat tttgataacg aaagaccctc tggggtccct   180
gatcggttct ctggctccat cgacagctcc tccaactctg cctccctcac catctctgga   240
ctgaagactg aggacgaggc tgactactac tgtcagacct acgacaccag cctgtatggt   300
tgggtgttcg gcggagggac caagctgacc gtccta                             336
```

<210> SEQ ID NO 212
<211> LENGTH: 112
<212> TYPE: PRT
<213> ORGANISM: Artificial Sequence
<220> FEATURE:
<223> OTHER INFORMATION: anti-CD19 C6 lambda variable light domain

<400> SEQUENCE: 212

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Asn Asp Lys
            20                  25                  30

Tyr Val Gln Trp Tyr Gln Gln Arg Pro Gly Ser Ser Pro Thr Ile Val
        35                  40                  45

Ile Tyr Phe Asp Asn Glu Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Thr Tyr Asp Thr
                85                  90                  95

Ser Leu Tyr Gly Trp Val Phe Gly Gly Gly Thr Lys Leu Thr Val Leu
            100                 105                 110

<210> SEQ ID NO 213
<211> LENGTH: 336
<212> TYPE: DNA
<213> ORGANISM: Artificial Sequence
<220> FEATURE:
<223> OTHER INFORMATION: anti-CD19 C9 lambda variable light domain

<400> SEQUENCE: 213
aattttatgc tgactcagcc ccactctgtg tcggagtctc cggggaagac ggtaaccatc     60
tcctgcaccc gcagcagtgg ctctatcgct gataagtatg tgcagtggta ccagcagcgc    120
ccgggcagtt cccccaccat tgtgatctat tatgataacg aaagaccctc aggggtccct    180
gatcggttct ctggctccat cgacagctcc tccaactctg cctccctcac catctctgga    240
ctgaagactg aggacgaggc tgactactac tgtcagacct acgacgagag cctgtatggt    300
tgggtgttcg gcggagggac caagctgacc gtccta                             336

<210> SEQ ID NO 214
<211> LENGTH: 112
<212> TYPE: PRT
<213> ORGANISM: Artificial Sequence
<220> FEATURE:
<223> OTHER INFORMATION: anti-CD19 C9 lambda variable light domain

<400> SEQUENCE: 214

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Asp Lys
            20                  25                  30

Tyr Val Gln Trp Tyr Gln Gln Arg Pro Gly Ser Ser Pro Thr Ile Val
        35                  40                  45

Ile Tyr Tyr Asp Asn Glu Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Thr Tyr Asp Glu
                85                  90                  95

Ser Leu Tyr Gly Trp Val Phe Gly Gly Gly Thr Lys Leu Thr Val Leu
            100                 105                 110

<210> SEQ ID NO 215
<211> LENGTH: 336
<212> TYPE: DNA
<213> ORGANISM: Artificial Sequence
<220> FEATURE:
<223> OTHER INFORMATION: anti-CD19 B11 lambda variable light domain

<400> SEQUENCE: 215

```
aattttatgc tgactcagcc ccactctgtg tcggagtctc cggggaagac ggtaaccatc      60
tcctgcaccc gcagcagtgg ctctatcgaa gataagtatg tgcagtggta ccagcagcgc     120
ccgggcagtt cccccaccat tgtgatctat tatgataacg aaagaccctc tggggtccct     180
gatcggttct ctggctccat cgacagctcc tccaactctg cctccctcac catctctgga     240
ctgaagactg aggacgaggc tgactactac tgtcagacct acgacaacag cctgtatggt     300
tgggtgttcg gcggagggac caagctgacc gtccta                               336
```

<210> SEQ ID NO 216
<211> LENGTH: 112
<212> TYPE: PRT
<213> ORGANISM: Artificial Sequence
<220> FEATURE:
<223> OTHER INFORMATION: anti-CD19 B11 lambda variable light domain

<400> SEQUENCE: 216

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Glu Asp Lys
            20                  25                  30

Tyr Val Gln Trp Tyr Gln Gln Arg Pro Gly Ser Ser Pro Thr Ile Val
        35                  40                  45

Ile Tyr Tyr Asp Asn Glu Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Thr Tyr Asp Asn
                85                  90                  95

Ser Leu Tyr Gly Trp Val Phe Gly Gly Gly Thr Lys Leu Thr Val Leu
            100                 105                 110
```

<210> SEQ ID NO 217
<211> LENGTH: 336
<212> TYPE: DNA
<213> ORGANISM: Artificial Sequence
<220> FEATURE:
<223> OTHER INFORMATION: anti-CD19 D11 lambda variable light domain

<400> SEQUENCE: 217

```
aattttatgc tgactcagcc ccactctgtg tcggagtctc cggggaagac ggtaaccatc      60
tcctgcaccc gcagcagtgg cagcatcgat gataagtttg tgcagtggta ccagcagcgc     120
ccgggcagtt cccccaccac tgtgatctat tatgataaca ttagaccctc tggggtccct     180
gatcggttct ctggctccat cgacagctcc tccaactctg cctccctcac catctctgga     240
ctgaagactg aggacgaggc tgactactac tgtcagtcct atgacgcgag cctgtatggt     300
tgggtgttcg gcggagggac caagctgacc gtccta                               336
```

<210> SEQ ID NO 218
<211> LENGTH: 112
<212> TYPE: PRT
<213> ORGANISM: Artificial Sequence
<220> FEATURE:
<223> OTHER INFORMATION: anti-CD19 D11 lambda variable light domain

<400> SEQUENCE: 218

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Asp Asp Lys
                20                  25                  30

Phe Val Gln Trp Tyr Gln Gln Arg Pro Gly Ser Ser Pro Thr Thr Val
            35                  40                  45

Ile Tyr Tyr Asp Asn Ile Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ala
                85                  90                  95

Ser Leu Tyr Gly Trp Val Phe Gly Gly Gly Thr Lys Leu Thr Val Leu
                100                 105                 110

<210> SEQ ID NO 219
<211> LENGTH: 336
<212> TYPE: DNA
<213> ORGANISM: Artificial Sequence
<220> FEATURE:
<223> OTHER INFORMATION: anti-CD19 B7 lambda variable light domain

<400> SEQUENCE: 219
aattttatgc tgactcagcc ccactctgtg tcggagtctc cggggaagac ggtaaccatc     60
tcctgcaccc gcagcagtgg ctctatcgcg gataagtatg tgcagtggta ccagcagcgc    120
ccgggcagtt cccccaccac tgtgatctat gaggataacc aaagaccctc tggggtccct    180
gatcggttct ctggctccat cgacagctcc tccaactctg cctccctcac catctctgga    240
ctgaagactg aggacgaggc tgactactac tgtcagtcct atgacagcag cctgtatggt    300
tgggtgttcg gcggagggac caagctgacc gtccta                              336

<210> SEQ ID NO 220
<211> LENGTH: 112
<212> TYPE: PRT
<213> ORGANISM: Artificial Sequence
<220> FEATURE:
<223> OTHER INFORMATION: anti-CD19 B7 lambda variable light domain

<400> SEQUENCE: 220

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Asp Lys
                20                  25                  30

Tyr Val Gln Trp Tyr Gln Gln Arg Pro Gly Ser Ser Pro Thr Thr Val
            35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Leu Tyr Gly Trp Val Phe Gly Gly Gly Thr Lys Leu Thr Val Leu
                100                 105                 110

<210> SEQ ID NO 221
<211> LENGTH: 330
<212> TYPE: DNA

<213> ORGANISM: Artificial Sequence
<220> FEATURE:
<223> OTHER INFORMATION: dummy variable light domain 1

<400> SEQUENCE: 221

```
cagtctgtgt tgacgcagcc gccctcagtg tctgcggccc caggacagaa ggtcaccatc      60
tcctgctctg gaagcagctc caatattgag actggttctg tatcctggta ccagcagctc     120
ccaggaacag cccccaaact cctcatttat gacaataata agcgaccctc agggattcct     180
gaccgattct ctggctccaa gtctggcacg tcagccaccc tgggcatcac cggactccag     240
actggggacg aggccgatta ttactgcgga acatgggatg acagcctgcc tggatgggtg     300
ttcggcggag ggaccaagct gaccgtccta                                       330
```

<210> SEQ ID NO 222
<211> LENGTH: 110
<212> TYPE: PRT
<213> ORGANISM: Artificial Sequence
<220> FEATURE:
<223> OTHER INFORMATION: dummy variable light domain 1

<400> SEQUENCE: 222

```
Gln Ser Val Leu Thr Gln Pro Pro Ser Val Ser Ala Ala Pro Gly Gln
1               5                   10                  15
Lys Val Thr Ile Ser Cys Ser Gly Ser Ser Asn Ile Glu Thr Gly
            20                  25                  30
Ser Val Ser Trp Tyr Gln Gln Leu Pro Gly Thr Ala Pro Lys Leu Leu
        35                  40                  45
Ile Tyr Asp Asn Asn Lys Arg Pro Ser Gly Ile Pro Asp Arg Phe Ser
    50                  55                  60
Gly Ser Lys Ser Gly Thr Ser Ala Thr Leu Gly Ile Thr Gly Leu Gln
65                  70                  75                  80
Thr Gly Asp Glu Ala Asp Tyr Tyr Cys Gly Thr Trp Asp Asp Ser Leu
                85                  90                  95
Pro Gly Trp Val Phe Gly Gly Gly Thr Lys Leu Thr Val Leu
            100                 105                 110
```

<210> SEQ ID NO 223
<211> LENGTH: 333
<212> TYPE: DNA
<213> ORGANISM: Artificial Sequence
<220> FEATURE:
<223> OTHER INFORMATION: dummy variable light domain 2

<400> SEQUENCE: 223

```
gaaatagtga tgacgcagtc tccagccacc ctgtctgtgt ctccagggga aagagccacc      60
ctctcctgca gggccagtca gacggttaag aataatttag cctggtacca gcagaaacct     120
ggccaggctc ccaggctcct catctatggt gcatccacca gggccactgg tatcccagcc     180
aggttcagtg gcagtgggtc tgggacagag ttcactctca ccatcagcag cctgcagtct     240
gaagattttg cagtttatta ctgtcagcag tataacaact ggttgcccat caacccctat     300
accttcggcc aagggaccaa ggtggaaatc aaa                                   333
```

<210> SEQ ID NO 224
<211> LENGTH: 111
<212> TYPE: PRT
<213> ORGANISM: Artificial Sequence
<220> FEATURE:
<223> OTHER INFORMATION: dummy variable light domain 2

<400> SEQUENCE: 224

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Thr Val Lys Asn Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Leu Pro
                85                  90                  95

Ile Asn Pro Tyr Thr Phe Gly Gly Gly Thr Lys Val Glu Ile Lys
            100                 105                 110

<210> SEQ ID NO 225
<211> LENGTH: 8
<212> TYPE: PRT
<213> ORGANISM: Artificial Sequence
<220> FEATURE:
<223> OTHER INFORMATION: anti-CD47 heavy chain CDHR1

<400> SEQUENCE: 225

Gly Phe Thr Phe Ser Ser Tyr Ala
1               5

<210> SEQ ID NO 226
<211> LENGTH: 8
<212> TYPE: PRT
<213> ORGANISM: Artificial Sequence
<220> FEATURE:
<223> OTHER INFORMATION: anti-CD47 heavy chain CDHR2

<400> SEQUENCE: 226

Ile Ser Gly Ser Gly Gly Ser Thr
1               5

<210> SEQ ID NO 227
<211> LENGTH: 9
<212> TYPE: PRT
<213> ORGANISM: Artificial Sequence
<220> FEATURE:
<223> OTHER INFORMATION: anti-CD47 heavy chain CDHR3

<400> SEQUENCE: 227

Ala Lys Ser Tyr Gly Ala Phe Asp Tyr
1               5

<210> SEQ ID NO 228
<211> LENGTH: 6
<212> TYPE: PRT
<213> ORGANISM: Artificial Sequence
<220> FEATURE:
<223> OTHER INFORMATION: anti-CD47 kappa light chain CDRL1

<400> SEQUENCE: 228

Gln Asp Ile Asn Lys Tyr
1               5

<210> SEQ ID NO 229
<211> LENGTH: 6
<212> TYPE: PRT

```
<213> ORGANISM: Artificial Sequence
<220> FEATURE:
<223> OTHER INFORMATION: anti-CD47 kappa light chain CDRL1

<400> SEQUENCE: 229

Gln Asp Ile Asn Arg Tyr
1               5

<210> SEQ ID NO 230
<211> LENGTH: 6
<212> TYPE: PRT
<213> ORGANISM: Artificial Sequence
<220> FEATURE:
<223> OTHER INFORMATION: anti-CD47 kappa light chain CDRL1

<400> SEQUENCE: 230

Gln Asn Ile Gly Lys Tyr
1               5

<210> SEQ ID NO 231
<211> LENGTH: 6
<212> TYPE: PRT
<213> ORGANISM: Artificial Sequence
<220> FEATURE:
<223> OTHER INFORMATION: anti-CD47 kappa light chain CDRL1

<400> SEQUENCE: 231

Gln Ser Ile Ala Arg Tyr
1               5

<210> SEQ ID NO 232
<211> LENGTH: 6
<212> TYPE: PRT
<213> ORGANISM: Artificial Sequence
<220> FEATURE:
<223> OTHER INFORMATION: anti-CD47 kappa light chain CDRL1

<400> SEQUENCE: 232

Gln Ser Ile Ala Ser Tyr
1               5

<210> SEQ ID NO 233
<211> LENGTH: 6
<212> TYPE: PRT
<213> ORGANISM: Artificial Sequence
<220> FEATURE:
<223> OTHER INFORMATION: anti-CD47 kappa light chain CDRL1

<400> SEQUENCE: 233

Gln Ser Ile Asp Lys Tyr
1               5

<210> SEQ ID NO 234
<211> LENGTH: 6
<212> TYPE: PRT
<213> ORGANISM: Artificial Sequence
<220> FEATURE:
<223> OTHER INFORMATION: anti-CD47 kappa light chain CDRL1

<400> SEQUENCE: 234

Gln Ser Ile Asp Arg Tyr
1               5

<210> SEQ ID NO 235
<211> LENGTH: 6
<212> TYPE: PRT
<213> ORGANISM: Artificial Sequence
```

```
<220> FEATURE:
<223> OTHER INFORMATION: anti-CD47 kappa light chain CDRL1

<400> SEQUENCE: 235

Gln Ser Ile Gly Lys Tyr
1               5

<210> SEQ ID NO 236
<211> LENGTH: 6
<212> TYPE: PRT
<213> ORGANISM: Artificial Sequence
<220> FEATURE:
<223> OTHER INFORMATION: anti-CD47 kappa light chain CDRL1

<400> SEQUENCE: 236

Gln Ser Ile Gly Arg Tyr
1               5

<210> SEQ ID NO 237
<211> LENGTH: 6
<212> TYPE: PRT
<213> ORGANISM: Artificial Sequence
<220> FEATURE:
<223> OTHER INFORMATION: anti-CD47 kappa light chain CDRL1

<400> SEQUENCE: 237

Gln Ser Ile Asn Arg Tyr
1               5

<210> SEQ ID NO 238
<211> LENGTH: 6
<212> TYPE: PRT
<213> ORGANISM: Artificial Sequence
<220> FEATURE:
<223> OTHER INFORMATION: anti-CD47 kappa light chain CDRL1

<400> SEQUENCE: 238

Gln Ser Ile Ser Lys Tyr
1               5

<210> SEQ ID NO 239
<211> LENGTH: 6
<212> TYPE: PRT
<213> ORGANISM: Artificial Sequence
<220> FEATURE:
<223> OTHER INFORMATION: anti-CD47 kappa light chain CDRL1

<400> SEQUENCE: 239

Gln Ser Ile Ser Arg Tyr
1               5

<210> SEQ ID NO 240
<211> LENGTH: 6
<212> TYPE: PRT
<213> ORGANISM: Artificial Sequence
<220> FEATURE:
<223> OTHER INFORMATION: anti-CD47 kappa light chain CDRL1

<400> SEQUENCE: 240

Gln Ser Ile Ser Ser Tyr
1               5

<210> SEQ ID NO 241
<211> LENGTH: 6
<212> TYPE: PRT
<213> ORGANISM: Artificial Sequence
<220> FEATURE:
```

<223> OTHER INFORMATION: anti-CD47 kappa light chain CDRL1

<400> SEQUENCE: 241

Gln Ser Ile Ala Lys Tyr
1               5

<210> SEQ ID NO 242
<211> LENGTH: 3
<212> TYPE: PRT
<213> ORGANISM: Artificial Sequence
<220> FEATURE:
<223> OTHER INFORMATION: anti-CD47 kappa light chain CDRL2

<400> SEQUENCE: 242

Ala Ala Ser
1

<210> SEQ ID NO 243
<211> LENGTH: 3
<212> TYPE: PRT
<213> ORGANISM: Artificial Sequence
<220> FEATURE:
<223> OTHER INFORMATION: anti-CD47 kappa light chain CDRL2

<400> SEQUENCE: 243

Gly Ala Ser
1

<210> SEQ ID NO 244
<211> LENGTH: 3
<212> TYPE: PRT
<213> ORGANISM: Artificial Sequence
<220> FEATURE:
<223> OTHER INFORMATION: anti-CD47 kappa light chain CDRL2

<400> SEQUENCE: 244

Asn Ala Ser
1

<210> SEQ ID NO 245
<211> LENGTH: 3
<212> TYPE: PRT
<213> ORGANISM: Artificial Sequence
<220> FEATURE:
<223> OTHER INFORMATION: anti-CD47 kappa light chain CDRL2

<400> SEQUENCE: 245

Ser Ala Ser
1

<210> SEQ ID NO 246
<211> LENGTH: 10
<212> TYPE: PRT
<213> ORGANISM: Artificial Sequence
<220> FEATURE:
<223> OTHER INFORMATION: anti-CD47 kappa light chain CDRL3

<400> SEQUENCE: 246

Gln Gln Lys His Pro Arg Gly Pro Arg Thr
1               5                   10

<210> SEQ ID NO 247
<211> LENGTH: 10
<212> TYPE: PRT
<213> ORGANISM: Artificial Sequence
<220> FEATURE:
<223> OTHER INFORMATION: anti-CD47 kappa light chain CDRL3

```
<400> SEQUENCE: 247

Gln Gln Phe His Lys Arg Ala Pro Gln Thr
1               5                   10

<210> SEQ ID NO 248
<211> LENGTH: 10
<212> TYPE: PRT
<213> ORGANISM: Artificial Sequence
<220> FEATURE:
<223> OTHER INFORMATION: anti-CD47 kappa light chain CDRL3

<400> SEQUENCE: 248

Gln Gln Phe His Lys Arg Arg Pro Gln Thr
1               5                   10

<210> SEQ ID NO 249
<211> LENGTH: 10
<212> TYPE: PRT
<213> ORGANISM: Artificial Sequence
<220> FEATURE:
<223> OTHER INFORMATION: anti-CD47 kappa light chain CDRL3

<400> SEQUENCE: 249

Gln Gln Phe His Lys Arg Ser Pro Gln Thr
1               5                   10

<210> SEQ ID NO 250
<211> LENGTH: 10
<212> TYPE: PRT
<213> ORGANISM: Artificial Sequence
<220> FEATURE:
<223> OTHER INFORMATION: anti-CD47 kappa light chain CDRL3

<400> SEQUENCE: 250

Gln Gln Lys His Pro Arg Ala Pro Arg Thr
1               5                   10

<210> SEQ ID NO 251
<211> LENGTH: 10
<212> TYPE: PRT
<213> ORGANISM: Artificial Sequence
<220> FEATURE:
<223> OTHER INFORMATION: anti-CD47 kappa light chain CDRL3

<400> SEQUENCE: 251

Gln Gln Lys His Pro Arg Ser Pro Arg Thr
1               5                   10

<210> SEQ ID NO 252
<211> LENGTH: 10
<212> TYPE: PRT
<213> ORGANISM: Artificial Sequence
<220> FEATURE:
<223> OTHER INFORMATION: anti-CD47 kappa light chain CDRL3

<400> SEQUENCE: 252

Gln Gln Lys His Pro Arg Tyr Pro Arg Thr
1               5                   10

<210> SEQ ID NO 253
<211> LENGTH: 10
<212> TYPE: PRT
<213> ORGANISM: Artificial Sequence
<220> FEATURE:
<223> OTHER INFORMATION: anti-CD47 kappa light chain CDRL3
```

<400> SEQUENCE: 253

Gln Gln Lys His Pro Arg Asn Pro Arg Thr
1               5                   10

<210> SEQ ID NO 254
<211> LENGTH: 10
<212> TYPE: PRT
<213> ORGANISM: Artificial Sequence
<220> FEATURE:
<223> OTHER INFORMATION: anti-CD47 kappa light chain CDRL3

<400> SEQUENCE: 254

Gln Gln Met His Pro Arg Ala Pro Lys Thr
1               5                   10

<210> SEQ ID NO 255
<211> LENGTH: 10
<212> TYPE: PRT
<213> ORGANISM: Artificial Sequence
<220> FEATURE:
<223> OTHER INFORMATION: anti-CD47 kappa light chain CDRL3

<400> SEQUENCE: 255

Gln Gln Met His Pro Arg Gly Pro Lys Thr
1               5                   10

<210> SEQ ID NO 256
<211> LENGTH: 10
<212> TYPE: PRT
<213> ORGANISM: Artificial Sequence
<220> FEATURE:
<223> OTHER INFORMATION: anti-CD47 kappa light chain CDRL3

<400> SEQUENCE: 256

Gln Gln Met His Pro Arg Ser Pro Lys Thr
1               5                   10

<210> SEQ ID NO 257
<211> LENGTH: 10
<212> TYPE: PRT
<213> ORGANISM: Artificial Sequence
<220> FEATURE:
<223> OTHER INFORMATION: anti-CD47 kappa light chain CDRL3

<400> SEQUENCE: 257

Gln Gln Arg His Pro Arg Ala Pro Arg Thr
1               5                   10

<210> SEQ ID NO 258
<211> LENGTH: 10
<212> TYPE: PRT
<213> ORGANISM: Artificial Sequence
<220> FEATURE:
<223> OTHER INFORMATION: anti-CD47 kappa light chain CDRL3

<400> SEQUENCE: 258

Gln Gln Arg His Lys Arg Ser Pro Gln Thr
1               5                   10

<210> SEQ ID NO 259
<211> LENGTH: 10
<212> TYPE: PRT
<213> ORGANISM: Artificial Sequence
<220> FEATURE:
<223> OTHER INFORMATION: anti-CD47 kappa light chain CDRL3

<400> SEQUENCE: 259

Gln Gln Arg His Pro Arg Gly Pro Arg Thr
1               5                   10

<210> SEQ ID NO 260
<211> LENGTH: 10
<212> TYPE: PRT
<213> ORGANISM: Artificial Sequence
<220> FEATURE:
<223> OTHER INFORMATION: anti-CD47 kappa light chain CDRL3

<400> SEQUENCE: 260

Gln Gln Arg His Pro Arg Gly Pro Ser Thr
1               5                   10

<210> SEQ ID NO 261
<211> LENGTH: 10
<212> TYPE: PRT
<213> ORGANISM: Artificial Sequence
<220> FEATURE:
<223> OTHER INFORMATION: anti-CD47 kappa light chain CDRL3

<400> SEQUENCE: 261

Gln Gln Arg His Pro Arg Gly Pro Thr Thr
1               5                   10

<210> SEQ ID NO 262
<211> LENGTH: 9
<212> TYPE: PRT
<213> ORGANISM: Artificial Sequence
<220> FEATURE:
<223> OTHER INFORMATION: anti-CD47 lambda light chain CDRL1

<400> SEQUENCE: 262

Ser Ser Asp Val Gly Gly Tyr Asn Tyr
1               5

<210> SEQ ID NO 263
<211> LENGTH: 9
<212> TYPE: PRT
<213> ORGANISM: Artificial Sequence
<220> FEATURE:
<223> OTHER INFORMATION: anti-CD47 lambda light chain CDRL1

<400> SEQUENCE: 263

Ser Ser Asp Val Glu Arg Lys Asn Tyr
1               5

<210> SEQ ID NO 264
<211> LENGTH: 9
<212> TYPE: PRT
<213> ORGANISM: Artificial Sequence
<220> FEATURE:
<223> OTHER INFORMATION: anti-CD47 lambda light chain CDRL1

<400> SEQUENCE: 264

Ser Ser Asp Val Arg Ala Asn Asn Tyr
1               5

<210> SEQ ID NO 265
<211> LENGTH: 9
<212> TYPE: PRT
<213> ORGANISM: Artificial Sequence
<220> FEATURE:
<223> OTHER INFORMATION: anti-CD47 lambda light chain CDRL1

<400> SEQUENCE: 265

```
Ser Ser Asp Val Tyr Tyr Asn Lys Tyr
1               5

<210> SEQ ID NO 266
<211> LENGTH: 9
<212> TYPE: PRT
<213> ORGANISM: Artificial Sequence
<220> FEATURE:
<223> OTHER INFORMATION: anti-CD47 lambda light chain CDRL1

<400> SEQUENCE: 266

Ser Ser Asp Val Gly Lys Ala Asn Tyr
1               5

<210> SEQ ID NO 267
<211> LENGTH: 9
<212> TYPE: PRT
<213> ORGANISM: Artificial Sequence
<220> FEATURE:
<223> OTHER INFORMATION: anti-CD47 lambda light chain CDRL1

<400> SEQUENCE: 267

Ser Ser Asp Val Arg Gly Asn Asn Tyr
1               5

<210> SEQ ID NO 268
<211> LENGTH: 9
<212> TYPE: PRT
<213> ORGANISM: Artificial Sequence
<220> FEATURE:
<223> OTHER INFORMATION: anti-CD47 lambda light chain CDRL1

<400> SEQUENCE: 268

Ser Ser Asp Val Ser Ala Arg Asn Tyr
1               5

<210> SEQ ID NO 269
<211> LENGTH: 9
<212> TYPE: PRT
<213> ORGANISM: Artificial Sequence
<220> FEATURE:
<223> OTHER INFORMATION: anti-CD47 lambda light chain CDRL1

<400> SEQUENCE: 269

Ser Ser Asp Val Asn Ser Ala Asn Tyr
1               5

<210> SEQ ID NO 270
<211> LENGTH: 9
<212> TYPE: PRT
<213> ORGANISM: Artificial Sequence
<220> FEATURE:
<223> OTHER INFORMATION: anti-CD47 lambda light chain CDRL1

<400> SEQUENCE: 270

Ser Ser Asp Val Arg Ala Ala Asn Tyr
1               5

<210> SEQ ID NO 271
<211> LENGTH: 9
<212> TYPE: PRT
<213> ORGANISM: Artificial Sequence
<220> FEATURE:
<223> OTHER INFORMATION: anti-CD47 lambda light chain CDRL1

<400> SEQUENCE: 271

Ser Ser Asp Val Arg Arg Ala Asn Tyr
```

```
<210> SEQ ID NO 272
<211> LENGTH: 9
<212> TYPE: PRT
<213> ORGANISM: Artificial Sequence
<220> FEATURE:
<223> OTHER INFORMATION: anti-CD47 lambda light chain CDRL1

<400> SEQUENCE: 272

Ser Ser Asp Val Asn Asn Thr Asn Tyr
1               5

<210> SEQ ID NO 273
<211> LENGTH: 3
<212> TYPE: PRT
<213> ORGANISM: Artificial Sequence
<220> FEATURE:
<223> OTHER INFORMATION: anti-CD47 lambda light chain CDRL2

<400> SEQUENCE: 273

Glu Asn Ser
1

<210> SEQ ID NO 274
<211> LENGTH: 3
<212> TYPE: PRT
<213> ORGANISM: Artificial Sequence
<220> FEATURE:
<223> OTHER INFORMATION: anti-CD47 lambda light chain CDRL2

<400> SEQUENCE: 274

Glu Ser Ser
1

<210> SEQ ID NO 275
<211> LENGTH: 3
<212> TYPE: PRT
<213> ORGANISM: Artificial Sequence
<220> FEATURE:
<223> OTHER INFORMATION: anti-CD47 lambda light chain CDRL2

<400> SEQUENCE: 275

Glu Val Ser
1

<210> SEQ ID NO 276
<211> LENGTH: 3
<212> TYPE: PRT
<213> ORGANISM: Artificial Sequence
<220> FEATURE:
<223> OTHER INFORMATION: anti-CD47 lambda light chain CDRL2

<400> SEQUENCE: 276

Lys Asp Ser
1

<210> SEQ ID NO 277
<211> LENGTH: 3
<212> TYPE: PRT
<213> ORGANISM: Artificial Sequence
<220> FEATURE:
<223> OTHER INFORMATION: anti-CD47 lambda light chain CDRL2

<400> SEQUENCE: 277

Lys Asn Ser
1
```

<210> SEQ ID NO 278
<211> LENGTH: 3
<212> TYPE: PRT
<213> ORGANISM: Artificial Sequence
<220> FEATURE:
<223> OTHER INFORMATION: anti-CD47 lambda light chain CDRL2

<400> SEQUENCE: 278

Lys Ser Ser
1

<210> SEQ ID NO 279
<211> LENGTH: 3
<212> TYPE: PRT
<213> ORGANISM: Artificial Sequence
<220> FEATURE:
<223> OTHER INFORMATION: anti-CD47 lambda light chain CDRL2

<400> SEQUENCE: 279

Lys Thr Ser
1

<210> SEQ ID NO 280
<211> LENGTH: 3
<212> TYPE: PRT
<213> ORGANISM: Artificial Sequence
<220> FEATURE:
<223> OTHER INFORMATION: anti-CD47 lambda light chain CDRL2

<400> SEQUENCE: 280

Gln Asp Ser
1

<210> SEQ ID NO 281
<211> LENGTH: 11
<212> TYPE: PRT
<213> ORGANISM: Artificial Sequence
<220> FEATURE:
<223> OTHER INFORMATION: anti-CD47 lambda light chain CDRL3

<400> SEQUENCE: 281

Ser Ser Tyr Asp Trp Trp Phe Arg Pro Lys Val
1               5                   10

<210> SEQ ID NO 282
<211> LENGTH: 94
<212> TYPE: PRT
<213> ORGANISM: Homo sapiens

<400> SEQUENCE: 282

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Tyr Asp Asn Leu Pro
                85                  90

<210> SEQ ID NO 283
<211> LENGTH: 21
<212> TYPE: DNA
<213> ORGANISM: Artificial Sequence
<220> FEATURE:
<223> OTHER INFORMATION: pNDS1 mycseq primer

<400> SEQUENCE: 283
ctcttctgag atgagttttt g                                              21

<210> SEQ ID NO 284
<211> LENGTH: 30
<212> TYPE: DNA
<213> ORGANISM: Artificial Sequence
<220> FEATURE:
<223> OTHER INFORMATION: pNDS1 gene3leader primer

<400> SEQUENCE: 284
ttattattcg caattccttt agttgttcct                                     30

<210> SEQ ID NO 285
<211> LENGTH: 110
<212> TYPE: PRT
<213> ORGANISM: Artificial Sequence
<220> FEATURE:
<223> OTHER INFORMATION: 5A3-VL

<400> SEQUENCE: 285

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Lys Tyr
            20                  25                  30

Leu Asn Trp Tyr Gln Gln Lys Pro Gly Lys Ala Pro Lys Leu Leu Ile
        35                  40                  45

Tyr Gly Ala Ser Arg Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Lys His Pro Arg Gly Pro
                85                  90                  95

Arg Thr Phe Gly Gln Gly Thr Lys Val Glu Ile Lys Arg Thr
            100                 105                 110

<210> SEQ ID NO 286
<211> LENGTH: 110
<212> TYPE: PRT
<213> ORGANISM: Artificial Sequence
<220> FEATURE:
<223> OTHER INFORMATION: 5A3-M3-VL

<400> SEQUENCE: 286

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

```
Glu Asp Ile Ala Thr Tyr Tyr Cys Gln Gln Lys His Pro Arg Gly Pro
                85                  90                  95

Arg Thr Phe Gly Gln Gly Thr Lys Val Glu Ile Lys Arg Thr
            100                 105                 110

<210> SEQ ID NO 287
<211> LENGTH: 110
<212> TYPE: PRT
<213> ORGANISM: Artificial Sequence
<220> FEATURE:
<223> OTHER INFORMATION: 5A3-M5-VL

<400> SEQUENCE: 287

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Lys Tyr
            20                  25                  30

Leu Asn Trp Tyr Gln Gln Lys Pro Gly Lys Ala Pro Lys Leu Leu Ile
        35                  40                  45

Tyr Gly Ala Ser Arg Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Lys His Pro Arg Tyr Pro
                85                  90                  95

Arg Thr Phe Gly Gln Gly Thr Lys Val Glu Ile Lys Arg Thr
            100                 105                 110
```

ANTI-CD47 ANTIBODIES AND METHODS OF USE THEREOF

RELATED APPLICATIONS

This application is a continuation of U.S. application Ser. No. 14/095,395, filed Dec. 3, 2013, which claims the benefit of U.S. Provisional Application No. 61/732,452, filed Dec. 3, 2012; of U.S. Provisional Application No. 61/816,788, filed Apr. 28, 2013; of U.S. Provisional Application No. 61/863,106, filed Aug. 7, 2013; of U.S. Provisional Application No. 61/881,523, filed Sep. 24, 2013; and of U.S. Provisional Application No. 61/898,710, filed Nov. 1, 2013; each of which is incorporated herein by reference in its entirety.

INCORPORATION BY REFERENCE OF SEQUENCE LISTING

The contents of the text file named "NOVI-030_C02US_SeqList_ST25.txt" which was created on Mar. 2, 2021 and is 272 KB in size, are hereby incorporated by reference in their entirety.

FIELD OF THE INVENTION

The invention relates to monoclonal and/or monovalent antibodies that bind CD47. The invention relates to monoclonal and/or monovalent antibodies that bind CD19. The invention also relates to novel bispecific monoclonal antibodies carrying a different specificity for each binding site of the immunoglobulin molecule, where one of the binding sites is specific for CD47. The invention also relates to novel bispecific monoclonal antibodies carrying a different specificity for each binding site of the immunoglobulin molecule, where one of the binding sites is specific for CD19.

BACKGROUND OF THE INVENTION

CD47 or Integrin-Associated-Protein (IAP) is a ubiquitous 50 kDa transmembrane glycoprotein with multiple functions in cell-cell communication. It interacts with multiple ligands, such as integrins, SIRPα (Signal Regulatory Protein alpha), SIRPγ and thrombospondins (Oldenborg, P. A., CD47: A Cell Surface Glycoprotein Which Regulates Multiple Functions of Hematopoietic Cells in Health and Disease, ISRN Hematol. 2013; 2013:614619; Soto-Pantoj a DR, et al., Therapeutic opportunities for targeting the ubiquitous cell surface receptor CD47 (2012), Expert Opin Ther Targets. 2013 January; 17(1):89-103; Sick E, et al., CD47 Update: a multifaced actor in the tumor microenvironment of potential therapeutic interest, Br J Pharmacol. 2012 December; 167(7):1415-30). In the context of the innate immune system, CD47 functions as a marker of self, transmitting an inhibitory "don't kill me" signal through binding to SIRPα expressed by myeloid cells, such as macrophages, neutrophils, and dendritic cells. The role of widespread expression of CD47 in the physiological situation is therefore to protect healthy cells against the elimination by the innate immune system (Oldenborg P A, et al., CD47-Signal Regulatory Protein α (Sirpα) Regulates Fcγ and Complement Receptor—Mediated Phagocytosis, J Exp Med. 2001 Apr. 2; 193(7):855-62; Mattias Olsson, Role of the CD47/SIRPα-interaction in regulation of macrophage phagocytosis, Department of Integrative Medical Biology, Section for Histology and CellBiology, UmeåUniversity, Umeå, Sweden, Thesis; Oldenborg P A., Role of CD47 in erythroid cells and in autoimmunity, Leuk Lymphoma. 2004 July; 45(7):1319-27; Oldenborg P A, et al., Role of CD47 as a Marker of Self on Red Blood Cells., Science. 2000 Jun. 16; 288 (5473):2051-4; Brown E J, Frazier W A., integrin-associated protein (CD47) and its ligands., Trends Cell Biol. 2001 March; 11(3):130-5).

Tumor cells hijack this immunosuppressive mechanism by overexpressing CD47, which efficiently helps them to escape immune surveillance and killing by innate immune cells. (Majeti R, Ch et al., CD47 is an adverse prognostic factor and therapeutic antibody target on human acute myeloid leukemia stem cells, Cell. 2009 Jul. 23; 138(2):286-99; S. Jaiswal et al., CD47 is upregulated on circulating hematopoietic stem cells and leukemia cells to avoid phagocytosis, Cell. 2009 Jul. 23; 138(2):271-85). CD47 expression is upregulated in most human cancers (e.g., NHL, AML, breast, colon, glioblastoma, glioma, ovarian, bladder and prostate cancers) and increased levels of CD47 expression clearly correlate with aggressive disease and poor survival. (Majeti R, et al., Cell. 2009 Jul. 23; 138(2):286-99; S. Jaiswal et al., Cell. 2009 Jul. 23; 138(2):271-85; Willingham S B, et al., The CD47-signal regulatory protein alpha (SIRPα) interaction is a therapeutic target for human solid tumors, Proc Natl Acad Sci USA. 2012 Apr. 24; 109(17): 6662-7; Chao M P, et al., Therapeutic antibody targeting of CD47 eliminates human acute lymphoblastic leukemia, Cancer Res. 2011 Feb. 15; 71(4):1374-84).

The widespread expression of CD47 in healthy tissues brings the question of treatment safety and efficacy: First, targeting CD47 with a neutralizing monoclonal antibody (Mab) could affect healthy cells, resulting in severe toxicities as shown in preclinical studies with mice and cynomolgus monkeys (Willingham S B, et al., Proc Natl Acad Sci USA. 2012 Apr. 24; 109(17):6662-7; Weiskopf K, et al., Engineered SIRPα Variants as Immunotherapeutic Adjuvants to Anticancer Antibodies, Science. 2013 Jul. 5; 341 (6141):88-91). Second, even if severe toxicities could be avoided or mitigated by using alternative formats (Weiskopf K, et al., Science. 2013 Jul. 5; 341(6141):88-91), broad expression of CD47 could still cause a rapid elimination of CD47-binding molecules through target-mediated drug disposition resulting in poor pharmacokinetics and decreased efficacy.

Accordingly, there exists a need for antibodies and therapeutics that enable targeting of CD47 and overcome these obstacles.

SUMMARY OF THE INVENTION

The invention provides monoclonal antibodies that bind CD47. These antibodies are collectively referred to herein as anti-CD47 monoclonal antibodies or anti-CD47 mAbs. Preferably, the monoclonal antibodies are specific for at least human CD47. In some embodiments, the monoclonal antibodies that recognize human CD47 are also cross-reactive for at least one other non-human CD47 protein, such as, by way of non-limiting example, non-human primate CD47, e.g., cynomolgus monkey CD47, and/or rodent CD47. In some embodiments, these anti-CD47 monoclonal antibodies inhibit the interaction between CD47 and signal-regulatory protein alpha (SIRPα). In some embodiments, these anti-CD47 monoclonal antibodies inhibit the interaction between human CD47 and human SIRPα. The invention also include antibodies that bind to the same epitope as an anti-CD47 monoclonal antibody disclosed herein and inhibits the interaction between CD47 and SIRPα, e.g., between human CD47 and human SIRPα.

The invention also provides monovalent antibodies and/or bispecific antibodies that include at least a first arm that is specific for CD47. Preferably, the monovalent antibodies and/or bispecific antibodies are specific for at least human CD47. In some embodiments, the monovalent antibodies and/or bispecific antibodies that recognize human CD47 are also cross-reactive for at least one other non-human CD47 protein, such as, by way of non-limiting example, non-human primate CD47, e.g., cynomolgus monkey CD47, and/or rodent CD47. In some embodiments, these anti-CD47 monovalent antibodies and/or anti-CD47 bispecific antibodies inhibit the interaction between CD47 and signal-regulatory protein alpha (SIRPα). In some embodiments, these anti-CD47 monovalent antibodies and/or anti-CD47 bispecific antibodies inhibit the interaction between human CD47 and human SIRPα. The invention also include antibodies that bind to the same epitope as an anti-CD47 monovalent and/or an anti-CD47 bispecific antibody disclosed herein and inhibits the interaction between CD47 and SIRPα, e.g., between human CD47 and human SIRPα.

The invention provides bispecific antibodies that recognize CD47 and a second target. The invention allows for the identification, production and purification of bispecific antibodies that are undistinguishable in sequence from standard antibodies and where one of the binding sites is specific for CD47 and the second binding site is specific for another target, for example a tumor-associated antigen (TAA). In some embodiments, the TAA is an antigen that is expressed on the cell surface of a cancer cell. In some embodiments, the cancer cell is selected from a lung cancer cell, a bronchial cancer cell, a prostate cancer cell, a breast cancer cell, a colorectal cancer cell, a pancreatic cancer cell, an ovarian, a leukemia cancer cell, a lymphoma cancer cell, an esophageal cancer cell, a liver cancer cell, a urinary and/or bladder cancer cell, a renal cancer cell, an oral cavity cancer cell, a pharyngeal cancer cell, a uterine cancer cell, and/or a melanoma cancer cell.

In some embodiments, suitable TAA, by way of non-limiting example, include CD20, HER2, HER3, EGFR, IGF1R, c-Met, PDGFR1, CD40, CD40L, CD30, CS1, CD70, glypican, mesothelin, PSMA, PSCA, MUC1, CA125, CEA, FRA, EpCAM, DR5, HGFR1, and/or 5T4.

CD47 (Cluster of Differentiation 47) functions as a "don't eat me" signal for phagocytic cells and is known to be over-expressed by many tumors (immune escape). CD47 interacts with SIRPα, which is expressed on phagocytic cells. CD47 down-regulates phagocytic activity. CD47 inhibits dendritic cell (DC) maturation and activation. CD47 has also been implicated in processes such as, for example, apoptosis, survival, proliferation, adhesion, migration, and regulation of angiogenesis, blood pressure, tissue perfusion, and/or platelet homeostasis.

CD47 has also been implicated in cancer. For example, CD47 is overexpressed in various hematological and solid malignancies. CD47 is a documented cancer stem cell/tumor initiating cell marker. It is thought that CD47 overexpression may help tumor cells to escape immune surveillance and killing by innate immune cells. High levels of CD47 are also associated with poor clinical outcome in cancers such as, for example, leukemias, lymphomas, breast cancer, colon cancer, ovarian cancer, bladder cancer, prostate cancer, and/or glioma. Thus, targeting CD47 would be useful in treating, delaying the progression of, or otherwise ameliorating a symptom of cancer.

As CD47 is ubiquitously expressed, it is a difficult target for a monoclonal antibody (mAb). Nevertheless, the antibodies that are specific for CD47 described herein are useful as monospecific antibodies and can be used for therapeutic intervention or as a research or diagnostic reagent. Monospecific antibodies of the invention that bind CD47, as well as fragments of these monospecific antibodies that are immunologically active and still bind CD47, include the exemplary antibodies described herein, e.g., the 5A3 antibody, the 5A3M4 antibody, the 5A3M3 antibody, the 5A3M5 antibody, the KE8 antibody, the KE8-P6H5 antibody (also referred to herein as KE8H5), the KE8-P3B2 antibody (also referred to herein as KE8B2), the KE8-P2A2 antibody (also referred to herein as KE8A25), the KE8F2 antibody, the KE8G2 antibody, the KE84G9 antibody, the KE81G9 antibody, the KE81A3 antibody, the KE8E8 antibody, the KE8G6 antibody, the KE8H3 antibody, the KE8C7 antibody, the KE8A4 antibody, the KE8A8 antibody, the KE8G11 antibody, the KE8B7 antibody, the KE8F1 antibody, the KE8C4 antibody, the KE8A3 antibody, the KE86G9 antibody, the KE8H6 antibody, the KA3 antibody, the KA3-P5G2 antibody (also referred to herein as KA3G2), the KA3-P1A3 antibody (also referred to herein as KA3A3), the KA3-P5C5 antibody (also referred to herein as KA3C5), the KA3H8 antibody, the KA3B2 antibody, the KA3A2 antibody, the KA3D3 antibody, the KA3H3 antibody, the KC4 antibody, the KC4-P1G11KC4-P4C11 antibody, the KC4-P6B1KC4-P4F4 antibody, and the KC4-P2E2 antibody (also referred to herein as KC4E2), the KC4 antibody, the KC4F4 antibody, the KC4A1 antibody, the KC4C11 antibody, the KC4E10 antibody, the KC4B1 antibody, the KC4C3 antibody, the KC4A4 antibody, the KC4G11 antibody, the KC4G9 antibody and fragments thereof.

The antibodies of the invention that bind CD47 and fragments thereof serve to modulate, block, inhibit, reduce, antagonize, neutralize or otherwise interfere with the functional activity of CD47. Functional activities of CD47 include, by way of non-limiting example, interaction with SIRPα. The antibodies are considered to completely modulate, block, inhibit, reduce, antagonize, neutralize or otherwise interfere with the CD47-SIRPα interaction when the level of CD47-SIRPα interaction in the presence of the antibody is decreased by at least 95%, e.g., by 96%, 97%, 98%, 99% or 100% as compared to the level of CD47-SIRPα interaction in the absence of binding with an antibody described herein. The antibodies are considered to partially modulate, block, inhibit, reduce, antagonize, neutralize or otherwise interfere with the CD47-SIRPα interaction when the level of CD47-SIRPα interaction in the presence of the antibody is decreased by less than 95%, e.g., 10%, 20%, 25%, 30%, 40%, 50%, 60%, 75%, 80%, 85% or 90% as compared to the level of CD47-SIRPα interaction in the absence of binding with an antibody described herein.

The invention also provides bispecific antibodies in which at least one binding site is specific for CD47. The bispecific antibodies of the invention target CD47 and a second antigen, e.g., a tumor-associated antigen (TAA). In some embodiments, the bispecific antibody includes a functional Fc portion. The TAA-binding arm of the bispecific antibody targets the CD47 arm to the tumor cell or cancer stem cell. The CD47 arm blocks, inhibits or otherwise reduces the interaction between CD47 and SIRPα, thereby conveying an "eat me" signal to the phagocyte. In some embodiments, the TAA-binding arm of the bispecific antibody includes an anti-CD19 antibody sequence or antigen-binding fragment thereof.

In some embodiments, the bispecific antibody exhibits a "balanced" affinity for each of the two targets. In other embodiments, the bispecific antibody exhibits an "unbalanced" affinity for each of the two targets. For example, in an anti-CD47/CD19 bispecific antibody, the affinity of the anti-CD19 arm is increased. For example, in an anti-CD47/CD19 bispecific antibody, the affinity of the anti-CD47 arm is decreased. For example, in an anti-CD47/CD19 bispecific antibody, the affinity of the anti-CD19 arm is increased and the affinity of the anti-CD47 arm is decreased. These unbalanced affinity bispecific antibodies are useful, for example, to improve selectivity for a target cell or group of target cells.

In some embodiments, the affinity of the anti-CD19 arm is increased by at least 100 fold following affinity maturation. In some embodiments, the affinity of the anti-CD47 arm is decreased by at least 2 fold following affinity dematuration. For example, in some embodiments, the anti-CD47 arm exhibits an affinity for CD47 that is between about 2 fold and 100 fold lower following affinity dematuration.

The bispecific antibodies of the invention that include at least one anti-CD47 arm serve to modulate, block, inhibit, reduce, antagonize, neutralize or otherwise interfere with the functional activity of CD47. Functional activities of CD47 include, by way of non-limiting example, interaction with SIRPα. The bispecific antibodies are considered to completely modulate, block, inhibit, reduce, antagonize, neutralize or otherwise interfere with the CD47-SIRPα interaction when the level of CD47-SIRPα interaction in the presence of the bispecific antibody is decreased by at least 95%, e.g., by 96%, 97%, 98%, 99% or 100% as compared to the level of CD47-SIRPα interaction in the absence of binding with a bispecific antibody described herein. The bispecific antibodies are considered to partially modulate, block, inhibit, reduce, antagonize, neutralize or otherwise interfere with the CD47-SIRPα interaction when the level of CD47-SIRPα interaction in the presence of the bispecific antibody is decreased by less than 95%, e.g., 10%, 20%, 25%, 30%, 40%, 50%, 60%, 75%, 80%, 85% or 90% as compared to the level of CD47-SIRPα interaction in the absence of binding with a bispecific antibody described herein.

The anti-CD47 arms of the bispecific antibodies of the invention are useful with a number of arms that bind other antigens, e.g., TAAs. Exemplary anti-CD47 arms, anti-CD47 monovalent antibodies and/or bispecific antibodies of the invention include the antibodies referred to herein as the 5A3 antibody, the 5A3M4 antibody, the 5A3M3 antibody, the 5A3M5 antibody, the KE8 antibody, the KE8-P6H5 antibody (also referred to herein as KE8H5), the KE8-P3B2 antibody (also referred to herein as KE8B2), the KE8-P2A2 antibody (also referred to herein as KE8A25), the KE8F2 antibody, the KE8G2 antibody, the KE84G9 antibody, the KE81G9 antibody, the KE81A3 antibody, the KE8E8 antibody, the KE8G6 antibody, the KE8H3 antibody, the KE8C7 antibody, the KE8A4 antibody, the KE8A8 antibody, the KE8G11 antibody, the KE8B7 antibody, the KE8F1 antibody, the KE8C4 antibody, the KE8A3 antibody, the KE86G9 antibody, the KE8H6 antibody, the KA3 antibody, the KA3-P5G2 antibody (also referred to herein as KA3G2), the KA3-P1A3 antibody (also referred to herein as KA3A3), the KA3-P5C5 antibody (also referred to herein as KA3C5), the KA3H8 antibody, the KA3B2 antibody, the KA3A2 antibody, the KA3D3 antibody, the KA3H3 antibody, the KC4 antibody, the KC4-P1G11KC4-P4C11 antibody, the KC4-P6B1KC4-P4F4 antibody, and the KC4-P2E2 antibody (also referred to herein as KC4E2), the KC4 antibody, the KC4F4 antibody, the KC4A1 antibody, the KC4C11 antibody, the KC4E10 antibody, the KC4B1 antibody, the KC4C3 antibody, the KC4A4 antibody, the KC4G11 antibody, the KC4G9 antibody and fragments thereof. In some embodiments, the TAA-binding arm of the bispecific antibody includes an anti-CD19 antibody sequence or antigen-binding fragment thereof.

The invention provides isolated bispecific antibodies having a first arm that includes a first amino acid sequence that binds CD47 and a second arm that includes a second amino acid sequence that does not bind CD47, wherein the bispecific antibody inhibits interaction between CD47 and signal-regulatory protein alpha (SIRPα). In some embodiments, the second amino acid sequence binds a tumor associated antigen (TAA). In some embodiments, the bispecific antibody inhibits interaction between human CD47 and human SIRPα.

In some embodiments, the bispecific antibody inhibits interaction between human CD47 and human SIRPα at a level that is at least ten times more potent than a corresponding level of inhibition of human CD47/human SIRPα interaction exhibited by a monovalent anti-CD47 antibody that includes the first amino acid sequence that binds CD47 and a second amino acid sequence that does not bind a human protein.

In some embodiments, the bispecific antibody inhibits interaction between human CD47 and human SIRPα at a level that is at least 100 times more potent than a corresponding level of inhibition of human CD47/human SIRPα interaction exhibited by a monovalent anti-CD47 antibody that includes the first amino acid sequence that binds CD47 and a second amino acid sequence that does not bind a human protein.

In some embodiments, the bispecific antibody inhibits interaction between human CD47 and human SIRPα at a level that is at least 1,000 times more potent than a corresponding level of inhibition of human CD47/human SIRPα interaction exhibited by a monovalent anti-CD47 antibody that includes the first amino acid sequence that binds CD47 and a second amino acid sequence that does not bind a human protein.

In some embodiments, the bispecific antibody includes a first arm that inhibits the interaction between human CD47 at the surface of cells and soluble human SIRPα with an IC50 greater than 5 nM in the assay described in Example 4 and in which the monovalent antibody 5A3M3 has an IC50 of approximately 13 nM.

In some embodiments, the bispecific antibody includes a first arm that is recovered at more than 80% after incubation at 37° C. for 30 minutes in human whole blood at a concentration of 10 μg/ml as described in Example 15.

In some embodiments, the bispecific antibody inhibits interaction between human CD47 and human SIRPα at a level that is at least ten times, at least 100 times or at least 1,000 times more potent than a corresponding level of inhibition of human CD47/human SIRPα interaction exhibited by a monovalent anti-CD47 antibody that includes the first amino acid sequence that binds CD47 and a second amino acid sequence that does not bind a human protein, and includes a first arm that inhibits the interaction between human CD47 at the surface of cells and soluble human SIRPα with an IC50 greater than 5 nM in the assay described in Example 4 and in which the monovalent antibody 5A3M3 has an IC50 of approximately 13 nM.

In some embodiments, the bispecific antibody inhibits interaction between human CD47 and human SIRPα at a level that is at least ten times, at least 100 times or at least 1,000 times more potent than a corresponding level of inhibition of human CD47/human SIRPα interaction exhibited by a monovalent anti-CD47 antibody that includes the first amino acid sequence that binds CD47 and a second amino acid sequence that does not bind a human protein, and includes a first arm that is recovered at more than 80% after incubation at 37° C. for 30 minutes in human whole blood at a concentration of 10 µg/ml as described in Example 15.

In some embodiments, the TAA is CD19. In some embodiments, the second amino acid sequence does not bind a human protein.

In some embodiments, the first amino acid sequence includes a variable heavy chain complementarity determining region 1 (CDRH1) amino acid sequence of SEQ ID NO: 225, a variable heavy chain complementarity determining region 2 (CDRH2) amino acid sequence of SEQ ID NO: 226, a variable heavy chain complementarity determining region 3 (CDRH3) amino acid sequence of SEQ ID NO: 227, a variable light chain complementarity determining region 1 (CDRL1) amino acid sequence selected from SEQ ID NO: 228-241 and 262-272, a variable light chain complementarity determining region 2 (CDRL2) amino acid sequence selected from 242-245 and 273-280, and a variable light chain complementarity determining region 3 (CDRH3) amino acid sequence selected from 246-261 and 281.

In some embodiments, the first amino acid sequence includes a variable heavy chain amino acid sequence of SEQ ID NO: 114 and a variable light chain amino acid sequence selected from SEQ ID NO: 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204 and 206.

In some embodiments, the bispecific antibody includes two copies of a single heavy chain polypeptide and a first light chain and a second light chain, wherein the first and second light chains are different.

In some embodiments, at least a portion of the first light chain is of the Kappa type and at least a portion of the second light chain is of the Lambda type. In some embodiments, the first light chain includes at least a Kappa constant region. In some embodiments, the first light chain further includes a Kappa variable region. In some embodiments, the first light chain further includes a Lambda variable region. In some embodiments, the second light chain includes at least a Lambda constant region. In some embodiments, the second light chain further includes a Lambda variable region. In some embodiments, the second light chain further includes a Kappa variable region. In some embodiments, the first light chain includes a Kappa constant region and a Kappa variable region, and wherein the second light chain includes a Lambda constant region and a Lambda variable region.

In some embodiments, the constant and variable framework region sequences are human.

The invention also provides bispecific antibodies and/or monovalent antibodies that include at least a first arm that inhibits the interaction between human CD47 at the surface of cells and soluble human SIRPα with an IC50 greater than 5 nM in the assay described in Example 4 and in which the antibody 5A3M3 has an IC50 of approximately 13 nM.

The invention also provides bispecific antibodies and/or monovalent antibodies that include at least a first arm that is recovered at more than 80% after incubation at 37° C. for 30 minutes in human whole blood at a concentration of 10 µg/ml as described in Example 15. In some embodiments, the bispecific antibody and/or monovalent antibody inhibits interaction between CD47 and signal-regulatory protein alpha (SIRPα). In some embodiments, the bispecific antibody and/or monovalent antibody inhibits interaction between human CD47 and human SIRPα.

The invention also provides isolated bispecific antibodies having a first arm that includes a first amino acid sequence that binds CD47 and a second arm that includes a second amino acid sequence that binds CD19, wherein the bispecific antibody inhibits interaction between CD47 and signal-regulatory protein alpha (SIRPα).

In some embodiments, the bispecific antibody inhibits interaction between human CD47 and human SIRPα. In some embodiments, the bispecific antibody inhibits interaction between human CD47 and human SIRPα at a level that is selected from the group consisting of at least ten times more potent, at least 100 times more potent and at least 1,000 times more potent than a corresponding level of inhibition of human CD47/human SIRPα interaction exhibited by a monovalent anti-CD47 antibody that includes the first amino acid sequence that binds CD47 and a second amino acid sequence that does not bind a human protein.

In some embodiments, the first amino acid sequence includes a variable heavy chain complementarity determining region 1 (CDRH1) amino acid sequence of SEQ ID NO: 225, a variable heavy chain complementarity determining region 2 (CDRH2) amino acid sequence of SEQ ID NO: 226, a variable heavy chain complementarity determining region 3 (CDRH3) amino acid sequence of SEQ ID NO: 227, a variable light chain complementarity determining region 1 (CDRL1) amino acid sequence selected from SEQ ID NO: 228-241 and 262-272, a variable light chain complementarity determining region 2 (CDRL2) amino acid sequence selected from 242-245 and 273-280, and a variable light chain complementarity determining region 3 (CDRH3) amino acid sequence selected from 246-261 and 281.

In some embodiments, the first amino acid sequence includes a variable heavy chain amino acid sequence of SEQ ID NO: 114 and a variable light chain amino acid sequence selected from SEQ ID NO: 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204 and 206.

In some embodiments, the bispecific antibody includes two copies of a single heavy chain polypeptide and a first light chain and a second light chain, wherein the first and second light chains are different.

In some embodiments, at least a portion of the first light chain is of the Kappa type and at least a portion of the second light chain is of the Lambda type. In some embodiments, the first light chain includes at least a Kappa constant region. In some embodiments, the first light chain further includes a Kappa variable region. In some embodiments, the first light chain further includes a Lambda variable region. In some embodiments, the second light chain includes at least a Lambda constant region. In some embodiments, the second light chain further includes a Lambda variable region. In some embodiments, the second light chain further includes a Kappa variable region. In some embodiments, the first light chain includes a Kappa constant region and a Kappa variable region, and wherein the second light chain includes a Lambda constant region and a Lambda variable region.

In some embodiments, the constant and variable framework region sequences are human.

The invention also provides monovalent antibodies that bind CD47. These antibodies are collectively referred to herein as anti-CD47 monovalent antibodies or anti-CD47 monov mAbs. The monovalent antibodies of the invention include one arm that specific recognizes CD47, and a second arm referred to herein as a dummy arm. The dummy arm includes an amino acid sequence that does not bind or otherwise cross-react with a human protein. In some embodiments, the dummy arm includes an amino acid sequence that does not bind or otherwise cross-react with a human protein that is found in whole blood. Those of ordinary skill in the art will appreciate that human proteins found in the blood are a proxy that represent all, or substantially all, antigens present in system circulation. In some embodiments, the dummy arm includes an amino acid sequence that does not bind or otherwise cross-react with a human protein that is found in solid tissue. Preferably, the monovalent antibodies are specific for at least human CD47. In some embodiments, the monovalent antibodies that recognize human CD47 are also cross-reactive for at least one other non-human CD47 protein, such as, by way of non-limiting example, non-human primate CD47, e.g., cynomolgus monkey CD47, and/or rodent CD47.

The anti-CD47 arms of the monovalent antibodies of the invention are useful with any dummy arm. Exemplary anti-CD47 arms of the monovalent antibodies of the invention include the antibodies referred to herein as the 5A3 antibody, the 5A3M4 antibody, the 5A3M3 antibody, the 5A3M5 antibody, the KE8 antibody, the KE8-P6H5 antibody (also referred to herein as KE8H5), the KE8-P3B2 antibody (also referred to herein as KE8B2), the KE8-P2A2 antibody (also referred to herein as KE8A25), the KE8F2 antibody, the KE8G2 antibody, the KE84G9 antibody, the KE81G9 antibody, the KE81A3 antibody, the KE8E8 antibody, the KE8G6 antibody, the KE8H3 antibody, the KE8C7 antibody, the KE8A4 antibody, the KE8A8 antibody, the KE8G11 antibody, the KE8B7 antibody, the KE8F1 antibody, the KE8C4 antibody, the KE8A3 antibody, the KE86G9 antibody, the KE8H6 antibody, the KA3 antibody, the KA3-P5G2 antibody (also referred to herein as KA3G2), the KA3-P1A3 antibody (also referred to herein as KA3A3), the KA3-P5C5 antibody (also referred to herein as KA3C5), the KA3H8 antibody, the KA3B2 antibody, the KA3A2 antibody, the KA3D3 antibody, the KA3H3 antibody, the KC4 antibody, the KC4-P1G11KC4-P4C11 antibody, the KC4-P6B1KC4-P4F4 antibody, and the KC4-P2E2 antibody (also referred to herein as KC4E2), the KC4 antibody, the KC4F4 antibody, the KC4A1 antibody, the KC4C11 antibody, the KC4E10 antibody, the KC4B1 antibody, the KC4C3 antibody, the KC4A4 antibody, the KC4G11 antibody, the KC4G9 antibody and fragments thereof. In some embodiments, the TAA-binding arm of the bispecific antibody includes an anti-CD19 antibody sequence or antigen-binding fragment thereof.

In some embodiments, the monovalent antibody inhibits interaction between human CD47 and human SIRPα.

In some embodiments, the anti-CD47 arm of the monovalent antibody includes a first amino acid sequence that includes a variable heavy chain complementarity determining region 1 (CDRH1) amino acid sequence of SEQ ID NO: 225, a variable heavy chain complementarity determining region 2 (CDRH2) amino acid sequence of SEQ ID NO: 226, a variable heavy chain complementarity determining region 3 (CDRH3) amino acid sequence of SEQ ID NO: 227, a variable light chain complementarity determining region 1 (CDRL1) amino acid sequence selected from SEQ ID NO: 228-241 and 262-272, a variable light chain complementarity determining region 2 (CDRL2) amino acid sequence selected from 242-245 and 273-280, and a variable light chain complementarity determining region 3 (CDRH3) amino acid sequence selected from 246-261 and 281.

In some embodiments, the anti-CD47 arm of the monovalent antibody includes a first amino acid sequence that includes a variable heavy chain amino acid sequence of SEQ ID NO: 114 and a variable light chain amino acid sequence selected from SEQ ID NO: 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204 and 206.

In some embodiments, the monovalent antibody includes two copies of a single heavy chain polypeptide and a first light chain and a second light chain, wherein the first and second light chains are different.

In some embodiments, at least a portion of the first light chain is of the Kappa type and at least a portion of the second light chain is of the Lambda type. In some embodiments, the first light chain includes at least a Kappa constant region. In some embodiments, the first light chain further includes a Kappa variable region. In some embodiments, the first light chain further includes a Lambda variable region. In some embodiments, the second light chain includes at least a Lambda constant region. In some embodiments, the second light chain further includes a Lambda variable region. In some embodiments, the second light chain further includes a Kappa variable region. In some embodiments, the first light chain includes a Kappa constant region and a Kappa variable region, and wherein the second light chain includes a Lambda constant region and a Lambda variable region.

In some embodiments, the constant and variable framework region sequences are human.

The bispecific antibodies of the invention are generated using any methods known in the art such as, by way of non-limiting example, the use of cross-linked fragments, quadromas, and/or any of a variety of recombinant formats such as, by way of non-limiting examples, linked antibody fragments, forced heterodimers, and or recombinant formats based on single domains. Examples of Bispecific formats include but are not limited to bispecific IgG based on Fab arm exchange (Gramer et al., 2013 MAbs. 5(6)); the CrossMab format (Klein C et al., 2012 MAbs 4(6)); multiple formats based on forced heterodimerization approaches such as SEED technology (Davis J H et al., 2010 Protein Eng Des Sel. 23(4):195-202), electrostatic steering (Gunasekaran K et al., J Biol Chem. 2010 285(25):19637-46.) or knob-into-hole (Ridgway J B et al., Protein Eng. 1996 9(7):617-21.) or other sets of mutations preventing homodimer formation (Von Kreudenstein T S et al., 2013 MAbs. 5(5):646-54.); fragment based bispecific formats such as tandem scFv (such asBiTEs) (Wolf E et al., 2005 Drug Discov. Today 10(18):1237-44.); bispecific tetravalent antibodies (Portner L M et al., 2012 Cancer Immunol Immunother. 61(10):1869-75.); dual affinity retargeting molecules (Moore P A et al., 2011 Blood. 117(17):4542-51), diabodies (Kontermann R E et al., Nat Biotechnol. 1997 15(7):629-31).

In some embodiments, the bispecific antibodies carry a different specificity in each combining site and including two copies of a single heavy chain polypeptide and a first light chain and a second light chain, wherein the first and second light chains are different.

In some antibodies, at least a first portion of the first light chain is of the Kappa type and at least a portion of the second light chain is of the Lambda type. In some antibodies, the first light chain includes at least a Kappa constant region. In some antibodies, the first light chain further includes a Kappa variable region. In some antibodies, the first light chain further includes a Lambda variable region. In some antibodies, the second light chain includes at least a Lambda constant region. In some antibodies, the second light chain further includes a Lambda variable region. In some antibodies, the second light chain further includes a Kappa variable region. In some antibodies, the first light chain includes a Kappa constant region and a Kappa variable region, and the second light chain includes a Lambda constant region and a Lambda variable region. In some embodiments, the constant and variable framework region sequences are human.

These anti-CD47 arms, monospecific anti-CD47 antibodies, monovalent anti-CD47 antibodies, and/or bispecific antibodies in which at least one binding site is specific for CD47 contain a variable heavy chain amino acid sequence that is at least 90%, 91%, 92%, 93%, 94%, 95%, 96%, 97%, 98%, 99% or more identical to the amino acid sequence of SEQ ID NO: 114 and a variable light chain amino acid sequence that is at least 90%, 91%, 92%, 93%, 94%, 95%, 96%, 97%, 98%, 99% or more identical to an amino acid sequence selected from SEQ ID NO: 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204 and 206.

The invention provides monoclonal antibodies that bind CD47. For example, the invention provides monoclonal antibodies that inhibit the interaction between human CD47 at the surface of cells and soluble human SIRPα with an IC50 greater than 0.3 nM in the assay described in Example 4 and in which the antibody 5A3M3 has an IC50 of approximately 0.36 nM.

The invention also provides monoclonal antibodies that bind CD47 and are recovered at more than 80% after incubation at 37° C. for 30 minutes in human whole blood at a concentration of 10 μg/ml as described in Example 15. In some embodiments, the monoclonal antibody inhibits interaction between CD47 and signal-regulatory protein alpha (SIRPα). In some embodiments, the monoclonal antibody inhibits interaction between human CD47 and human SIRPα.

The invention also provides anti-CD47 monoclonal antibodies that include a variable heavy chain complementarity determining region 1 (CDRH1) amino acid sequence of SEQ ID NO: 225, a variable heavy chain complementarity determining region 2 (CDRH2) amino acid sequence of SEQ ID NO: 226, a variable heavy chain complementarity determining region 3 (CDRH3) amino acid sequence of SEQ ID NO: 227, a variable light chain complementarity determining region 1 (CDRL1) amino acid sequence selected from SEQ ID NO: 228-241 and 262-272, a variable light chain complementarity determining region 2 (CDRL2) amino acid sequence selected from 242-245 and 273-280, and a variable light chain complementarity determining region 3 (CDRH3) amino acid sequence selected from 246-261 and 281.

In some embodiments, the anti-CD47 monoclonal antibody includes a variable heavy chain amino acid sequence that is at least 90%, 91%, 92%, 93%, 94%, 95%, 96%, 97%, 98%, 99% or more identical to the amino acid sequence of SEQ ID NO: 114. In some embodiments, the anti-CD47 monoclonal antibody includes a variable light chain amino acid sequence that is at least 90%, 91%, 92%, 93%, 94%, 95%, 96%, 97%, 98%, 99% or more identical to an amino acid sequence selected from SEQ ID NO: 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204 and 206. In some embodiments, the anti-CD47 monoclonal antibody includes a variable heavy chain amino acid sequence that is at least 90%, 91%, 92%, 93%, 94%, 95%, 96%, 97%, 98%, 99% or more identical to the amino acid sequence of SEQ ID NO: 114, and a variable light chain amino acid sequence that is at least 90%, 91%, 92%, 93%, 94%, 95%, 96%, 97%, 98%, 99% or more identical to an amino acid sequence selected from SEQ ID NO: 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204 and 206.

In some embodiments, the anti-CD47 monoclonal antibody includes a variable heavy chain amino acid sequence of SEQ ID NO: 114 and a variable light chain amino acid sequence selected from SEQ ID NO: 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204 and 206.

In some embodiments, the anti-CD47 antibody includes a combination of a variable heavy chain sequence and a variable light chain sequence selected from the group consisting of the combinations shown in 5A3, 5A3M4, 5A3M3, 5A3M5, KE8, KE8F2, KE8G2, KE84G9, KE81G9, KE81A3, KE8E8, KE8G6, KE8H5, KE8A2, KE8H3, KE8C7, KE8B2, KE8A4, KE8A8, KE8G11, KE8B7, KE8F1, KE8C4, KE8A3, KE86G9, KE8H6, KA3, KA3H8, KA3A3, KA3C5, KA3B2, KA3A2, KA3D3, KA3G2, KA3H3, KC4, KC4E2, KC4F4, KC4A1, KC4C11, KC4E10, KC4B1, KC4C3, KC4A4, KC4G11, and KC4G9.

The invention provides monoclonal antibodies that bind CD19. These antibodies are collectively referred to herein as anti-CD19 monoclonal antibodies or anti-CD19 mAbs. Preferably, the monoclonal antibodies are specific for at least human CD19. In some embodiments, the monoclonal antibodies that recognize human CD19 are also cross-reactive for at least one other non-human CD19 protein, such as, by way of non-limiting example, non-human primate CD19, e.g., cynomolgus monkey CD19, and/or rodent CD19.

In some embodiments, the anti-CD19 monoclonal antibody includes a variable heavy chain amino acid sequence that is at least 90%, 91%, 92%, 93%, 94%, 95%, 96%, 97%, 98%, 99% or more identical to the amino acid sequence of SEQ ID NO: 114. In some embodiments, the anti-CD19 monoclonal antibody includes a variable light chain amino acid sequence that is at least 90%, 91%, 92%, 93%, 94%, 95%, 96%, 97%, 98%, 99% or more identical to an amino acid sequence selected from SEQ ID NO: 208, 210, 212, 214, 216, 218, and 220. In some embodiments, the anti-CD19 monoclonal antibody includes a variable heavy chain amino acid sequence that is at least 90%, 91%, 92%, 93%, 94%, 95%, 96%, 97%, 98%, 99% or more identical to the amino acid sequence of SEQ ID NO: 114, and a variable light chain amino acid sequence that is at least 90%, 91%, 92%, 93%, 94%, 95%, 96%, 97%, 98%, 99% or more identical to an amino acid sequence selected from SEQ ID NO: 208, 210, 212, 214, 216, 218, and 220.

In some embodiments, the anti-CD19 monoclonal antibody includes a variable heavy chain amino acid sequence of SEQ ID NO: 114 and a variable light chain amino acid sequence selected from SEQ ID NO: 208, 210, 212, 214, 216, 218, and 220.

The invention also provides monovalent antibodies that bind CD19. These antibodies are collectively referred to herein as anti-CD19 monovalent antibodies or anti-CD19 monov mAbs. The monovalent antibodies of the invention include one arm that specific recognizes CD19, and a second arm referred to herein as a dummy arm. The dummy arm includes an amino acid sequence that does not bind or otherwise cross-react with a human protein. In some embodiments, the dummy arm includes an amino acid sequence that does not bind or otherwise cross-react with a human protein that is found in whole blood. In some embodiments, the dummy arm includes an amino acid sequence that does not bind or otherwise cross-react with a human protein that is found in solid tissue. Preferably, the monovalent antibodies are specific for at least human CD19. In some embodiments, the monovalent antibodies that recognize human CD19 are also cross-reactive for at least one other non-human CD19 protein, such as, by way of non-limiting example, non-human primate CD19, e.g., cynomolgus monkey CD19, and/or rodent CD19.

The invention also provides bispecific antibodies that recognize CD19 and a second target. In some embodiments, the second target is an antigen known to be associated or otherwise implicated in autoimmune diseases and/or inflammatory diseases, such as, for example, B-cell mediated autoimmune diseases and/or inflammatory diseases, including by way of non-limiting example, systemic lupus erythematosus (SLE), rheumatoid arthritis (RA), idiopathic thrombocytopenic purpura (ITP), Waldenstrom's hypergammaglobulinaemia, Sjogren's syndrome, multiple sclerosis (MS), and/or lupus nephritis.

In some embodiments, suitable second targets include, by way of non-limiting example, CD20, CD22, CD40, BAFFR, CD5, CD32b, ICOSL, IL6R, and/or IL21R.

The bispecific antibodies of the invention that recognize CD19 and a second target are generated using any methods known in the art such as, by way of non-limiting example, the use of cross-linked fragments, quadromas, and/or any of a variety of recombinant formats such as, by way of non-limiting examples, linked antibody fragments, forced heterodimers, and or recombinant formats based on single domains. The invention allows for the identification, production and purification of bispecific antibodies that are undistinguishable in sequence from standard antibodies and where one of the binding sites is specific for CD19 and the second binding site is specific for another target, for example a tumor-associated antigen (TAA). The unmodified nature of the antibodies of the invention provides them with favorable manufacturing and biochemical characteristics similar to standard monoclonal antibodies.

In some embodiments, the bispecific antibodies carry a different specificity in each combining site and including two copies of a single heavy chain polypeptide and a first light chain and a second light chain, wherein the first and second light chains are different.

In some antibodies, at least a first portion of the first light chain is of the Kappa type and at least a portion of the second light chain is of the Lambda type. In some antibodies, the first light chain includes at least a Kappa constant region. In some antibodies, the first light chain further includes a Kappa variable region. In some antibodies, the first light chain further includes a Lambda variable region. In some antibodies, the second light chain includes at least a Lambda constant region. In some antibodies, the second light chain further includes a Lambda variable region. In some antibodies, the second light chain further includes a Kappa variable region. In some antibodies, the first light chain includes a Kappa constant region and a Kappa variable region, and the second light chain includes a Lambda constant region and a Lambda variable region. In some embodiments, the constant and variable framework region sequences are human.

The monoclonal, monovalent and/or bispecific antibodies of the invention can be used for therapeutic intervention or as a research or diagnostic reagent. For example, the monoclonal, monovalent and/or bispecific antibodies of the invention are useful in methods of treating, preventing and/or delaying the progression of pathologies associated with aberrant CD47 and/or aberrant CD47-SIRPα expression and/or activity or alleviating a symptom associated with such pathologies, by administering an antibody of the invention to a subject in which such treatment or prevention is desired. The subject to be treated is, e.g., human. The monoclonal, monovalent and/or bispecific antibody is administered in an amount sufficient to treat, prevent, delay the progression or alleviate a symptom associated with the pathology.

In some embodiments, the monoclonal, monovalent and/or bispecific antibodies described herein are used in conjunction with one or more additional agents or a combination of additional agents. Suitable additional agents include current pharmaceutical and/or surgical therapies for an intended application, such as, for example, cancer, inflammation and/or autoimmune diseases. In some embodiments, the monoclonal, monovalent and/or bispecific antibodies can be used in conjunction with rituximab.

In some embodiments, the monoclonal, monovalent and/or bispecific antibodies and the additional agent are formulated into a single therapeutic composition, and the monoclonal, monovalent and/or bispecific antibody and additional agent are administered simultaneously. Alternatively, the ac monoclonal, monovalent and/or bispecific antibodies and additional agent are separate from each other, e.g., each is formulated into a separate therapeutic composition, and the monoclonal, monovalent and/or bispecific antibody and the additional agent are administered simultaneously, or the monoclonal, monovalent and/or bispecific antibodies and the additional agent are administered at different times during a treatment regimen. For example, the monoclonal, monovalent and/or bispecific antibody is administered prior to the administration of the additional agent, the monoclonal, monovalent and/or bispecific antibody is administered subsequent to the administration of the additional agent, or the monoclonal, monovalent and/or bispecific antibody and the additional agent are administered in an alternating fashion. As described herein, the monoclonal, monovalent and/or bispecific antibody and additional agent are administered in single doses or in multiple doses.

Pathologies treated and/or prevented using the antibodies of the invention include, for example, cancer or any other disease or disorder associated with aberrant CD47 expression and/or activity.

The invention also provides methods of producing bispecific antibodies that exhibit an "unbalanced" affinity for each of the two targets. For example, in some embodiments of an anti-CD47/CD19 bispecific antibody, the affinity of the anti-CD19 arm is increased using affinity maturation. For example, in some embodiments of an anti-CD47/CD19 bispecific antibody, the affinity of the anti-CD47 arm is decreased using affinity dematuration. For example, in some embodiments an anti-CD47/CD19 bispecific antibody, the affinity of the anti-CD19 arm is increased using affinity maturation, and the affinity of the anti-CD47 arm is decreased using affinity de-maturation. These unbalanced affinity bispecific antibodies are useful, for example, to improve selectivity for a target cell or group of target cells.

FIG. 1 is an illustration of the sequence alignment between the variable light chain (VL) sequence of the anti-CD47 antibody 5A3 (SEQ ID NO: 285) to its closest germline sequence (SEQ ID NO: 282), the human IGKV1-33 according to the IMGT nomenclature, and to the variable light chain (VL) sequence of the anti-CD47 antibody 5A3-

M3-VL (SEQ ID NO: 286) and to the variable light chain (VL) sequence of the anti-CD47 antibody 5A3-M5-VL (SEQ ID NO: 287)).

BRIEF DESCRIPTION OF THE DRAWINGS

FIG. 1 is an illustration of the sequence alignment between the variable light chain (VL) sequence of the anti-CD47 antibody 5A3 (SEQ ID NO: 116) to its closest germline sequence (SEQ ID NO: 282), the human IGKV1-33 according to the IMGT nomenclature.

FIG. 7 demonstrates that high-affinity CD47 Mabs of the 5A3, Ke8, and Ka3 families induce hemagglutination; in contrast to the other three families, Kc4 family antibodies tested in this experiment do not induce hemagglutination.

FIGS. 9A-9C are a series of graphs the ability of a CD47xCD19 BsAb to co-engage the two targets at the surface of cells. The graphs in FIGS. 9A-9C present FACS profiles generated with monovalent and bispecific antibodies binding to CD19-negative B-NHL cells (DS-1) and CD19-positive Burkitt lymphoma cells (Raji). All antibodies were human IgG1 format and were tested at four concentrations as indicated.

FIG. 10 demonstrates the co-engagement of CD19 and CD47 on the surface of the target cell, by showing that the neutralization of CD47-SIRPα interaction by CD47xCD19 BsAbs is CD19-dependent. The experiments were done in quadruplicates Mean and SEM are shown. Dose-response inhibition curves were fitted with GraphPad software.

FIGS. 11A-11B demonstrate the ability of CD47xCD19 BsAbs to kill CD19-positive cells in a CD19-dependent manner, as the corresponding CD47 monovalent antibodies were much less efficient or not efficient at all. FIG. 11C demonstrates that the efficacy of killing of Raji cells with CD47xCD19 antibodies was comparable to rituximab and much higher than with the CD19 Mab C2.

FIG. 13 shows that the efficacy of BsAB is similar to B6H12 or rituximab and that tumor eradication was CD19-dependent, as the corresponding monovalent was less efficacious.

DETAILED DESCRIPTION

Figure 2:
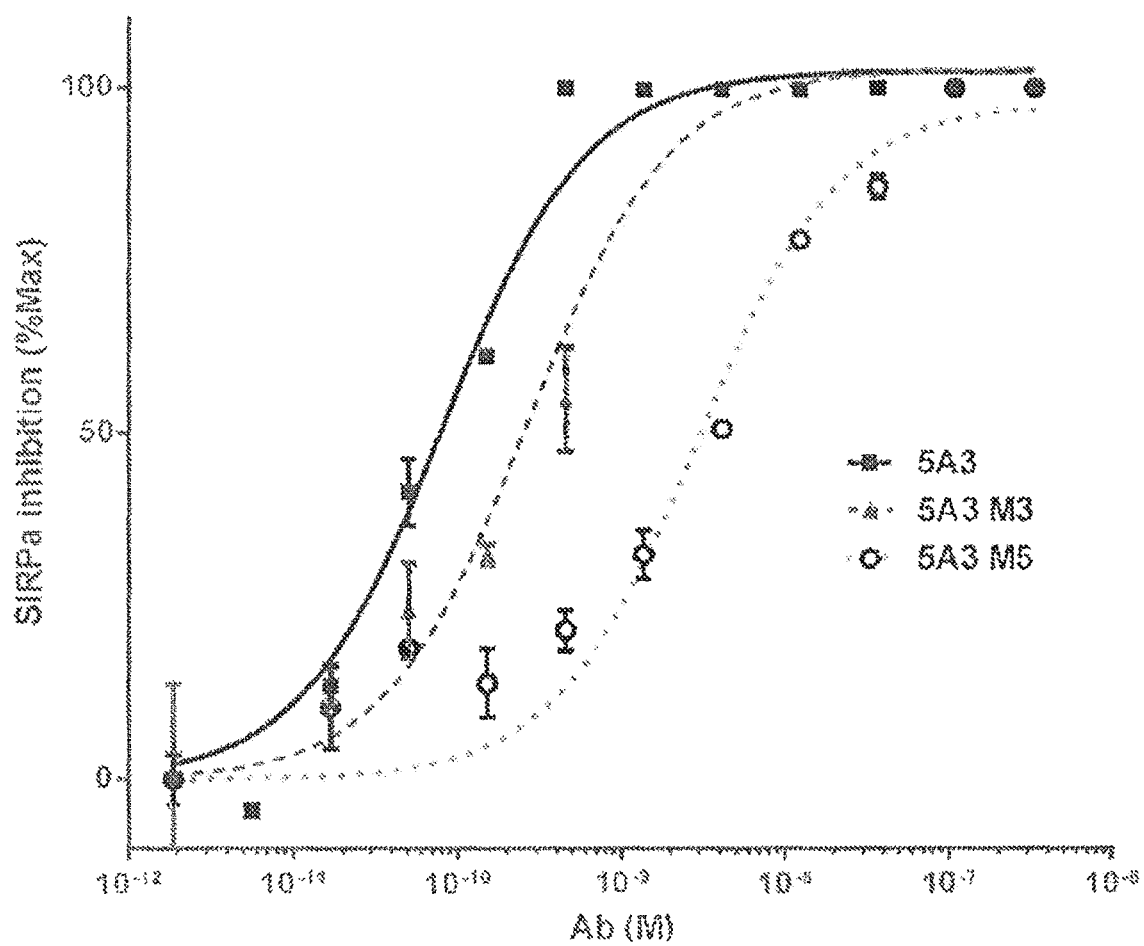
FIG. 2 is a graph depicting the blocking potency of the 5A3-M3 and 5A3-M5 antibody variants as compared to the parental antibody 5A3 in a CD47/SIRPα binding assay.

The invention provides monoclonal antibodies that bind CD47. These antibodies are collectively referred to herein as anti-CD47 monoclonal antibodies or anti-CD47 mAbs. Preferably, the monoclonal antibodies are specific for at least human CD47. In some embodiments, the monoclonal antibodies that recognize human CD47 are also cross-reactive for at least one other non-human CD47 protein, such as, by way of non-limiting example, non-human primate CD47, e.g., cynomolgus monkey CD47, and/or rodent CD47. In some embodiments, these anti-CD47 monoclonal antibodies inhibit the interaction between CD47 and signal-regulatory protein alpha (SIRPα). In some embodiments, these anti-CD47 monoclonal antibodies inhibit the interaction between human CD47 and human SIRPα. The invention also include antibodies that bind to the same epitope as an anti-CD47 monoclonal antibody disclosed herein and inhibits the interaction between CD47 and SIRPα, e.g., between human CD47 and human SIRPα.

The invention also provides monovalent antibodies and/or bispecific antibodies that include at least a first arm that is specific for CD47. Preferably, the monovalent antibodies and/or bispecific antibodies are specific for at least human CD47. In some embodiments, the monovalent antibodies and/or bispecific antibodies that recognize human CD47 are also cross-reactive for at least one other non-human CD47 protein, such as, by way of non-limiting example, non-human primate CD47, e.g., cynomolgus monkey CD47, and/or rodent CD47. In some embodiments, these anti-CD47 monovalent antibodies and/or anti-CD47 bispecific antibodies inhibit the interaction between CD47 and signal-regulatory protein alpha (SIRPα). In some embodiments, these anti-CD47 monovalent antibodies and/or anti-CD47 bispecific antibodies inhibit the interaction between human CD47 and human SIRPα. The invention also include antibodies that bind to the same epitope as an anti-CD47 monovalent and/or an anti-CD47 bispecific antibody disclosed herein and inhibits the interaction between CD47 and SIRPα, e.g., between human CD47 and human SIRPα.

The bispecific antibodies of the invention allow for simultaneous binding of the two antibody arms to two antigens on the surface of the cell (termed co-engagement), which results in additive or synergistic increase of affinity due to avidity mechanism. As a consequence, co-engagement confers high selectivity towards cells expressing both antigens as compared to cells that express just one single antigen. In addition, the affinities of the two arms of a bispecific antibody to their respective targets can be set up in a way that binding to target cells is principally driven by one of the antibody arms. In some embodiments, the bispecific antibody includes a first arm that binds CD47 and a second arm that binds a tumor associated antigen (TAA), where the second arm binds to the TAA with high affinity, and the first arm binds to CD47 with low affinity, i.e., an affinity that is sufficient to inhibit CD47/SIRPα upon TAA co-engagement. This design allows the bispecific antibodies of the invention to preferentially inhibit CD47 in cancer versus normal cells. In the examples provided herein, a bispecific antibody with a first arm that binds CD47 with low affinity and a second arm that binds CD19 with high affinity (termed a CD47xCD19 bispecific) allow preferential inhibition of CD47 in cancer versus normal cells. Besides the two antigen-binding arms, the CD47 x TAA bispecific antibody requires a functional Fc portion to recruit macrophages and/or other immune effector cells. A fully human bispecific IgG format (such as the κλ-body format described herein) is well suited for the generation of dual targeting CD47 x TAA bispecific antibodies. As shown in the examples provided herein, the ability of dual targeting bispecific antibodies to co-engage CD47 and CD19 results in a significant increase in the affinity of binding to CD19-positive cells and in CD19-dependent neutralization of the CD47-SIRPα interaction. This, in turn, translates into efficient and selective cancer cell killing mediated by the CD47xCD19 bispecific antibody, as demonstrated in the ADCC and ADCP experiments provided herein.

Exemplary anti-CD47 monoclonal, monospecific anti-CD47 antibodies, anti-CD47 monovalent antibodies, and/or bispecific antibodies of the invention in which at least one binding site is specific for CD47 include, for example, the 5A3 antibody, the 5A3M4 antibody, the 5A3M3 antibody, the 5A3M5 antibody, the KE8 antibody, the KE8-P6H5 antibody (also referred to herein as KE8H5), the KE8-P3B2 antibody (also referred to herein as KE8B2), the KE8-P2A2 antibody (also referred to herein as KE8A25), the KE8F2 antibody, the KE8G2 antibody, the KE84G9 antibody, the KE81G9 antibody, the KE81A3 antibody, the KE8E8 antibody, the KE8G6 antibody, the KE8H3 antibody, the KE8C7 antibody, the KE8A4 antibody, the KE8A8 antibody, the KE8G11 antibody, the KE8B7 antibody, the KE8F1 antibody, the KE8C4 antibody, the KE8A3 antibody, the KE86G9 antibody, the KE8H6 antibody, the KA3 antibody, the KA3-P5G2 antibody (also referred to herein as KA3G2), the KA3-P1A3 antibody (also referred to herein as KA3A3), the KA3-P5C5 antibody (also referred to herein as KA3C5), the KA3H8 antibody, the KA3B2 antibody, the KA3A2 antibody, the KA3D3 antibody, the KA3H3 antibody, the KC4 antibody, the KC4-P1G11KC4-P4C11 antibody, the KC4-P6B1KC4-P4F4 antibody, and the KC4-P2E2 antibody (also referred to herein as KC4E2), the KC4 antibody, the KC4F4 antibody, the KC4A1 antibody, the KC4C11 antibody, the KC4E10 antibody, the KC4B1 antibody, the KC4C3 antibody, the KC4A4 antibody, the KC4G11 antibody, and the KC4G9 antibody, as well as immunologically active and/or antigen-binding fragments thereof.

In some embodiments, exemplary anti-CD47 monoclonal, monospecific anti-CD47 antibodies, anti-CD47 monovalent antibodies, and/or bispecific antibodies of the invention include a combination of heavy chain and light chain complementarity determining regions (CDRs) selected from the CDR sequences shown in Tables 1, 2 and 3, where the CDRs shown in Tables 1, 2 and 3 are defined according to the IMGT nomenclature.

In some embodiments, exemplary anti-CD47 monoclonal, monospecific anti-CD47 antibodies, anti-CD47 monovalent antibodies, and/or bispecific antibodies of the invention include the combination of heavy chain CDR sequences from Table 1 and two sets of light chain CDRs selected from the CDRL1, CDRL2 and CDRL3 sequences shown in Tables 2 and 3.

In some embodiments, exemplary anti-CD47 monoclonal, monospecific anti-CD47 antibodies, anti-CD47 monovalent antibodies, and/or bispecific antibodies of the invention include the combination of heavy chain CDR sequences from Table 1 and a first set of light chain CDRs selected from the CDRL1, CDRL2 and CDRL3 sequences shown in Table 2 and a second set of light chain CDRs selected from the CDRL1, CDRL2 and CDRL3 sequences shown in Table 3.

TABLE 1

Anti-CD47 Heavy Chain CDRs

| CDRH1 | CDRH2 | CDRH3 |
|---|---|---|
| GFTF----SSYA (SEQ ID NO: 225) | ISGS--GGST (SEQ ID NO: 226) | AKSYGAF----DY (SEQ ID NO: 227) |

TABLE 2

Anti-CD47 Kappa Light Chain CDRs

| CDRL1 | CDRL2 | CDRL3 |
|---|---|---|
| QDI------NKY (SEQ ID NO: 228) | AA-------S (SEQ ID NO: 242) | QQKHPRGP---RT (SEQ ID NO: 246) |
| QDI------NRY (SEQ ID NO: 229) | GA-------S (SEQ ID NO: 243) | QQFHKRAP---QT (SEQ ID NO: 247) |

TABLE 2-continued

Anti-CD47 Kappa Light Chain CDRs

| CDRL1 | CDRL2 | CDRL3 |
|---|---|---|
| QNI------GKY (SEQ ID NO: 230) | NA-------S (SEQ ID NO: 244) | QQFHKRRP---QT (SEQ ID NO: 248) |
| QSI------ARY (SEQ ID NO: 231) | SA-------S (SEQ ID NO: 245) | QQFHKRSP---QT (SEQ ID NO: 249) |
| QSI------ASY (SEQ ID NO: 232) | | QQKHPRAP---RT (SEQ ID NO: 250) |
| QSI------DKY (SEQ ID NO: 233) | | QQKHPRSP---RT (SEQ ID NO: 251) |
| QSI------DRY (SEQ ID NO: 234) | | QQKHPRYP---RT (SEQ ID NO: 252) |
| QSI------GKY (SEQ ID NO: 235) | | QQKHPRNP---RT (SEQ ID NO: 253) |
| QSI------GRY (SEQ ID NO: 236) | | QQMHPRAP---KT (SEQ ID NO: 254) |
| QSI------NRY (SEQ ID NO: 237) | | QQMHPRGP---KT (SEQ ID NO: 255) |
| QSI------SKY (SEQ ID NO: 238) | | QQMHPRSP---KT (SEQ ID NO: 256) |
| QSI------SRY (SEQ ID NO: 239) | | QQRHPRAP---RT (SEQ ID NO: 257) |
| QSI------SSY (SEQ ID NO: 240) | | QQRHKRSP---QT (SEQ ID NO: 258) |
| QSI------AKY (SEQ ID NO: 241) | | QQRHPRGP---RT (SEQ ID NO: 259) |
| | | QQRHPRGP---ST (SEQ ID NO: 260) |
| | | QQRHPRGP---TT (SEQ ID NO: 261) |

TABLE 3

Anti-CD47 Lambda Light Chain CDRs

| CDRL1 | CDRL2 | CDRL3 |
|---|---|---|
| SSDVG---GYNY (SEQ ID NO: 262) | EN-------S (SEQ ID NO: 273) | SSYDWWFRP--KV (SEQ ID NO: 281) |
| SSDVE---RKNY (SEQ ID NO: 263) | ES-------S (SEQ ID NO: 274) | |
| SSDVR---ANNY (SEQ ID NO: 264) | EV-------S (SEQ ID NO: 275) | |
| SSDVY---YNKY (SEQ ID NO: 265) | KD-------S (SEQ ID NO: 276) | |
| SSDVG---KANY (SEQ ID NO: 266) | KN-------S (SEQ ID NO: 277) | |
| SSDVR---GNNY (SEQ ID NO: 267) | KS-------S (SEQ ID NO: 278) | |
| SSDVS---ARNY (SEQ ID NO: 268) | KT-------S (SEQ ID NO: 279) | |
| SSDVN---SANY (SEQ ID NO: 269) | QD-------S (SEQ ID NO: 280) | |
| SSDVR---AANY (SEQ ID NO: 270) | | |
| SSDVR---RANY (SEQ ID NO: 271) | | |
| SSDVN---NTNY (SEQ ID NO: 272) | | |

Each of the exemplary anti-CD47, anti-CD19, monovalent and bispecific antibodies described herein include a common heavy chain (HC), one kappa chain or one lambda chain for anti-CD47 and anti-CD19 antibodies, one kappa and one lambda light chains (LC) for monovalent and bispecific antibodies, as shown in the amino acid and corresponding nucleic acid sequences listed below. Each of the exemplary anti-CD47, anti-CD19, monovalent and bispecific antibodies described below includes a common variable heavy domain (VH), one kappa variable light domain or one lambda variable light domain for anti-CD47 and anti-CD19 antibodies, one kappa and one lambda variable light domains (VL) for monovalent and bispecific antibodies, as shown in the amino acid and corresponding nucleic acid sequences listed below.

While antibody sequences below are provided herein as examples, it is to be understood that these sequences can be used to generate bispecific antibodies using any of a variety of art-recognized techniques. Examples of bispecific formats include but are not limited to bispecific IgG based on Fab arm exchange (Gramer et al., 2013 MAbs. 5(6)); the CrossMab format (Klein C et al., 2012 MAbs 4(6)); multiple formats based on forced heterodimerization approaches such as SEED technology (Davis J H et al., 2010 Protein Eng Des Sel. 23(4):195-202), electrostatic steering (Gunasekaran K et al., J Biol Chem. 2010 285(25):19637-46.) or knob-into-hole (Ridgway J B et al., Protein Eng. 1996 9(7):617-21.) or other sets of mutations preventing homodimer formation (Von Kreudenstein T S et al., 2013 MAbs. 5(5):646-54.); fragment based bispecific formats such as tandem scFv (such asBiTEs) (Wolf E et al., 2005 Drug Discov. Today 10(18):1237-44.); bispecific tetravalent antibodies (Portner L M et al., 2012 Cancer Immunol Immunother. 61(10):1869-75.); dual affinity retargeting molecules (Moore P A et al., 2011 Blood. 117(17):4542-51), diabodies (Kontermann R E et al., Nat Biotechnol. 1997 15(7):629-31).

The exemplary anti-CD47, anti-CD19, monovalent and bispecific antibodies include a common heavy chain (SEQ ID NO: 2) encoded by the nucleic acid sequence shown in SEQ ID NO: 1.

>COMMON-HC-NT
(SEQ ID NO: 1)
GAGGTGCAGCTGTTGGAGTCTGGGGGAGGCTTGGTACAGCCTGGGGGGTC

CCTGAGACTCTCCTGTGCAGCCTCTGGATTCACCTTTAGCAGCTATGCCA

TGAGCTGGGTCCGCCAGGCTCCAGGGAAGGGGCTGGAGTGGGTCTCAGCT

ATTAGTGGTAGTGGTGGTAGCACATACTACGCAGACTCCGTGAAGGGCCG

GTTCACCATCTCCAGAGACAATTCCAAGAACACGCTGTATCTGCAAATGA

ACAGCCTGAGAGCCGAGGACACGGCCGTATATTACTGTGCGAAAAGTTAT

```
GGTGCTTTTGACTACTGGGGCCAGGGAACCCTGGTCACAGTCTCGAGCGC

CTCCACCAAGGGCCCATCGGTCTTCCCCCTGGCACCCTCCTCCAAGAGCA

CCTCTGGGGGCACAGCGGCCCTGGGCTGCCTGGTCAAGGACTACTTCCCC

GAACCGGTGACAGTCTCGTGGAACTCAGGAGCCCTGACCAGCGGCGTGCA

CACCTTCCCGGCTGTCCTACAGTCCTCAGGACTCTACTCCCTCAGCAGCG

TGGTGACTGTGCCCTCCAGCAGCTTGGGCACCCAGACCTACATCTGCAAC

GTGAATCACAAGCCCAGCAACACCAAGGTGGACAAGAGAGTTGAGCCCAA

ATCTTGTGACAAAACTCACACATGCCCACCGTGCCCAGCACCTGAACTCC

TGGGGGGACCGTCAGTCTTCCTCTTCCCCCCAAAACCCAAGGACACCCTC

ATGATCTCCCGGACCCCTGAGGTCACATGCGTGGTGGTGGACGTGAGCCA

CGAAGACCCTGAGGTCAAGTTCAACTGGTACGTGGACGGCGTGGAGGTGC

ATAATGCCAAGACAAAGCCGCGGGAGGAGCAGTACAACAGCACGTACCGT

GTGGTCAGCGTCCTCACCGTCCTGCACCAGGACTGGCTGAATGGCAAGGA

GTACAAGTGCAAGGTCTCCAACAAAGCCCTCCCAGCCCCCATCGAGAAAA

CCATCTCCAAAGCCAAAGGGCAGCCCCGAGAACCACAGGTGTATACCCTG

CCCCCATCTCGGGAGGAGATGACCAAGAACCAGGTCAGCCTGACTTGCCT

GGTCAAAGGCTTCTATCCCAGCGACATCGCCGTGGAGTGGGAGAGCAACG

GGCAGCCGGAGAACAACTACAAGACCACGCCTCCCGTGCTGGACTCCGAC

GGCTCCTTCTTCCTCTATAGCAAGCTCACCGTGGACAAGTCCAGGTGGCA

GCAGGGGAACGTCTTCTCATGCTCCGTGATGCATGAGGCTCTGCACAACC

ACTACACGCAGAAGAGCCTCTCCCTGTCTCCGGGTTAA

>COMMON-HC-AA
                                    (SEQ ID NO: 2)
EVQLLESGGGLVQPGGSLRLSCAASGFTFSSYAMSWVRQAPGKGLEWVSA

ISGSGGSTYYADSVKGRFTISRDNSKNTLYLQMNSLRAEDTAVYYCAKSY

GAFDYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKRVEPKSCDKTHTCPPCPAPELLGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG
```

The anti-CD47, anti-CD19, monovalent and bispecific antibodies include a common variable heavy domain (SEQ ID NO: 114) encoded by the nucleic acid sequence shown in SEQ ID NO: 113.

```
>COMMON-VH-NT
                                    (SEQ ID NO: 113)
GAGGTGCAGCTGTTGGAGTCTGGGGGAGGCTTGGTACAGCCTGGGGGGTC

CCTGAGACTCTCCTGTGCAGCCTCTGGATTCACCTTTAGCAGCTATGCCA

TGAGCTGGGTCCGCCAGGCTCCAGGGAAGGGGCTGGAGTGGGTCTCAGCT

ATTAGTGGTAGTGGTGGTAGCACATACTACGCAGACTCCGTGAAGGGCCG

GTTCACCATCTCCAGAGACAATTCCAAGAACACGCTGTATCTGCAAATGA

ACAGCCTGAGAGCCGAGGACACGGCCGTATATTACTGTGCGAAAAGTTAT

GGTGCTTTTGACTACTGGGGCCAGGGAACCCTGGTCACAGTCTCGAGC

>COMMON-VH-AA
                                    (SEQ ID NO: 114)
EVQLLESGGGLVQPGGSLRLSCAASGFTFSSYAMSWVRQAPGKGLEWVSA

ISGSGGSTYYADSVKGRFTISRDNSKNTLYLQMNSLRAEDTAVYYCAKSY

GAFDYWGQGTLVTVSS
```

Anti-CD47 Antibodies

The 5A3 antibody includes a common heavy chain (SEQ ID NO: 2) encoded by the nucleic acid sequence shown in SEQ ID NO: 1 and includes a kappa light chain (SEQ ID NO: 4) encoded by the nucleic acid sequence shown in SEQ ID NO: 3.

```
>5A3-LC-NT
                                    (SEQ ID NO: 3)
GACATCCAGATGACCCAGTCTCCATCCTCCCTGTCTGCATCTGTAGGAGA

CAGAGTCACCATCACTTGCCAGGCGAGTCAGGACATTAATAAGTATTTAA

ATTGGTATCAGCAGAAACCAGGGAAAGCCCCTAAGCTCCTGATCTACGGT

GCATCCAGGTTGGAAACAGGGGTCCCATCAAGGTTCAGTGGAAGTGGATC

TGGGACAGATTTTACTTTCACCATCAGCAGCCTGCAGCCTGAAGATATTG

CAACATATTACTGTCAGCAGAAGCACCCCCGGGGCCGAGGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>5A3-LC-AA
                                    (SEQ ID NO: 4)
DIQMTQSPSSLSASVGDRVTITCQASQDINKYLNWYQQKPGKAPKLLIYG

ASRLETGVPSRFSGSGSGTDFTFTISSLQPEDIATYYCQQKHPRGPRTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC
```

The 5A3 antibody includes a common variable heavy domain (SEQ ID NO: 114) encoded by the nucleic acid sequence shown in SEQ ID NO: 113 and includes a kappa variable light domain (SEQ ID NO: 116) encoded by the nucleic acid sequence shown in SEQ ID NO: 115.

```
>5A3-VL-NT
                                    (SEQ ID NO: 115)
GACATCCAGATGACCCAGTCTCCATCCTCCCTGTCTGCATCTGTAGGAGA

CAGAGTCACCATCACTTGCCAGGCGAGTCAGGACATTAATAAGTATTTAA

ATTGGTATCAGCAGAAACCAGGGAAAGCCCCTAAGCTCCTGATCTACGGT

GCATCCAGGTTGGAAACAGGGGTCCCATCAAGGTTCAGTGGAAGTGGATC

TGGGACAGATTTTACTTTCACCATCAGCAGCCTGCAGCCTGAAGATATTG
```

-continued

CAACATATTACTGTCAGCAGAAGCACCCCCGGGGGCCGAGGACCTTCGGC

CAAGGGACCAAGGTGGAAATCAAA

>5A3-VL-AA
(SEQ ID NO: 116)
DIQMTQSPSSLSASVGDRVTITCQASQDINKYLNWYQQKPGKAPKLLIYG

ASRLETGVPSRFSGSGSGTDFTFTISSLQPEDIATYYCQQKHPRGPRTFG

QGTKVEIK

The 5A3-M4 antibody includes a common heavy chain (SEQ ID NO: 2) encoded by the nucleic acid sequence shown in SEQ ID NO: 1 and includes a kappa light chain (SEQ ID NO: 6) encoded by the nucleic acid sequence shown in SEQ ID NO: 5.

>5A3-M4-LC-NT
(SEQ ID NO: 5)
GACATCCAGATGACCCAGTCTCCATCCTCCCTGTCTGCATCTGTAGGAGA

CAGAGTCACCATCACTTGCCAGGCGAGTCAGGACATTAATAAGTATTTAA

ATTGGTATCAGCAGAAACCAGGGAAAGCCCCTAAGCTCCTGATCTACGGT

GCATCCAGGTTGGAAACAGGGGTCCCATCAAGGTTCAGTGGAAGTGGATC

TGGGACAGATTTTACTTTCACCATCAGCAGCCTGCAGCCTGAAGATATTG

CAACATATTACTGTCAGCAGAAGCACCCCCGGAACCCGAGGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>5A3-M4-LC-AA
(SEQ ID NO: 6)
DIQMTQSPSSLSASVGDRVTITCQASQDINKYLNWYQQKPGKAPKLLIYG

ASRLETGVPSRFSGSGSGTDFTFTISSLQPEDIATYYCQQKHPRNPRTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The 5A3-M4 antibody includes a common variable heavy domain (SEQ ID NO: 114) encoded by the nucleic acid sequence shown in SEQ ID NO: 113 and includes a kappa variable light domain (SEQ ID NO: 118) encoded by the nucleic acid sequence shown in SEQ ID NO: 117.

>5A3-M4-VL-NT
(SEQ ID NO: 117)
GACATCCAGATGACCCAGTCTCCATCCTCCCTGTCTGCATCTGTAGGAGA

CAGAGTCACCATCACTTGCCAGGCGAGTCAGGACATTAATAAGTATTTAA

ATTGGTATCAGCAGAAACCAGGGAAAGCCCCTAAGCTCCTGATCTACGGT

GCATCCAGGTTGGAAACAGGGGTCCCATCAAGGTTCAGTGGAAGTGGATC

TGGGACAGATTTTACTTTCACCATCAGCAGCCTGCAGCCTGAAGATATTG

-continued

CAACATATTACTGTCAGCAGAAGCACCCCCGGAACCCGAGGACCTTCGGC

CAAGGGACCAAGGTGGAAATCAAA

>5A3-M4-VL-AA
(SEQ ID NO: 118)
DIQMTQSPSSLSASVGDRVTITCQASQDINKYLNWYQQKPGKAPKLLIYG

ASRLETGVPSRFSGSGSGTDFTFTISSLQPEDIATYYCQQKHPRNPRTFG

QGTKVEIK

The 5A3-M3 antibody includes a common heavy chain (SEQ ID NO: 2) encoded by the nucleic acid sequence shown in SEQ ID NO: 1 and includes a kappa light chain (SEQ ID NO: 8) encoded by the nucleic acid sequence shown in SEQ ID NO: 7.

>5A3-M3-LC-NT
(SEQ ID NO: 7)
GACATCCAGATGACCCAGTCTCCATCCTCCCTGTCTGCATCTGTAGGAGA

CAGAGTCACCATCACTTGCCAGGCGAGTCAGTCCATTAGTAGTTATTTAA

ATTGGTATCAGCAGAAACCAGGGAAAGCCCCTAAGCTCCTGATCTACGCT

GCATCCTCGTTGGAAACAGGGGTCCCATCAAGGTTCAGTGGAAGTGGATC

TGGGACAGATTTTACTTTCACCATCAGCAGCCTGCAGCCTGAAGATATTG

CAACATATTACTGTCAGCAGAAGCACCCCCGGGGCCGAGGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>5A3-M3-LC-AA
(SEQ ID NO: 8)
DIQMTQSPSSLSASVGDRVTITCQASQSISSYLNWYQQKPGKAPKLLIYA

ASSLETGVPSRFSGSGSGTDFTFTISSLQPEDIATYYCQQKHPRGPRTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The 5A3-M3 antibody includes a common variable heavy domain (SEQ ID NO: 114) encoded by the nucleic acid sequence shown in SEQ ID NO: 113 and includes a kappa variable light domain (SEQ ID NO: 120) encoded by the nucleic acid sequence shown in SEQ ID NO: 119.

>5A3-M3-VL-NT
(SEQ ID NO: 119)
GACATCCAGATGACCCAGTCTCCATCCTCCCTGTCTGCATCTGTAGGAGA

CAGAGTCACCATCACTTGCCAGGCGAGTCAGTCCATTAGTAGTTATTTAA

ATTGGTATCAGCAGAAACCAGGGAAAGCCCCTAAGCTCCTGATCTACGCT

GCATCCTCGTTGGAAACAGGGGTCCCATCAAGGTTCAGTGGAAGTGGATC

TGGGACAGATTTTACTTTCACCATCAGCAGCCTGCAGCCTGAAGATATTG

```
>5A3-M3-VL-AA
                                (SEQ ID NO: 120)
DIQMTQSPSSLSASVGDRVTITCQASQSISSYLNWYQQKPGKAPKLLIYA

ASSLETGVPSRFSGSGSGTDFTFTISSLQPEDIATYYCQQKHPRGPRTFG

QGTKVEIK
```

The 5A3-M5 antibody includes a common heavy chain (SEQ ID NO: 2) encoded by the nucleic acid sequence shown in SEQ ID NO: 1 and includes a kappa light chain (SEQ ID NO: 10) encoded by the nucleic acid sequence shown in SEQ ID NO: 9.

```
>5A3-M5-LC-NT
                                (SEQ ID NO: 9)
GACATCCAGATGACCCAGTCTCCATCCTCCCTGTCTGCATCTGTAGGAGA

CAGAGTCACCATCACTTGCCAGGCGAGTCAGGACATTAATAAGTATTTAA

ATTGGTATCAGCAGAAACCAGGGAAAGCCCCTAAGCTCCTGATCTACGGT

GCATCCAGGTTGGAAACAGGGGTCCCATCAAGGTTCAGTGGAAGTGGATC

TGGGACAGATTTTACTTTCACCATCAGCAGCCTGCAGCCTGAAGATATTG

CAACATATTACTGTCAGCAGAAGCACCCCGGTACCCGAGGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>5A3-M5-LC-AA
                                (SEQ ID NO: 10)
DIQMTQSPSSLSASVGDRVTITCQASQDINKYLNWYQQKPGKAPKLLIYG

ASRLETGVPSRFSGSGSGTDFTFTISSLQPEDIATYYCQQKHPRYPRTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC
```

The 5A3-M5 antibody includes a common variable heavy domain (SEQ ID NO: 114) encoded by the nucleic acid sequence shown in SEQ ID NO: 113 and includes a kappa variable light domain (SEQ ID NO: 122) encoded by the nucleic acid sequence shown in SEQ ID NO: 121.

```
>5A3-M5-VL-NT
                                (SEQ ID NO: 121)
GACATCCAGATGACCCAGTCTCCATCCTCCCTGTCTGCATCTGTAGGAGA

CAGAGTCACCATCACTTGCCAGGCGAGTCAGGACATTAATAAGTATTTAA

ATTGGTATCAGCAGAAACCAGGGAAAGCCCCTAAGCTCCTGATCTACGGT

GCATCCAGGTTGGAAACAGGGGTCCCATCAAGGTTCAGTGGAAGTGGATC

TGGGACAGATTTTACTTTCACCATCAGCAGCCTGCAGCCTGAAGATATTG

CAACATATTACTGTCAGCAGAAGCACCCCGGTACCCGAGGACCTTCGGC

CAAGGGACCAAGGTGGAAATCAAA

>5A3-M5-VL-AA
                                (SEQ ID NO: 122)
DIQMTQSPSSLSASVGDRVTITCQASQDINKYLNWYQQKPGKAPKLLIYG

ASRLETGVPSRFSGSGSGTDFTFTISSLQPEDIATYYCQQKHPRYPRTFG

QGTKVEIK
```

The Ke8 antibody includes a common heavy chain (SEQ ID NO: 2) encoded by the nucleic acid sequence shown in SEQ ID NO: 1 and includes a kappa light chain (SEQ ID NO: 12) encoded by the nucleic acid sequence shown in SEQ ID NO: 11.

```
>Ke8-LC-NT
                                (SEQ ID NO: 11)
GACATCCAGATGACCCAGTCTCCATCCTCCCTGTCTGCATCTGTAGGAGA

CAGAGTCACCATCACTTGCCGGGCAAGTCAGAGCATTAGCAGCTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGTTCCACAAGCGGCGGCCGCAGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8-LC-AA
                                (SEQ ID NO: 12)
DIQMTQSPSSLSASVGDRVTITCRASQSISSYLNWYQQKPGKAPKLLIYA

ASSLQSGVPSRFSGSGSGTDFTLTISSLQPEDFATYYCQQFHKRRPQTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC
```

The Ke8 antibody includes a common variable heavy domain (SEQ ID NO: 114) encoded by the nucleic acid sequence shown in SEQ ID NO: 113 and includes a kappa variable light domain (SEQ ID NO: 124) encoded by the nucleic acid sequence shown in SEQ ID NO: 123.

```
>Ke8-VL-NT
                                (SEQ ID NO: 123)
GACATCCAGATGACCCAGTCTCCATCCTCCCTGTCTGCATCTGTAGGAGA

CAGAGTCACCATCACTTGCCGGGCAAGTCAGAGCATTAGCAGCTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG
```

>KE8-VL-AA
(SEQ ID NO: 124)
DIQMTQSPSSLSASVGDRVTITCRASQSISSYLNWYQQKPGKAPKLLIYA

ASSLQSGVPSRFSGSGSGTDFTLTISSLQPEDFATYYCQQFHKRRPQTFG

QGTKVEIK

The Ke8H5 antibody includes a common heavy chain (SEQ ID NO: 2) encoded by the nucleic acid sequence shown in SEQ ID NO: 1 and includes a kappa light chain (SEQ ID NO: 14) encoded by the nucleic acid sequence shown in SEQ ID NO: 13.

>KE8H5-LC-NT
(SEQ ID NO: 13)
GACATCCAGATGACCCAGTCTCCATCCTCCCTGTCTGCATCTGTAGGAGA

CAGAGTCACCATCACTTGCCGGGCAAGTCAGAGCATTGCGAGGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGTTCCATAAGCGTGCGCCGCAGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8H5-LC-AA
(SEQ ID NO: 14)
DIQMTQSPSSLSASVGDRVTITCRASQSIARYLNWYQQKPGKAPKLLIYA

ASSLQSGVPSRFSGSGSGTDFTLTISSLQPEDFATYYCQQFHKRAPQTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke8H5 antibody includes a common variable heavy domain (SEQ ID NO: 114) encoded by the nucleic acid sequence shown in SEQ ID NO: 113 and includes a kappa variable light domain (SEQ ID NO: 126) encoded by the nucleic acid sequence shown in SEQ ID NO: 125.

>KE8H5-VL-NT
(SEQ ID NO: 125)
GACATCCAGATGACCCAGTCTCCATCCTCCCTGTCTGCATCTGTAGGAGA

CAGAGTCACCATCACTTGCCGGGCAAGTCAGAGCATTGCGAGGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGTTCCACAAGCGGCGGCCGCAGACCTTCGGC

CAAGGGACCAAGGTGGAAATCAAA

>KE8H5-VL-AA
(SEQ ID NO: 126)
DIQMTQSPSSLSASVGDRVTITCRASQSIARYLNWYQQKPGKAPKLLIYA

ASSLQSGVPSRFSGSGSGTDFTLTISSLQPEDFATYYCQQFHKRAPQTFG

QGTKVEIK

The Ke8B2 antibody includes a common heavy chain (SEQ ID NO: 2) encoded by the nucleic acid sequence shown in SEQ ID NO: 1 and includes a kappa light chain (SEQ ID NO: 16) encoded by the nucleic acid sequence shown in SEQ ID NO: 15.

>KE8B2-LC-NT
(SEQ ID NO: 15)
GACATCCAGATGACCCAGTCTCCATCCTCCCTGTCTGCATCTGTAGGAGA

CAGAGTCACCATCACTTGCCGGGCAAGTCAGAGCATTGGTAAGTATTTAA

ATTGGTATCAGCAGAAACCAGGGAAAGCCCCTAAGCTCCTGATCTATGCG

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAAGCACCCGCGTGCCCCGCGGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8B2-LC-AA
(SEQ ID NO: 16)
DIQMTQSPSSLSASVGDRVTITCRASQSIGKYLNWYQQKPGKAPKLLIYA

ASRLQSGVPSRFSGSGSGTDFTLTISSLQPEDFATYYCQQKHPRAPRTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke8B2 antibody includes a common variable heavy domain (SEQ ID NO: 114) encoded by the nucleic acid sequence shown in SEQ ID NO: 113 and includes a kappa variable light domain (SEQ ID NO: 128) encoded by the nucleic acid sequence shown in SEQ ID NO: 127.

>KE8B2-VL-NT
(SEQ ID NO: 127)
GACATCCAGATGACCCAGTCTCCATCCTCCCTGTCTGCATCTGTAGGAGA

CAGAGTCACCATCACTTGCCGGGCAAGTCAGAGCATTGGTAAGTATTTAA

ATTGGTATCAGCAGAAACCAGGGAAAGCCCCTAAGCTCCTGATCTATGCG

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

```
>KE8B2-VL-AA
                                         (SEQ ID NO: 128)
DIQMTQSPSSLSASVGDRVTITCRASQSIGKYLNWYQQKPGKAPKLLIYA

ASRLQSGVPSRFSGSGSGTDFTLTISSLQPEDFATYYCQQKHPRAPRTFG

QGTKVEIK
```

The Ke8A2 antibody includes a common heavy chain (SEQ ID NO: 2) encoded by the nucleic acid sequence shown in SEQ ID NO: 1 and includes a kappa light chain (SEQ ID NO: 18) encoded by the nucleic acid sequence shown in SEQ ID NO: 17.

```
>KE8A2-LC-NT
                                          (SEQ ID NO: 17)
GACATCCAGATGACCCAGTCTCCATCCTCCCTGTCTGCATCTGTAGGAGA

CAGAGTCACCATCACTTGCCGGGCAAGTCAGAGCATTGATAGGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAAGCATCCCCGTGGGCCGAGGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8A2-LC-AA
                                          (SEQ ID NO: 18)
DIQMTQSPSSLSASVGDRVTITCRASQSIDRYLNWYQQKPGKAPKLLIYA

ASSLQSGVPSRFSGSGSGTDFTLTISSLQPEDFATYYCQQKHPRGPRTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC
```

The Ke8A2 antibody includes a common variable heavy domain (SEQ ID NO: 114) encoded by the nucleic acid sequence shown in SEQ ID NO: 113 and includes a kappa variable light domain (SEQ ID NO: 130) encoded by the nucleic acid sequence shown in SEQ ID NO: 129.

```
>KE8A2-VL-NT
                                         (SEQ ID NO: 129)
GACATCCAGATGACCCAGTCTCCATCCTCCCTGTCTGCATCTGTAGGAGA

CAGAGTCACCATCACTTGCCGGGCAAGTCAGAGCATTGATAGGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAAGCACCCGCGTGCCCCGCGGACCTTCGGC

CAAGGGACCAAGGTGGAAATCAAA

>KE8A2-VL-AA
                                         (SEQ ID NO: 130)
DIQMTQSPSSLSASVGDRVTITCRASQSIDRYLNWYQQKPGKAPKLLIYA

ASSLQSGVPSRFSGSGSGTDFTLTISSLQPEDFATYYCQQKHPRGPRTFG

QGTKVEIK
```

The Ke8E8 antibody includes a common heavy chain (SEQ ID NO: 2) encoded by the nucleic acid sequence shown in SEQ ID NO: 1 and includes a kappa light chain (SEQ ID NO: 20) encoded by the nucleic acid sequence shown in SEQ ID NO: 19.

```
>KE8E8-LC-NT
                                          (SEQ ID NO: 19)
GACATCCAGATGACCCAGTCTCCATCCTCCCTGTCTGCATCTGTAGGAGA

CAGAGTCACCATCACTTGCCAGGCGAGTCAGGACATTAATAAGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAAGCATCCCCGTGGGCCGCGGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8E8-LC-AA
                                          (SEQ ID NO: 20)
DIQMTQSPSSLSASVGDRVTITCQASQDINKYLNWYQQKPGKAPKLLIYA

ASSLQSGVPSRFSGSGSGTDFTLTISSLQPEDFATYYCQQKHPRGPRTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC
```

The Ke8E8 antibody includes a common variable heavy domain (SEQ ID NO: 114) encoded by the nucleic acid sequence shown in SEQ ID NO: 113 and includes a kappa variable light domain (SEQ ID NO: 132) encoded by the nucleic acid sequence shown in SEQ ID NO: 131.

```
>KE8E8-VL-NT
                                         (SEQ ID NO: 131)
GACATCCAGATGACCCAGTCTCCATCCTCCCTGTCTGCATCTGTAGGAGA

CAGAGTCACCATCACTTGCCAGGCGAGTCAGGACATTAATAAGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG
```

CAACTTACTACTGTCAGCAGAAGCATCCCCGTGGCCCGCGGACCTTCGGC

CAAGGGACCAAGGTGGAAATCAAA

>KE8E8-VL-AA
(SEQ ID NO: 132)
DIQMTQSPSSLSASVGDRVTITCQASQDINKYLNWYQQKPGKAPKLLIYA

ASSLQSGVPSRFSGSGSGTDFTLTISSLQPEDFATYYCQQKHPRGPRTFG

QGTKVEIK

The Ke8H3 antibody includes a common heavy chain (SEQ ID NO: 2) encoded by the nucleic acid sequence shown in SEQ ID NO: 1 and includes a kappa light chain (SEQ ID NO: 22) encoded by the nucleic acid sequence shown in SEQ ID NO: 21.

>KE8H3-LC-NT
(SEQ ID NO: 21)
GACATCCAGATGACCCAGTCTCCATCCTCCCTGTCTGCATCTGTAGGAGA

CAGAGTCACCATCACTTGCCGGGCAAGTCAGAGCATTAATAGGTATTTAA

ATTGGTATCAGCAGAAACCAGGGAAAGCCCCTAAGCTCCTGATCTATGCT

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAAGCATCCGCGTGGGCCGAGGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8H3-LC-AA
(SEQ ID NO: 22)
DIQMTQSPSSLSASVGDRVTITCRASQSINRYLNWYQQKPGKAPKLLIYA

ASRLQSGVPSRFSGSGSGTDFTLTISSLQPEDFATYYCQQKHPRGPRTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke8H3 antibody includes a common variable heavy domain (SEQ ID NO: 114) encoded by the nucleic acid sequence shown in SEQ ID NO: 113 and includes a kappa variable light domain (SEQ ID NO: 134) encoded by the nucleic acid sequence shown in SEQ ID NO: 133.

>KE8H3-VL-NT
(SEQ ID NO: 133)
GACATCCAGATGACCCAGTCTCCATCCTCCCTGTCTGCATCTGTAGGAGA

CAGAGTCACCATCACTTGCCGGGCAAGTCAGAGCATTAATAGGTATTTAA

ATTGGTATCAGCAGAAACCAGGGAAAGCCCCTAAGCTCCTGATCTATGCT

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAAGCATCCGCGTGGGCCGAGGACCTTCGGC

CAAGGGACCAAGGTGGAAATCAAA

>KE8H3-VL-AA
(SEQ ID NO: 134)
DIQMTQSPSSLSASVGDRVTITCRASQSINRYLNWYQQKPGKAPKLLIYA

ASRLQSGVPSRFSGSGSGTDFTLTISSLQPEDFATYYCQQKHPRGPRTFG

QGTKVEIK

The Ke8G6 antibody includes a common heavy chain (SEQ ID NO: 2) encoded by the nucleic acid sequence shown in SEQ ID NO: 1 and includes a kappa light chain (SEQ ID NO: 24) encoded by the nucleic acid sequence shown in SEQ ID NO: 23.

>KE8G6-LC-NT
(SEQ ID NO: 23)
GACATCCAGATGACCCAGTCTCCATCCTCCCTGTCTGCATCTGTAGGAGA

CAGAGTCACCATCACTTGCCGGGCAAGTCAGAGCATTGGTAGGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCGCGTGCGCCGAAGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8G6-LC-AA
(SEQ ID NO: 24)
DIQMTQSPSSLSASVGDRVTITCRASQSIGRYLNWYQQKPGKAPKLLIYA

ASSLQSGVPSRFSGSGSGTDFTLTISSLQPEDFATYYCQQMHPRAPKTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke8G6 antibody includes a common variable heavy domain (SEQ ID NO: 114) encoded by the nucleic acid sequence shown in SEQ ID NO: 113 and includes a kappa variable light domain (SEQ ID NO: 136) encoded by the nucleic acid sequence shown in SEQ ID NO: 135.

>KE8G6-VL-NT
(SEQ ID NO: 135)
GACATCCAGATGACCCAGTCTCCATCCTCCCTGTCTGCATCTGTAGGAGA

CAGAGTCACCATCACTTGCCGGGCAAGTCAGAGCATTGGTAGGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

```
CAACTTACTACTGTCAGCAGATGCATCCGCGTGCGCCGAAGACCTTCGGC

CAAGGGACCAAGGTGGAAATCAAA

>KE8G6-VL-AA
                                    (SEQ ID NO: 136)
DIQMTQSPSSLSASVGDRVTITCRASQSIGRYLNWYQQKPGKAPKLLIYA

ASSLQSGVPSRFSGSGSGTDFTLTISSLQPEDFATYYCQQMHPRAPKTFG

QGTKVEIK
```

The Ke8A3 antibody includes a common heavy chain (SEQ ID NO: 2) encoded by the nucleic acid sequence shown in SEQ ID NO: 1 and includes a kappa light chain (SEQ ID NO: 26) encoded by the nucleic acid sequence shown in SEQ ID NO: 25.

```
>KE8A3-LC-NT
                                    (SEQ ID NO: 25)
GACATCCAGATGACCCAGTCTCCATCCTCCCTGTCTGCATCTGTAGGAGA

CAGAGTCACCATCACTTGCCGGGTAAGTCAGAGCATTAGTAAGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAGGCATCCCCGTGGGCCGAGCACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8A3-LC-AA
                                    (SEQ ID NO: 26)
DIQMTQSPSSLSASVGDRVTITCRVSQSISKYLNWYQQKPGKAPKLLIYA

ASSLQSGVPSRFSGSGSGTDFTLTISSLQPEDFATYYCQQRHPRGPSTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC
```

The Ke8A3 antibody includes a common variable heavy domain (SEQ ID NO: 114) encoded by the nucleic acid sequence shown in SEQ ID NO: 113 and includes a kappa variable light domain (SEQ ID NO: 138) encoded by the nucleic acid sequence shown in SEQ ID NO: 137.

```
>KE8A3-VL-NT
                                    (SEQ ID NO: 137)
GACATCCAGATGACCCAGTCTCCATCCTCCCTGTCTGCATCTGTAGGAGA

CAGAGTCACCATCACTTGCCGGGTAAGTCAGAGCATTAGTAAGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG
```

```
CAACTTACTACTGTCAGCAGAGGCATCCCCGTGGGCCGAGCACCTTCGGC

CAAGGGACCAAGGTGGAAATCAAA

>KE8A3-VL-AA
                                    (SEQ ID NO: 138)
DIQMTQSPSSLSASVGDRVTITCRVSQSISKYLNWYQQKPGKAPKLLIYA

ASSLQSGVPSRFSGSGSGTDFTLTISSLQPEDFATYYCQQRHPRGPSTFG

QGTKVEIK
```

The Ke81A3 antibody includes a common heavy chain (SEQ ID NO: 2) encoded by the nucleic acid sequence shown in SEQ ID NO: 1 and includes a kappa light chain (SEQ ID NO: 28) encoded by the nucleic acid sequence shown in SEQ ID NO: 27.

```
>KE81A3-LC-NT
                                    (SEQ ID NO: 27)
GACATCCAGATGACCCAGTCTCCATCCTCCCTGTCTGCATCTGTAGGAGA

CAGAGTCACCATCACTTGCCAGGCGAGTCAGGACATTAATAGGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAGGCATCCGCGTGCCCCGCGGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE81A3-LC-AA
                                    (SEQ ID NO: 28)
DIQMTQSPSSLSASVGDRVTITCQASQDINRYLNWYQQKPGKAPKLLIYA

ASSLQSGVPSRFSGSGSGTDFTLTISSLQPEDFATYYCQQRHPRAPRTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC
```

The Ke81A3 antibody includes a common variable heavy domain (SEQ ID NO: 114) encoded by the nucleic acid sequence shown in SEQ ID NO: 113 and includes a kappa variable light domain (SEQ ID NO: 140) encoded by the nucleic acid sequence shown in SEQ ID NO: 139.

```
>KE81A3-VL-NT
                                    (SEQ ID NO: 139)
GACATCCAGATGACCCAGTCTCCATCCTCCCTGTCTGCATCTGTAGGAGA

CAGAGTCACCATCACTTGCCAGGCGAGTCAGGACATTAATAGGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG
```

```
>KE81A3-VL-AA
                                       (SEQ ID NO: 140)
DIQMTQSPSSLSASVGDRVTITCQASQDINRYLNWYQQKPGKAPKLLIYA

ASSLQSGVPSRFSGSGSGTDFTLTISSLQPEDFATYYCQQRHPRAPRTFG

QGTKVEIK
```

The Ke8A8 antibody includes a common heavy chain (SEQ ID NO: 2) encoded by the nucleic acid sequence shown in SEQ ID NO: 1 and includes a kappa light chain (SEQ ID NO: 30) encoded by the nucleic acid sequence shown in SEQ ID NO: 29.

```
>KE8A8-LC-NT
                                        (SEQ ID NO: 29)
GACATCCAGATGACCCAGTCTCCATCCTCCCTGTCTGCATCTGTAGGAGA

CAGAGTCACCATCACTTGCCGGGCAAGTCAGAGCATTAGTAAGTATTTAA

ATTGGTATCAGCAGAAACCAGGGAAAGCCCCTAAGCTCCTGATCTATGCT

GCATCCACTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCGCGTGCGCCGAAGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8A8-LC-AA
                                        (SEQ ID NO: 30)
DIQMTQSPSSLSASVGDRVTITCRASQSISKYLNWYQQKPGKAPKLLIYA

ASTLQSGVPSRFSGSGSGTDFTLTISSLQPEDFATYYCQQMHPRAPKTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC
```

The Ke8A8 antibody includes a common variable heavy domain (SEQ ID NO: 114) encoded by the nucleic acid sequence shown in SEQ ID NO: 113 and includes a kappa variable light domain (SEQ ID NO: 142) encoded by the nucleic acid sequence shown in SEQ ID NO: 141.

```
>KE8A8-VL-NT
                                       (SEQ ID NO: 141)
GACATCCAGATGACCCAGTCTCCATCCTCCCTGTCTGCATCTGTAGGAGA

CAGAGTCACCATCACTTGCCGGGCAAGTCAGAGCATTAGTAAGTATTTAA

ATTGGTATCAGCAGAAACCAGGGAAAGCCCCTAAGCTCCTGATCTATGCT

GCATCCACTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCGCGTGCCCCGCGGACCTTCGGC

CAAGGGACCAAGGTGGAAATCAAA

>KE8A8-VL-AA
                                       (SEQ ID NO: 142)
DIQMTQSPSSLSASVGDRVTITCRASQSISKYLNWYQQKPGKAPKLLIYA

ASTLQSGVPSRFSGSGSGTDFTLTISSLQPEDFATYYCQQMHPRAPKTFG

QGTKVEIK
```

The Ke8C7 antibody includes a common heavy chain (SEQ ID NO: 2) encoded by the nucleic acid sequence shown in SEQ ID NO: 1 and includes a kappa light chain (SEQ ID NO: 32) encoded by the nucleic acid sequence shown in SEQ ID NO: 31.

```
>KE8C7-LC-NT
                                        (SEQ ID NO: 31)
GACATCCAGATGACCCAGTCTCCATCCTCCCTGTCTGCATCTGTAGGAGA

CAGAGTCACCATCACTTGCCAGGCGAGTCAGGACATTAATAGGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGCGCCATCCGCGTGGCCCGAGGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8C7-LC-AA
                                        (SEQ ID NO: 32)
DIQMTQSPSSLSASVGDRVTITCQASQDINRYLNWYQQKPGKAPKLLIYA

ASSLQSGVPSRFSGSGSGTDFTLTISSLQPEDFATYYCQQRHPRGPRTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC
```

The Ke8C7 antibody includes a common variable heavy domain (SEQ ID NO: 114) encoded by the nucleic acid sequence shown in SEQ ID NO: 113 and includes a kappa variable light domain (SEQ ID NO: 144) encoded by the nucleic acid sequence shown in SEQ ID NO: 143.

```
>KE8C7-VL-NT
                                       (SEQ ID NO: 143)
GACATCCAGATGACCCAGTCTCCATCCTCCCTGTCTGCATCTGTAGGAGA

CAGAGTCACCATCACTTGCCAGGCGAGTCAGGACATTAATAGGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG
```

```
CAACTTACTACTGTCAGCAGCGCCATCCGCGTGGCCCGAGGACCTTCGGC

CAAGGGACCAAGGTGGAAATCAAA

>KE8C7-VL-AA
                                        (SEQ ID NO: 144)
DIQMTQSPSSLSASVGDRVTITCQASQDINRYLNWYQQKPGKAPKLLIYA

ASSLQSGVPSRFSGSGSGTDFTLTISSLQPEDFATYYCQQRHPRGPRTFG

QGTKVEIK
```

The Ke8G2 antibody includes a common heavy chain (SEQ ID NO: 2) encoded by the nucleic acid sequence shown in SEQ ID NO: 1 and includes a kappa light chain (SEQ ID NO: 34) encoded by the nucleic acid sequence shown in SEQ ID NO: 33.

```
>KE8G2-LC-NT
                                        (SEQ ID NO: 33)
GACATCCAGATGACCCAGTCTCCATCCTCCCTGTCTGCATCTGTAGGAGA

CAGAGTCACCATCACTTGCCGGGCAAGTCAGAGCATTGGTAGGTATTTAA

ATTGGTATCAGCAGAAACCAGGGAAAGCCCCTAAGCTCCTGATCTATGCG

GCATCCAGGTTGCAAAGTGGGGTCCCATCAAGGTTCAGTGGCAGTGGATC

TGGGACAGATTTCACTCTCACCATCAACAGTCTGCAACCTGAAGATTTTG

CAACTTACTACTGTCAGCAGAAGCATCCCCGTGCGCCGAGGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8G2-LC-AA
                                        (SEQ ID NO: 34)
DIQMTQSPSSLSASVGDRVTITCRASQSIGRYLNWYQQKPGKAPKLLIYA

ASRLQSGVPSRFSGSGSGTDFTLTINSLQPEDFATYYCQQKHPRAPRTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC
```

The Ke8G2 antibody includes a common variable heavy domain (SEQ ID NO: 114) encoded by the nucleic acid sequence shown in SEQ ID NO: 113 and includes a kappa variable light domain (SEQ ID NO: 146) encoded by the nucleic acid sequence shown in SEQ ID NO: 145.

```
>KE8G2-VL-NT
                                        (SEQ ID NO: 145)
GACATCCAGATGACCCAGTCTCCATCCTCCCTGTCTGCATCTGTAGGAGA

CAGAGTCACCATCACTTGCCGGGCAAGTCAGAGCATTGGTAGGTATTTAA

ATTGGTATCAGCAGAAACCAGGGAAAGCCCCTAAGCTCCTGATCTATGCG

GCATCCAGGTTGCAAAGTGGGGTCCCATCAAGGTTCAGTGGCAGTGGATC

TGGGACAGATTTCACTCTCACCATCAACAGTCTGCAACCTGAAGATTTTG
```

```
CAACTTACTACTGTCAGCAGAAGCATCCCCGTGCGCCGAGGACCTTCGGC

CAAGGGACCAAGGTGGAAATCAAA

>KE8G2-VL-AA
                                        (SEQ ID NO: 146)
DIQMTQSPSSLSASVGDRVTITCRASQSIGRYLNWYQQKPGKAPKLLIYA

ASRLQSGVPSRFSGSGSGTDFTLTINSLQPEDFATYYCQQKHPRAPRTFG

QGTKVEIK
```

The Ke81G9 antibody includes a common heavy chain (SEQ ID NO: 2) encoded by the nucleic acid sequence shown in SEQ ID NO: 1 and includes a kappa light chain (SEQ ID NO: 36) encoded by the nucleic acid sequence shown in SEQ ID NO: 35.

```
>KE81G9-LC-NT
                                        (SEQ ID NO: 35)
GACATCCAGATGACCCAGTCTCCATCCTCCCTGTCTGCATCTGTAGGAGA

CAGAGTCACCATCACTTGCCGGGCAAGTCAGAGCATTGATAAGTATTTAA

ATTGGTATCAGCAGAAACCAGGGAAAGCCCCTAAGCTCCTGATCTATGCG

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGCGGCATAAGCGTTCCCCGCAGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE81G9-LC-AA
                                        (SEQ ID NO: 36)
DIQMTQSPSSLSASVGDRVTITCRASQSIDKYLNWYQQKPGKAPKLLIYA

ASRLQSGVPSRFSGSGSGTDFTLTISSLQPEDFATYYCQQRHKRSPQTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC
```

The Ke81G9 antibody includes a common variable heavy domain (SEQ ID NO: 114) encoded by the nucleic acid sequence shown in SEQ ID NO: 113 and includes a kappa variable light domain (SEQ ID NO: 148) encoded by the nucleic acid sequence shown in SEQ ID NO: 147.

```
>KE81G9-VL-NT
                                        (SEQ ID NO: 147)
GACATCCAGATGACCCAGTCTCCATCCTCCCTGTCTGCATCTGTAGGAGA

CAGAGTCACCATCACTTGCCGGGCAAGTCAGAGCATTGATAAGTATTTAA

ATTGGTATCAGCAGAAACCAGGGAAAGCCCCTAAGCTCCTGATCTATGCG

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG
```

-continued

CAACTTACTACTGTCAGCAGCGGCATAAGCGTTCCCCGCAGACCTTCGGC

CAAGGGACCAAGGTGGAAATCAAA

>KE81G9-VL-AA
(SEQ ID NO: 148)
DIQMTQSPSSLSASVGDRVTITCRASQSIDKYLNWYQQKPGKAPKLLIYA

ASRLQSGVPSRFSGSGSGTDFTLTISSLQPEDFATYYCQQRHKRSPQTFG

QGTKVEIK

The Ke8F2 antibody includes a common heavy chain (SEQ ID NO: 2) encoded by the nucleic acid sequence shown in SEQ ID NO: 1 and includes a kappa light chain (SEQ ID NO: 38) encoded by the nucleic acid sequence shown in SEQ ID NO: 37.

>KE8F2-LC-NT
(SEQ ID NO: 37)
GACATCCAGATGACCCAGTCTCCATCCTCCCTGTCTGCATCTGTAGGAGA

CAGAGTCACCATCACTTGCCGGGCAAGTCAGAGCATTGATAAGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAAGCATCCGCGTGCGCCGCGGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8F2-LC-AA
(SEQ ID NO: 38)
DIQMTQSPSSLSASVGDRVTITCRASQSIDKYLNWYQQKPGKAPKLLIYA

ASSLQSGVPSRFSGSGSGTDFTLTISSLQPEDFATYYCQQKHPRAPRTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke8F2 antibody includes a common variable heavy domain (SEQ ID NO: 114) encoded by the nucleic acid sequence shown in SEQ ID NO: 113 and includes a kappa variable light domain (SEQ ID NO: 150) encoded by the nucleic acid sequence shown in SEQ ID NO: 149.

>KE8F2-VL-NT
(SEQ ID NO: 149)
GACATCCAGATGACCCAGTCTCCATCCTCCCTGTCTGCATCTGTAGGAGA

CAGAGTCACCATCACTTGCCGGGCAAGTCAGAGCATTGATAAGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAAGCATCCGCGTGCGCCGCGGACCTTCGGC

CAAGGGACCAAGGTGGAAATCAAA

>KE8F2-VL-AA
(SEQ ID NO: 150)
DIQMTQSPSSLSASVGDRVTITCRASQSIDKYLNWYQQKPGKAPKLLIYA

ASSLQSGVPSRFSGSGSGTDFTLTISSLQPEDFATYYCQQKHPRAPRTFG

QGTKVEIK

The Ke8B7 antibody includes a common heavy chain (SEQ ID NO: 2) encoded by the nucleic acid sequence shown in SEQ ID NO: 1 and includes a kappa light chain (SEQ ID NO: 40) encoded by the nucleic acid sequence shown in SEQ ID NO: 39.

>KE8B7-LC-NT
(SEQ ID NO: 39)
GACATCCAGATGACCCAGTCTCCATCCTCCCTGTCTGCATCTGTAGGAGA

CAGAGTCACCATCACTTGCCGGGCAAGTCAGAGCATTGGGAAGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCGCGTAGCCCGAAGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8B7-LC-AA
(SEQ ID NO: 40)
DIQMTQSPSSLSASVGDRVTITCRASQSIGKYLNWYQQKPGKAPKLLIYA

ASSLQSGVPSRFSGSGSGTDFTLTISSLQPEDFATYYCQQMHPRSPKTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke8B7 antibody includes a common variable heavy domain (SEQ ID NO: 114) encoded by the nucleic acid sequence shown in SEQ ID NO: 113 and includes a kappa variable light domain (SEQ ID NO: 152) encoded by the nucleic acid sequence shown in SEQ ID NO: 151.

>KE8B7-VL-NT
(SEQ ID NO: 151)
GACATCCAGATGACCCAGTCTCCATCCTCCCTGTCTGCATCTGTAGGAGA

CAGAGTCACCATCACTTGCCGGGCAAGTCAGAGCATTGGGAAGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCGCGTAGCCCGAAGACCTTCGGC

CAAGGGACCAAGGTGGAAATCAAA

>KE8B7-VL-AA
(SEQ ID NO: 152)
DIQMTQSPSSLSASVGDRVTITCRASQSIGKYLNWYQQKPGKAPKLLIYA

ASSLQSGVPSRFSGSGSGTDFTLTISSLQPEDFATYYCQQMHPRSPKTFG

QGTKVEIK

The Ke8C4 antibody includes a common heavy chain (SEQ ID NO: 2) encoded by the nucleic acid sequence shown in SEQ ID NO: 1 and includes a kappa light chain (SEQ ID NO: 42) encoded by the nucleic acid sequence shown in SEQ ID NO: 41.

>KE8C4-LC-NT
(SEQ ID NO: 41)
GACATCCAGATGACCCAGTCTCCATCCTCCCTGTCTGCATCTGTAGGAGA

CAGAGTCACCATCACTTGCCGGGCAAGTCAGAGCATTAGTAGGTATTTAA

ATTGGTATCAGCAGAAACCAGGGAAAGCCCCTAAGCTCCTGATCTATGCT

GCATCCAATTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCGCGTGGGCCGAAGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8C4-LC-AA
(SEQ ID NO: 42)
DIQMTQSPSSLSASVGDRVTITCRASQSISRYLNWYQQKPGKAPKLLIYA

ASNLQSGVPSRFSGSGSGTDFTLTISSLQPEDFATYYCQQMHPRGPKTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke8C4 antibody includes a common variable heavy domain (SEQ ID NO: 114) encoded by the nucleic acid sequence shown in SEQ ID NO: 113 and includes a kappa variable light domain (SEQ ID NO: 154) encoded by the nucleic acid sequence shown in SEQ ID NO: 153.

>KE8C4-VL-NT
(SEQ ID NO: 153)
GACATCCAGATGACCCAGTCTCCATCCTCCCTGTCTGCATCTGTAGGAGA

CAGAGTCACCATCACTTGCCGGGCAAGTCAGAGCATTAGTAGGTATTTAA

ATTGGTATCAGCAGAAACCAGGGAAAGCCCCTAAGCTCCTGATCTATGCT

GCATCCAATTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCGCGTGGGCCGAAGACCTTCGGC

CAAGGGACCAAGGTGGAAATCAAA

>KE8C4-VL-AA
(SEQ ID NO: 154)
DIQMTQSPSSLSASVGDRVTITCRASQSISRYLNWYQQKPGKAPKLLIYA

ASNLQSGVPSRFSGSGSGTDFTLTISSLQPEDFATYYCQQMHPRGPKTFG

QGTKVEIK

The Ke8F1 antibody includes a common heavy chain (SEQ ID NO: 2) encoded by the nucleic acid sequence shown in SEQ ID NO: 1 and includes a kappa light chain (SEQ ID NO: 44) encoded by the nucleic acid sequence shown in SEQ ID NO: 43.

>KE8F1-LC-NT
(SEQ ID NO: 43)
GACATCCAGATGACCCAGTCTCCATCCTCCCTGTCTGCATCTGTAGGAGA

CAGAGTCACCATCACTTGCCGGGCAAGTCAGAGCATTGCTTCTTATGTAA

ATTGGTATCAGCAGAAACCAGGGAAAGCCCCTAAGCTCCTGATCTATGCT

GCATCCGGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGTTCCATAAGCGTCGGCCGCAGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8F1-LC-AA
(SEQ ID NO: 44)
DIQMTQSPSSLSASVGDRVTITCRASQSIASYVNWYQQKPGKAPKLLIYA

ASGLQSGVPSRFSGSGSGTDFTLTISSLQPEDFATYYCQQFHKRRPQTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke8F1 antibody includes a common variable heavy domain (SEQ ID NO: 114) encoded by the nucleic acid sequence shown in SEQ ID NO: 113 and includes a kappa variable light domain (SEQ ID NO: 156) encoded by the nucleic acid sequence shown in SEQ ID NO: 155.

>KE8F1-VL-NT
(SEQ ID NO: 155)
GACATCCAGATGACCCAGTCTCCATCCTCCCTGTCTGCATCTGTAGGAGA

CAGAGTCACCATCACTTGCCGGGCAAGTCAGAGCATTGCTTCTTATGTAA

ATTGGTATCAGCAGAAACCAGGGAAAGCCCCTAAGCTCCTGATCTATGCT

GCATCCGGTTTGCAAAGTGGGGTCCCATCAAGGTTCAGTGGCAGTGGATC

TGGGACAGATTTCACTCTCACCATCAGCAGTCTGCAACCTGAAGATTTTG

```
CAACTTACTACTGTCAGCAGTTCCATAAGCGTCGGCCGCAGACCTTCGGC

CAAGGGACCAAGGTGGAAATCAAA

>KE8F1-VL-AA
                                        (SEQ ID NO: 156)
DIQMTQSPSSLSASVGDRVTITCRASQSIASYVNWYQQKPGKAPKLLIYA

ASGLQSGVPSRFSGSGSGTDFTLTISSLQPEDFATYYCQQFHKRRPQTFG

QGTKVEIK
```

The Ke8G11 antibody includes a common heavy chain (SEQ ID NO: 2) encoded by the nucleic acid sequence shown in SEQ ID NO: 1 and includes a kappa light chain (SEQ ID NO: 46) encoded by the nucleic acid sequence shown in SEQ ID NO: 45.

```
>KE8G11-LC-NT
                                        (SEQ ID NO: 45)
GACATCCAGATGACCCAGTCTCCATCCTCCCTGTCTGCATCTGTAGGAGA

CAGAGTCACCATCACTTGCCGGGCAAGTCAGAGCATTGGGAGGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCGCGTGGGCCGAAGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8G11-LC-AA
                                        (SEQ ID NO: 46)
DIQMTQSPSSLSASVGDRVTITCRASQSIGRYLNWYQQKPGKAPKLLIYA

ASSLQSGVPSRFSGSGSGTDFTLTISSLQPEDFATYYCQQMHPRGPKTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC
```

The Ke8G11 antibody includes a common variable heavy domain (SEQ ID NO: 114) encoded by the nucleic acid sequence shown in SEQ ID NO: 113 and includes a kappa variable light domain (SEQ ID NO: 158) encoded by the nucleic acid sequence shown in SEQ ID NO: 157.

```
>KE8G11-VL-NT
                                        (SEQ ID NO: 157)
GACATCCAGATGACCCAGTCTCCATCCTCCCTGTCTGCATCTGTAGGAGA

CAGAGTCACCATCACTTGCCGGGCAAGTCAGAGCATTGGGAGGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG
```

```
CAACTTACTACTGTCAGCAGATGCATCCGCGTGGGCCGAAGACCTTCGGC

CAAGGGACCAAGGTGGAAATCAAA

>KE8G11-VL-AA
                                        (SEQ ID NO: 158)
DIQMTQSPSSLSASVGDRVTITCRASQSIGRYLNWYQQKPGKAPKLLIYA

ASSLQSGVPSRFSGSGSGTDFTLTISSLQPEDFATYYCQQMHPRGPKTFG

QGTKVEIK
```

The Ke8H6 antibody includes a common heavy chain (SEQ ID NO: 2) encoded by the nucleic acid sequence shown in SEQ ID NO: 1 and includes a kappa light chain (SEQ ID NO: 48) encoded by the nucleic acid sequence shown in SEQ ID NO: 47.

```
>KE8H6-LC-NT
                                        (SEQ ID NO: 47)
GACATCCAGATGACCCAGTCTCCATCCTCCCTGTCTGCATCTGTAGGAGA

CAGAGTCACCATCACTTGCCGGGCAAGTCAGAGCATTAGTAAGTATTTAA

ATTGGTATCAGCAGAAACCAGGGAAAGCCCCTAAGCTCCTGATCTATAAT

GCATCCACTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAGGCATCCGCGTGGGCCGCGCACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8H6-LC-AA
                                        (SEQ ID NO: 48)
DIQMTQSPSSLSASVGDRVTITCRASQSISKYLNWYQQKPGKAPKLLIYN

ASTLQSGVPSRFSGSGSGTDFTLTISSLQPEDFATYYCQQRHPRGPRTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC
```

The Ke8H6 antibody includes a common variable heavy domain (SEQ ID NO: 114) encoded by the nucleic acid sequence shown in SEQ ID NO: 113 and includes a kappa variable light domain (SEQ ID NO: 160) encoded by the nucleic acid sequence shown in SEQ ID NO: 159.

```
>KE8H6-VL-NT
                                        (SEQ ID NO: 159)
GACATCCAGATGACCCAGTCTCCATCCTCCCTGTCTGCATCTGTAGGAGA

CAGAGTCACCATCACTTGCCGGGCAAGTCAGAGCATTAGTAAGTATTTAA

ATTGGTATCAGCAGAAACCAGGGAAAGCCCCTAAGCTCCTGATCTATAAT

GCATCCACTTTGCAAAGTGGGGTCCCATCAAGGTTCAGTGGCAGTGGATC

TGGGACAGATTTCACTCTCACCATCAGCAGTCTGCAACCTGAAGATTTTG
```

CAACTTACTACTGTCAGCAGAGGCATCCGCGTGGGCCGCGCACCTTCGGC

CAAGGGACCAAGGTGGAAATCAAA

>KE8H6-VL-AA (SEQ ID NO: 160)
DIQMTQSPSSLSASVGDRVTITCRASQSISKYLNWYQQKPGKAPKLLIYN

ASTLQSGVPSRFSGSGSGTDFTLTISSLQPEDFATYYCQQRHPRGPRTFG

QGTKVEIK

The Ke84G9 antibody includes a common heavy chain (SEQ ID NO: 2) encoded by the nucleic acid sequence shown in SEQ ID NO: 1 and includes a kappa light chain (SEQ ID NO: 50) encoded by the nucleic acid sequence shown in SEQ ID NO: 49.

>KE84G9-LC-NT (SEQ ID NO: 49)
GACATCCAGATGACCCAGTCTCCATCCTCCCTGTCTGCATCTGTAGGAGA

CAGAGTCACCATCACTTGCCGGGCAAGTCAGAGCATTAGTAAGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAAGCATCCGCGTAGCCCGCGGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE84G9-LC-AA (SEQ ID NO: 50)
DIQMTQSPSSLSASVGDRVTITCRASQSISKYLNWYQQKPGKAPKLLIYA

ASSLQSGVPSRFSGSGSGTDFTLTISSLQPEDFATYYCQQKHPRSPRTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke84G9 antibody includes a common variable heavy domain (SEQ ID NO: 114) encoded by the nucleic acid sequence shown in SEQ ID NO: 113 and includes a kappa variable light domain (SEQ ID NO: 162) encoded by the nucleic acid sequence shown in SEQ ID NO: 161.

>KE84G9-VL-NT (SEQ ID NO: 161)
GACATCCAGATGACCCAGTCTCCATCCTCCCTGTCTGCATCTGTAGGAGA

CAGAGTCACCATCACTTGCCGGGCAAGTCAGAGCATTAGTAAGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAAGCATCCGCGTAGCCCGCGGACCTTCGGC

CAAGGGACCAAGGTGGAAATCAAA

>KE84G9-VL-AA (SEQ ID NO: 162)
DIQMTQSPSSLSASVGDRVTITCRASQSISKYLNWYQQKPGKAPKLLIYA

ASSLQSGVPSRFSGSGSGTDFTLTISSLQPEDFATYYCQQKHPRSPRTFG

QGTKVEIK

The Ke8A4 antibody includes a common heavy chain (SEQ ID NO: 2) encoded by the nucleic acid sequence shown in SEQ ID NO: 1 and includes a kappa light chain (SEQ ID NO: 52) encoded by the nucleic acid sequence shown in SEQ ID NO: 51.

>KE8A4-LC-NT (SEQ ID NO: 51)
GACATCCAGATGACCCAGTCTCCATCCTCCCTGTCTGCATCTGTAGGAGA

CAGAGTCACCATCACTTGCCGGGCAAGTCAGAGCATTGCTAAGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGTTCCATAAGCGTAGCCCGCAGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE8A4-LC-AA (SEQ ID NO: 52)
DIQMTQSPSSLSASVGDRVTITCRASQSIAKYLNWYQQKPGKAPKLLIYA

ASSLQSGVPSRFSGSGSGTDFTLTISSLQPEDFATYYCQQFHKRSPQTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke8A4 antibody includes a common variable heavy domain (SEQ ID NO: 114) encoded by the nucleic acid sequence shown in SEQ ID NO: 113 and includes a kappa variable light domain (SEQ ID NO: 164) encoded by the nucleic acid sequence shown in SEQ ID NO: 163.

>KE8A4-VL-NT (SEQ ID NO: 163)
GACATCCAGATGACCCAGTCTCCATCCTCCCTGTCTGCATCTGTAGGAGA

CAGAGTCACCATCACTTGCCGGGCAAGTCAGAGCATTGCTAAGTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGTTCCATAAGCGTAGCCCGCAGACCTTCGGC

CAAGGGACCAAGGTGGAAATCAAA

>KE8A4-VL-AA
(SEQ ID NO: 164)
DIQMTQSPSSLSASVGDRVTITCRASQSIAKYLNWYQQKPGKAPKLLIYA

ASSLQSGVPSRFSGSGSGTDFTLTISSLQPEDFATYYCQQFHKRSPQTFG

QGTKVEIK

The Ke86G9 antibody includes a common heavy chain (SEQ ID NO: 2) encoded by the nucleic acid sequence shown in SEQ ID NO: 1 and includes a kappa light chain (SEQ ID NO: 54) encoded by the nucleic acid sequence shown in SEQ ID NO: 53.

>KE86G9-LC-NT
(SEQ ID NO: 53)
GACATCCAGATGACCCAGTCTCCATCCTCCCTGTCTGCATCTGTAGGAGA

CAGAGTCACCATCACTTGCCGGGCAAGTCAGAGCATTAGTAAGTATTTAA

ATTGGTATCAGCAGAAACCAGGGAAAGCCCCTAAGCTCCTGATCTATAAT

GCATCCAATTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAGGCATCCGCGTGGGCCGACCACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KE86G9-LC-AA
(SEQ ID NO: 54)
DIQMTQSPSSLSASVGDRVTITCRASQSISKYLNWYQQKPGKAPKLLIYN

ASNLQSGVPSRFSGSGSGTDFTLTISSLQPEDFATYYCQQRHPRGPTTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ke86G9 antibody includes a common variable heavy domain (SEQ ID NO: 114) encoded by the nucleic acid sequence shown in SEQ ID NO: 113 and includes a kappa variable light domain (SEQ ID NO: 166) encoded by the nucleic acid sequence shown in SEQ ID NO: 165.

>KE86G9-VL-NT
(SEQ ID NO: 165)
GACATCCAGATGACCCAGTCTCCATCCTCCCTGTCTGCATCTGTAGGAGA

CAGAGTCACCATCACTTGCCGGGCAAGTCAGAGCATTAGTAAGTATTTAA

ATTGGTATCAGCAGAAACCAGGGAAAGCCCCTAAGCTCCTGATCTATAAT

GCATCCAATTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGAGGCATCCGCGTGGGCCGACCACCTTCGGC

CAAGGGACCAAGGTGGAAATCAAA

>KE86G9-VL-AA
(SEQ ID NO: 166)
DIQMTQSPSSLSASVGDRVTITCRASQSISKYLNWYQQKPGKAPKLLIYN

ASNLQSGVPSRFSGSGSGTDFTLTISSLQPEDFATYYCQQRHPRGPTTFG

QGTKVEIK

The Ka3 antibody includes a common heavy chain (SEQ ID NO: 2) encoded by the nucleic acid sequence shown in SEQ ID NO: 1 and includes a kappa light chain (SEQ ID NO: 56) encoded by the nucleic acid sequence shown in SEQ ID NO: 55.

>KA3-LC-NT
(SEQ ID NO: 55)
GACATCCAGATGACCCAGTCTCCATCCTCCCTGTCTGCATCTGTAGGAGA

CAGAGTCACCATCACTTGCCGGGCAAGTCAGAGCATTAGCAGCTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCACCCGCGCGCCCCGAAGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KA3-LC-AA
(SEQ ID NO: 56)
DIQMTQSPSSLSASVGDRVTITCRASQSISSYLNWYQQKPGKAPKLLIYA

ASSLQSGVPSRFSGSGSGTDFTLTISSLQPEDFATYYCQQMHPRAPKTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ka3 antibody includes a common variable heavy domain (SEQ ID NO: 114) encoded by the nucleic acid sequence shown in SEQ ID NO: 113 and includes a kappa variable light domain (SEQ ID NO: 168) encoded by the nucleic acid sequence shown in SEQ ID NO: 167.

>KA3-VL-NT
(SEQ ID NO: 167)
GACATCCAGATGACCCAGTCTCCATCCTCCCTGTCTGCATCTGTAGGAGA

CAGAGTCACCATCACTTGCCGGGCAAGTCAGAGCATTAGCAGCTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCACCCGCGCGCCCCGAAGACCTTCGGC

CAAGGGACCAAGGTGGAAATCAAA

>KA3-VL-AA
(SEQ ID NO: 168)
DIQMTQSPSSLSASVGDRVTITCRASQSISSYLNWYQQKPGKAPKLLIYA

ASSLQSGVPSRFSGSGSGTDFTLTISSLQPEDFATYYCQQMHPRAPKTFG

QGTKVEIK

The Ka3A2 antibody includes a common heavy chain (SEQ ID NO: 2) encoded by the nucleic acid sequence shown in SEQ ID NO: 1 and includes a kappa light chain (SEQ ID NO: 58) encoded by the nucleic acid sequence shown in SEQ ID NO: 57.

>KA3A2-LC-NT
(SEQ ID NO: 57)
GACATCCAGATGACCCAGTCTCCATCCTCCCTGTCTGCATCTGTAGGAGA

CAGAGTCACCATCACTTGCCGGGCAAGTCAGAGCATTAGTAAGTATTTAA

ATTGGTATCAGCAGAAACCAGGGAAAGCCCCTAAGCTCCTGATCTATGCT

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCTCGCTCGCCGAAAACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KA3A2-LC-AA
(SEQ ID NO: 58)
DIQMTQSPSSLSASVGDRVTITCRASQSISKYLNWYQQKPGKAPKLLIYA

ASRLQSGVPSRFSGSGSGTDFTLTISSLQPEDFATYYCQQMHPRSPKTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ka3A2 antibody includes a common variable heavy domain (SEQ ID NO: 114) encoded by the nucleic acid sequence shown in SEQ ID NO: 113 and includes a kappa variable light domain (SEQ ID NO: 170) encoded by the nucleic acid sequence shown in SEQ ID NO: 169.

>KA3A2-VL-NT
(SEQ ID NO: 169)
GACATCCAGATGACCCAGTCTCCATCCTCCCTGTCTGCATCTGTAGGAGA

CAGAGTCACCATCACTTGCCGGGCAAGTCAGAGCATTAGTAAGTATTTAA

ATTGGTATCAGCAGAAACCAGGGAAAGCCCCTAAGCTCCTGATCTATGCT

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCTCGCTCGCCGAAAACCTTCGGC

CAAGGGACCAAGGTGGAAATCAAA

>KA3A2-VL-AA
(SEQ ID NO: 170)
DIQMTQSPSSLSASVGDRVTITCRASQSISKYLNWYQQKPGKAPKLLIYA

ASRLQSGVPSRFSGSGSGTDFTLTISSLQPEDFATYYCQQMHPRSPKTFG

QGTKVEIK

The Ka3H3 antibody includes a common heavy chain (SEQ ID NO: 2) encoded by the nucleic acid sequence shown in SEQ ID NO: 1 and includes a kappa light chain (SEQ ID NO: 60) encoded by the nucleic acid sequence shown in SEQ ID NO: 59.

>KA3H3-LC-NT
(SEQ ID NO: 59)
GACATCCAGATGACCCAGTCTCCATCCTCCCTGTCTGCATCTGTAGGAGA

CAGAGTCACCATCACTTGCCAGGCGAGTCAGGACATTGCTAAGTATTTAA

ATTGGTATCAGCAGAAACCAGGGAAAGCCCCTAAGCTCCTGATCTATGCT

GCATCCGCTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCTCGCTCGCCGAAAACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KA3H3-LC-AA
(SEQ ID NO: 60)
DIQMTQSPSSLSASVGDRVTITCQASQDIAKYLNWYQQKPGKAPKLLIYA

ASALQSGVPSRFSGSGSGTDFTLTISSLQPEDFATYYCQQMHPRSPKTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ka3H3 antibody includes a common variable heavy domain (SEQ ID NO: 114) encoded by the nucleic acid sequence shown in SEQ ID NO: 113 and includes a kappa variable light domain (SEQ ID NO: 172) encoded by the nucleic acid sequence shown in SEQ ID NO: 171.

>KA3H3-VL-NT
(SEQ ID NO: 171)
GACATCCAGATGACCCAGTCTCCATCCTCCCTGTCTGCATCTGTAGGAGA

CAGAGTCACCATCACTTGCCAGGCGAGTCAGGACATTGCTAAGTATTTAA

ATTGGTATCAGCAGAAACCAGGGAAAGCCCCTAAGCTCCTGATCTATGCT

GCATCCGCTTTGCAAAGTGGGGTCCCATCAAGGTTCAGTGGCAGTGGATC

TGGGACAGATTTCACTCTCACCATCAGCAGTCTGCAACCTGAAGATTTTG

-continued
```
CAACTTACTACTGTCAGCAGATGCATCCTCGCTCGCCGAAAACCTTCGGC

CAAGGGACCAAGGTGGAAATCAAA
```
>KA3H3-VL-AA
(SEQ ID NO: 172)
```
DIQMTQSPSSLSASVGDRVTITCQASQDIAKYLNWYQQKPGKAPKLLIYA

ASALQSGVPSRFSGSGSGTDFTLTISSLQPEDFATYYCQQMHPRSPKTFG

QGTKVEIK
```

The Ka3A3 antibody includes a common heavy chain (SEQ ID NO: 2) encoded by the nucleic acid sequence shown in SEQ ID NO: 1 and includes a kappa light chain (SEQ ID NO: 62) encoded by the nucleic acid sequence shown in SEQ ID NO: 61.

>KA3A3-LC-NT
(SEQ ID NO: 61)
```
GACATCCAGATGACCCAGTCTCCATCCTCCCTGTCTGCATCTGTAGGAGA

CAGAGTCACCATCACTTGCCGGGCAAGTCAGAGCATTGCTAGTTATTTAA

ATTGGTATCAGCAGAAACCAGGGAAAGCCCCTAAGCTCCTGATCTATGCG

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCTCGCGCGCCGAAAACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA
```
>KA3A3-LC-AA
(SEQ ID NO: 62)
```
DIQMTQSPSSLSASVGDRVTITCRASQSIASYLNWYQQKPGKAPKLLIYA

ASRLQSGVPSRFSGSGSGTDFTLTISSLQPEDFATYYCQQMHPRAPKTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC
```

The Ka3A3 antibody includes a common variable heavy domain (SEQ ID NO: 114) encoded by the nucleic acid sequence shown in SEQ ID NO: 113 and includes a kappa variable light domain (SEQ ID NO: 174) encoded by the nucleic acid sequence shown in SEQ ID NO: 173.

>KA3A3-VL-NT
(SEQ ID NO: 173)
```
GACATCCAGATGACCCAGTCTCCATCCTCCCTGTCTGCATCTGTAGGAGA

CAGAGTCACCATCACTTGCCGGGCAAGTCAGAGCATTGCTAGTTATTTAA

ATTGGTATCAGCAGAAACCAGGGAAAGCCCCTAAGCTCCTGATCTATGCG

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG
```

```
CAACTTACTACTGTCAGCAGATGCATCCTCGCGCGCCGAAAACCTTCGGC

CAAGGGACCAAGGTGGAAATCAAA
```
>KA3A3-VL-AA
(SEQ ID NO: 174)
```
DIQMTQSPSSLSASVGDRVTITCRASQSIASYLNWYQQKPGKAPKLLIYA

ASRLQSGVPSRFSGSGSGTDFTLTISSLQPEDFATYYCQQMHPRAPKTFG

QGTKVEIK
```

The Ka3H8 antibody includes a common heavy chain (SEQ ID NO: 2) encoded by the nucleic acid sequence shown in SEQ ID NO: 1 and includes a kappa light chain (SEQ ID NO: 64) encoded by the nucleic acid sequence shown in SEQ ID NO: 63.

>KA3H8-LC-NT
(SEQ ID NO: 63)
```
GACATCCAGATGACCCAGTCTCCATCCTCCCTGTCTGCATCTGTAGGAGA

CAGAGTCACCATCACTTGCCGGGCAAGTCAGAGCATTGCGAGTTATTTAA

ATTGGTATCAGCAGAAACCAGGGAAAGCCCCTAAGCTCCTGATCTATGCG

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCTCGCTCGCCGAAAACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA
```
>KA3H8-LC-AA
(SEQ ID NO: 64)
```
DIQMTQSPSSLSASVGDRVTITCRASQSIASYLNWYQQKPGKAPKLLIYA

ASRLQSGVPSRFSGSGSGTDFTLTISSLQPEDFATYYCQQMHPRSPKTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC
```

The Ka3H8 antibody includes a common variable heavy domain (SEQ ID NO: 114) encoded by the nucleic acid sequence shown in SEQ ID NO: 113 and includes a kappa variable light domain (SEQ ID NO: 176) encoded by the nucleic acid sequence shown in SEQ ID NO: 175.

>KA3H8-VL-NT
(SEQ ID NO: 175)
```
GACATCCAGATGACCCAGTCTCCATCCTCCCTGTCTGCATCTGTAGGAGA

CAGAGTCACCATCACTTGCCGGGCAAGTCAGAGCATTGCGAGTTATTTAA

ATTGGTATCAGCAGAAACCAGGGAAAGCCCCTAAGCTCCTGATCTATGCG

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG
```

CAACTTACTACTGTCAGCAGATGCATCCTCGCTCGCCGAAAACCTTCGGC

CAAGGGACCAAGGTGGAAATCAAA

>KA3H8-VL-AA (SEQ ID NO: 176)
DIQMTQSPSSLSASVGDRVTITCRASQSIASYLNWYQQKPGKAPKLLIYA

ASRLQSGVPSRFSGSGSGTDFTLTISSLQPEDFATYYCQQMHPRSPKTFG

QGTKVEIK

The Ka3B2 antibody includes a common heavy chain (SEQ ID NO: 2) encoded by the nucleic acid sequence shown in SEQ ID NO: 1 and includes a kappa light chain (SEQ ID NO: 66) encoded by the nucleic acid sequence shown in SEQ ID NO: 65.

>KA3B2-LC-NT (SEQ ID NO: 65)
GACATCCAGATGACCCAGTCTCCATCCTCCCTGTCTGCATCTGTAGGAGA

CAGAGTCACCATCACTTGCCGGGCAAGTCAGAACATTGGTAAGTATTTAA

ATTGGTATCAGCAGAAACCAGGGAAAGCCCCTAAGCTCCTGATCTATAGT

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCTCGCGCGCCGAAAACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KA3B2-LC-AA (SEQ ID NO: 66)
DIQMTQSPSSLSASVGDRVTITCRASQNIGKYLNWYQQKPGKAPKLLIYS

ASRLQSGVPSRFSGSGSGTDFTLTISSLQPEDFATYYCQQMHPRAPKTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ka3B2 antibody includes a common variable heavy domain (SEQ ID NO: 114) encoded by the nucleic acid sequence shown in SEQ ID NO: 113 and includes a kappa variable light domain (SEQ ID NO: 178) encoded by the nucleic acid sequence shown in SEQ ID NO: 177.

>KA3B2-VL-NT (SEQ ID NO: 177)
GACATCCAGATGACCCAGTCTCCATCCTCCCTGTCTGCATCTGTAGGAGA

CAGAGTCACCATCACTTGCCGGGCAAGTCAGAACATTGGTAAGTATTTAA

ATTGGTATCAGCAGAAACCAGGGAAAGCCCCTAAGCTCCTGATCTATAGT

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCTCGCGCGCCGAAAACCTTCGGC

CAAGGGACCAAGGTGGAAATCAAA

>KA3B2-VL-AA (SEQ ID NO: 178)
DIQMTQSPSSLSASVGDRVTITCRASQNIGKYLNWYQQKPGKAPKLLIYS

ASRLQSGVPSRFSGSGSGTDFTLTISSLQPEDFATYYCQQMHPRAPKTFG

QGTKVEIK

The Ka3C5 antibody includes a common heavy chain (SEQ ID NO: 2) encoded by the nucleic acid sequence shown in SEQ ID NO: 1 and includes a kappa light chain (SEQ ID NO: 68) encoded by the nucleic acid sequence shown in SEQ ID NO: 67.

>KA3C5-LC-NT (SEQ ID NO: 67)
GACATCCAGATGACCCAGTCTCCATCCTCCCTGTCTGCATCTGTAGGAGA

CAGAGTCACCATCACTTGCCGGGCAAGTCAGAGCATTAGTAGGTATTTAA

ATTGGTATCAGCAGAAACCAGGGAAAGCCCCTAAGCTCCTGATCTATTCT

GCATCCTCTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCTCGCGCCCGAAAACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KA3C5-LC-AA (SEQ ID NO: 68)
DIQMTQSPSSLSASVGDRVTITCRASQSISRYLNWYQQKPGKAPKLLIYS

ASSLQSGVPSRFSGSGSGTDFTLTISSLQPEDFATYYCQQMHPRAPKTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ka3C5 antibody includes a common variable heavy domain (SEQ ID NO: 114) encoded by the nucleic acid sequence shown in SEQ ID NO: 113 and includes a kappa variable light domain (SEQ ID NO: 180) encoded by the nucleic acid sequence shown in SEQ ID NO: 179.

>KA3C5-VL-NT (SEQ ID NO: 179)
GACATCCAGATGACCCAGTCTCCATCCTCCCTGTCTGCATCTGTAGGAGA

CAGAGTCACCATCACTTGCCGGGCAAGTCAGAGCATTAGTAGGTATTTAA

ATTGGTATCAGCAGAAACCAGGGAAAGCCCCTAAGCTCCTGATCTATTCT

GCATCCTCTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCTCGCGCCCCGAAAACCTTCGGC

CAAGGGACCAAGGTGGAAATCAAA

>KA3C5-VL-AA
(SEQ ID NO: 180)
DIQMTQSPSSLSASVGDRVTITCRASQSISRYLNWYQQKPGKAPKLLIYS

ASSLQSGVPSRFSGSGSGTDFTLTISSLQPEDFATYYCQQMHPRAPKTFG

QGTKVEIK

The Ka3G2 antibody includes a common heavy chain (SEQ ID NO: 2) encoded by the nucleic acid sequence shown in SEQ ID NO: 1 and includes a kappa light chain (SEQ ID NO: 70) encoded by the nucleic acid sequence shown in SEQ ID NO: 69.

>KA3G2-LC-NT
(SEQ ID NO: 69)
GACATCCAGATGACCCAGTCTCCATCCTCCCTGTCTGCATCTGTAGGAGA

CAGAGTCACCATCACTTGCCGGGCAAGTCAGAGCATTGATAAGTATTTAA

ATTGGTATCAGCAGAAACCAGGGAAAGCCCCTAAGCTCCTGATCTATGCT

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCTCGCGGGCCGAAAACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KA3G2-LC-AA
(SEQ ID NO: 70)
DIQMTQSPSSLSASVGDRVTITCRASQSIDKYLNWYQQKPGKAPKLLIYA

ASRLQSGVPSRFSGSGSGTDFTLTISSLQPEDFATYYCQQMHPRGPKTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ka3G2 antibody includes a common variable heavy domain (SEQ ID NO: 114) encoded by the nucleic acid sequence shown in SEQ ID NO: 113 and includes a kappa variable light domain (SEQ ID NO: 182) encoded by the nucleic acid sequence shown in SEQ ID NO: 181.

>KA3G2-VL-NT
(SEQ ID NO: 181)
GACATCCAGATGACCCAGTCTCCATCCTCCCTGTCTGCATCTGTAGGAGA

CAGAGTCACCATCACTTGCCGGGCAAGTCAGAGCATTGATAAGTATTTAA

ATTGGTATCAGCAGAAACCAGGGAAAGCCCCTAAGCTCCTGATCTATGCT

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCTCGCGGGCCGAAAACCTTCGGC

CAAGGGACCAAGGTGGAAATCAAA

>KA3G2-VL-AA
(SEQ ID NO: 182)
DIQMTQSPSSLSASVGDRVTITCRASQSIDKYLNWYQQKPGKAPKLLIYA

ASRLQSGVPSRFSGSGSGTDFTLTISSLQPEDFATYYCQQMHPRGPKTFG

QGTKVEIK

The Ka3D3 antibody includes a common heavy chain (SEQ ID NO: 2) encoded by the nucleic acid sequence shown in SEQ ID NO: 1 and includes a kappa light chain (SEQ ID NO: 72) encoded by the nucleic acid sequence shown in SEQ ID NO: 71.

>KA3D3-LC-NT
(SEQ ID NO: 71)
GACATCCAGATGACCCAGTCTCCATCCTCCCTGTCTGCATCTGTAGGAGA

CAGAGTCACCATCACTTGCCGGGCAAGTCAGAGCATTGGTAAGTATTTAA

ATTGGTATCAGCAGAAACCAGGGAAAGCCCCTAAGCTCCTGATCTATGCT

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCATCCTCGCGCGCCGAAAACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>KA3D3-LC-AA
(SEQ ID NO: 72)
DIQMTQSPSSLSASVGDRVTITCRASQSIGKYLNWYQQKPGKAPKLLIYA

ASRLQSGVPSRFSGSGSGTDFTLTISSLQPEDFATYYCQQMHPRAPKTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The Ka3D3 antibody includes a common variable heavy domain (SEQ ID NO: 114) encoded by the nucleic acid sequence shown in SEQ ID NO: 113 and includes a kappa variable light domain (SEQ ID NO: 184) encoded by the nucleic acid sequence shown in SEQ ID NO: 183.

>KA3D3-VL-NT
(SEQ ID NO: 183)
GACATCCAGATGACCCAGTCTCCATCCTCCCTGTCTGCATCTGTAGGAGA

CAGAGTCACCATCACTTGCCGGGCAAGTCAGAGCATTGGTAAGTATTTAA

ATTGGTATCAGCAGAAACCAGGGAAAGCCCCTAAGCTCCTGATCTATGCT

GCATCCAGGTTGCAAAGTGGGGTCCCATCAAGGTTCAGTGGCAGTGGATC

TGGGACAGATTTCACTCTCACCATCAGCAGTCTGCAACCTGAAGATTTTG

```
CAACTTACTACTGTCAGCAGATGCATCCTCGCGCGCCGAAAACCTTCGGC

CAAGGGACCAAGGTGGAAATCAAA

>KA3D3-VL-AA
                                        (SEQ ID NO: 184)
DIQMTQSPSSLSASVGDRVTITCRASQSIGKYLNWYQQKPGKAPKLLIYA

ASRLQSGVPSRFSGSGSGTDFTLTISSLQPEDFATYYCQQMHPRAPKTFG

QGTKVEIK
```

The Kc4 antibody includes a common heavy chain (SEQ ID NO: 2) encoded by the nucleic acid sequence shown in SEQ ID NO: 1 and includes a lambda light chain (SEQ ID NO: 74) encoded by the nucleic acid sequence shown in SEQ ID NO: 73.

```
>KC4-LC-NT
                                         (SEQ ID NO: 73)
CAGTCTGCCCTGACTCAGCCTGCCTCCGTGTCTGGGTCTCCTGGACAGTC

GATCACCATCTCCTGCACTGGAACCAGCAGTGACGTTGGTGGTTATAACT

ATGTCTCCTGGTACCAACAGCACCCAGGCAAAGCCCCCAAACTCATGATT

TATGAGGTCAGTAATCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATGATTGGTGGTTCCGCCCCAAG

GTGTTCGGCGGAGGGACCAAGCTGACCGTCCTAGGTCAGCCCAAGGCTGC

CCCCTCGGTCACTCTGTTCCCGCCCTCCTCTGAGGAGCTTCAAGCCAACA

AGGCCACACTGGTGTGTCTCATAAGTGACTTCTACCCGGGAGCCGTGACA

GTGGCTTGGAAAGCAGATAGCAGCCCCGTCAAGGCGGGAGTGGAGACCAC

CACACCCTCCAAACAAAGCAACAACAAGTACGCGGCCAGCAGCTATCTGA

GCCTGACGCCTGAGCAGTGGAAGTCCCACAGAAGCTACAGCTGCCAGGTC

ACGCATGAAGGGAGCACCGTGGAGAAGACAGTGGCCCCTACAGAATGTTC

ATAA

>KC4-LC-AA
                                         (SEQ ID NO: 74)
QSALTQPASVSGSPGQSITISCTGTSSDVGGYNYVSWYQQHPGKAPKLMI

YEVSNRPSGVSNRFSGSKSGNTASLTISGLQAEDEADYYCSSYDWWFRPK

VFGGGTKLTVLGQPKAAPSVTLFPPSSEELQANKATLVCLISDFYPGAVT

VAWKADSSPVKAGVETTTPSKQSNNKYAASSYLSLTPEQWKSHRSYSCQV

THEGSTVEKTVAPTECS
```

The Kc4 antibody includes a common variable heavy domain (SEQ ID NO: 114) encoded by the nucleic acid sequence shown in SEQ ID NO: 113 and includes a lambda variable light domain (SEQ ID NO: 186) encoded by the nucleic acid sequence shown in SEQ ID NO: 185.

```
>KC4-VL-NT
                                        (SEQ ID NO: 185)
CAGTCTGCCCTGACTCAGCCTGCCTCCGTGTCTGGGTCTCCTGGACAGTC

GATCACCATCTCCTGCACTGGAACCAGCAGTGACGTTGGTGGTTATAACT

ATGTCTCCTGGTACCAACAGCACCCAGGCAAAGCCCCCAAACTCATGATT

TATGAGGTCAGTAATCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATGATTGGTGGTTCCGCCCCAAG

GTGTTCGGCGGAGGGACCAAGCTGACCGTCCTA

>KC4-VL-AA
                                        (SEQ ID NO: 186)
QSALTQPASVSGSPGQSITISCTGTSSDVGGYNYVSWYQQHPGKAPKLMI

YEVSNRPSGVSNRFSGSKSGNTASLTISGLQAEDEADYYCSSYDWWFRPK

VFGGGTKLTVL
```

The Kc4G11 antibody includes a common heavy chain (SEQ ID NO: 2) encoded by the nucleic acid sequence shown in SEQ ID NO: 1 and includes a lambda light chain (SEQ ID NO: 76) encoded by the nucleic acid sequence shown in SEQ ID NO: 75.

```
>KC4G11-LC-NT
                                         (SEQ ID NO: 75)
CAGTCTGCCCTGACTCAGCCTGCCTCCGTGTCTGGGTCTCCTGGACAGTC

GATCACCATCTCCTGCACTGGAACCAGCAGTGACGTTGGGAAGGCGAACT

ATGTCTCCTGGTACCAACAGCACCCAGGCAAAGCCCCCAAACTCATGATT

TATAAGGATAGTGATCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATGATTGGTGGTTCCGCCCCAAG

GTGTTCGGCGGAGGGACCAAGCTGACCGTCCTAGGTCAGCCCAAGGCTGC

CCCCTCGGTCACTCTGTTCCCGCCCTCCTCTGAGGAGCTTCAAGCCAACA

AGGCCACACTGGTGTGTCTCATAAGTGACTTCTACCCGGGAGCCGTGACA

GTGGCTTGGAAAGCAGATAGCAGCCCCGTCAAGGCGGGAGTGGAGACCAC

CACACCCTCCAAACAAAGCAACAACAAGTACGCGGCCAGCAGCTATCTGA

GCCTGACGCCTGAGCAGTGGAAGTCCCACAGAAGCTACAGCTGCCAGGTC

ACGCATGAAGGGAGCACCGTGGAGAAGACAGTGGCCCCTACAGAATGTTC

ATAA

>KC4G11-LC-AA
                                         (SEQ ID NO: 76)
QSALTQPASVSGSPGQSITISCTGTSSDVGKANYVSWYQQHPGKAPKLMI

YKDSDRPSGVSNRFSGSKSGNTASLTISGLQAEDEADYYCSSYDWWFRPK

VFGGGTKLTVLGQPKAAPSVTLFPPSSEELQANKATLVCLISDFYPGAVT

VAWKADSSPVKAGVETTTPSKQSNNKYAASSYLSLTPEQWKSHRSYSCQV

THEGSTVEKTVAPTECS
```

The Kc4G11 antibody includes a common variable heavy domain (SEQ ID NO: 114) encoded by the nucleic acid sequence shown in SEQ ID NO: 113 and includes a lambda variable light domain (SEQ ID NO: 188) encoded by the nucleic acid sequence shown in SEQ ID NO: 187.

```
>KC4G11-VL-NT
                                        (SEQ ID NO: 187)
CAGTCTGCCCTGACTCAGCCTGCCTCCGTGTCTGGGTCTCCTGGACAGTC

GATCACCATCTCCTGCACTGGAACCAGCAGTGACGTTGGGAAGGCGAACT

ATGTCTCCTGGTACCAACAGCACCCAGGCAAAGCCCCCAAACTCATGATT
```

TATAAGGATAGTGATCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATGATTGGTGGTTCCGCCCCAAG

GTGTTCGGCGGAGGGACCAAGCTGACCGTCCTA

>KC4G11-VL-AA
(SEQ ID NO: 188)
QSALTQPASVSGSPGQSITISCTGTSSDVGKANYVSWYQQHPGKAPKLMI

YKDSDRPSGVSNRFSGSKSGNTASLTISGLQAEDEADYYCSSYDWWFRPK

VFGGGTKLTVL

The Kc4C11 antibody includes a common heavy chain (SEQ ID NO: 2) encoded by the nucleic acid sequence shown in SEQ ID NO: 1 and includes a lambda light chain (SEQ ID NO: 78) encoded by the nucleic acid sequence shown in SEQ ID NO: 77.

>KC4C11-LC-NT
(SEQ ID NO: 77)
CAGTCTGCCCTGACTCAGCCTGCCTCCGTGTCTGGGTCTCCTGGACAGTC

GATCACCATCTCCTGCACTGGAACCAGCAGTGACGTTAGGGGGAATAACT

ATGTCTCCTGGTACCAACAGCACCCAGGCAAAGCCCCCAAACTCATGATT

TATGAGAATAGTAAGCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATGATTGGTGGTTCCGCCCCAAG

GTGTTCGGCGGAGGGACCAAGCTGACCGTCCTAGGTCAGCCCAAGGCTGC

CCCCTCGGTCACTCTGTTCCCGCCCTCCTCTGAGGAGCTTCAAGCCAACA

AGGCCACACTGGTGTGTCTCATAAGTGACTTCTACCCGGGAGCCGTGACA

GTGGCTTGGAAAGCAGATAGCAGCCCCGTCAAGGCGGGAGTGGAGACCAC

CACACCCTCCAAACAAAGCAACAACAAGTACGCGGCCAGCAGCTATCTGA

GCCTGACGCCTGAGCAGTGGAAGTCCCACAGAAGCTACAGCTGCCAGGTC

ACGCATGAAGGGAGCACCGTGGAGAAGACAGTGGCCCCTACAGAATGTTC

ATAA

>KC4C11-LC-AA
(SEQ ID NO: 78)
QSALTQPASVSGSPGQSITISCTGTSSDVRGNNYVSWYQQHPGKAPKLMI

YENSKRPSGVSNRFSGSKSGNTASLTISGLQAEDEADYYCSSYDWWFRPK

VFGGGTKLTVLGQPKAAPSVTLFPPSSEELQANKATLVCLISDFYPGAVT

VAWKADSSPVKAGVETTTPSKQSNNKYAASSYLSLTPEQWKSHRSYSCQV

THEGSTVEKTVAPTECS

The Kc4C11 antibody includes a common variable heavy domain (SEQ ID NO: 114) encoded by the nucleic acid sequence shown in SEQ ID NO: 113 and includes a lambda variable light domain (SEQ ID NO: 190) encoded by the nucleic acid sequence shown in SEQ ID NO: 189.

>KC4C11-VL-NT
(SEQ ID NO: 189)
CAGTCTGCCCTGACTCAGCCTGCCTCCGTGTCTGGGTCTCCTGGACAGTC

GATCACCATCTCCTGCACTGGAACCAGCAGTGACGTTAGGGGGAATAACT

ATGTCTCCTGGTACCAACAGCACCCAGGCAAAGCCCCCAAACTCATGATT

TATGAGAATAGTAAGCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATGATTGGTGGTTCCGCCCCAAG

GTGTTCGGCGGAGGGACCAAGCTGACCGTCCTA

>KC4C11-VL-AA
(SEQ ID NO: 190)
QSALTQPASVSGSPGQSITISCTGTSSDVRGNNYVSWYQQHPGKAPKLMI

YENSKRPSGVSNRFSGSKSGNTASLTISGLQAEDEADYYCSSYDWWFRPK

VFGGGTKLTVL

The Kc4A1 antibody includes a common heavy chain (SEQ ID NO: 2) encoded by the nucleic acid sequence shown in SEQ ID NO: 1 and includes a lambda light chain (SEQ ID NO: 80) encoded by the nucleic acid sequence shown in SEQ ID NO: 79.

>KC4A1-LC-NT
(SEQ ID NO: 79)
CAGTCTGCCCTGACTCAGCCTGCCTCCGTGTCTGGGTCTCCTGGACAGTC

GATCACCATCTCCTGCACTGGAACCAGCAGTGACGTTAGTGCGAGGAACT

ATGTCTCCTGGTACCAACAGCACCCAGGCAAAGCCCCCAAACTCATGATT

TATGAGAGTAGTAAGCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATGATTGGTGGTTCCGCCCCAAG

GTGTTCGGCGGAGGGACCAAGCTGACCGTCCTAGGTCAGCCCAAGGCTGC

CCCCTCGGTCACTCTGTTCCCGCCCTCCTCTGAGGAGCTTCAAGCCAACA

AGGCCACACTGGTGTGTCTCATAAGTGACTTCTACCCGGGAGCCGTGACA

GTGGCTTGGAAAGCAGATAGCAGCCCCGTCAAGGCGGGAGTGGAGACCAC

CACACCCTCCAAACAAAGCAACAACAAGTACGCGGCCAGCAGCTATCTGA

GCCTGACGCCTGAGCAGTGGAAGTCCCACAGAAGCTACAGCTGCCAGGTC

ACGCATGAAGGGAGCACCGTGGAGAAGACAGTGGCCCCTACAGAATGTTC

ATAA

>KC4A1-LC-AA
(SEQ ID NO: 80)
QSALTQPASVSGSPGQSITISCTGTSSDVSARNYVSWYQQHPGKAPKLMI

YESSKRPSGVSNRFSGSKSGNTASLTISGLQAEDEADYYCSSYDWWFRPK

VFGGGTKLTVLGQPKAAPSVTLFPPSSEELQANKATLVCLISDFYPGAVT

VAWKADSSPVKAGVETTTPSKQSNNKYAASSYLSLTPEQWKSHRSYSCQV

THEGSTVEKTVAPTECS

The Kc4A1 antibody includes a common variable heavy domain (SEQ ID NO: 114) encoded by the nucleic acid sequence shown in SEQ ID NO: 113 and includes a lambda variable light domain (SEQ ID NO: 192) encoded by the nucleic acid sequence shown in SEQ ID NO: 191.

>KC4A1-VL-NT
(SEQ ID NO: 191)
CAGTCTGCCCTGACTCAGCCTGCCTCCGTGTCTGGGTCTCCTGGACAGTC
GATCACCATCTCCTGCACTGGAACCAGCAGTGACGTTAGTGCGAGGAACT
ATGTCTCCTGGTACCAACAGCACCCAGGCAAAGCCCCCAAACTCATGATT
TATGAGAGTAGTAAGCGGCCCTCAGGGGTTTCTAATCGCTTCTCTGGCTC
CAAGTCTGGCAACACGGCCTCCCTGACCATCTCTGGGCTCCAGGCTGAGG
ACGAGGCTGATTATTACTGCAGCTCATATGATTGGTGGTTCCGCCCCAAG
GTGTTCGGCGGAGGGACCAAGCTGACCGTCCTA

>KC4A1-VL-AA
(SEQ ID NO: 192)
QSALTQPASVSGSPGQSITISCTGTSSDVSARNYVSWYQQHPGKAPKLMI
YESSKRPSGVSNRFSGSKSGNTASLTISGLQAEDEADYYCSSYDWWFRPK
VFGGGTKLTVL

The Kc4A4 antibody includes a common heavy chain (SEQ ID NO: 2) encoded by the nucleic acid sequence shown in SEQ ID NO: 1 and includes a lambda light chain (SEQ ID NO: 82) encoded by the nucleic acid sequence shown in SEQ ID NO: 81.

>KC4A4-LC-NT
(SEQ ID NO: 81)
CAGTCTGCCCTGACTCAGCCTGCCTCCGTGTCTGGGTCTCCTGGACAGTC
GATCACCATCTCCTGCACTAGAACCAGCAGTGACGTTAATAATACTAACT
ATGTCTCCTGGTACCAACAGCACCCAGGCAAAGCCCCCAAACTCATGATT
TATAAGACTAGTGGTCGGCCCTCAGGGGTTTCTAATCGCTTCTCTGGCTC
CAAGTCTGGCAACACGGCCTCCCTGACCATCTCTGGGCTCCAGGCTGAGG
ACGAGGCTGATTATTACTGCAGCTCATATGATTGGTGGTTCCGCCCCAAG
GTGTTCGGCGGAGGGACCAAGCTGACCGTCCTAGGTCAGCCCAAGGCTGC
CCCCTCGGTCACTCTGTTCCCGCCCTCCTCTGAGGAGCTTCAAGCCAACA
AGGCCACACTGGTGTGTCTCATAAGTGACTTCTACCCGGGAGCCGTGACA
GTGGCTTGGAAAGCAGATAGCAGCCCCGTCAAGGCGGGAGTGGAGACCAC
CACACCCTCCAAACAAAGCAACAACAAGTACGCGGCCAGCAGCTATCTGA
GCCTGACGCCTGAGCAGTGGAAGTCCCACAGAAGCTACAGCTGCCAGGTC
ACGCATGAAGGGAGCACCGTGGAGAAGACAGTGGCCCCTACAGAATGTTC
ATAA

>KC4A4-LC-AA
(SEQ ID NO: 82)
QSALTQPASVSGSPGQSITISCTRTSSDVNNTNYVSWYQQHPGKAPKLMI
YKTSGRPSGVSNRFSGSKSGNTASLTISGLQAEDEADYYCSSYDWWFRPK
VFGGGTKLTVLGQPKAAPSVTLFPPSSEELQANKATLVCLISDFYPGAVT
VAWKADSSPVKAGVETTTPSKQSNNKYAASSYLSLTPEQWKSHRSYSCQV
THEGSTVEKTVAPTECS

The Kc4A4 antibody includes a common variable heavy domain (SEQ ID NO: 114) encoded by the nucleic acid sequence shown in SEQ ID NO: 113 and includes a lambda variable light domain (SEQ ID NO: 194) encoded by the nucleic acid sequence shown in SEQ ID NO: 193.

>KC4A4-VL-NT
(SEQ ID NO: 193)
CAGTCTGCCCTGACTCAGCCTGCCTCCGTGTCTGGGTCTCCTGGACAGTC
GATCACCATCTCCTGCACTAGAACCAGCAGTGACGTTAATAATACTAACT
ATGTCTCCTGGTACCAACAGCACCCAGGCAAAGCCCCCAAACTCATGATT
TATAAGACTAGTGGTCGGCCCTCAGGGGTTTCTAATCGCTTCTCTGGCTC
CAAGTCTGGCAACACGGCCTCCCTGACCATCTCTGGGCTCCAGGCTGAGG
ACGAGGCTGATTATTACTGCAGCTCATATGATTGGTGGTTCCGCCCCAAG
GTGTTCGGCGGAGGGACCAAGCTGACCGTCCTA

>KC4A4-VL-AA
(SEQ ID NO: 194)
QSALTQPASVSGSPGQSITISCTRTSSDVNNTNYVSWYQQHPGKAPKLMI
YKTSGRPSGVSNRFSGSKSGNTASLTISGLQAEDEADYYCSSYDWWFRPK
VFGGGTKLTVL

The Kc4E10 antibody includes a common heavy chain (SEQ ID NO: 2) encoded by the nucleic acid sequence shown in SEQ ID NO: 1 and includes a lambda light chain (SEQ ID NO: 84) encoded by the nucleic acid sequence shown in SEQ ID NO: 83.

>KC4E10-LC-NT
(SEQ ID NO: 83)
CAGTCTGCCCTGACTCAGCCTGCCTCCGTGTCTGGGTCTCCTGGACAGTC
GATCACCATCTCCTGCACTGGAACCAGCAGTGACGTTAATTCTGCTAACT
ATGTCTCCTGGTACCAACAGCACCCAGGCAAAGCCCCCAAACTCATGATT
TATAAGAGTAGTAGTCGGCCCTCAGGGGTTTCTAATCGCTTCTCTGGCTC
CAAGTCTGGCAACACGGCCTCCCTGACCATCTCTGGGCTCCAGGCTGAGG
ACGAGGCTGATTATTACTGCAGCTCATATGATTGGTGGTTCCGCCCCAAG
GTGTTCGGCGGAGGGACCAAGCTGACCGTCCTAGGTCAGCCCAAGGCTGC
CCCCTCGGTCACTCTGTTCCCGCCCTCCTCTGAGGAGCTTCAAGCCAACA
AGGCCACACTGGTGTGTCTCATAAGTGACTTCTACCCGGGAGCCGTGACA
GTGGCTTGGAAAGCAGATAGCAGCCCCGTCAAGGCGGGAGTGGAGACCAC
CACACCCTCCAAACAAAGCAACAACAAGTACGCGGCCAGCAGCTATCTGA
GCCTGACGCCTGAGCAGTGGAAGTCCCACAGAAGCTACAGCTGCCAGGTC
ACGCATGAAGGGAGCACCGTGGAGAAGACAGTGGCCCCTACAGAATGTTC
ATAA

>KC4E10-LC-AA
(SEQ ID NO: 84)
QSALTQPASVSGSPGQSITISCTGTSSDVNSANYVSWYQQHPGKAPKLMI
YKSSSRPSGVSNRFSGSKSGNTASLTISGLQAEDEADYYCSSYDWWFRPK
VFGGGTKLTVLGQPKAAPSVTLFPPSSEELQANKATLVCLISDFYPGAVT
VAWKADSSPVKAGVETTTPSKQSNNKYAASSYLSLTPEQWKSHRSYSCQV
THEGSTVEKTVAPTECS

The Kc4E10 antibody includes a common variable heavy domain (SEQ ID NO: 114) encoded by the nucleic acid sequence shown in SEQ ID NO: 113 and includes a lambda variable light domain (SEQ ID NO: 196) encoded by the nucleic acid sequence shown in SEQ ID NO: 195.

>KC4E10-VL-NT
(SEQ ID NO: 195)
CAGTCTGCCCTGACTCAGCCTGCCTCCGTGTCTGGGTCTCCTGGACAGTC

GATCACCATCTCCTGCACTGGAACCAGCAGTGACGTTAATTCTGCTAACT

ATGTCTCCTGGTACCAACAGCACCCAGGCAAAGCCCCCAAACTCATGATT

TATAAGAGTAGTAGTCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATGATTGGTGGTTCCGCCCCAAG

GTGTTCGGCGGAGGGACCAAGCTGACCGTCCTA

>KC4E10-VL-AA
(SEQ ID NO: 196)
QSALTQPASVSGSPGQSITISCTGTSSDVNSANYVSWYQQHPGKAPKLMI

YKSSSRPSGVSNRFSGSKSGNTASLTISGLQAEDEADYYCSSYDWWFRPK

VFGGGTKLTVL

The Kc4G9 antibody includes a common heavy chain (SEQ ID NO: 2) encoded by the nucleic acid sequence shown in SEQ ID NO: 1 and includes a lambda light chain (SEQ ID NO: 86) encoded by the nucleic acid sequence shown in SEQ ID NO: 85.

>KC4G9-LC-NT
(SEQ ID NO: 85)
CAGTCTGCCCTGACTCAGCCTGCCTCCGTGTCCGGGTCTCCTGGACAGTC

GATCACCATCTCCTGCACTGGAACCAGCAGTGACGTTGAGAGGAAGAACT

ATGTCTCCTGGTACCAACAGCACCCAGGCAAAGCCCCCAAACTCATGATT

TATAAGAATAGTACTCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATGATTGGTGGTTCCGCCCCAAG

GTGTTCGGCGGAGGGACCAAGCTGACCGTCCTAGGTCAGCCCAAGGCTGC

CCCCTCGGTCACTCTGTTCCCGCCCTCCTCTGAGGAGCTTCAAGCCAACA

AGGCCACACTGGTGTGTCTCATAAGTGACTTCTACCCGGGAGCCGTGACA

GTGGCTTGGAAAGCAGATAGCAGCCCCGTCAAGGCGGGAGTGGAGACCAC

CACACCCTCCAAACAAAGCAACAACAAGTACGCGGCCAGCAGCTATCTGA

GCCTGACGCCTGAGCAGTGGAAGTCCCACAGAAGCTACAGCTGCCAGGTC

ACGCATGAAGGGAGCACCGTGGAGAAGACAGTGGCCCCTACAGAATGTTC

ATAA

>KC4G9-LC-AA
(SEQ ID NO: 86)
QSALTQPASVSGSPGQSITISCTGTSSDVERKNYVSWYQQHPGKAPKLMI

YKNSTRPSGVSNRFSGSKSGNTASLTISGLQAEDEADYYCSSYDWWFRPK

VFGGGTKLTVLGQPKAAPSVTLFPPSSEELQANKATLVCLISDFYPGAVT

VAWKADSSPVKAGVETTTPSKQSNNKYAASSYLSLTPEQWKSHRSYSCQV

THEGSTVEKTVAPTECS

The Kc4G9 antibody includes a common variable heavy domain (SEQ ID NO: 114) encoded by the nucleic acid sequence shown in SEQ ID NO: 113 and includes a lambda variable light domain (SEQ ID NO: 198) encoded by the nucleic acid sequence shown in SEQ ID NO: 197.

>KC4G9-VL-NT
(SEQ ID NO: 197)
CAGTCTGCCCTGACTCAGCCTGCCTCCGTGTCCGGGTCTCCTGGACAGTC

GATCACCATCTCCTGCACTGGAACCAGCAGTGACGTTGAGAGGAAGAACT

ATGTCTCCTGGTACCAACAGCACCCAGGCAAAGCCCCCAAACTCATGATT

TATAAGAATAGTACTCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATGATTGGTGGTTCCGCCCCAAG

GTGTTCGGCGGAGGGACCAAGCTGACCGTCCTA

>KC4G9-VL-AA
(SEQ ID NO: 198)
QSALTQPASVSGSPGQSITISCTGTSSDVERKNYVSWYQQHPGKAPKLMI

YKNSTRPSGVSNRFSGSKSGNTASLTISGLQAEDEADYYCSSYDWWFRPK

VFGGGTKLTVL

The Kc4C3 antibody includes a common heavy chain (SEQ ID NO: 2) encoded by the nucleic acid sequence shown in SEQ ID NO: 1 and includes a lambda light chain (SEQ ID NO: 88) encoded by the nucleic acid sequence shown in SEQ ID NO: 87.

>KC4C3-LC-NT
(SEQ ID NO: 87)
CAGTCTGCCCTGACTCAGCCTGCCTCCGTGTCTGGGTCTCCTGGACAGTC

GATCACCATCTCCTGCACTGGAACCAGCAGTGACGTTAGGGCGGCTAACT

ATGTCTCCTGGTACCAACAGCACCCAGGCAAAGCCCCCAAACTCATGATT

TATAAGAATAGTACTCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATGATTGGTGGTTCCGCCCCAAG

GTGTTCGGCGGAGGGACCAAGCTGACCGTCCTAGGTCAGCCCAAGGCTGC

CCCCTCGGTCACTCTGTTCCCGCCCTCCTCTGAGGAGCTTCAAGCCAACA

AGGCCACACTGGTGTGTCTCATAAGTGACTTCTACCCGGGAGCCGTGACA

GTGGCTTGGAAAGCAGATAGCAGCCCCGTCAAGGCGGGAGTGGAGACCAC

CACACCCTCCAAACAAAGCAACAACAAGTACGCGGCCAGCAGCTATCTGA

GCCTGACGCCTGAGCAGTGGAAGTCCCACAGAAGCTACAGCTGCCAGGTC

ACGCATGAAGGGAGCACCGTGGAGAAGACAGTGGCCCCTACAGAATGTTC

ATAA

>KC4C3-LC-AA
(SEQ ID NO: 88)
QSALTQPASVSGSPGQSITISCTGTSSDVRAANYVSWYQQHPGKAPKLMI

YKNSTRPSGVSNRFSGSKSGNTASLTISGLQAEDEADYYCSSYDWWFRPK

VFGGGTKLTVLGQPKAAPSVTLFPPSSEELQANKATLVCLISDFYPGAVT

VAWKADSSPVKAGVETTTPSKQSNNKYAASSYLSLTPEQWKSHRSYSCQV

THEGSTVEKTVAPTECS

The Kc4C3 antibody includes a common variable heavy domain (SEQ ID NO: 114) encoded by the nucleic acid sequence shown in SEQ ID NO: 113 and includes a lambda variable light domain (SEQ ID NO: 200) encoded by the nucleic acid sequence shown in SEQ ID NO: 199.

>KC4C3-VL-NT
(SEQ ID NO: 199)
CAGTCTGCCCTGACTCAGCCTGCCTCCGTGTCTGGGTCTCCTGGACAGTC
GATCACCATCTCCTGCACTGGAACCAGCAGTGACGTTAGGGCGGCTAACT
ATGTCTCCTGGTACCAACAGCACCCAGGCAAAGCCCCCAAACTCATGATT
TATAAGAATAGTACTCGGCCCTCAGGGGTTTCTAATCGCTTCTCTGGCTC
CAAGTCTGGCAACACGGCCTCCCTGACCATCTCTGGGCTCCAGGCTGAGG
ACGAGGCTGATTATTACTGCAGCTCATATGATTGGTGGTTCCGCCCCAAG
GTGTTCGGCGGAGGGACCAAGCTGACCGTCCTA

>KC4C3-VL-AA
(SEQ ID NO: 200)
QSALTQPASVSGSPGQSITISCTGTSSDVRAANYVSWYQQHPGKAPKLMI
YKNSTRPSGVSNRFSGSKSGNTASLTISGLQAEDEADYYCSSYDWWFRPK
VFGGGTKLTVL

The Kc4F4 antibody includes a common heavy chain (SEQ ID NO: 2) encoded by the nucleic acid sequence shown in SEQ ID NO: 1 and includes a lambda light chain (SEQ ID NO: 90) encoded by the nucleic acid sequence shown in SEQ ID NO: 89.

>KC4F4-LC-NT
(SEQ ID NO: 89)
CAGTCTGCCCTGACTCAGCCTGCCTCCGTGTCTGGGTCTCCTGGACAGTC
GATCACCATCTCCTGCACTGGAACCAGCAGTGACGTTAGGAGGGCTAACT
ATGTCTCCTGGTACCAACAGCACCCAGGCAAAGCCCCCAAACTCATGATT
TATCAGGATAGTAGTCGGCCCTCAGGGGTTTCTAATCGCTTCTCTGGCTC
CAAGTCTGGCAACACGGCCTCCCTGACCATCTCTGGGCTCCAGGCTGAGG
ACGAGGCTGATTATTACTGCAGCTCATATGATTGGTGGTTCCGCCCCAAG
GTGTTCGGCGGAGGGACCAAGCTGACCGTCCTAGGTCAGCCCAAGGCTGC
CCCCTCGGTCACTCTGTTCCCGCCCTCCTCTGAGGAGCTTCAAGCCAACA
AGGCCACACTGGTGTGTCTCATAAGTGACTTCTACCCGGGAGCCGTGACA
GTGGCTTGGAAAGCAGATAGCAGCCCCGTCAAGGCGGGAGTGGAGACCAC
CACACCCTCCAAACAAAGCAACAACAAGTACGCGGCCAGCAGCTATCTGA
GCCTGACGCCTGAGCAGTGGAAGTCCCACAGAAGCTACAGCTGCCAGGTC
ACGCATGAAGGGAGCACCGTGGAGAAGACAGTGGCCCCTACAGAATGTTC
ATAA

>KC4F4-LC-AA
(SEQ ID NO: 90)
QSALTQPASVSGSPGQSITISCTGTSSDVRRANYVSWYQQHPGKAPKLMI
YQDSSRPSGVSNRFSGSKSGNTASLTISGLQAEDEADYYCSSYDWWFRPK
VFGGGTKLTVLGQPKAAPSVTLFPPSSEELQANKATLVCLISDFYPGAVT
VAWKADSSPVKAGVETTTPSKQSNNKYAASSYLSLTPEQWKSHRSYSCQV
THEGSTVEKTVAPTECS

The Kc4F4 antibody includes a common variable heavy domain (SEQ ID NO: 114) encoded by the nucleic acid sequence shown in SEQ ID NO: 113 and includes a lambda variable light domain (SEQ ID NO: 202) encoded by the nucleic acid sequence shown in SEQ ID NO: 201.

>KC4F4-VL-NT
(SEQ ID NO: 201)
CAGTCTGCCCTGACTCAGCCTGCCTCCGTGTCTGGGTCTCCTGGACAGTC
GATCACCATCTCCTGCACTGGAACCAGCAGTGACGTTAGGAGGGCTAACT
ATGTCTCCTGGTACCAACAGCACCCAGGCAAAGCCCCCAAACTCATGATT
TATCAGGATAGTAGTCGGCCCTCAGGGGTTTCTAATCGCTTCTCTGGCTC
CAAGTCTGGCAACACGGCCTCCCTGACCATCTCTGGGCTCCAGGCTGAGG
ACGAGGCTGATTATTACTGCAGCTCATATGATTGGTGGTTCCGCCCCAAG
GTGTTCGGCGGAGGGACCAAGCTGACCGTCCTA

>KC4F4-VL-AA
(SEQ ID NO: 202)
QSALTQPASVSGSPGQSITISCTGTSSDVRRANYVSWYQQHPGKAPKLMI
YQDSSRPSGVSNRFSGSKSGNTASLTISGLQAEDEADYYCSSYDWWFRPK
VFGGGTKLTVL

The Kc4B1 antibody includes a common heavy chain (SEQ ID NO: 2) encoded by the nucleic acid sequence shown in SEQ ID NO: 1 and includes a lambda light chain (SEQ ID NO: 92) encoded by the nucleic acid sequence shown in SEQ ID NO: 91.

>KC4B1-LC-NT
(SEQ ID NO: 91)
CAGTCTGCCCTGACTCAGCCTGCCTCCGTGTCTGGGTCTCCTGGACAGTC
GATCACCATCTCCTGCACTGGAACCAGCAGTGACGTTAGGGCTAATAACT
ATGTCTCCTGGTACCAACAGCACCCAGGCAAAGCCCCCAAACTCATGATT
TATGAGAGTAGTGCGCGGCCCTCAGGGGTTTCTAATCGCTTCTCTGGCTC
CAAGTCTGGCAACACGGCCTCCCTGACCATCTCTGGGCTCCAGGCTGAGG
ACGAGGCTGATTATTACTGCAGCTCATATGATTGGTGGTTCCGCCCCAAG
GTGTTCGGCGGAGGGACCAAGCTGACCGTCCTAGGTCAGCCCAAGGCTGC
CCCCTCGGTCACTCTGTTCCCGCCCTCCTCTGAGGAGCTTCAAGCCAACA
AGGCCACACTGGTGTGTCTCATAAGTGACTTCTACCCGGGAGCCGTGACA
GTGGCTTGGAAAGCAGATAGCAGCCCCGTCAAGGCGGGAGTGGAGACCAC
CACACCCTCCAAACAAAGCAACAACAAGTACGCGGCCAGCAGCTATCTGA
GCCTGACGCCTGAGCAGTGGAAGTCCCACAGAAGCTACAGCTGCCAGGTC
ACGCATGAAGGGAGCACCGTGGAGAAGACAGTGGCCCCTACAGAATGTTC
ATAA

>KC4B1-LC-AA
(SEQ ID NO: 92)
QSALTQPASVSGSPGQSITISCTGTSSDVRANNYVSWYQQHPGKAPKLMI
YESSARPSGVSNRFSGSKSGNTASLTISGLQAEDEADYYCSSYDWWFRPK
VFGGGTKLTVLGQPKAAPSVTLFPPSSEELQANKATLVCLISDFYPGAVT
VAWKADSSPVKAGVETTTPSKQSNNKYAASSYLSLTPEQWKSHRSYSCQV
THEGSTVEKTVAPTECS

The Kc4B1 antibody includes a common variable heavy domain (SEQ ID NO: 114) encoded by the nucleic acid sequence shown in SEQ ID NO: 113 and includes a lambda variable light domain (SEQ ID NO: 204) encoded by the nucleic acid sequence shown in SEQ ID NO: 203.

>KC4B1-VL-NT
(SEQ ID NO: 203)
CAGTCTGCCCTGACTCAGCCTGCCTCCGTGTCTGGGTCTCCTGGACAGTC

GATCACCATCTCCTGCACTGGAACCAGCAGTGACGTTAGGGCTAATAACT

ATGTCTCCTGGTACCAACAGCACCCAGGCAAAGCCCCCAAACTCATGATT

TATGAGAGTAGTGCGCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATGATTGGTGGTTCCGCCCCAAG

GTGTTCGGCGGAGGGACCAAGCTGACCGTCCTA

>KC4B1-VL-AA
(SEQ ID NO: 204)
QSALTQPASVSGSPGQSITISCTGTSSDVRANNYVSWYQQHPGKAPKLMI

YESSARPSGVSNRFSGSKSGNTASLTISGLQAEDEADYYCSSYDWWFRPK

VFGGGTKLTVL

The Kc4E2 antibody includes a common heavy chain (SEQ ID NO: 2) encoded by the nucleic acid sequence shown in SEQ ID NO: 1 and includes a lambda light chain (SEQ ID NO: 94) encoded by the nucleic acid sequence shown in SEQ ID NO: 93.

>KC4E2-LC-NT
(SEQ ID NO: 93)
CAGTCTGCCCTGACTCAGCCTGCCTCCGTGTCTGGGTCTCCTGGACAGTC

GATCACCATCTCCTGCACTGGAACCAGCAGTGACGTTTATTATAATAAGT

ATGTCTCCTGGTACCAACAGCACCCAGGCAAAGCCCCCAAACTCATGATT

TATGAGAGTAGTAAGCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATGATTGGTGGTTCCGCCCCAAG

GTGTTCGGCGGAGGGACCAAGCTGACCGTCCTAGGTCAGCCCAAGGCTGC

CCCCTCGGTCACTCTGTTCCCGCCCTCCTCTGAGGAGCTTCAAGCCAACA

AGGCCACACTGGTGTGTCTCATAAGTGACTTCTACCCGGGAGCCGTGACA

GTGGCTTGGAAAGCAGATAGCAGCCCCGTCAAGGCGGGAGTGGAGACCAC

CACACCCTCCAAACAAAGCAACAACAAGTACGCGGCCAGCAGCTATCTGA

GCCTGACGCCTGAGCAGTGGAAGTCCCACAGAAGCTACAGCTGCCAGGTC

ACGCATGAAGGGAGCACCGTGGAGAAGACAGTGGCCCCTACAGAATGTTC

ATAA

>KC4E2-LC-AA
(SEQ ID NO: 94)
QSALTQPASVSGSPGQSITISCTGTSSDVYYNKYVSWYQQHPGKAPKLMI

YESSKRPSGVSNRFSGSKSGNTASLTISGLQAEDEADYYCSSYDWWFRPK

VFGGGTKLTVLGQPKAAPSVTLFPPSSEELQANKATLVCLISDFYPGAVT

VAWKADSSPVKAGVETTTPSKQSNNKYAASSYLSLTPEQWKSHRSYSCQV

THEGSTVEKTVAPTECS

The Kc4E2 antibody includes a common variable heavy domain (SEQ ID NO: 114) encoded by the nucleic acid sequence shown in SEQ ID NO: 113 and includes a lambda variable light domain (SEQ ID NO: 206) encoded by the nucleic acid sequence shown in SEQ ID NO: 205.

>KC4E2-VL-NT
(SEQ ID NO: 205)
CAGTCTGCCCTGACTCAGCCTGCCTCCGTGTCTGGGTCTCCTGGACAGTC

GATCACCATCTCCTGCACTGGAACCAGCAGTGACGTTTATTATAATAAGT

ATGTCTCCTGGTACCAACAGCACCCAGGCAAAGCCCCCAAACTCATGATT

TATGAGAGTAGTAAGCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATGATTGGTGGTTCCGCCCCAAG

GTGTTCGGCGGAGGGACCAAGCTGACCGTCCTA

>KC4E2-VL-AA
(SEQ ID NO: 206)
QSALTQPASVSGSPGQSITISCTGTSSDVYYNKYVSWYQQHPGKAPKLMI

YESSKRPSGVSNRFSGSKSGNTASLTISGLQAEDEADYYCSSYDWWFRPK

VFGGGTKLTVL

Anti-CD19 Antibodies

The C2 antibody includes a common heavy chain (SEQ ID NO: 2) encoded by the nucleic acid sequence shown in SEQ ID NO: 1 and includes a lambda light chain (SEQ ID NO: 96) encoded by the nucleic acid sequence shown in SEQ ID NO: 95.

>C2-LC-NT
(SEQ ID NO: 95)
AATTTTATGCTGACTCAGCCCCACTCTGTGTCGGAGTCTCCGGGGAAGAC

GGTAACCATCTCCTGCACCCGCAGCAGTGGCTCTATCGAAGATAAGTATG

TGCAGTGGTACCAGCAGCGCCCGGGCAGTTCCCCCACCATTGTGATCTAT

TATGATAACGAAAGACCCTCTGGGGTCCCTGATCGGTTCTCTGGCTCCAT

CGACAGCTCCTCCAACTCTGCCTCCCTCACCATCTCTGGACTGAAGACTG

AGGACGAGGCTGACTACTACTGTCAGACCTACGACCAGAGCCTGTATGGT

TGGGTGTTCGGCGGAGGGACCAAGCTGACCGTCCTAGGTCAGCCCAAGGC

TGCCCCCTCGGTCACTCTGTTCCCGCCCTCCTCTGAGGAGCTTCAAGCCA

ACAAGGCCACACTGGTGTGTCTCATAAGTGACTTCTACCCGGGAGCCGTG

ACAGTGGCTTGGAAAGCAGATAGCAGCCCCGTCAAGGCGGGAGTGGAGAC

CACCACACCCTCCAAACAAAGCAACAACAAGTACGCGGCCAGCAGCTATC

TGAGCCTGACGCCTGAGCAGTGGAAGTCCCACAGAAGCTACAGCTGCCAG

GTCACGCATGAAGGGAGCACCGTGGAGAAGACAGTGGCCCCTACAGAATG

TTCATAA

>C2-LC-AA
(SEQ ID NO: 96)
NFMLTQPHSVSESPGKTVTISCTRSSGSIEDKYVQWYQRPGSSPTIVIY

YDNERPSGVPDRFSGSIDSSSNSASLTISGLKTEDEADYYCQTYDQSLYG

```
WVFGGGTKLTVLGQPKAAPSVTLFPPSSEELQANKATLVCLISDFYPGAV

TVAWKADSSPVKAGVETTTPSKQSNNKYAASSYLSLTPEQWKSHRSYSCQ

VTHEGSTVEKTVAPTECS
```

The C2 antibody includes a common variable heavy domain (SEQ ID NO: 114) encoded by the nucleic acid sequence shown in SEQ ID NO: 113 and includes a lambda variable light domain (SEQ ID NO: 208) encoded by the nucleic acid sequence shown in SEQ ID NO: 207.

```
>C2-VL-NT
                                        (SEQ ID NO: 207)
AATTTTATGCTGACTCAGCCCCACTCTGTGTCGGAGTCTCCGGGGAAGAC

GGTAACCATCTCCTGCACCCGCAGCAGTGGCTCTATCGAAGATAAGTATG

TGCAGTGGTACCAGCAGCGCCCGGGCAGTTCCCCCACCATTGTGATCTAT

TATGATAACGAAAGACCCTCTGGGGTCCCTGATCGGTTCTCTGGCTCCAT

CGACAGCTCCTCCAACTCTGCCTCCCTCACCATCTCTGGACTGAAGACTG

AGGACGAGGCTGACTACTACTGTCAGACCTACGACCAGAGCCTGTATGGT

TGGGTGTTCGGCGGAGGGACCAAGCTGACCGTCCTA

>C2-VL-AA
                                        (SEQ ID NO: 208)
NFMLTQPHSVSESPGKTVTISCTRSSGSIEDKYVQWYQQRPGSSPTIVIY

YDNERPSGVPDRFSGSIDSSSNSASLTISGLKTEDEADYYCQTYDQSLYG

WVFGGGTKLTVL
```

The A6 antibody includes a common heavy chain (SEQ ID NO: 2) encoded by the nucleic acid sequence shown in SEQ ID NO: 1 and includes a lambda light chain (SEQ ID NO: 98) encoded by the nucleic acid sequence shown in SEQ ID NO: 97.

```
>A6-LC-NT
                                        (SEQ ID NO: 97)
AATTTTATGCTGACTCAGCCCCACTCTGTGTCGGAGTCTCCGGGGAAGAC

GGTAACCATCTCCTGCACCCGCAGCAGTGGCTCTATCGGTGATAAGTATG

TGCAGTGGTACCAGCAGCGCCCGGGCAGTTCCCCCACCATTGTGATCTAT

TATGATAACGAAAGACCCTCTGGGGTCCCTGATCGGTTCTCTGGCTCCAT

CGACAGCTCCTCCAACTCTGCCTCCCTCACCATCTCTGGACTGAAGACTG

AGGACGAGGCTGACTACTACTGTCAGACGTACGACGAGAGCCTGTATGGT

TGGGTGTTCGGCGGAGGGACCAAGCTGACCGTCCTAGGTCAGCCCAAGGC

TGCCCCCTCGGTCACTCTGTTCCCGCCCTCCTCTGAGGAGCTTCAAGCCA

ACAAGGCCACACTGGTGTGTCTCATAAGTGACTTCTACCCGGGAGCCGTG

ACAGTGGCTTGGAAAGCAGATAGCAGCCCCGTCAAGGCGGGAGTGGAGAC

CACCACACCCTCCAAACAAAGCAACAACAAGTACGCGGCCAGCAGCTATC

TGAGCCTGACGCCTGAGCAGTGGAAGTCCCACAGAAGCTACAGCTGCCAG

GTCACGCATGAAGGGAGCACCGTGGAGAAGACAGTGGCCCCTACAGAATG

TTCATAA

>A6-LC-AA
                                        (SEQ ID NO: 98)
NFMLTQPHSVSESPGKTVTISCTRSSGSIGDKYVQWYQQRPGSSPTIVIY

YDNERPSGVPDRFSGSIDSSSNSASLTISGLKTEDEADYYCQTYDESLYG

WVFGGGTKLTVLGQPKAAPSVTLFPPSSEELQANKATLVCLISDFYPGAV

TVAWKADSSPVKAGVETTTPSKQSNNKYAASSYLSLTPEQWKSHRSYSCQ

VTHEGSTVEKTVAPTECS
```

The A6 antibody includes a common variable heavy domain (SEQ ID NO: 114) encoded by the nucleic acid sequence shown in SEQ ID NO: 113 and includes a lambda variable light domain (SEQ ID NO: 210) encoded by the nucleic acid sequence shown in SEQ ID NO: 209.

```
>A6-VL-NT
                                        (SEQ ID NO: 209)
AATTTTATGCTGACTCAGCCCCACTCTGTGTCGGAGTCTCCGGGGAAGAC

GGTAACCATCTCCTGCACCCGCAGCAGTGGCTCTATCGGTGATAAGTATG

TGCAGTGGTACCAGCAGCGCCCGGGCAGTTCCCCCACCATTGTGATCTAT

TATGATAACGAAAGACCCTCTGGGGTCCCTGATCGGTTCTCTGGCTCCAT

CGACAGCTCCTCCAACTCTGCCTCCCTCACCATCTCTGGACTGAAGACTG

AGGACGAGGCTGACTACTACTGTCAGACGTACGACGAGAGCCTGTATGGT

TGGGTGTTCGGCGGAGGGACCAAGCTGACCGTCCTA

>A6-VL-AA
                                        (SEQ ID NO: 210)
NFMLTQPHSVSESPGKTVTISCTRSSGSIGDKYVQWYQQRPGSSPTIVIY

YDNERPSGVPDRFSGSIDSSSNSASLTISGLKTEDEADYYCQTYDESLYG

WVFGGGTKLTVL
```

The C6 antibody includes a common heavy chain (SEQ ID NO: 2) encoded by the nucleic acid sequence shown in SEQ ID NO: 1 and includes a lambda light chain (SEQ ID NO: 100) encoded by the nucleic acid sequence shown in SEQ ID NO: 99.

```
>C6-LC-NT
                                        (SEQ ID NO: 99)
AATTTTATGCTGACTCAGCCCCACTCTGTGTCGGAGTCTCCGGGGAAGAC

GGTAACCATCTCCTGCACCCGCAGCAGTGGCTCTATCAATGATAAGTATG

TGCAGTGGTACCAGCAGCGCCCGGGCAGTTCCCCCACCATTGTGATCTAT

TTTGATAACGAAAGACCCTCTGGGGTCCCTGATCGGTTCTCTGGCTCCAT

CGACAGCTCCTCCAACTCTGCCTCCCTCACCATCTCTGGACTGAAGACTG

AGGACGAGGCTGACTACTACTGTCAGACCTACGACACCAGCCTGTATGGT

TGGGTGTTCGGCGGAGGGACCAAGCTGACCGTCCTAGGTCAGCCCAAGGC

TGCCCCCTCGGTCACTCTGTTCCCGCCCTCCTCTGAGGAGCTTCAAGCCA

ACAAGGCCACACTGGTGTGTCTCATAAGTGACTTCTACCCGGGAGCCGTG

ACAGTGGCTTGGAAAGCAGATAGCAGCCCCGTCAAGGCGGGAGTGGAGAC

CACCACACCCTCCAAACAAAGCAACAACAAGTACGCGGCCAGCAGCTATC
```

```
TGAGCCTGACGCCTGAGCAGTGGAAGTCCCACAGAAGCTACAGCTGCCAG

GTCACGCATGAAGGGAGCACCGTGGAGAAGACAGTGGCCCCTACAGAATG

TTCATAA

>C6-LC-AA
                                        (SEQ ID NO: 100)
NFMLTQPHSVSESPGKTVTISCTRSSGSINDKYVQWYQQRPGSSPTIVIY

FDNERPSGVPDRFSGSIDSSSNSASLTISGLKTEDEADYYCQTYDTSLYG

WVFGGGTKLTVLGQPKAAPSVTLFPPSSEELQANKATLVCLISDFYPGAV

TVAWKADSSPVKAGVETTTPSKQSNNKYAASSYLSLTPEQWKSHRSYSCQ

VTHEGSTVEKTVAPTECS
```

The C6 antibody includes a common variable heavy domain (SEQ ID NO: 114) encoded by the nucleic acid sequence shown in SEQ ID NO: 113 and includes a lambda variable light domain (SEQ ID NO: 212) encoded by the nucleic acid sequence shown in SEQ ID NO: 211.

```
>C6-VL-NT
                                        (SEQ ID NO: 211)
AATTTTATGCTGACTCAGCCCCACTCTGTGTCGGAGTCTCCGGGGAAGAC

GGTAACCATCTCCTGCACCCGCAGCAGTGGCTCTATCAATGATAAGTATG

TGCAGTGGTACCAGCAGCGCCCGGGCAGTTCCCCCACCATTGTGATCTAT

TTTGATAACGAAAGACCCTCTGGGGTCCCTGATCGGTTCTCTGGCTCCAT

CGACAGCTCCTCCAACTCTGCCTCCCTCACCATCTCTGGACTGAAGACTG

AGGACGAGGCTGACTACTACTGTCAGACCTACGACACCAGCCTGTATGGT

TGGGTGTTCGGCGGAGGGACCAAGCTGACCGTCCTA

>C6-VL-AA
                                        (SEQ ID NO: 212)
NFMLTQPHSVSESPGKTVTISCTRSSGSINDKYVQWYQQRPGSSPTIVIY

FDNERPSGVPDRFSGSIDSSSNSASLTISGLKTEDEADYYCQTYDTSLYG

WVFGGGTKLTVL
```

The C9 antibody includes a common heavy chain (SEQ ID NO: 2) encoded by the nucleic acid sequence shown in SEQ ID NO: 1 and includes a lambda light chain (SEQ ID NO: 102) encoded by the nucleic acid sequence shown in SEQ ID NO: 101.

```
>C9-LC-NT
                                        (SEQ ID NO: 101)
AATTTTATGCTGACTCAGCCCCACTCTGTGTCGGAGTCTCCGGGGAAGAC

GGTAACCATCTCCTGCACCCGCAGCAGTGGCTCTATCGCTGATAAGTATG

TGCAGTGGTACCAGCAGCGCCCGGGCAGTTCCCCCACCATTGTGATCTAT

TATGATAACGAAAGACCCTCTGGGGTCCCTGATCGGTTCTCTGGCTCCAT

CGACAGCTCCTCCAACTCTGCCTCCCTCACCATCTCTGGACTGAAGACTG

AGGACGAGGCTGACTACTACTGTCAGACCTACGACGAGAGCCTGTATGGT

TGGGTGTTCGGCGGAGGGACCAAGCTGACCGTCCTAGGTCAGCCCAAGGC

TGCCCCCTCGGTCACTCTGTTCCCGCCCTCCTCTGAGGAGCTTCAAGCCA

ACAAGGCCACACTGGTGTGTCTCATAAGTGACTTCTACCCGGGAGCCGTG

ACAGTGGCTTGGAAAGCAGATAGCAGCCCCGTCAAGGCGGGAGTGGAGAC

CACCACACCCTCCAAACAAAGCAACAACAAGTACGCGGCCAGCAGCTATC

TGAGCCTGACGCCTGAGCAGTGGAAGTCCCACAGAAGCTACAGCTGCCAG

GTCACGCATGAAGGGAGCACCGTGGAGAAGACAGTGGCCCCTACAGAATG

TTCATAA

>C9-LC-AA
                                        (SEQ ID NO: 102)
NFMLTQPHSVSESPGKTVTISCTRSSGSIADKYVQWYQQRPGSSPTIVIY

YDNERPSGVPDRFSGSIDSSSNSASLTISGLKTEDEADYYCQTYDESLYG

WVFGGGTKLTVLGQPKAAPSVTLFPPSSEELQANKATLVCLISDFYPGAV

TVAWKADSSPVKAGVETTTPSKQSNNKYAASSYLSLTPEQWKSHRSYSCQ

VTHEGSTVEKTVAPTECS
```

The C9 antibody includes a common variable heavy domain (SEQ ID NO: 114) encoded by the nucleic acid sequence shown in SEQ ID NO: 113 and includes a lambda variable light domain (SEQ ID NO: 214) encoded by the nucleic acid sequence shown in SEQ ID NO: 213.

```
>C9-VL-NT
                                        (SEQ ID NO: 213)
AATTTTATGCTGACTCAGCCCCACTCTGTGTCGGAGTCTCCGGGGAAGAC

GGTAACCATCTCCTGCACCCGCAGCAGTGGCTCTATCGCTGATAAGTATG

TGCAGTGGTACCAGCAGCGCCCGGGCAGTTCCCCCACCATTGTGATCTAT

TATGATAACGAAAGACCCTCTGGGGTCCCTGATCGGTTCTCTGGCTCCAT

CGACAGCTCCTCCAACTCTGCCTCCCTCACCATCTCTGGACTGAAGACTG

AGGACGAGGCTGACTACTACTGTCAGACCTACGACGAGAGCCTGTATGGT

TGGGTGTTCGGCGGAGGGACCAAGCTGACCGTCCTA

>C9-VL-AA
                                        (SEQ ID NO: 214)
NFMLTQPHSVSESPGKTVTISCTRSSGSIADKYVQWYQQRPGSSPTIVIY

YDNERPSGVPDRFSGSIDSSSNSASLTISGLKTEDEADYYCQTYDESLYG

WVFGGGTKLTVL
```

The B11 antibody includes a common heavy chain (SEQ ID NO: 2) encoded by the nucleic acid sequence shown in SEQ ID NO: 1 and includes a lambda light chain (SEQ ID NO: 104) encoded by the nucleic acid sequence shown in SEQ ID NO: 103.

```
>B11-LC-NT
                                        (SEQ ID NO: 103)
AATTTTATGCTGACTCAGCCCCACTCTGTGTCGGAGTCTCCGGGGAAGAC

GGTAACCATCTCCTGCACCCGCAGCAGTGGCTCTATCGAAGATAAGTATG

TGCAGTGGTACCAGCAGCGCCCGGGCAGTTCCCCCACCATTGTGATCTAT

TATGATAACGAAAGACCCTCTGGGGTCCCTGATCGGTTCTCTGGCTCCAT

CGACAGCTCCTCCAACTCTGCCTCCCTCACCATCTCTGGACTGAAGACTG

AGGACGAGGCTGACTACTACTGTCAGACCTACGACAACAGCCTGTATGGT

TGGGTGTTCGGCGGAGGGACCAAGCTGACCGTCCTAGGTCAGCCCAAGGC

TGCCCCCTCGGTCACTCTGTTCCCGCCCTCCTCTGAGGAGCTTCAAGCCA

ACAAGGCCACACTGGTGTGTCTCATAAGTGACTTCTACCCGGGAGCCGTG
```

```
ACAGTGGCTTGGAAAGCAGATAGCAGCCCCGTCAAGGCGGGAGTGGAGAC

CACCACACCCTCCAAACAAAGCAACAACAAGTACGCGGCCAGCAGCTATC

TGAGCCTGACGCCTGAGCAGTGGAAGTCCCACAGAAGCTACAGCTGCCAG

GTCACGCATGAAGGGAGCACCGTGGAGAAGACAGTGGCCCCTACAGAATG

TTCATAA

>B11-LC-AA
                                       (SEQ ID NO: 104)
NFMLTQPHSVSESPGKTVTISCTRSSGSIEDKYVQWYQQRPGSSPTIVIY

YDNERPSGVPDRFSGSIDSSSNSASLTISGLKTEDEADYYCQTYDNSLYG

WVFGGGTKLTVLGQPKAAPSVTLFPPSSEELQANKATLVCLISDFYPGAV

TVAWKADSSPVKAGVETTTPSKQSNNKYAASSYLSLTPEQWKSHRSYSCQ

VTHEGSTVEKTVAPTECS
```

The B11 antibody includes a common variable heavy domain (SEQ ID NO: 114) encoded by the nucleic acid sequence shown in SEQ ID NO: 113 and includes a lambda variable light domain (SEQ ID NO: 216) encoded by the nucleic acid sequence shown in SEQ ID NO: 215.

```
>B11-VL-NT
                                       (SEQ ID NO: 215)
AATTTTATGCTGACTCAGCCCCACTCTGTGTCGGAGTCTCCGGGGAAGAC

GGTAACCATCTCCTGCACCCGCAGCAGTGGCTCTATCGAAGATAAGTATG

TGCAGTGGTACCAGCAGCGCCCGGGCAGTTCCCCCACCATTGTGATCTAT

TATGATAACGAAAGACCCTCTGGGGTCCCTGATCGGTTCTCTGGCTCCAT

CGACAGCTCCTCCAACTCTGCCTCCCTCACCATCTCTGGACTGAAGACTG

AGGACGAGGCTGACTACTACTGTCAGACCTACGACAACAGCCTGTATGGT

TGGGTGTTCGGCGGAGGGACCAAGCTGACCGTCCTA

>B11-VL-AA
                                       (SEQ ID NO: 216)
NFMLTQPHSVSESPGKTVTISCTRSSGSIEDKYVQWYQQRPGSSPTIVIY

YDNERPSGVPDRFSGSIDSSSNSASLTISGLKTEDEADYYCQTYDNSLYG

WVFGGGTKLTVL
```

The D11 antibody includes a common heavy chain (SEQ ID NO: 2) encoded by the nucleic acid sequence shown in SEQ ID NO: 1 and includes a lambda light chain (SEQ ID NO: 106) encoded by the nucleic acid sequence shown in SEQ ID NO: 105.

```
>D11-LC-NT
                                       (SEQ ID NO: 105)
AATTTTATGCTGACTCAGCCCCACTCTGTGTCGGAGTCTCCGGGGAAGAC

GGTAACCATCTCCTGCACCCGCAGCAGTGGCAGCATCGATGATAAGTTTG

TGCAGTGGTACCAGCAGCGCCCGGGCAGTTCCCCCACCACTGTGATCTAT

TATGATAACATTAGACCCTCTGGGGTCCCTGATCGGTTCTCTGGCTCCAT

CGACAGCTCCTCCAACTCTGCCTCCCTCACCATCTCTGGACTGAAGACTG

AGGACGAGGCTGACTACTACTGTCAGTCCTATGACGCGAGCCTGTATGGT

TGGGTGTTCGGCGGAGGGACCAAGCTGACCGTCCTAGGTCAGCCCAAGGC

TGCCCCCTCGGTCACTCTGTTCCCGCCCTCCTCTGAGGAGCTTCAAGCCA

ACAAGGCCACACTGGTGTGTCTCATAAGTGACTTCTACCCGGGAGCCGTG

ACAGTGGCTTGGAAAGCAGATAGCAGCCCCGTCAAGGCGGGAGTGGAGAC

CACCACACCCTCCAAACAAAGCAACAACAAGTACGCGGCCAGCAGCTATC

TGAGCCTGACGCCTGAGCAGTGGAAGTCCCACAGAAGCTACAGCTGCCAG

GTCACGCATGAAGGGAGCACCGTGGAGAAGACAGTGGCCCCTACAGAATG

TTCATAA

>D11-LC-AA
                                       (SEQ ID NO: 106)
NFMLTQPHSVSESPGKTVTISCTRSSGSIDDKFVQWYQQRPGSSPTTVIY

YDNIRPSGVPDRFSGSIDSSSNSASLTISGLKTEDEADYYCQSYDASLYG

WVFGGGTKLTVLGQPKAAPSVTLFPPSSEELQANKATLVCLISDFYPGAV

TVAWKADSSPVKAGVETTTPSKQSNNKYAASSYLSLTPEQWKSHRSYSCQ

VTHEGSTVEKTVAPTECS
```

The D11 antibody includes a common variable heavy domain (SEQ ID NO: 114) encoded by the nucleic acid sequence shown in SEQ ID NO: 113 and includes a lambda variable light domain (SEQ ID NO: 218) encoded by the nucleic acid sequence shown in SEQ ID NO: 217.

```
>D11-VL-NT
                                       (SEQ ID NO: 217)
AATTTTATGCTGACTCAGCCCCACTCTGTGTCGGAGTCTCCGGGGAAGAC

GGTAACCATCTCCTGCACCCGCAGCAGTGGCAGCATCGATGATAAGTTTG

TGCAGTGGTACCAGCAGCGCCCGGGCAGTTCCCCCACCACTGTGATCTAT

TATGATAACATTAGACCCTCTGGGGTCCCTGATCGGTTCTCTGGCTCCAT

CGACAGCTCCTCCAACTCTGCCTCCCTCACCATCTCTGGACTGAAGACTG

AGGACGAGGCTGACTACTACTGTCAGTCCTATGACGCGAGCCTGTATGGT

TGGGTGTTCGGCGGAGGGACCAAGCTGACCGTCCTA

>D11-VL-AA
                                       (SEQ ID NO: 218)
NFMLTQPHSVSESPGKTVTISCTRSSGSIDDKFVQWYQQRPGSSPTTVIY

YDNIRPSGVPDRFSGSIDSSSNSASLTISGLKTEDEADYYCQSYDASLYG

WVFGGGTKLTVL
```

The B7 antibody includes a common heavy chain (SEQ ID NO: 2) encoded by the nucleic acid sequence shown in SEQ ID NO: 1 and includes a lambda light chain (SEQ ID NO: 108) encoded by the nucleic acid sequence shown in SEQ ID NO: 107.

```
>B7-LC-NT
                                       (SEQ ID NO: 107)
AATTTTATGCTGACTCAGCCCCACTCTGTGTCGGAGTCTCCGGGGAAGAC

GGTAACCATCTCCTGCACCCGCAGCAGTGGCTCTATCGCGGATAAGTATG

TGCAGTGGTACCAGCAGCGCCCGGGCAGTTCCCCCACCACTGTGATCTAT

GAGGATAACCAAAGACCCTCTGGGGTCCCTGATCGGTTCTCTGGCTCCAT

CGACAGCTCCTCCAACTCTGCCTCCCTCACCATCTCTGGACTGAAGACTG

AGGACGAGGCTGACTACTACTGTCAGTCCTATGACAGCAGCCTGTATGGT

TGGGTGTTCGGCGGAGGGACCAAGCTGACCGTCCTAGGTCAGCCCAAGGC
```

```
TGCCCCCTCGGTCACTCTGTTCCCGCCCTCCTCTGAGGAGCTTCAAGCCA

ACAAGGCCACACTGGTGTGTCTCATAAGTGACTTCTACCCGGGAGCCGTG

ACAGTGGCTTGGAAAGCAGATAGCAGCCCCGTCAAGGCGGGAGTGGAGAC

CACCACACCCTCCAAACAAAGCAACAACAAGTACGCGGCCAGCAGCTATC

TGAGCCTGACGCCTGAGCAGTGGAAGTCCCACAGAAGCTACAGCTGCCAG

GTCACGCATGAAGGGAGCACCGTGGAGAAGACAGTGGCCCCTACAGAATG

TTCATAA
```

>B7-LC-AA
(SEQ ID NO: 108)
```
NFMLTQPHSVSESPGKTVTISCTRSSGSIADKYVQWYQQRPGSSPTTVIY

EDNQRPSGVPDRFSGSIDSSSNSASLTISGLKTEDEADYYCQSYDSSLYG

WVFGGGTKLTVLGQPKAAPSVTLFPPSSEELQANKATLVCLISDFYPGAV

TVAWKADSSPVKAGVETTTPSKQSNNKYAASSYLSLTPEQWKSHRSYSCQ

VTHEGSTVEKTVAPTECS
```

The B7 antibody includes a common variable heavy domain (SEQ ID NO: 114) encoded by the nucleic acid sequence shown in SEQ ID NO: 113 and includes a lambda variable light domain (SEQ ID NO: 220) encoded by the nucleic acid sequence shown in SEQ ID NO: 219.

>B7-VL-NT
(SEQ ID NO: 219)
```
AATTTTATGCTGACTCAGCCCCACTCTGTGTCGGAGTCTCCGGGGAAGAC

GGTAACCATCTCCTGCACCCGCAGCAGTGGCTCTATCGCGGATAAGTATG

TGCAGTGGTACCAGCAGCGCCCGGGCAGTTCCCCCACCACTGTGATCTAT

GAGGATAACCAAAGACCCTCTGGGGTCCCTGATCGGTTCTCTGGCTCCAT

CGACAGCTCCTCCAACTCTGCCTCCCTCACCATCTCTGGACTGAAGACTG

AGGACGAGGCTGACTACTACTGTCAGTCCTATGACAGCAGCCTGTATGGT

TGGGTGTTCGGCGGAGGGACCAAGCTGACCGTCCTA
```

>B7-VL-AA
(SEQ ID NO: 220)
```
NFMLTQPHSVSESPGKTVTISCTRSSGSIADKYVQWYQQRPGSSPTTVIY

EDNQRPSGVPDRFSGSIDSSSNSASLTISGLKTEDEADYYCQSYDSSLYG

WVFGGGTKLTVL
```

Dummy Light Chains

The Dummy light chain 1 (SEQ ID NO: 110) is encoded by the nucleic acid sequence shown in SEQ ID NO: 109.

>DUMMY-LC1-NT
(SEQ ID NO: 109)
```
CAGTCTGTGTTGACGCAGCCGCCCTCAGTGTCTGCGGCCCCAGGACAGAA

GGTCACCATCTCCTGCTCTGGAAGCAGCTCCAATATTGAGACTGGTTCTG

TATCCTGGTACCAGCAGCTCCCAGGAACAGCCCCCAAACTCCTCATTTAT

GACAATAATAAGCGACCCTCAGGGATTCCTGACCGATTCTCTGGCTCCAA

GTCTGGCACGTCAGCCACCCTGGGCATCACCGGACTCCAGACTGGGGACG

AGGCCGATTATTACTGCGGAACATGGGATGACAGCCTGCCTGGATGGGTG

TTCGGCGGAGGGACCAAGCTGACCGTCCTAGGTCAGCCCAAGGCTGCCCC

CTCGGTCACTCTGTTCCCGCCCTCCTCTGAGGAGCTTCAAGCCAACAAGG

CCACACTGGTGTGTCTCATAAGTGACTTCTACCCGGGAGCCGTGACAGTG

GCTTGGAAAGCAGATAGCAGCCCCGTCAAGGCGGGAGTGGAGACCACCAC

ACCCTCCAAACAAAGCAACAACAAGTACGCGGCCAGCAGCTATCTGAGCC

TGACGCCTGAGCAGTGGAAGTCCCACAGAAGCTACAGCTGCCAGGTCACG

CATGAAGGGAGCACCGTGGAGAAGACAGTGGCCCCTACAGAATGTTCATA

A
```

>DUMMY-LC1-AA
(SEQ ID NO: 110)
```
QSVLTQPPSVSAAPGQKVTISCSGSSSNIETGSVSWYQQLPGTAPKLLIY

DNNKRPSGIPDRFSGSKSGTSATLGITGLQTGDEADYYCGTWDDSLPGWV

FGGGTKLTVLGQPKAAPSVTLFPPSSEELQANKATLVCLISDFYPGAVTV

AWKADSSPVKAGVETTTPSKQSNNKYAASSYLSLTPEQWKSHRSYSCQVT

HEGSTVEKTVAPTECS
```

The Dummy variable light domain 1 (SEQ ID NO: 222) is encoded by the nucleic acid sequence shown in SEQ ID NO: 221.

>DUMMY-VL1-NT
(SEQ ID NO: 221)
```
CAGTCTGTGTTGACGCAGCCGCCCTCAGTGTCTGCGGCCCCAGGACAGAA

GGTCACCATCTCCTGCTCTGGAAGCAGCTCCAATATTGAGACTGGTTCTG

TATCCTGGTACCAGCAGCTCCCAGGAACAGCCCCCAAACTCCTCATTTAT

GACAATAATAAGCGACCCTCAGGGATTCCTGACCGATTCTCTGGCTCCAA

GTCTGGCACGTCAGCCACCCTGGGCATCACCGGACTCCAGACTGGGGACG

AGGCCGATTATTACTGCGGAACATGGGATGACAGCCTGCCTGGATGGGTG

TTCGGCGGAGGGACCAAGCTGACCGTCCTA
```

>DUMMY-VL1-AA
(SEQ ID NO: 222)
```
QSVLTQPPSVSAAPGQKVTISCSGSSSNIETGSVSWYQQLPGTAPKLLIY

DNNKRPSGIPDRFSGSKSGTSATLGITGLQTGDEADYYCGTWDDSLPGWV

FGGGTKLTVL
```

The Dummy light chain 2 (SEQ ID NO: 112) is encoded by the nucleic acid sequence shown in SEQ ID NO: 111.

>DUMMY-LC2-NT
(SEQ ID NO: 111)
```
GAAATAGTGATGACGCAGTCTCCAGCCACCCTGTCTGTGTCTCCAGGGGA

AAGAGCCACCCTCTCCTGCAGGGCCAGTCAGACGGTTAAGAATAATTTAG

CCTGGTACCAGCAGAAACCTGGCCAGGCTCCCAGGCTCCTCATCTATGGT

GCATCCACCAGGGCCACTGGTATCCCAGCCAGGTTCAGTGGCAGTGGGTC

TGGGACAGAGTTCACTCTCACCATCAGCAGCCTGCAGTCTGAAGATTTTG

CAGTTTATTACTGTCAGCAGTATAACAACTGGTTGCCCATCAACCCCTAT

ACCTTCGGCCAAGGGACCAAGGTGGAAATCAAACGTACGGTGGCTGCACC

ATCTGTCTTCATCTTCCCGCCATCTGATGAGCAGTTGAAATCTGGAACTG

CCTCTGTTGTGTGCCTGCTGAATAACTTCTATCCCAGAGAGGCCAAAGTA
```

-continued
```
CAGTGGAAGGTGGATAACGCCCTCCAATCGGGTAACTCCCAGGAGAGTGT

CACAGAGCAGGACAGCAAGGACAGCACCTACAGCCTCAGCAGCACCCTGA

CGCTGAGCAAAGCAGACTACGAGAAACACAAAGTCTACGCCTGCGAAGTC

ACCCATCAGGGCCTGAGCTCGCCCGTCACAAAGAGCTTCAACAGGGGAGA

GTGTTAA

>DUMMY-LC2-AA
                                        (SEQ ID NO: 112)
EIVMTQSPATLSVSPGERATLSCRASQTVKNNLAWYQQKPGQAPRLLIYG

ASTRATGIPARFSGSGSGTEFTLTISSLQSEDFAVYYCQQYNNWLPINPY

TFGQGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC
```

The Dummy variable light domain 2 (SEQ ID NO: 224) is encoded by the nucleic acid sequence shown in SEQ ID NO: 223.

```
>DUMMY-VL2-NT
                                        (SEQ ID NO: 223)
GAAATAGTGATGACGCAGTCTCCAGCCACCCTGTCTGTGTCTCCAGGGGA

AAGAGCCACCCTCTCCTGCAGGGCCAGTCAGACGGTTAAGAATAATTTAG

CCTGGTACCAGCAGAAACCTGGCCAGGCTCCCAGGCTCCTCATCTATGGT

GCATCCACCAGGGCCACTGGTATCCCAGCCAGGTTCAGTGGCAGTGGGTC

TGGGACAGAGTTCACTCTCACCATCAGCAGCCTGCAGTCTGAAGATTTTG

CAGTTTATTACTGTCAGCAGTATAACAACTGGTTGCCCATCAACCCCTAT

ACCTTCGGCCAAGGGACCAAGGTGGAAATCAAA

>DUMMY-VL2-AA
                                        (SEQ ID NO: 224)
EIVMTQSPATLSVSPGERATLSCRASQTVKNNLAWYQQKPGQAPRLLIYG

ASTRATGIPARFSGSGSGTEFTLTISSLQSEDFAVYYCQQYNNWLPINPY

TFGQGTKVEIK
```

Monovalent Antibodies

In some embodiments, the monovalent antibody 5A3 includes a common heavy chain (SEQ ID NO: 2) encoded by the nucleic acid sequence shown in SEQ ID NO: 1, a kappa light chain (SEQ ID NO: 4) encoded by the nucleic acid sequence shown in SEQ ID NO: 3 and a lambda dummy light chain 1 (SEQ ID NO: 110) encoded by the nucleic acid sequence shown in SEQ ID NO: 109. In some embodiments, the monovalent antibody 5A3 includes a common variable heavy domain (SEQ ID NO: 114) encoded by the nucleic acid sequence shown in SEQ ID NO: 113, a kappa variable light domain (SEQ ID NO: 116) encoded by the nucleic acid sequence shown in SEQ ID NO: 115 and a lambda dummy variable light domain 1 (SEQ ID NO: 222) encoded by the nucleic acid sequence shown in SEQ ID NO: 221.

In some embodiments, the monovalent antibody 5A3-M3 includes a common heavy chain (SEQ ID NO: 2) encoded by the nucleic acid sequence shown in SEQ ID NO: 1, a kappa light chain (SEQ ID NO: 8) encoded by the nucleic acid sequence shown in SEQ ID NO: 7 and a lambda dummy light chain 1 (SEQ ID NO: 110) encoded by the nucleic acid sequence shown in SEQ ID NO: 109. In some embodiments, the monovalent antibody 5A3-M3 includes a common variable heavy domain (SEQ ID NO: 114) encoded by the nucleic acid sequence shown in SEQ ID NO: 113, a kappa variable light domain (SEQ ID NO: 120) encoded by the nucleic acid sequence shown in SEQ ID NO: 119 and a lambda dummy variable light domain 1 (SEQ ID NO: 222) encoded by the nucleic acid sequence shown in SEQ ID NO: 221.

In some embodiments, the monovalent antibody 5A3-M5 includes a common heavy chain (SEQ ID NO: 2) encoded by the nucleic acid sequence shown in SEQ ID NO: 1, a kappa light chain (SEQ ID NO: 10) encoded by the nucleic acid sequence shown in SEQ ID NO: 9 and a lambda dummy light chain 1 (SEQ ID NO: 110) encoded by the nucleic acid sequence shown in SEQ ID NO: 109. In some embodiments, the monovalent antibody 5A3-M5 includes a common variable heavy domain (SEQ ID NO: 114) encoded by the nucleic acid sequence shown in SEQ ID NO: 113, a kappa variable light domain (SEQ ID NO: 122) encoded by the nucleic acid sequence shown in SEQ ID NO: 121 and a lambda dummy variable light domain 1 (SEQ ID NO: 222) encoded by the nucleic acid sequence shown in SEQ ID NO: 221.

In some embodiments, the monovalent antibody Ke8 includes a common heavy chain (SEQ ID NO: 2) encoded by the nucleic acid sequence shown in SEQ ID NO: 1, a kappa light chain (SEQ ID NO: 12) encoded by the nucleic acid sequence shown in SEQ ID NO: 11 and a lambda dummy light chain 1 (SEQ ID NO: 110) encoded by the nucleic acid sequence shown in SEQ ID NO: 109. In some embodiments, the monovalent antibody Ke8 includes a common variable heavy domain (SEQ ID NO: 114) encoded by the nucleic acid sequence shown in SEQ ID NO: 113, a kappa variable light domain (SEQ ID NO: 124) encoded by the nucleic acid sequence shown in SEQ ID NO: 123 and a lambda dummy variable light domain 1 (SEQ ID NO: 222) encoded by the nucleic acid sequence shown in SEQ ID NO: 221.

In some embodiments, the monovalent antibody Ke8A2 includes a common heavy chain (SEQ ID NO: 2) encoded by the nucleic acid sequence shown in SEQ ID NO: 1, a kappa light chain (SEQ ID NO: 18) encoded by the nucleic acid sequence shown in SEQ ID NO: 17 and a lambda dummy light chain 1 (SEQ ID NO: 110) encoded by the nucleic acid sequence shown in SEQ ID NO: 109. In some embodiments, the monovalent antibody Ke8A2 includes a common variable heavy domain (SEQ ID NO: 114) encoded by the nucleic acid sequence shown in SEQ ID NO: 113, a kappa variable light domain (SEQ ID NO: 130) encoded by the nucleic acid sequence shown in SEQ ID NO: 129 and a lambda dummy variable light domain 1 (SEQ ID NO: 222) encoded by the nucleic acid sequence shown in SEQ ID NO: 221.

In some embodiments, the monovalent antibody Ke8B2 includes a common heavy chain (SEQ ID NO: 2) encoded by the nucleic acid sequence shown in SEQ ID NO: 1, a kappa light chain (SEQ ID NO: 16) encoded by the nucleic acid sequence shown in SEQ ID NO: 15 and a lambda dummy light chain 1 (SEQ ID NO: 110) encoded by the nucleic acid sequence shown in SEQ ID NO: 109. In some embodiments, the monovalent antibody Ke8B2 includes a common variable heavy domain (SEQ ID NO: 114) encoded by the nucleic acid sequence shown in SEQ ID NO: 113, a kappa variable light domain (SEQ ID NO: 128) encoded by the nucleic acid sequence shown in SEQ ID NO: 127 and a lambda dummy variable light domain 1 (SEQ ID NO: 222) encoded by the nucleic acid sequence shown in SEQ ID NO: 221.

In some embodiments, the monovalent antibody Ke8G11 includes a common heavy chain (SEQ ID NO: 2) encoded by the nucleic acid sequence shown in SEQ ID NO: 1, a kappa light chain (SEQ ID NO: 46) encoded by the nucleic acid sequence shown in SEQ ID NO: 45 and a lambda dummy light chain 1 (SEQ ID NO: 110) encoded by the nucleic acid sequence shown in SEQ ID NO: 109. In some embodiments, the monovalent antibody Ke8G11 includes a common variable heavy domain (SEQ ID NO: 114) encoded by the nucleic acid sequence shown in SEQ ID NO: 113, a kappa variable light domain (SEQ ID NO: 158) encoded by the nucleic acid sequence shown in SEQ ID NO: 157 and a lambda dummy variable light domain 1 (SEQ ID NO: 222) encoded by the nucleic acid sequence shown in SEQ ID NO: 221.

In some embodiments, the monovalent antibody Ke8C4 includes a common heavy chain (SEQ ID NO: 2) encoded by the nucleic acid sequence shown in SEQ ID NO: 1, a kappa light chain (SEQ ID NO: 42) encoded by the nucleic acid sequence shown in SEQ ID NO: 41 and a lambda dummy light chain 1 (SEQ ID NO: 110) encoded by the nucleic acid sequence shown in SEQ ID NO: 109. In some embodiments, the monovalent antibody Ke8C4 includes a common variable heavy domain (SEQ ID NO: 114) encoded by the nucleic acid sequence shown in SEQ ID NO: 113, a kappa variable light domain (SEQ ID NO: 154) encoded by the nucleic acid sequence shown in SEQ ID NO: 153 and a lambda dummy variable light domain 1 (SEQ ID NO: 222) encoded by the nucleic acid sequence shown in SEQ ID NO: 221.

In some embodiments, the monovalent antibody Ke8A3 includes a common heavy chain (SEQ ID NO: 2) encoded by the nucleic acid sequence shown in SEQ ID NO: 1, a kappa light chain (SEQ ID NO: 26) encoded by the nucleic acid sequence shown in SEQ ID NO: 25 and a lambda dummy light chain 1 (SEQ ID NO: 110) encoded by the nucleic acid sequence shown in SEQ ID NO: 109. In some embodiments, the monovalent antibody Ke8A3 includes a common variable heavy domain (SEQ ID NO: 114) encoded by the nucleic acid sequence shown in SEQ ID NO: 113, a kappa variable light domain (SEQ ID NO: 138) encoded by the nucleic acid sequence shown in SEQ ID NO: 137 and a lambda dummy variable light domain 1 (SEQ ID NO: 222) encoded by the nucleic acid sequence shown in SEQ ID NO: 221.

In some embodiments, the monovalent antibody Ka3 includes a common heavy chain (SEQ ID NO: 2) encoded by the nucleic acid sequence shown in SEQ ID NO: 1, a kappa light chain (SEQ ID NO: 56) encoded by the nucleic acid sequence shown in SEQ ID NO: 55 and a lambda dummy light chain 1 (SEQ ID NO: 110) encoded by the nucleic acid sequence shown in SEQ ID NO: 109. In some embodiments, the monovalent antibody Ka3 includes a common variable heavy domain (SEQ ID NO: 114) encoded by the nucleic acid sequence shown in SEQ ID NO: 113, a kappa variable light domain (SEQ ID NO: 168) encoded by the nucleic acid sequence shown in SEQ ID NO: 167 and a lambda dummy variable light domain 1 (SEQ ID NO: 222) encoded by the nucleic acid sequence shown in SEQ ID NO: 221.

In some embodiments, the monovalent antibody Ka3A3 includes a common heavy chain (SEQ ID NO: 2) encoded by the nucleic acid sequence shown in SEQ ID NO: 1, a kappa light chain (SEQ ID NO: 62) encoded by the nucleic acid sequence shown in SEQ ID NO: 61 and a lambda dummy light chain 1 (SEQ ID NO: 110) encoded by the nucleic acid sequence shown in SEQ ID NO: 109. In some embodiments, the monovalent antibody Ka3A3 includes a common variable heavy domain (SEQ ID NO: 114) encoded by the nucleic acid sequence shown in SEQ ID NO: 113, a kappa variable light domain (SEQ ID NO: 174) encoded by the nucleic acid sequence shown in SEQ ID NO: 173 and a lambda dummy variable light domain 1 (SEQ ID NO: 222) encoded by the nucleic acid sequence shown in SEQ ID NO: 221.

In some embodiments, the monovalent antibody Ka3G2 includes a common heavy chain (SEQ ID NO: 2) encoded by the nucleic acid sequence shown in SEQ ID NO: 1, a kappa light chain (SEQ ID NO: 70) encoded by the nucleic acid sequence shown in SEQ ID NO: 69 and a lambda dummy light chain 1 (SEQ ID NO: 110) encoded by the nucleic acid sequence shown in SEQ ID NO: 109. In some embodiments, the monovalent antibody Ka3G2 includes a common variable heavy domain (SEQ ID NO: 114) encoded by the nucleic acid sequence shown in SEQ ID NO: 113, a kappa variable light domain (SEQ ID NO: 182) encoded by the nucleic acid sequence shown in SEQ ID NO: 181 and a lambda dummy variable light domain 1 (SEQ ID NO: 222) encoded by the nucleic acid sequence shown in SEQ ID NO: 221.

In some embodiments, the monovalent antibody Ka3H3 includes a common heavy chain (SEQ ID NO: 2) encoded by the nucleic acid sequence shown in SEQ ID NO: 1, a kappa light chain (SEQ ID NO: 60) encoded by the nucleic acid sequence shown in SEQ ID NO: 59 and a lambda dummy light chain 1 (SEQ ID NO: 110) encoded by the nucleic acid sequence shown in SEQ ID NO: 109. In some embodiments, the monovalent antibody Ka3H3 includes a common variable heavy domain (SEQ ID NO: 114) encoded by the nucleic acid sequence shown in SEQ ID NO: 113, a kappa variable light domain (SEQ ID NO: 172) encoded by the nucleic acid sequence shown in SEQ ID NO: 171 and a lambda dummy variable light domain 1 (SEQ ID NO: 222) encoded by the nucleic acid sequence shown in SEQ ID NO: 221.

In some embodiments, the monovalent antibody C2 includes a common heavy chain (SEQ ID NO: 2) encoded by the nucleic acid sequence shown in SEQ ID NO: 1, a kappa dummy light chain 2 (SEQ ID NO: 112) encoded by the nucleic acid sequence shown in SEQ ID NO: 111 and a lambda light chain (SEQ ID NO: 96) encoded by the nucleic acid sequence shown in SEQ ID NO: 95. In some embodiments, the monovalent antibody C2 includes a common variable heavy domain (SEQ ID NO: 114) encoded by the nucleic acid sequence shown in SEQ ID NO: 113, a kappa dummy variable light domain 2 (SEQ ID NO: 224) encoded by the nucleic acid sequence shown in SEQ ID NO: 223 and a lambda variable light domain (SEQ ID NO: 208) encoded by the nucleic acid sequence shown in SEQ ID NO: 207.

Bispecific Antibodies

In some embodiments, the bispecific antibody 5A3xD11 includes a common heavy chain (SEQ ID NO: 2) encoded by the nucleic acid sequence shown in SEQ ID NO: 1, a kappa light chain (SEQ ID NO: 4) encoded by the nucleic acid sequence shown in SEQ ID NO: 3 and a lambda light chain (SEQ ID NO: 106) encoded by the nucleic acid sequence shown in SEQ ID NO: 105. In some embodiments, the bispecific antibody 5A3xD11 includes a common variable heavy domain (SEQ ID NO: 114) encoded by the nucleic acid sequence shown in SEQ ID NO: 113, a kappa variable light domain (SEQ ID NO: 116) encoded by the nucleic acid sequence shown in SEQ ID NO: 115 and a lambda variable light domain (SEQ ID NO: 218) encoded by the nucleic acid sequence shown in SEQ ID NO: 217.

In some embodiments, the bispecific antibody 5A3-M3xD11 includes a common heavy chain (SEQ ID NO: 2) encoded by the nucleic acid sequence shown in SEQ ID NO:

1, a kappa light chain (SEQ ID NO: 8) encoded by the nucleic acid sequence shown in SEQ ID NO: 7 and a lambda light chain (SEQ ID NO: 106) encoded by the nucleic acid sequence shown in SEQ ID NO: 105. In some embodiments, the bispecific antibody 5A3-M3xD11 includes a common variable heavy domain (SEQ ID NO: 114) encoded by the nucleic acid sequence shown in SEQ ID NO: 113, a kappa variable light domain (SEQ ID NO: 120) encoded by the nucleic acid sequence shown in SEQ ID NO: 119 and a lambda variable light domain (SEQ ID NO: 218) encoded by the nucleic acid sequence shown in SEQ ID NO: 217.

In some embodiments, the bispecific antibody 5A3-M3xC2 includes a common heavy chain (SEQ ID NO: 2) encoded by the nucleic acid sequence shown in SEQ ID NO: 1, a kappa light chain (SEQ ID NO: 8) encoded by the nucleic acid sequence shown in SEQ ID NO: 7 and a lambda light chain (SEQ ID NO: 96) encoded by the nucleic acid sequence shown in SEQ ID NO: 95. In some embodiments, the bispecific antibody 5A3-M3xC2 includes a common variable heavy domain (SEQ ID NO: 114) encoded by the nucleic acid sequence shown in SEQ ID NO: 113, a kappa variable light domain (SEQ ID NO: 120) encoded by the nucleic acid sequence shown in SEQ ID NO: 119 and a lambda variable light domain (SEQ ID NO: 208) encoded by the nucleic acid sequence shown in SEQ ID NO: 207.

In some embodiments, the bispecific antibody 5A3-M5xD11 includes a common heavy chain (SEQ ID NO: 2) encoded by the nucleic acid sequence shown in SEQ ID NO: 1, a kappa light chain (SEQ ID NO: 10) encoded by the nucleic acid sequence shown in SEQ ID NO: 9 and a lambda light chain (SEQ ID NO: 106) encoded by the nucleic acid sequence shown in SEQ ID NO: 105. In some embodiments, the bispecific antibody 5A3-M5xD11 includes a common variable heavy domain (SEQ ID NO: 114) encoded by the nucleic acid sequence shown in SEQ ID NO: 113, a kappa variable light domain (SEQ ID NO: 122) encoded by the nucleic acid sequence shown in SEQ ID NO: 121 and a lambda variable light domain (SEQ ID NO: 218) encoded by the nucleic acid sequence shown in SEQ ID NO: 217.

In some embodiments, the bispecific antibody 5A3-M5xC2 includes a common heavy chain (SEQ ID NO: 2) encoded by the nucleic acid sequence shown in SEQ ID NO: 1, a kappa light chain (SEQ ID NO: 10) encoded by the nucleic acid sequence shown in SEQ ID NO: 9 and a lambda light chain (SEQ ID NO: 96) encoded by the nucleic acid sequence shown in SEQ ID NO: 95. In some embodiments, the bispecific antibody 5A3-M5xC2 includes a common variable heavy domain (SEQ ID NO: 114) encoded by the nucleic acid sequence shown in SEQ ID NO: 113, a kappa variable light domain (SEQ ID NO: 122) encoded by the nucleic acid sequence shown in SEQ ID NO: 121 and a lambda variable light domain (SEQ ID NO: 208) encoded by the nucleic acid sequence shown in SEQ ID NO: 207.

In some embodiments, the bispecific antibody Ke8xD11 includes a common heavy chain (SEQ ID NO: 2) encoded by the nucleic acid sequence shown in SEQ ID NO: 1, a kappa light chain (SEQ ID NO: 12) encoded by the nucleic acid sequence shown in SEQ ID NO: 11 and a lambda light chain (SEQ ID NO: 106) encoded by the nucleic acid sequence shown in SEQ ID NO: 105. In some embodiments, the bispecific antibody Ke8xD11 includes a common variable heavy domain (SEQ ID NO: 114) encoded by the nucleic acid sequence shown in SEQ ID NO: 113, a kappa variable light domain (SEQ ID NO: 124) encoded by the nucleic acid sequence shown in SEQ ID NO: 123 and a lambda variable light domain (SEQ ID NO: 218) encoded by the nucleic acid sequence shown in SEQ ID NO: 217.

In some embodiments, the bispecific antibody Ke8xD11 includes a common heavy chain (SEQ ID NO: 2) encoded by the nucleic acid sequence shown in SEQ ID NO: 1, a kappa light chain (SEQ ID NO: 12) encoded by the nucleic acid sequence shown in SEQ ID NO: 11 and a lambda light chain (SEQ ID NO: 106) encoded by the nucleic acid sequence shown in SEQ ID NO: 105. In some embodiments, the bispecific antibody Ke8xD11 includes a common variable heavy domain (SEQ ID NO: 114) encoded by the nucleic acid sequence shown in SEQ ID NO: 113, a kappa variable light domain (SEQ ID NO: 124) encoded by the nucleic acid sequence shown in SEQ ID NO: 123 and a lambda variable light domain (SEQ ID NO: 218) encoded by the nucleic acid sequence shown in SEQ ID NO: 217.

In some embodiments, the bispecific antibody Ke8A2xD11 includes a common heavy chain (SEQ ID NO: 2) encoded by the nucleic acid sequence shown in SEQ ID NO: 1, a kappa light chain (SEQ ID NO: 18) encoded by the nucleic acid sequence shown in SEQ ID NO: 17 and a lambda light chain (SEQ ID NO: 106) encoded by the nucleic acid sequence shown in SEQ ID NO: 105. In some embodiments, the bispecific antibody Ke8A2xD11 includes a common variable heavy domain (SEQ ID NO: 114) encoded by the nucleic acid sequence shown in SEQ ID NO: 113, a kappa variable light domain (SEQ ID NO: 130) encoded by the nucleic acid sequence shown in SEQ ID NO: 129 and a lambda variable light domain (SEQ ID NO: 218) encoded by the nucleic acid sequence shown in SEQ ID NO: 217.

In some embodiments, the bispecific antibody Ke8B2xD11 includes a common heavy chain (SEQ ID NO: 2) encoded by the nucleic acid sequence shown in SEQ ID NO: 1, a kappa light chain (SEQ ID NO: 16) encoded by the nucleic acid sequence shown in SEQ ID NO: 15 and a lambda light chain (SEQ ID NO: 106) encoded by the nucleic acid sequence shown in SEQ ID NO: 105. In some embodiments, the bispecific antibody Ke8B2xD11 includes a common variable heavy domain (SEQ ID NO: 114) encoded by the nucleic acid sequence shown in SEQ ID NO: 113, a kappa variable light domain (SEQ ID NO: 128) encoded by the nucleic acid sequence shown in SEQ ID NO: 127 and a lambda variable light domain (SEQ ID NO: 218) encoded by the nucleic acid sequence shown in SEQ ID NO: 217.

In some embodiments, the bispecific antibody Ke8G11xC2 includes a common heavy chain (SEQ ID NO: 2) encoded by the nucleic acid sequence shown in SEQ ID NO: 1, a kappa light chain (SEQ ID NO: 46) encoded by the nucleic acid sequence shown in SEQ ID NO: 45 and a lambda light chain (SEQ ID NO: 96) encoded by the nucleic acid sequence shown in SEQ ID NO: 95. In some embodiments, the bispecific antibody Ke8GxC2 includes a common variable heavy domain (SEQ ID NO: 114) encoded by the nucleic acid sequence shown in SEQ ID NO: 113, a kappa variable light domain (SEQ ID NO: 158) encoded by the nucleic acid sequence shown in SEQ ID NO: 157 and a lambda variable light domain (SEQ ID NO: 208) encoded by the nucleic acid sequence shown in SEQ ID NO: 207.

In some embodiments, the bispecific antibody Ke8C4xD11 includes a common heavy chain (SEQ ID NO: 2) encoded by the nucleic acid sequence shown in SEQ ID NO: 1, a kappa light chain (SEQ ID NO: 42) encoded by the nucleic acid sequence shown in SEQ ID NO: 41 and a lambda light chain (SEQ ID NO: 106) encoded by the nucleic acid sequence shown in SEQ ID NO: 105. In some embodiments, the bispecific antibody Ke8C4xD11 includes a common variable heavy domain (SEQ ID NO: 114)

encoded by the nucleic acid sequence shown in SEQ ID NO: 113, a kappa variable light domain (SEQ ID NO: 154) encoded by the nucleic acid sequence shown in SEQ ID NO: 153 and a lambda variable light domain (SEQ ID NO: 218) encoded by the nucleic acid sequence shown in SEQ ID NO: 217.

In some embodiments, the bispecific antibody Ke8C4xC2 includes a common heavy chain (SEQ ID NO: 2) encoded by the nucleic acid sequence shown in SEQ ID NO: 1, a kappa light chain (SEQ ID NO: 42) encoded by the nucleic acid sequence shown in SEQ ID NO: 41 and a lambda light chain (SEQ ID NO: 96) encoded by the nucleic acid sequence shown in SEQ ID NO: 95. In some embodiments, the bispecific antibody Ke8C4xC2 includes a common variable heavy domain (SEQ ID NO: 114) encoded by the nucleic acid sequence shown in SEQ ID NO: 113, a kappa variable light domain (SEQ ID NO: 154) encoded by the nucleic acid sequence shown in SEQ ID NO: 153 and a lambda variable light domain (SEQ ID NO: 208) encoded by the nucleic acid sequence shown in SEQ ID NO: 207.

In some embodiments, the bispecific antibody Ke8A3xD11 includes a common heavy chain (SEQ ID NO: 2) encoded by the nucleic acid sequence shown in SEQ ID NO: 1, a kappa light chain (SEQ ID NO: 26) encoded by the nucleic acid sequence shown in SEQ ID NO: 25 and a lambda light chain (SEQ ID NO: 106) encoded by the nucleic acid sequence shown in SEQ ID NO: 105. In some embodiments, the bispecific antibody Ke8A3xD11 includes a common variable heavy domain (SEQ ID NO: 114) encoded by the nucleic acid sequence shown in SEQ ID NO: 113, a kappa variable light domain (SEQ ID NO: 138) encoded by the nucleic acid sequence shown in SEQ ID NO: 137 and a lambda variable light domain (SEQ ID NO: 218) encoded by the nucleic acid sequence shown in SEQ ID NO: 217.

In some embodiments, the bispecific antibody Ke8A3xC2 includes a common heavy chain (SEQ ID NO: 2) encoded by the nucleic acid sequence shown in SEQ ID NO: 1, a kappa light chain (SEQ ID NO: 26) encoded by the nucleic acid sequence shown in SEQ ID NO: 25 and a lambda light chain (SEQ ID NO: 96) encoded by the nucleic acid sequence shown in SEQ ID NO: 95. In some embodiments, the bispecific antibody Ke8A3xC2 includes a common variable heavy domain (SEQ ID NO: 114) encoded by the nucleic acid sequence shown in SEQ ID NO: 113, a kappa variable light domain (SEQ ID NO: 138) encoded by the nucleic acid sequence shown in SEQ ID NO: 137 and a lambda variable light domain (SEQ ID NO: 208) encoded by the nucleic acid sequence shown in SEQ ID NO: 207.

In some embodiments, the bispecific antibody Ka3xD11 includes a common heavy chain (SEQ ID NO: 2) encoded by the nucleic acid sequence shown in SEQ ID NO: 1, a kappa light chain (SEQ ID NO: 56) encoded by the nucleic acid sequence shown in SEQ ID NO: 55 and a lambda light chain (SEQ ID NO: 106) encoded by the nucleic acid sequence shown in SEQ ID NO: 105. In some embodiments, the bispecific antibody Ka3xD11 includes a common variable heavy domain (SEQ ID NO: 114) encoded by the nucleic acid sequence shown in SEQ ID NO: 113, a kappa variable light domain (SEQ ID NO: 168) encoded by the nucleic acid sequence shown in SEQ ID NO: 167 and a lambda variable light domain (SEQ ID NO: 218) encoded by the nucleic acid sequence shown in SEQ ID NO: 217.

In some embodiments, the bispecific antibody Ka3xC2 includes a common heavy chain (SEQ ID NO: 2) encoded by the nucleic acid sequence shown in SEQ ID NO: 1, a kappa light chain (SEQ ID NO: 56) encoded by the nucleic acid sequence shown in SEQ ID NO: 55 and a lambda light chain (SEQ ID NO: 96) encoded by the nucleic acid sequence shown in SEQ ID NO: 95. In some embodiments, the bispecific antibody Ka3xC2 includes a common variable heavy domain (SEQ ID NO: 114) encoded by the nucleic acid sequence shown in SEQ ID NO: 113, a kappa variable light domain (SEQ ID NO: 168) encoded by the nucleic acid sequence shown in SEQ ID NO: 167 and a lambda variable light domain (SEQ ID NO: 208) encoded by the nucleic acid sequence shown in SEQ ID NO: 207.

In some embodiments, the bispecific antibody Ka3A3xD11 includes a common heavy chain (SEQ ID NO: 2) encoded by the nucleic acid sequence shown in SEQ ID NO: 1, a kappa light chain (SEQ ID NO: 62) encoded by the nucleic acid sequence shown in SEQ ID NO: 61 and a lambda light chain (SEQ ID NO: 106) encoded by the nucleic acid sequence shown in SEQ ID NO: 105. In some embodiments, the bispecific antibody Ka3A3xD11 includes a common variable heavy domain (SEQ ID NO: 114) encoded by the nucleic acid sequence shown in SEQ ID NO: 113, a kappa variable light domain (SEQ ID NO: 174) encoded by the nucleic acid sequence shown in SEQ ID NO: 173 and a lambda variable light domain (SEQ ID NO: 218) encoded by the nucleic acid sequence shown in SEQ ID NO: 217.

In some embodiments, the bispecific antibody Ka3G2xD11 includes a common heavy chain (SEQ ID NO: 2) encoded by the nucleic acid sequence shown in SEQ ID NO: 1, a kappa light chain (SEQ ID NO: 70) encoded by the nucleic acid sequence shown in SEQ ID NO: 69 and a lambda light chain (SEQ ID NO: 106) encoded by the nucleic acid sequence shown in SEQ ID NO: 105. In some embodiments, the bispecific antibody Ka3G2xD11 includes a common variable heavy domain (SEQ ID NO: 114) encoded by the nucleic acid sequence shown in SEQ ID NO: 113, a kappa variable light domain (SEQ ID NO: 182) encoded by the nucleic acid sequence shown in SEQ ID NO: 181 and a lambda variable light domain (SEQ ID NO: 218) encoded by the nucleic acid sequence shown in SEQ ID NO: 217.

In some embodiments, the bispecific antibody Ka3G2xC2 includes a common heavy chain (SEQ ID NO: 2) encoded by the nucleic acid sequence shown in SEQ ID NO: 1, a kappa light chain (SEQ ID NO: 70) encoded by the nucleic acid sequence shown in SEQ ID NO: 69 and a lambda light chain (SEQ ID NO: 96) encoded by the nucleic acid sequence shown in SEQ ID NO: 95. In some embodiments, the bispecific antibody Ka3G2xC2 includes a common variable heavy domain (SEQ ID NO: 114) encoded by the nucleic acid sequence shown in SEQ ID NO: 113, a kappa variable light domain (SEQ ID NO: 182) encoded by the nucleic acid sequence shown in SEQ ID NO: 181 and a lambda variable light domain (SEQ ID NO: 208) encoded by the nucleic acid sequence shown in SEQ ID NO: 207.

In some embodiments, the bispecific antibody Ka3H3xD11 includes a common heavy chain (SEQ ID NO: 2) encoded by the nucleic acid sequence shown in SEQ ID NO: 1, a kappa light chain (SEQ ID NO: 60) encoded by the nucleic acid sequence shown in SEQ ID NO: 59 and a lambda light chain (SEQ ID NO: 106) encoded by the nucleic acid sequence shown in SEQ ID NO: 105. In some embodiments, the bispecific antibody Ka3H3xD11 includes a common variable heavy domain (SEQ ID NO: 114) encoded by the nucleic acid sequence shown in SEQ ID NO: 113, a kappa variable light domain (SEQ ID NO: 172) encoded by the nucleic acid sequence shown in SEQ ID NO:

171 and a lambda variable light domain (SEQ ID NO: 218) encoded by the nucleic acid sequence shown in SEQ ID NO: 217.

In some embodiments, the bispecific antibody Ka3H3xC2 includes a common heavy chain (SEQ ID NO: 2) encoded by the nucleic acid sequence shown in SEQ ID NO: 1, a kappa light chain (SEQ ID NO: 60) encoded by the nucleic acid sequence shown in SEQ ID NO: 59 and a lambda light chain (SEQ ID NO: 96) encoded by the nucleic acid sequence shown in SEQ ID NO: 95. In some embodiments, the bispecific antibody Ka3H3xC2 includes a common variable heavy domain (SEQ ID NO: 114) encoded by the nucleic acid sequence shown in SEQ ID NO: 113, a kappa variable light domain (SEQ ID NO: 172) encoded by the nucleic acid sequence shown in SEQ ID NO: 171 and a lambda variable light domain (SEQ ID NO: 208) encoded by the nucleic acid sequence shown in SEQ ID NO: 207.

Definitions:

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, dAb (domain antibody), single chain, $F_{ab}$, $F_{ab'}$ and $F_{(ab')2}$ fragments, scFvs, and an $F_{ab}$ expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide. An antibody is the to specifically bind an antigen when the dissociation constant is ≤1 µM; e.g., ≤100 nM, preferably ≤10 nM and more preferably ≤1 nM.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is the to specifically bind to its target, when the equilibrium binding constant ($K_d$) is ≤1 μM, e.g., 100 nM, preferably ≤10 nM, and more preferably ≤1 nM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Polynucleotides in accordance with the invention include the nucleic acid molecules encoding the heavy chain immunoglobulin molecules, and nucleic acid molecules encoding the light chain immunoglobulin molecules described herein.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of marine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the invention comprise the heavy chain immunoglobulin molecules, and the light chain immunoglobulin molecules described herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means a polymeric boron of nucleotides of at least 10 bases in length, either ribonucleotides or deoxynucleotides or a modified form of either type of nucleotide. The term includes single and double stranded forms of DNA.

As used herein, the twenty conventional amino acids and their abbreviations follow conventional usage. See Immunology—A Synthesis (2nd Edition, E. S. Golub and D. R. Gren, Eds., Sinauer Associates, Sunderland Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, 0-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present.

Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term patient includes human and veterinary subjects.

Antibodies

Various procedures known within the art may be used for the production of polyclonal or monoclonal antibodies directed against a given target, such as, for example, CD47, a tumor associated antigen or other target, or against derivatives, fragments, analogs homologs or orthologs thereof. (See, for example, Antibodies: A Laboratory Manual, Harlow E, and Lane D, 1988, Cold Spring Harbor Laboratory Press, Cold Spring Harbor, N.Y., incorporated herein by reference).

Antibodies are purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

In some embodiments, the antibodies of the invention are monoclonal antibodies. Monoclonal antibodies are generated, for example, by using the procedures set forth in the Examples provided herein. Antibodies are also generated, e.g., by immunizing BALB/c mice with combinations of cell transfectants expressing high levels of a given target on their surface. Hybridomas resulting from myeloma/B cell fusions are then screened for reactivity to the selected target.

Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (MA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-SEPHAROSE® (crosslinked, beaded-form of agarose), hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Monoclonal antibodies of the invention include humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization is performed, e.g., by following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. (See also U.S. Pat. No. 5,225,539). In some instances, Fv framework residues of the human immunoglobulin are replaced by corresponding non-human residues. Humanized antibodies also comprise, e.g., residues which are found neither in the recipient antibody nor in the imported CDR or framework sequences. In general, the humanized antibody includes substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also includes at least a portion of an immunoglobulin constant region (Fc), typically that of a human immunoglobulin (Jones et al., 1986; Riechmann et al., 1988; and Presta, Curr. Op. Struct. Biol., 2:593-596 (1992)).

Fully human antibodies are antibody molecules in which the entire sequence of both the light chain and the heavy chain, including the CDRs, arise from human genes. Such antibodies are termed "human antibodies", or "fully human antibodies" herein. Monoclonal antibodies can be prepared by using trioma technique; the human B-cell hybridoma technique (see Kozbor, et al., 1983 Immunol Today 4: 72); and the EBV hybridoma technique to produce monoclonal antibodies (see Cole, et al., 1985 In: MONOCLONAL ANTIBODIES AND CANCER THERAPY, Alan R. Liss, Inc., pp. 77-96). Monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. An example of such a nonhuman animal is a mouse termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen and a correlative method for selecting an antibody that binds specifically to the relevant epitope with high affinity are disclosed in PCT publication WO 99/53049.

The antibody can be expressed by a vector containing a DNA segment encoding the single chain antibody described above.

These can include vectors, liposomes, naked DNA, adjuvant-assisted DNA. gene gun, catheters, etc. Vectors include chemical conjugates such as described in WO 93/64701, which has targeting moiety (e.g., a ligand to a cellular surface receptor), and a nucleic acid binding moiety (e.g., polylysine), viral vector (e.g., a DNA or RNA viral vector), fusion proteins such as described in PCT/US 95/02140 (WO 95/22618) which is a fusion protein containing a target moiety (e.g., an antibody specific for a target cell) and a nucleic acid binding moiety (e.g., a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g., infection, transfection, transduction or transformation. Examples of modes of gene transfer include e.g., naked DNA, CaPO$_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g., adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266:292-305 (1994)). Other methods that can be used include catheters, intravenous, parenteral, intraperitoneal and subcutaneous injection, and oral or other known routes of administration.

Bispecific antibodies are antibodies that have binding specificities for at least two different antigens. In the present case, one of the binding specificities is for a target such as CD47 or any fragment thereof. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Bispecific and/or monovalent antibodies of the invention can be made using any of a variety of art-recognized techniques, including those disclosed in co-pending application WO 2012/023053, filed Aug. 16, 2011, the contents of which are hereby incorporated by reference in their entirety. The methods described in WO 2012/023053 generate bispecific antibodies that are identical in structure to a human immunoglobulin. This type of molecule is composed of two copies of a unique heavy chain polypeptide, a first light chain variable region fused to a constant Kappa domain and second light chain variable region fused to a constant Lambda domain. Each combining site displays a different antigen specificity to which both the heavy and light chain contribute. The light chain variable regions can be of the Lambda or Kappa family and are preferably fused to a Lambda and Kappa constant domains, respectively. This is preferred in order to avoid the generation of non-natural polypeptide junctions. However it is also possible to obtain bispecific antibodies of the invention by fusing a Kappa light chain variable domain to a constant Lambda domain for a first specificity and fusing a Lambda light chain variable domain to a constant Kappa domain for the second specificity. The bispecific antibodies described in WO 2012/023053 are referred to as IgGκλ antibodies or "κλ bodies," a new fully human bispecific IgG format. This κλ-body format allows the affinity purification of a bispecific antibody that is undistinguishable from a standard IgG molecule with characteristics that are undistinguishable from a standard monoclonal antibody and, therefore, favorable as compared to previous formats.

An essential step of the method is the identification of two antibody Fv regions (each composed by a variable light chain and variable heavy chain domain) having different antigen specificities that share the same heavy chain variable domain. Numerous methods have been described for the generation of monoclonal antibodies and fragments thereof. (See, e.g., Antibodies: A Laboratory Manual, Harlow E, and Lane D, 1988, Cold Spring Harbor Laboratory Press, Cold Spring Harbor, N.Y., incorporated herein by reference). Fully human antibodies are antibody molecules in which the sequence of both the light chain and the heavy chain, including the CDRs 1 and 2, arise from human genes. The CDR3 region can be of human origin or designed by synthetic means. Such antibodies are termed "human antibodies", or "fully human antibodies" herein. Human monoclonal antibodies can be prepared by using the trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

Monoclonal antibodies are generated, e.g., by immunizing an animal with a target antigen or an immunogenic fragment, derivative or variant thereof. Alternatively, the animal is immunized with cells transfected with a vector containing a nucleic acid molecule encoding the target antigen, such that the target antigen is expressed and associated with the surface of the transfected cells. A variety of techniques are well-known in the art for producing xenogenic non-human animals. For example, see U.S. Pat. Nos. 6,075,181 and 6,150,584, which is hereby incorporated by reference in its entirety.

Alternatively, the antibodies are obtained by screening a library that contains antibody or antigen binding domain sequences for binding to the target antigen. This library is prepared, e.g., in bacteriophage as protein or peptide fusions to a bacteriophage coat protein that is expressed on the surface of assembled phage particles and the encoding DNA sequences contained within the phage particles (i.e., "phage displayed library").

Hybridomas resulting from myeloma/B cell fusions are then screened for reactivity to the target antigen. Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

Although not strictly impossible, the serendipitous identification of different antibodies having the same heavy chain variable domain but directed against different antigens is highly unlikely. Indeed, in most cases the heavy chain contributes largely to the antigen binding surface and is also the most variable in sequence. In particular the CDR3 on the heavy chain is the most diverse CDR in sequence, length and structure. Thus, two antibodies specific for different antigens will almost invariably carry different heavy chain variable domains.

The methods disclosed in co-pending application WO 2012/023053 overcomes this limitation and greatly facilitates the isolation of antibodies having the same heavy chain variable domain by the use of antibody libraries in which the heavy chain variable domain is the same for all the library members and thus the diversity is confined to the light chain variable domain. Such libraries are described, for example, in co-pending applications WO 2010/135558 and WO 2011/084255, each of which is hereby incorporated by reference in its entirety. However, as the light chain variable domain is expressed in conjunction with the heavy variable domain, both domains can contribute to antigen binding. To further facilitate the process, antibody libraries containing the same heavy chain variable domain and either a diversity of Lambda variable light chains or Kappa variable light chains can be used in parallel for in vitro selection of antibodies against different antigens. This approach enables the identification of two antibodies having a common heavy chain but one carrying a Lambda light chain variable domain and the other a Kappa light chain variable domain that can be used as building blocks for the generation of a bispecific antibody in the full immunoglobulin format of the invention. The bispecific antibodies of the invention can be of different Isotypes and their Fc portion can be modified in order to alter the bind properties to different Fc receptors and in this way modify the effectors functions of the antibody as well as it pharmacokinetic properties. Numerous methods for the modification of the Fc portion have been described and are applicable to antibodies of the invention. (see for example Strohl, WR Curr Opin Biotechnol 2009 (6):685-91; U.S. Pat. No. 6,528,624; PCT/US2009/0191199 filed Jan. 9, 2009). The methods of the invention can also be used to generate bispecific antibodies and antibody mixtures in a F(ab')2 format that lacks the Fc portion.

The common heavy chain and two different light chains are co-expressed into a single cell to allow for the assembly of a bispecific antibody of the invention. If all the polypeptides get expressed at the same level and get assembled equally well to form an immunoglobulin molecule then the ratio of monospecific (same light chains) and bispecific (two different light chains) should be 50%. However, it is likely that different light chains are expressed at different levels and/or do not assemble with the same efficiency. Therefore, a means to modulate the relative expression of the different polypeptides is used to compensate for their intrinsic expression characteristics or different propensities to assemble with the common heavy chain. This modulation can be achieved via promoter strength, the use of internal ribosome entry sites (IRES) featuring different efficiencies or other types of regulatory elements that can act at transcriptional or translational levels as well as acting on mRNA stability. Different promoters of different strength could include CMV (Immediate-early Cytomegalovirus virus promoter); EF1-1α (Human elongation factor 1α-subunit promoter); Ubc (Human ubiquitin C promoter); SV40 (Simian virus 40 promoter). Different IRES have also been described from mammalian and viral origin. (See e.g., Hellen C U and Sarnow P. Genes Dev 2001 15: 1593-612). These IRES can greatly differ in their length and ribosome recruiting efficiency. Furthermore, it is possible to further tune the activity by introducing multiple copies of an IRES (Stephen et al. 2000 Proc Natl Acad Sci USA 97: 1536-1541). The modulation of the expression can also be achieved by multiple sequential transfections of cells to increase the copy number of individual genes expressing one or the other light chain and thus modify their relative expressions. The Examples provided herein demonstrate that controlling the relative expression of the different chains is critical for maximizing the assembly and overall yield of the bispecific antibody.

The co-expression of the heavy chain and two light chains generates a mixture of three different antibodies into the cell culture supernatant: two monospecific bivalent antibodies and one bispecific bivalent antibody. The latter has to be purified from the mixture to obtain the molecule of interest. The method described herein greatly facilitates this purification procedure by the use of affinity chromatography media that specifically interact with the Kappa or Lambda light chain constant domains such as the CAPTURESELECT™ Fab Kappa (Fab-Kappa affinity chromatography media) and CAPTURESELECT™ Fab Lambda (Fab-Lambda affinity chromatography media) affinity matrices (BAC BV, Holland). This multi-step affinity chromatography purification approach is efficient and generally applicable to antibodies of the invention. This is in sharp contrast to specific purification methods that have to be developed and optimized for each bispecific antibodies derived from quadromas or other cell lines expressing antibody mixtures. Indeed, if the biochemical characteristics of the different antibodies in the mixtures are similar, their separation using standard chromatography technique such as ion exchange chromatography can be challenging or not possible at all.

Other suitable purification methods include those disclosed in co-pending application PCT/M2012/003028, filed on Oct. 19, 2012, published as WO2013/088259, the contents of which are hereby incorporated by reference in their entirety.

In other embodiments of producing bispecific antibodies, antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface includes at least a part of the CH3 region of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Techniques for generating bispecific antibodies from antibody fragments have been described in the literature. For example, bispecific antibodies can be prepared using chemical linkage. The bispecific antibodies produced can be used as agents for the selective immobilization of enzymes.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g., CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the invention with respect to effector function, so as to enhance, e.g., the effectiveness of the antibody in treating cancer and/or other diseases and disorders associated with aberrant CD47 expression and/or activity. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{122}$Bi, $^{131}$I, $^{131}$In, $^{90}$Y and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987).

Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionami-do]hexanoate (Pierce Chem. Co., Cat #21651G); (iv) Sulfo-LC-SPDP (sulfosuccinimidyl 6 [3-(2-pyridyldithio)-propi-anamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NETS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Use of Anti-CD47 Antibodies

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as LIPOFECTIN™ (transfection reagent), DNA conjugates, anhydrous absorption pastes, oil-in-water and water-in-oil emulsions, emulsions carbowax (polyethylene glycols of various molecular weights), semi-solid gels, and semisolid mixtures containing carbo wax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311(1998) and the citations therein for additional information related to formulations, excipients and carriers well known to pharmaceutical chemists.

Therapeutic formulations of the invention, which include an antibody of the invention, are used to treat or alleviate a symptom associated with a cancer, such as, by way of non-limiting example, leukemias, lymphomas, breast cancer, colon cancer, ovarian cancer, bladder cancer, prostate cancer, glioma, lung & bronchial cancer, colorectal cancer, pancreatic cancer, esophageal cancer, liver cancer, urinary bladder cancer, kidney and renal pelvis cancer, oral cavity & pharynx cancer, uterine corpus cancer, and/or melanoma The present invention also provides methods of treating or alleviating a symptom associated with a cancer. A therapeutic regimen is carried out by identifying a subject, e.g., a human patient suffering from (or at risk of developing) a cancer, using standard methods.

Efficaciousness of treatment is determined in association with any known method for diagnosing or treating the particular immune-related disorder. Alleviation of one or more symptoms of the immune-related disorder indicates that the antibody confers a clinical benefit.

Methods for the screening of antibodies that possess the desired specificity include, but are not limited to, enzyme linked immunosorbent assay (ELISA) and other immunologically mediated techniques known within the art.

Antibodies directed against a target such as CD47, a tumor associated antigen or other antigen (or a fragment thereof) may be used in methods known within the art relating to the localization and/or quantitation of these targets, e.g., for use in measuring levels of these targets within appropriate physiological samples, for use in diagnostic methods, for use in imaging the protein, and the like). In a given embodiment, antibodies specific any of these targets, or derivative, fragment, analog or homolog thereof, that contain the antibody derived antigen binding domain, are utilized as pharmacologically active compounds (referred to hereinafter as "Therapeutics").

An antibody of the invention can be used to isolate a particular target using standard techniques, such as immunoaffinity, chromatography or immunoprecipitation. Antibodies of the invention (or a fragment thereof) can be used diagnostically to monitor protein levels in tissue as part of a clinical testing procedure, e.g., to determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{135}$S or $^{3}$H.

Antibodies of the invention, including polyclonal, monoclonal, humanized and fully human antibodies, may be used as therapeutic agents. Such agents will generally be employed to treat or prevent a disease or pathology associated with aberrant expression or activation of a given target in a subject. An antibody preparation, preferably one having high specificity and high affinity for its target antigen, is administered to the subject and will generally have an effect due to its binding with the target. Administration of the antibody may abrogate or inhibit or interfere with the signaling function of the target. Administration of the antibody may abrogate or inhibit or interfere with the binding of the target with an endogenous ligand to which it naturally binds. For example, the antibody binds to the target and neutralizes or otherwise inhibits the interaction between CD47 and SIRPα.

A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Antibodies or a fragment thereof of the invention can be administered for the treatment of a variety of diseases and disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods.

An antibody according to the invention can be used as an agent for detecting the presence of a given target (or a protein fragment thereof) in a sample. In some embodiments, the antibody contains a detectable label. Antibodies are polyclonal, or more preferably, monoclonal. An intact antibody, or a fragment thereof (e.g., $F_{ab}$, scFv, or $F_{(ab)2}$) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Pharmaceutical Compositions

The antibodies of the invention (also referred to herein as "active compounds"), and derivatives, fragments, analogs and homologs thereof, can be incorporated into pharmaceutical compositions suitable for administration. Such compositions typically comprise the antibody and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (non-ionic oil-in-water emulsifier and/or solubilizer) (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The invention will be further described in the following examples, which do not limit the scope of the invention described in the claims.

EXAMPLES

Example 1: Cloning, Expression and Purification of Human CD47

Cloning. The sequence corresponding to the extracellular domain of human CD47 (hCD47), was amplified from human CDNA by polymerase chain reaction (PCR) using specific oligonucleotides. The amplification production was gel-purified and cloned into the Peak8 mammalian expression vector (Edge Biosystems, Gaithersburg, Md.). The vector was further modified to introduce an AVITAG™ (biotin-conjugated peptide tag) (Avidity, Denver Colo.) and an hexa-histidine tag at the C-terminus allowing for single site biotinylation of the protein and purification by IMAC (Immobilized Metal Ion Affinity Chromatography). The constructs were verified by DNA sequencing.

Expression. The plasmid was then transfected into mammalian cells using a liposome based transfection reagent such as TransIT-LT1 (Minis, Madison, Wis.). The transfection step requires only small quantities of DNA and cells, typically $2 \times 10^5$ cells and 2 µg of plasmid DNA per well and the transfection carried out in a 6-well plate. Although different mammalian cell lines can be used, in the examples given below, transformed human embryo kidney monolayer epithelial cells (PEAK cells) were transfected. These cells stably express the EBNA-1 gene, further supporting the episomal replication process, are semi-adherent and can be grown under standard conditions cell culture incubator (5% CO2; 37° C. in DMEM medium supplemented with 10% fetal calf serum). After 24 h, cells were placed under selective conditions by adding medium containing 0.5-2 µg/mL puromycin, as cells harboring the episomal vector are resistant to this antibiotic.

Two to three weeks after transfection, were used to seed Tri-flasks or disposable CELLLINE™ bioreactors (membrane cell culture flask) for the production step. The CELL-LINE™ is a two compartment bioreactor that can be used in a standard cell culture incubator. The smaller compartment (15 ml) contains the cells and is separated from a larger (one liter) medium containing compartment by a semi-permeable membrane with a cut-off size of 10 kDa (Bruce et al. 2002, McDonald et al. 2005). This system allows for the diffusion of nutrients, gazes and metabolic waste products, while retaining cells and secreted proteins in the smaller compartment. The culture was maintained for 7-10 days before harvest of the supernatant. As the medium contains serum, the cells maintain good viability and several production runs can be generated using the same cells and containers.

Purification. After harvest, the cell culture supernatants were clarified by centrifugation and filtered through a 0.22 µm membrane. The supernatant from Tri-flasks were concentrated 20-40 times using a concentration device such as a SartoFlow 200 (Sartorius) with a membrane having an appropriate cut-off size to retain the protein of interest. This step was not required using the CELLline bioreactor due to the low volume recovered from the cell compartment. In addition, the concentration step increases the concentration of both the protein of interest and high molecular weight contaminants such as bovine serum albumin or immunoglobulins. In contrast, the supernatant retrieved from the cell compartment of the CELLine bioreactor contains concentrated recombinant protein and reduced levels of contaminants as they cannot cross the 10 kDa membrane separating the two chambers of the reactor. This increased recombinant protein to contaminant ratio greatly enhances the efficiency of purification using IMAC. The concentrated supernatant was then supplemented with 100 mM imidazole and loaded on Ni-NTA affinity chromatography resin (Qiagen). The relatively high concentration of imidazole minimizes binding of contaminants to the resin. After washing of the column, proteins are eluted at a flow rate of 2 mL/min using a 30 mL imidazole gradient (20-400 mM imidazole) on an ÄKTA Prime chromatography system (Amersham Pharmacia Biotech). The elution gradient further improves the purity of the recombinant protein but can be replaced by a step elution approach if a chromatography system is not available. The eluted fractions can be analyzed by SDS-PAGE or ELISA to determine their content in recombinant protein. The fractions of interest are pooled and desalted on PD-10 columns (GE Healthcare) equilibrated with phosphate buffered saline or another appropriate buffer. The desalted proteins can then be quantified using various techniques and their purity analyzed by SDS-PAGE. Recombinant CD47 was biotinylated in vitro using biotin ligase (Avidity, Denver Colo.) according to manufacturer's instructions. After desalting the biotinylation level was evaluated by pull-down assays using streptavidin magnetic beads and SDS-PAGE analysis.

Example 2: Cloning, Expression and Purification of Human CD19

Cloning. The sequence corresponding to the extracellular domain of human CD19 (hCD419), was amplified from human cDNA by polymerase chain reaction (PCR) using specific oligonucleotides. The amplification production was gel-purified and cloned into the pEAK8 mammalian expression vector (Edge Biosystems, Gaithersburg, Md.). The vector was further modified to introduce an Avitag™ (Avidity, Denver Colo.) and an hexa-histidine tag at the C-terminus allowing for single site biotinylation of the protein and purification by IMAC (Immobilized Metal Ion Affinity Chromatography). The constructs were verified by DNA sequencing.

Expression and Purification. The expression, purification and biotinylation of soluble hCD19 were performed as described in Example 1.

Example 3: Phage Display Selection Using Human scFv Libraries Containing Fixed Variable Heavy Chain General procedures for construction and handling of human scFv libraries displayed on M13 bacteriophage are described in Vaughan et al., (Nat. Biotech. 1996, 14:309-314), hereby incorporated by reference in its entirety. The libraries used for selection and screening encode scFv that all share the same VH domain and are solely diversified in the VL domain. Methods for the generation of fixed VH libraries and their use for the identification and assembly of bispecific antibodies are described in US 2012/0184716 and WO 2012/023053, each of which is hereby incorporated by reference in its entirety. The procedures to identify scFv binding to hCD19 or hCD47 are described below.

Liquid Phase Selections. Aliquots of scFv phage libraries ($10^{12}$ Pfu) were blocked with PBS containing 3% (w/v) skimmed milk for one hour at room temperature on a rotary mixer. Blocked phage was then deselected on streptavidin magnetic beads (Dynal M-280) for one hour at room temperature on a rotary mixer. Deselected phage was then incubated with in vivo biotinylated hCD19 or hCD4 7 (100 nM) for two hours at room temperature on a rotary mixer. Beads were captured using a magnetic stand followed by four washes with PBS/0.1% TWEEN® 20 (polysorbate 20) and 3 washes with PBS. Beads were then directly added to 10 ml of exponentially growing TG1 cells and incubated for one hour at 37° C. with slow shaking (100 rpm). An aliquot of the infected TG1 was serial diluted to titer the selection output. The remaining infected TG1 were spun at 3000 rpm for 15 minutes and resuspended in 0.5 ml 2xTY-AG (2xTY media containing 100 µg/ml ampicillin and 2% glucose) and spread on 2xTY AG agar Bioassay plates. After overnight incubation at 30° C. 10 ml of 2xTY AG was added to the plates and the cells were scraped form the surface and transferred to a 50 ml polypropylene tube. 2xTYAG containing 50% glycerol was added to the cell suspension to obtain a final concentration of 17% glycerol. Aliquots of the selection round were kept at −80° C.

Phage Rescue. 100 µl of cell suspension obtained from previous selection rounds were added to 20 ml of 2xTYAG and grown at 37° C. with agitation (240 rpm) until an $OD_{600}$ of 0.3 to 0.5 was reached. The culture was then super-infected with $3.3 \times 10^{10}$ MK13K07 helper phage and incubated for one hour at 37° C. (150 rpm). The medium was then changed by centrifuging the cells at 2000 rpm for 10 minutes, removing the medium and resuspending the pellet in 20 ml of 2xTY-AK (100 µg/ml ampicillin; 50 µg/ml kanamycin). The culture was then grown overnight at 30° C. (240 rpm). The next day, the phage containing supernatant was used for the next round of selection.

Cell Surface Selections. Phage containing supernatants were blocked with PBS containing 3% (w/v) skimmed milk for one hour at room temperature on a rotary mixer. Blocked phage was then deselected for one hour on Jukat T cells that do not express CD19 and that had been previously blocked with PBS containing 2% (w/v) skimmed milk. Deselected phage was then incubated with $2 \times 10^7$ Raji cells expressing CD19 for one hour at room temperature with gentle shaking. Cells were then pelleted and washed ten times with PBS. Bound phage was eluted by adding directly 10 ml of exponentially growing TG1 to the T75 flask and incubating for one hour at 37° C. with slow shaking. An aliquot of the infected TG1 was serial diluted to titer the selection output. Infected TG1 were spun at 3000 rpm for 15 minutes and re-suspended in 0.5 ml 2xTY-AG (2xTY media containing 100 µg/ml ampicillin and 2% glucose) and spread on 2xTYAG agar Bioassay plates. After overnight incubation at 30° C. 10 ml of 2xTYAG was added to the plates and the cells were scraped form the surface and transferred to a 50 ml polypropylene tube. 2xTYAG containing 50% glycerol was added to the cell suspension to obtain a final concentration of 17% glycerol. Aliquots of the selection round were kept at −80° C.

scFv periplasmic preparation for binding and functional tests. Individual clones were inoculated into a deep well microtiter plate containing 0.9 ml of 2xTYAG media (0.1% glucose) per well and grown at 37° C. for 5-6 h (250 rpm). 100 µl per well of 0.2 mM IPTG in 2xTY medium were then added to give a final concentration of 0.02 mM IPTG. Plates were then incubated overnight at 30° C. with shaking at 250 rpm. The deepwell plates were centrifuged at 2,500 rpm for 10 min and the supernatant carefully removed. The pellets were re-suspended in 150 µl TES buffer (50 mM Tris/HCl (pH 8), 1 mM EDTA (pH 8), 20% sucrose, complemented with COMPLETE™ protease inhibitor (protease inhibitor cocktail tablet), Roche). A hypotonic shock was produced by adding 150 µl of diluted TES buffer (1:5 TES:water dilution) and incubation on ice for 30 min. Plates were then centrifuged at 4000 rpm for 10 minutes to remove cells and debris. The supernatants were carefully transferred into another microtiter plate and kept on ice for immediate testing in functional assays or binding assays.

Phage clone sequencing. Single clones were placed in a microtiter plate containing 150 µl of 2xTYAG media (2% glucose) per well and grown at 30° C. (120 rpm) overnight. The next day 5 µl of culture was transferred into another plate containing 45 µl of $dH_2O$ and mixed. The plate was then frozen at −20° C. After thawing, 1 µl of this suspension was used for PCR amplification using standard PCR protocols with primer specific for pNDS1: mycseq, 5'-CTCTTCT-GAGATGAGTTTTTG-3' (SEQ ID NO: 283) and gene3leader, 5'-TTATTATTCGCAATTCCTT-TAGTTGTTCCT-3' (SEQ ID NO: 284). The PCR reactions were purified in 96 well format using the Montage PCµ96 system (Millipore). 5 µl of the eluted DNA was sequencing using the mycseq and gene3leader primers.

Example 4: Screening for scFv Binding to hCD47 and scFv Inhibiting SIRPα Interaction Binding: Screening of scFv for binding to hCD47 was tested in a homogenous assay using FMAT technology. The following reagents were mixed in each well of a 384 optical plate (Costar): 30 µl of a streptavidin polystyrene bead suspension (Spherotech; 3000 beads/well) coated with biotinylated hCD47 or a control biotinylated protein (NusA); 60 µl of scFv periplasmic preparation; 10 µl of detection buffer (PBS containing anti-cmyc antibody at 5 µg/mL; anti-mouse FC ALEXAFLUOR® 647 (photostable fluorescent dye) diluted 1:200). After mixing at 450 rpm for 5 minutes, the 384 well plates were incubated at room temperature and read after 1 and 3 hours on an FMAT 8200 Cellular Detection System (Applied Biosystems). Each scFv sample was tested in duplicate against hCD47 and NusA. Clones expressing scFv giving a specific signal for hCD47 and not NusA were selected for further analysis.

Inhibition of CD47-SIRPα Interaction: ScFv were also screened for their capacity to inhibit the interaction between CD47 and SIRPα in a bead based homogenous assay using FMAT technology. Protein A polystyrene beads (Spherotech) are incubated with 5 µg/mL of goat anti-human IgG Fcγ specific (Jackson Immunoresearch). After washing of the beads 5 µg/mL SIRPα-Fc (R&D Systems) was added so that the fusion protein can be captured at the bead surface. After blocking with PBS; 2% Tropix 1-block (Applied Biosystems), 30 µl of the beads suspension (3000 beads/well) coated were added to each well of a 384 optical plate (Costar). In a separate 96 well plate 120 µl of scFv periplasmic preparation were mixed with 24 µl of biotinylated hCD47 (300 ng/ml) and incubated for 50 minutes at room temperature so that the scFv can bind to hCD47. After incubation, 24 µl of Streptavidin Cy5 (1 µg/ml; Invitrogen) are added to the mix and 70 µl of this final mix are added to the 30 µl of beads in each well of the 384 well plate. After 3 hours of incubation at room temperature, the plate is then read on an FMAT 8200 Cellular Detection System (Applied Biosystems). Controls well containing no scFv or an irrelevant scFv not binding to CD47 were included in each plate so that clones expressing scFv leading to a reduction of the SIRPα-CD47 signal measured in controls were selected for further analysis.

Alternatively a cell based assay monitoring the interaction of soluble SIRPα with hCD47 expressed at the surface of stably transfected Chinese hamster ovary (CHO) cell line was also used for screening of candidates. 20 µl of PBS-BSA 2% azide 0.1% containing 3000 CHO expressing hCD47 cells were added to each well of a 384 optical plate (Costar). 50 µl of a twofold dilution of the scFv periplasmic preparation was then added to the well and incubated at room temperature for 30 minutes to allow the scFv to bind to CD47 on cells. After incubation 30 µl of PBS 2% BSA azide 0.1% containing long/ml of SIRPα-Fc (R&D systems) and Anti hIgG-Fc FMAT Blue coupled antibody (diluted 1:2000) were added and further incubated for 3 hours before reading on an FMAT 8200 Cellular Detection System (Applied Biosystems).

Example 5: Screening for scFv Binding to hCD19

Screening of scFv for binding to recombinant hCD19 was tested in a homogenous assay using FMAT technology as described in Example 4.

Screening was also performed on Raji cells for binding to the native form of hCD19. To each well of a 384 optical plate (Costar) 30 µl of PBS-BSA 2% azide 0.1% containing 3000 Raji cells (a human B cell line expressing CD19) or Jurkat cells (a human T cell line that do not express CD19) were added. Then, 30 µl of a twofold dilution of the scFv periplasmic preparation, 30 µl of PBS-BSA2% and 10 30 µl of 10× detection buffer (Qiagen Antibody pentaHis AF647 diluted 1:700 in PBS-BSA2%). After mixing at 450 rpm for 5 minutes, the 384 well plates were incubated at room temperature and read after 1 and 3 hours on an FMAT 8200 Cellular Detection System (Applied Biosystems). Clones expressing scFv giving a specific signal for Raji and not Jurkat cells were selected for further analysis.

Example 6: Fixed VII Candidates Reformatting into IgG and Transient Expression in Mammalian Cells After screening, scFv candidates against hCD19 or hCD47 were reformatted into IgG and expressed by transient transfection into PEAK cells. The VH and VL sequences of selected scFv were amplified with specific oligonucleotides and cloned into an expression vector containing the heavy and light chain constant regions and the constructions were verified by sequencing. The expression vectors were transfected into mammalian cells using the Fugene 6 Transfection Reagent (Roche, Basel, Switzerland). Briefly, Peak cells were cultured in 6-well plates at a concentration of $6\times10^5$ cells per well in 2 ml culture media containing fetal bovine serum. The expression vectors encoding the candidate VH and VL sequences were co-transfected into the cells using the Fugene 6 Transfection Reagent according to manufacturer's instructions. One day following transfection, the culture media was aspirated, and 3 ml of fresh serum-free media was added to cells and cultured for three days at 37° C. Following three days culture period, the supernatant was harvested for IgG purified on protein G-Sepharose 4B fast flow columns (Sigma, St. Louis, Mo.) according to manufacturer's instructions. Briefly, supernatants from transfected cells were incubated overnight at 4° C. with ImmunoPure (G) IgG binding buffer (Pierce, Rockford Ill.). Samples were then passed over Protein G-Sepharose 4B fast flow columns and the IgG consequently purified using elution buffer. The eluted IgG fraction was then dialyzed against PBS and the IgG content quantified by absorption at 280 nm. Purity and IgG integrity were verified by SDS-PAGE.

Example 7: Affinity Modulation of Anti-hCD47 Antibodies (a) Antibodies Ka3, Ke8, Kc4

Three antibodies identified during the screening process described in the Examples above were shown to be specific for human CD47 and able to block the interaction between CD47 and SIRPα were selected for affinity maturation in order to increase their affinity and potency. All these antibodies share the same variable heavy chain but have different variable light chains. Ka3 and Ke8 contain a kappa light chain (IGVK1-39 according to the IMGT nomenclature) whereas Kc4 contains a lambda light chain (IGVL2-14). Several phage libraries displaying scFv variants were generated by introducing diversity into the CDR1, CDR2 and CDR3 of the variable light chain region while the heavy chain variable region was kept unmodified. One library of $9\times10^7$ transformants covering a theoretical diversity of $7\times10^5$ was generated for Ka3; two libraries of $2\times10^8$ transformants each, partially covering a theoretical diversity of $2.4\times10^9$ were generated for Ke8 and one library of $3.6\times10^7$ transformants covering a theoretical diversity of $2.6\times10^5$ was generated for Kc4. These libraries were used for phage display selections as described in Example 3 except that the selection stringency was increased between rounds by reducing the concentration of hCD47 between different rounds: 10 nM and 1 nM of hCD47 were used in the first and second round of selection, respectively. The selected variants were screened for the capacity to inhibit the interaction between hCD47 and SIRPα using the assay described in Example 4. Positive clones were then reformatted as IgG and characterized as described in the following Examples. These affinity maturation efforts lead to the identification of the following anti-VD47 antibodies:

Ke8H6; Ke86G9; Ke8A3; Ke8C4; Ke8F1; Ke8B7; Ke8G11; Ke8A8; Ke8A4; Ke8B2; Ke8C7; Ke8H3; Ke8A2; Ke8H5; Ke8G6; Ke8E8; Ke81A3; Ke81G9; Ke84G9; Ke8G2; Ke8F2

Ka3G2; Ka3D3; Ka3A2; Ka3B2; Ka3C5; Ka3A3; Ka3H8; Ka3H3

Kc4E2; Kc4F4; Kc4A1; Kc4C11; Kc4E10; Kc4B1; Kc4C3; Kc4A4; Kc4G11; Kc4G9

(b) 5A3 Antibody Engineering for Affinity Modulation

Figure 1:
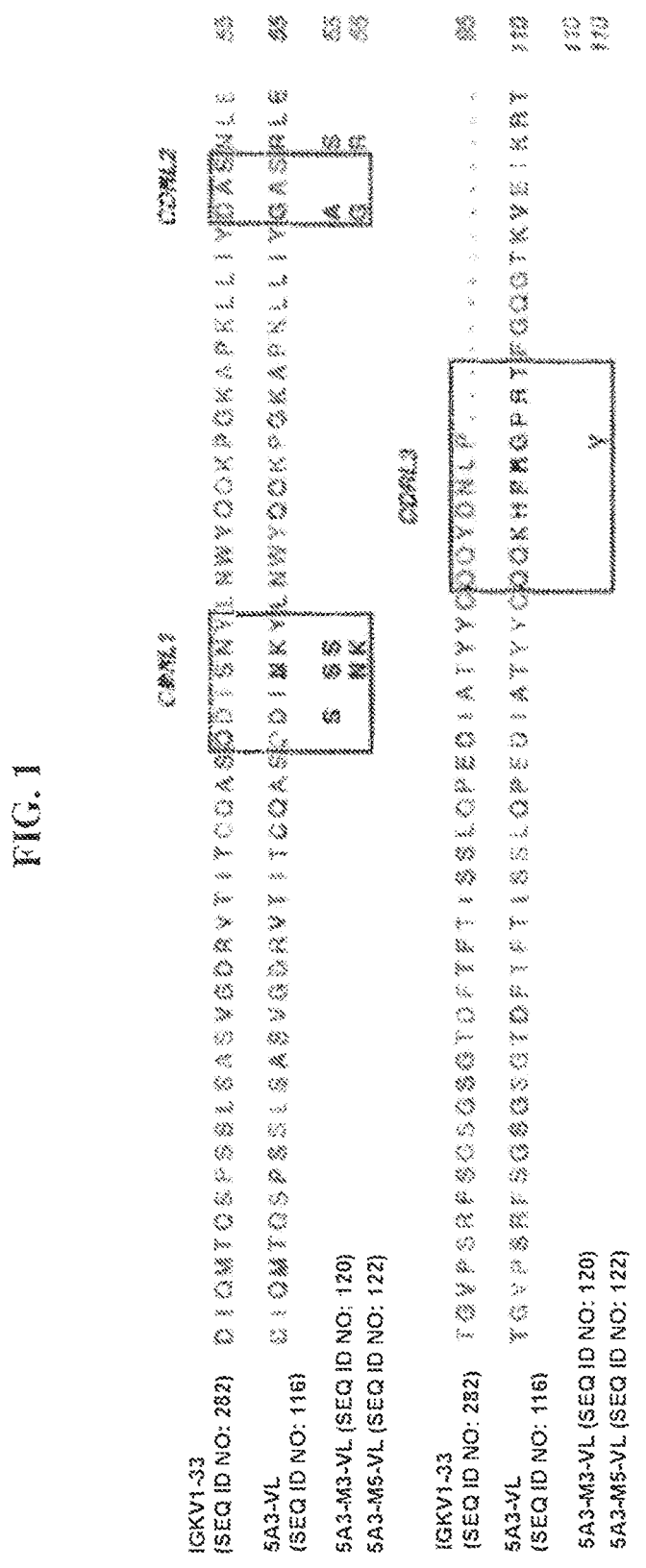

The VL sequence of anti-CD47 5A3 antibody was engineered to decrease its affinity toward its target. The 5A3-VL sequence was aligned to its closest germline sequence, the human IGKV1-33 according to the IMGT nomenclature (FIG. 1). Using this alignment, several residues were identified in the CDRL1 and CDRL2 of 5A3 VL which are not conserved with the germline sequence. Some of these amino acids were mutated in order to alter the binding affinity of the antibody. Residues of the 5A3 CDRL3 were also changed to modulate antibody binding while at the same time targeting the same epitope on CD47. These different strategies led to the identification of the 5A3-M3 and 5A3-M5 candidates.

These variants were first tested in a CD47/SIRPα binding assay to determine their blocking potency compared to the parental 5A3 antibody (FIG. 2). The 5A3-M3 and 5A3-M5 are both less potent at inhibiting the interaction between CD47 and SIRPα than 5A3 with 5A3-M5 showing the weakest inhibition potency profile.

The affinity of these variants for human CD47 was then evaluated by surface plasmon resonance technology. The $K_D$ of the 5A3, 5A3-M3 and 5A3-M5 antibodies are about 2.36E-08, 5.60E-08 and 2.84E-06 M, respectively. These data confirmed that the 5A3 variants are binding to CD47 with a lower affinity compared to the parental antibody and that the 5A3-M5 has the weakest affinity for human CD47 while the 5A3-M3 has an intermediate affinity.

Example 8: Characterization of CD47 Antibodies

Binding of CD47 Antibodies to huCD47-Transfected CHO Cells

Figure 3:
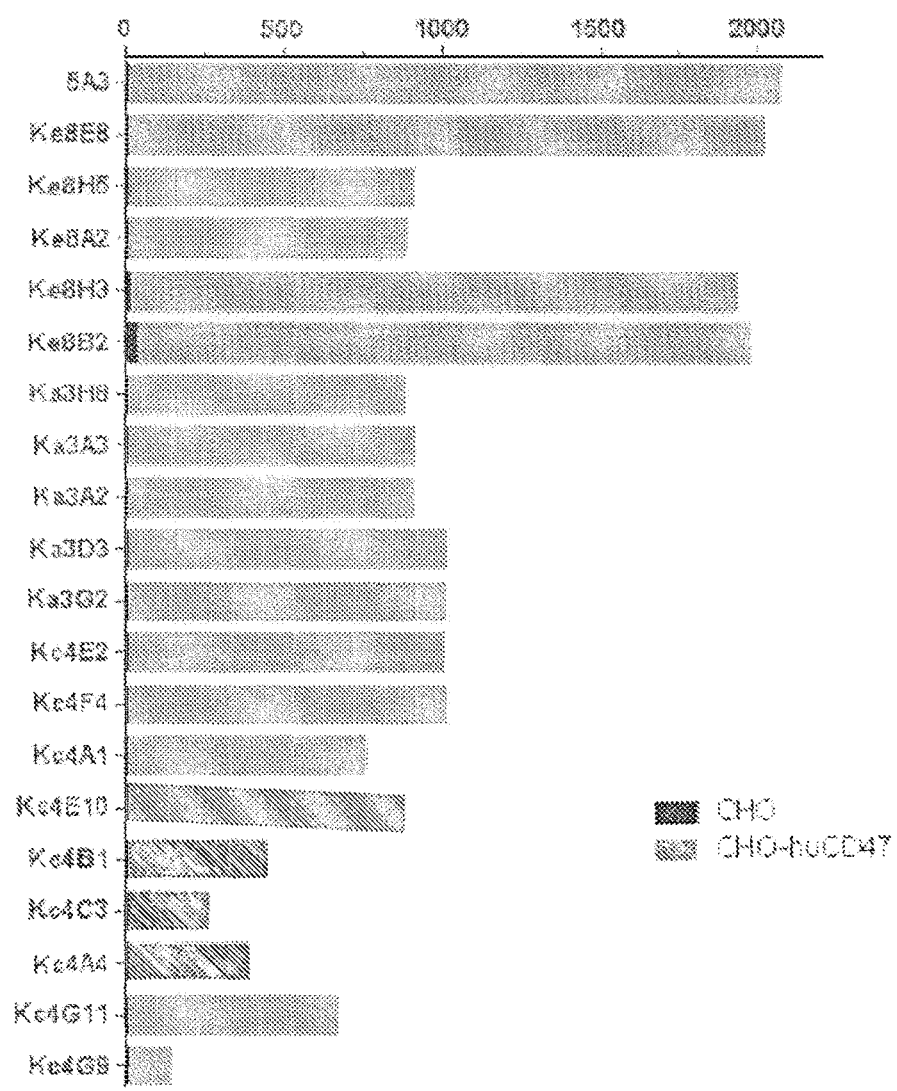
FIG. 3 is a graph depicting the specificity of various CD47 monoclonal antibodies (Mabs) as indicated by the binding of purified CD47 Mabs to CHO cells transfected with human CD47, assessed by flow cytometry (grey bars). CD47 MAbs did not bind to non-transfected CHO cells (black bars).

The specificity of CD47 monoclonal antibodies (Mabs) was shown by flow cytometry using CHO cells stably transfected with human CD47 (CHO-huCD47 cells). Non-transfected CHO cells were used as control. In brief, purified CD47 Mabs were incubated with CHO-huCD47 cells at a final concentration of 10 μg/ml for 30 minutes. After two washes, bound CD47 antibodies were detected using a Cy-5 conjugated anti-human Fc secondary antibody (BD biosciences). FIG. 3 shows a significant binding of CD47 MAbs to hu-CD47 transfected CHO cells, but no binding (or background-level binding) to non-transfected CHO cells, thus demonstrating the specificity of CD47 MAbs of the present invention.

Binding of CD47 Antibodies to HEK293-P Cells

Figure 4:
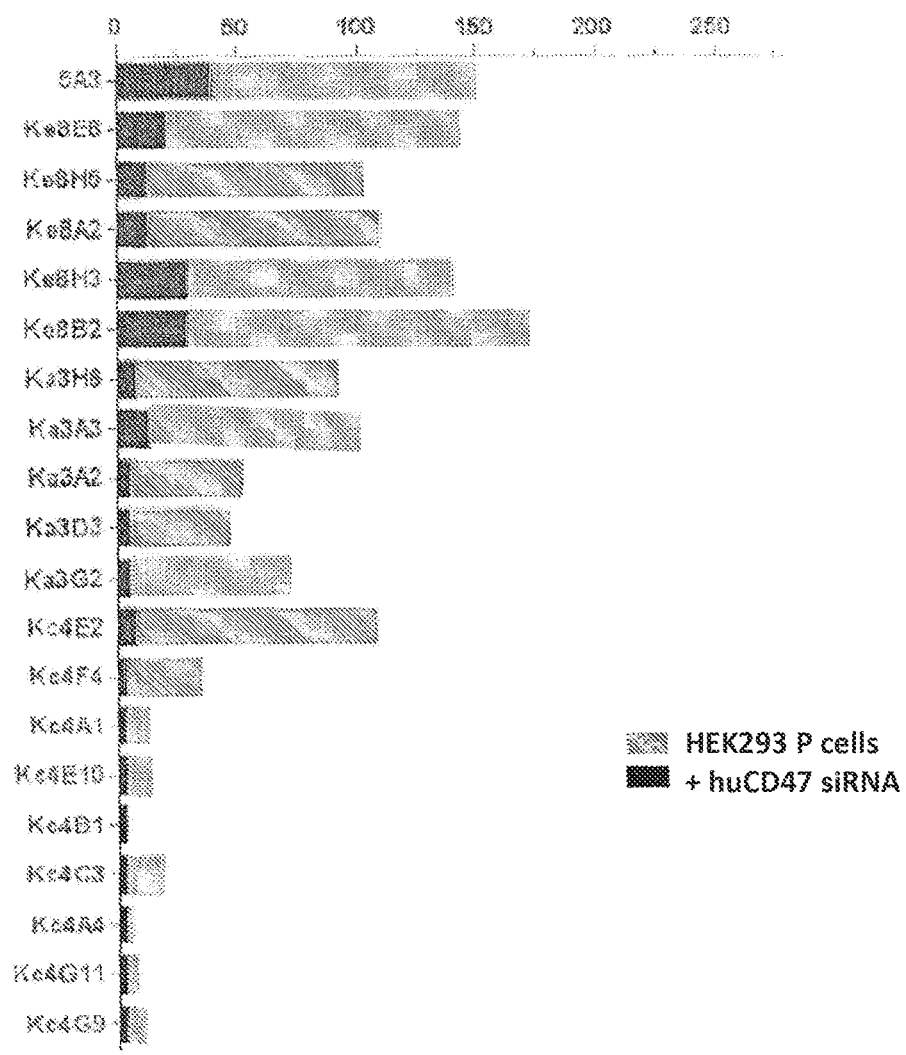
FIG. 4 is a graph depicting binding to native CD47 and specificity of CD47 MAbs as shown by binding of purified CD47 Mabs to HEK293-P cells as assessed by flow cytometry (grey bars). Binding to HEK293-P cells stably transfected with hCD47-specific siRNA is significantly decreased (black bars).

The specificity of CD47 Mabs was further confirmed in an experiment using HEK293-P cells with a siRNA mediated CD47 gene knock-down. The HEK293-P cells (Peak cells) were derived from human embryonic kidney cells and expresses low to moderate levels of CD47. A CD47-deficient variant of Peak cells has been generated by stably transfecting them with siRNA specific to the CD47 gene. Cell surface expression of CD47 antigen is reduced in these CD47 knock-down PEAK cells by more than 85% (data not shown). FIG. 4 demonstrates the binding of selected CD47 MAbs to non-transfected Peak cells and to CD47 knock-down Peak cells. Binding of CD47 Mabs to CD47 siRNA-transfected Peak cells is significantly reduced, thus confirming their antigen specificity.

Figure 5:
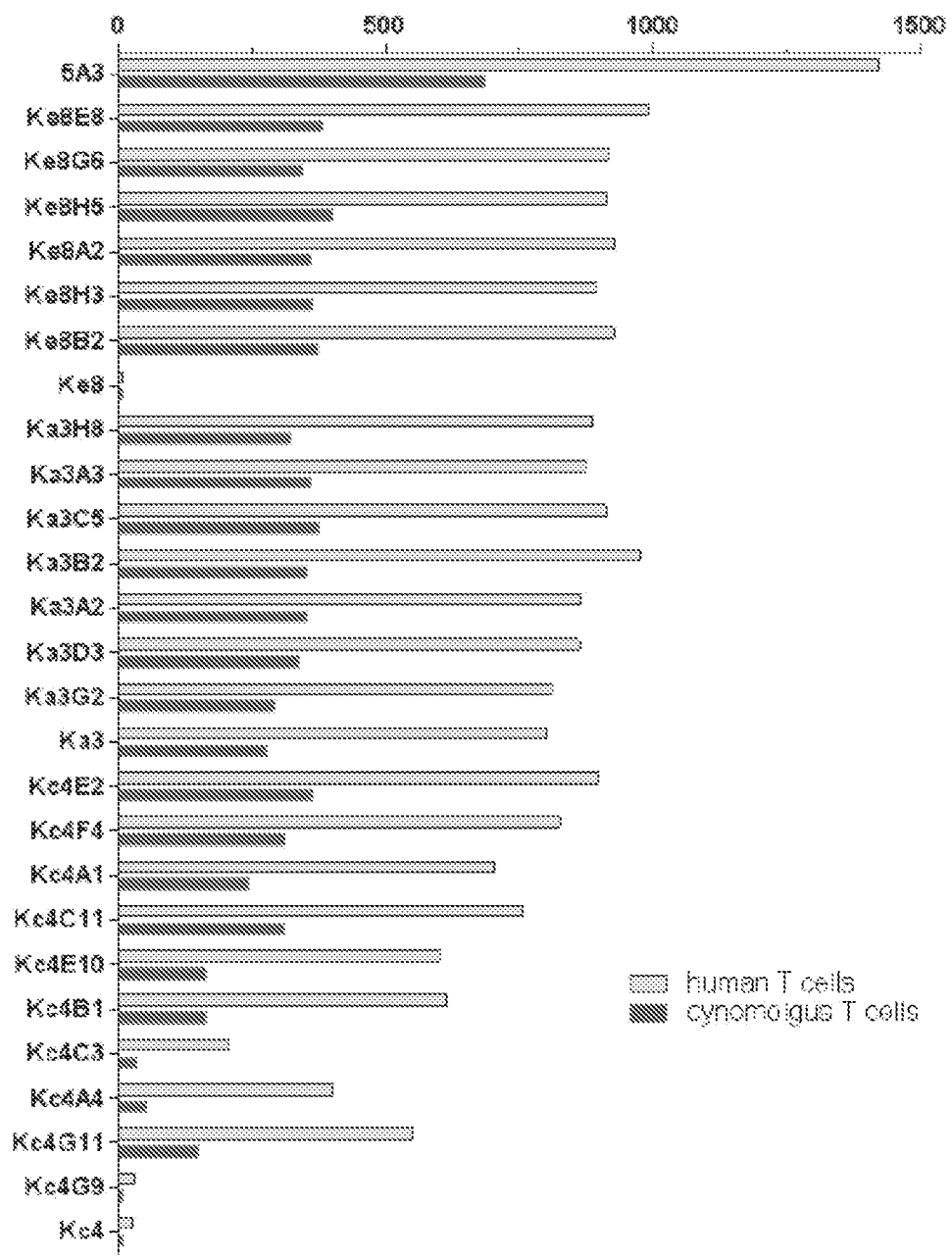
FIG. 5 is a graph depicting binding to native human CD47 and cross-reactivity with cynomolgus CD47. The binding of purified CD47 Mabs to human (light grey bars) and cynomolgus (dark grey bars) PBMC CD4+ T cells was evaluated.

Cross-Reactivity of CD47 Antibodies with Cynomolgus CD47; Binding of CD47 Antibodies to Human and Cynomolgus CD4+ T Cells The ability of CD47 monoclonal antibodies of the present invention to cross-react with native cynomolgus monkey CD47 was tested by flow cytometry. Binding of CD47 antibodies to cynomolgus CD4-positive T lymphocytes present in peripheral blood mononuclear cells (PBMCs) was compared to the binding to the corresponding human cell population. In brief, cynomolgus peripheral blood mononuclear cells (PBMCs) were obtained from Ricerca Biosciences. Human PBMCs were isolated from a buffy coat using CPT ficoll tubes (Beckton and Dickinson). For flow cytometry analysis, PBMCs were preincubated with FcgR Blocking Reagent, (Miltenyi Biotech.) for 20 minutes in order to block Fc gamma receptors before addition of CD47 antibodies (final concentration of 0.005 mg/ml). After an incubation period of 30 minutes cells were washed and reacted with PE-conjugated anti human CD4 antibody (clone L200, BD Pharmingen diluted 1/100) and FMAT-BLUE®-conjugated (monofunctional dye label) goat-anti human Fc antibody (Jackson Immuno Research, 109-005-098). The MFI for CD47 binding (FL4) was then determined by flow cytometry in the CD4+ positive population (gated on FL2). As shown in FIG. 5, CD47 monoclonal antibodies of the present invention bind to native human CD47 and cross-react with cynomolgus CD47.

SIRPα Blocking Activity of CD47 Antibodies

Figure 6:
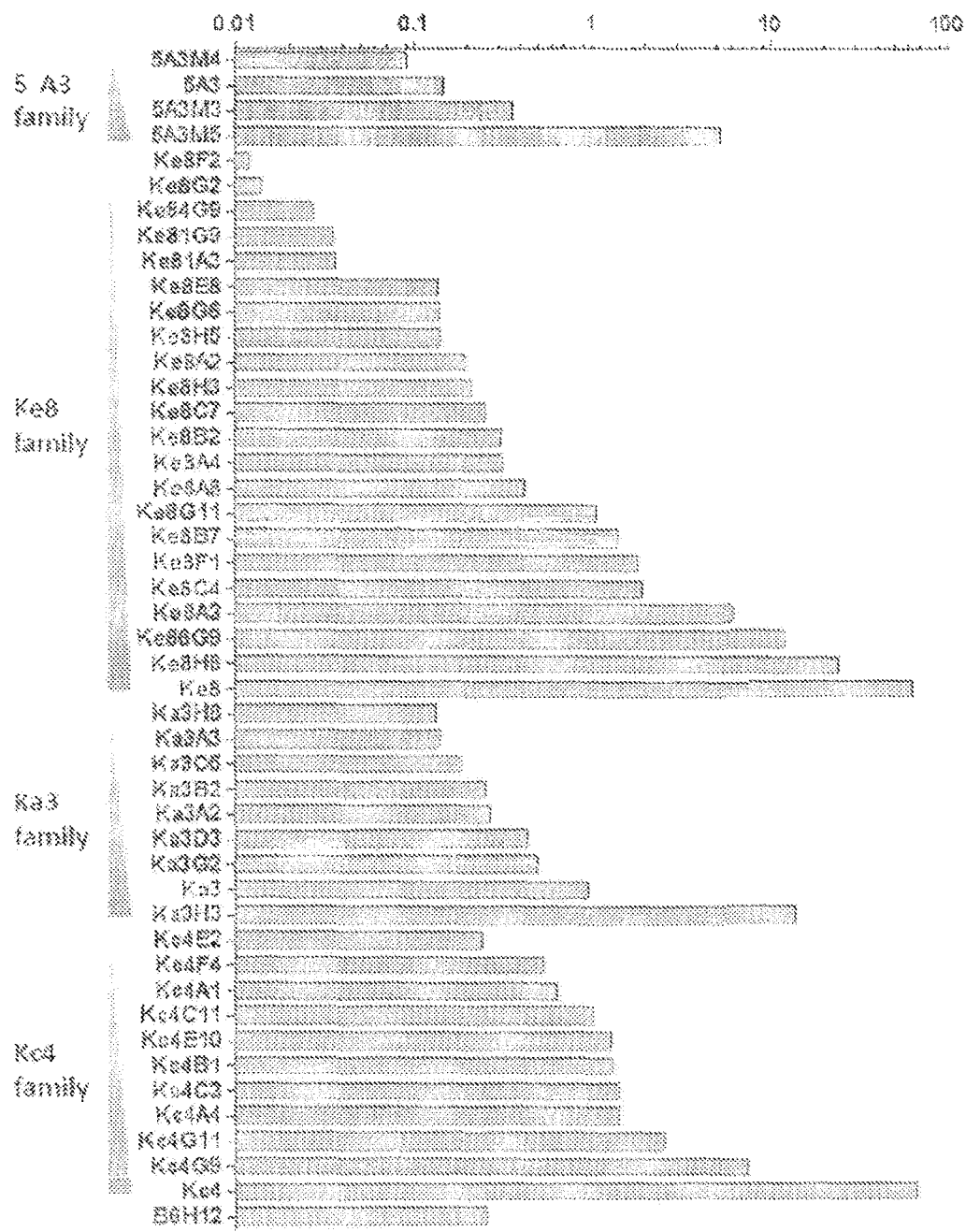
FIG. 6 is a graph depicting the potency of CD47 Mabs to block the CD47-SIRPα interaction, as tested in the CD47-SIRPα inhibition assay (competitive inhibition of the binding of recombinant soluble human SIRPα to hCD47-expressing CHO cells, as described in Example 4). IC50 values obtained in dose-response experiments are shown. CD47 Mabs are grouped by family and ranked from higher to lower potency. The neutralizing activity of the antibodies of the present invention is compared to the commercially available CD47 antibody B6H12.

The SIRPα blocking activity of CD47 was determined in the CD47-SIRPα competitive binding assay. Dose-response experiments with CD47 Mabs allowed determining an IC50 value for each of the CD47 MAbs of the present invention. In brief, human CD47 transfected CHO cells were incubated with His-tagged soluble human SIRPα (final concentration, 200 ng/ml) and increasing concentrations of CD47 Mab (3.3 pM to 330 nM, in quadruplicates) The detection of bound SIRPα was as described in example 4. FIG. 6 shows the potency of CD47 Mabs to block the CD47-SIRPα interaction, represented by IC50 values. CD47 Mabs are grouped by family and ranked from higher to lower potency. Their neutralizing activity was compared to the commercially available CD47 antibody B6H12. It is apparent from FIG. 6 that the neutralizing potencies of CD47 Mabs of the present invention vary over a wide range.

Hemagglutination Activity of CD47 Antibodies

Figure 7:
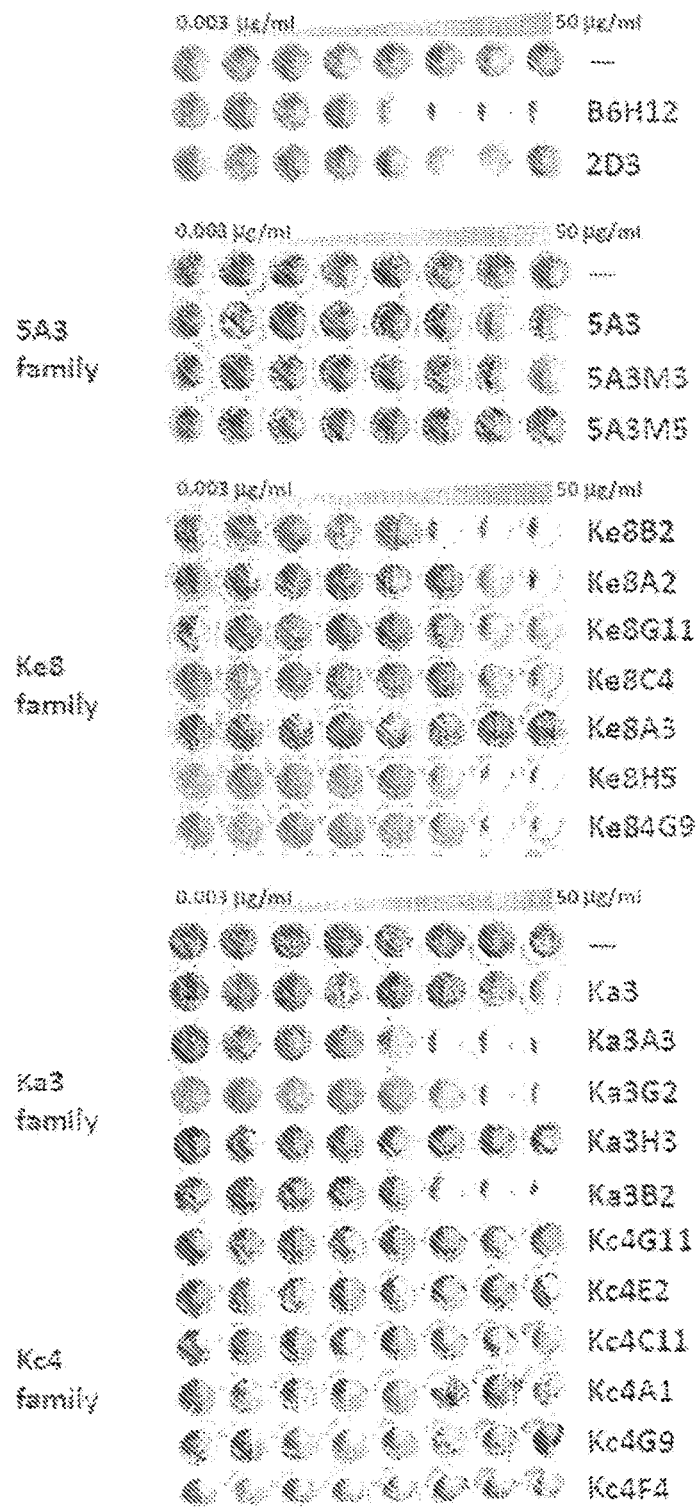
FIG. 7 is an illustration depicting the hemagglutination activity of CD47 antibodies. Hemagglutination is evidenced as a clumped deposit of RBC, in the form of a crescent at the bottom around the inferior border of the well, whereas non-agglutinated are do not form aggregates and are distributed evenly over the well surface area.
Figure 8:
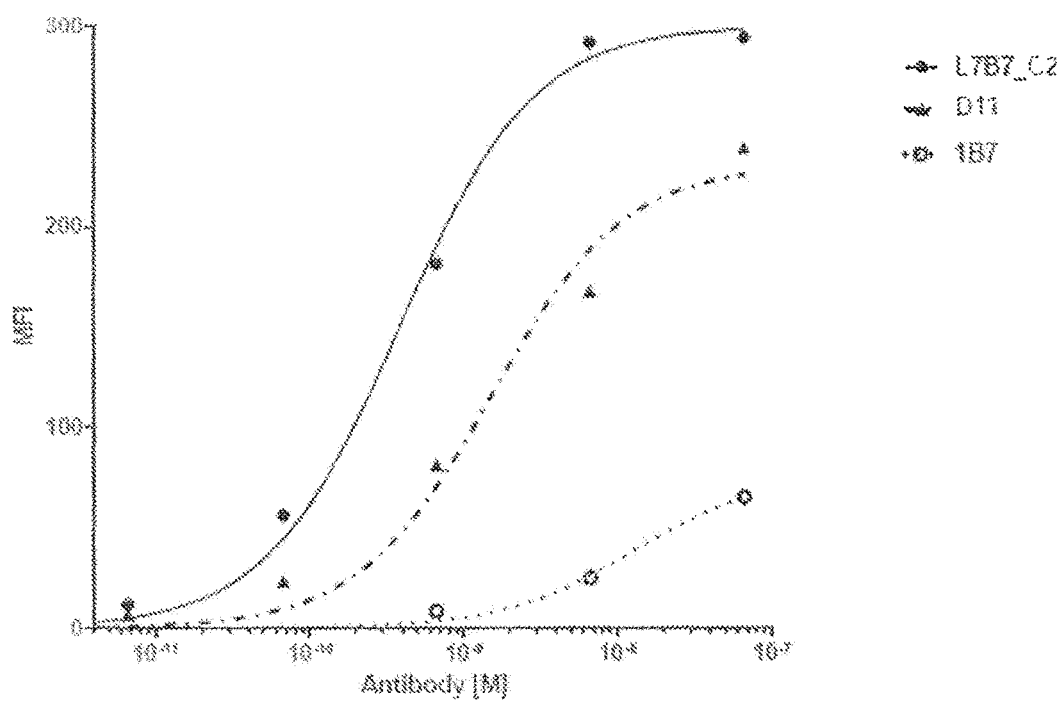
FIG. 8 is a graph depicting dose-response curve for a FACS-binding assay done with Raji cells and the original anti-CD19 clone 1B7, clone D11 identified following the first affinity maturation round, and the final clone L7B7_c2, issued form the second affinity maturation round.

FIG. 7 demonstrates that high-affinity CD47 Mabs of the 5A3, Ke8, and Ka3 families induce hemagglutination; in contrast to the other three families, Kc4 family antibodies tested in this experiment do not seem to induce hemagglutination even the one binding strongly to CD47 and inhibiting potently the CD47-SIRPα interaction.

CD47 MAbs were tested for their ability to induce homotypic clustering of erythrocytes (hemagglutination). 10 microliters of human whole blood was diluted in 40 microliters of antibody solution in PBS at different concentrations (range: 0.003 microg/ml to 50 microg/ml final Mab concentration) in flat-bottom 96 well plates. The blood-antibody mix was incubated O/N at 37° C. without shaking. At the end of the incubation, the plates were agitated manually, tilted at about 30° C., and let to rest for about 10 minutes.

Evidence of hemagglutination is demonstrated by the formation of a clumped deposit, in the form of a crescent at the bottom around the inferior border of the well. All but the lowest affinity CD47 antibodies of the 5A3, Ke8, and Ka3 families (specifically, 5A3M5, Ke8A3, Ka3A3) caused hemagglutination. In contrast, the CD47 antibodies of the Kc4 family did not cause hemagglutination, even the higher affinity ones (Kc4E2, Kc4F4).

Example 9: CD19 Antibody Affinity Maturation (a) Antibody B7

Amongst the antibodies identified during the screening process described in the Examples above B7 was selected for affinity maturation in order to increase its affinity for hCD19. Candidate B7 contains a lambda light chain (IGLV6-57) and several phage libraries displaying scFv variants were generated by introducing diversity into the CDR1, CDR2 and CDR3 of the variable light chain region while the heavy chain variable region was kept unmodified. Different diversification strategies were used to generate 20 libraries comprising a total of $2 \times 10^9$ transformants partially covering a theoretical diversity of $4 \times 10^{12}$.

(b) Antibody L7B7_D11

Antibody D11 was identified during the affinity maturation of B7 described above and binds to hCD19 with a higher affinity than the parental antibody B7. This antibody was selected for a second round of affinity maturation of its light chain. A total of 6 libraries comprising $2.8 \times 10^9$ transformants partially covering a theoretical diversity of $4 \times 10^9$ were generated and used for phage display selections as described above except that 1 nM of hCD19 was used for each round of selection. This second round of affinity maturation lead to the identification of the following antibodies with and improved binding to CD19: L7B7_C2; L7B7_A6; L7B7_B11; L7B7 C6 and L7B7_C9.

Example 10: Expression and Purification of Bispecific Antibodies Carrying a Lambda and a Kappa Light Chain The simultaneous expression of one heavy chain and two lights chain in the same cell can lead to the assembly of three different antibodies. Simultaneous expression can be achieved in different ways such as that the transfection of multiple vectors expressing one of the chains to be co-expressed or by using vectors that drive multiple gene expression. A vector pNovi κHλ was previously generated to allow for the co-expression of one heavy chain, one Kappa light chain and one Lambda light chain as described in US 2012/0184716 and WO 2012/023053, each of which is hereby incorporated by reference in its entirety. The expression of the three genes is driven by human cytomegalovirus promoters (hCMV) and the vector also contains a glutamine synthetase gene (GS) that enables the selection and establishment of stable cell lines. The VH and VL gene of the anti-hCD19 IgGπ or the anti-hCD47 IgGκ were cloned in the vector pNovi κHλ, for transient expression in mammalian cells. Peak cells were cultured in 6-well plates at a concentration of $6 \times 10^5$ cells per well in 2 ml culture media containing fetal bovine serum. 2 μg of plasmid DNA was transfected into the cells using TransIT-LT1 transfection reagent (Minis) according to manufacturer's instructions. Antibody concentration in the serum-containing supernatant of transfected cells was measured at several time points during the production using the Bio-Layer Interferometry (BLI) technology. An OctetRED96 instrument and Protein A biosensors were used for quantitation (Pall, Basel, Switzerland). 200 μL of supernatant were used to determine IgG concentration; biosensors were pre-conditioned and regenerated using 10 mM glycine pH 1.7 and IgG calibrators diluted in conditioned PEAK cell medium were prepared for standard curve generation. Concentrations were determined using the dose response 5PL weighted Y standard curve equation and an initial slope binding rate equation. According to antibody concentration, supernatants were harvested 7 to 10 days after transfection and clarified by centrifugation at 1300 g for 10 min. The purification process was composed of three affinity steps. First, the CaptureSelect™ IgG-CH1 affinity matrix (Life Technologies, Zug, Switzerland) was washed with PBS and then added in the clarified supernatant. After incubation overnight at +4° C., supernatants were centrifuged at 1000 g for 10 min, flow through was stored and resin washed twice with PBS. Then, the resin was transferred on spin columns and a solution containing 50 mM glycine at pH 2.7 was used for elution. Several elution fractions were generated, pooled and desalted against PBS using 50 kDa Amicon® Ultra Centrifugal filter units (Merck KGaA, Darmstadt, Germany). The final product, containing total human IgGs from the supernatant, was quantified using a Nanodrop spectrophotometer (NanoDrop Technologies, Wilmington, Del.) and incubated for 15 min at RT and 20 rpm with the appropriate volume of CaptureSelect™ LC-kappa (Hu) affinity matrix (Life Technologies, Zug, Switzerland). Incubation, resin recovery, elution and desalting steps were performed as described previously. The last affinity purification step was performed using the CaptureSelect™ LC-lambda (Hu) affinity matrix (Life Technologies, Zug, Switzerland) applying the same process as for the two previous purifications. The final product was quantified using the Nanodrop. Purified bispecific antibodies were analyzed by electrophoresis in denaturing and reducing conditions. The Agilent 2100 Bioanalyzer was used with the Protein 80 kit as described by the manufacturer (Agilent Technologies, Santa Clara, Calif., USA). 4 μL of purified samples were mixed with sample buffer supplemented with dithiothreitol (DTT; Sigma Aldrich, St. Louis, Mo.). Samples were heated at 95° C. for 5 min and then loaded on the chip. All samples were tested for endotoxin contamination using the Limulus Amebocyte Lysate test (LAL; Charles River Laboratories, Wilmington, Mass.).

Example 11: Characterization of Monovalent and Bispecific Antibodies

Dual-targeting bispecific antibodies bind to two different antigens on the surface of the same cell. Simultaneous binding of the two antibody arms to two antigens on the surface of the cell (termed co-engagement) results in additive or synergistic increase of affinity due to avidity mechanism. As a consequence, co-engagement confers high selectivity towards cells expressing both antigens as compared to cells that express just one single antigen. In addition, the affinities of the two arms of a bispecific antibody to their respective targets can be set up in a way that binding to target cells is principally driven by one of the antibody arms. For instance, a dual targeting κλ-body composed of one arm binding with high affinity to a tumor associated antigen (TAA), for example CD19, and a second arm binding with lower affinity to CD47—but sufficient to inhibit CD47/SIRPα upon TAA co-engagement—should allow preferential inhibition of CD47 in cancer versus normal cells. The experiments described below (FIGS. 9 to 13) compare the binding affinity, the CD47-SIRPα neutralization potency, and the tumor cell killing activity of CD47xCD19 bispecific κλ-body and the corresponding monovalent antibody, i.e., having the same CD47-binding arm plus a "dummy" non-binding arm.

Binding of Monovalent and Bispecific Antibodies to B Cell Lines

Figure 9A:
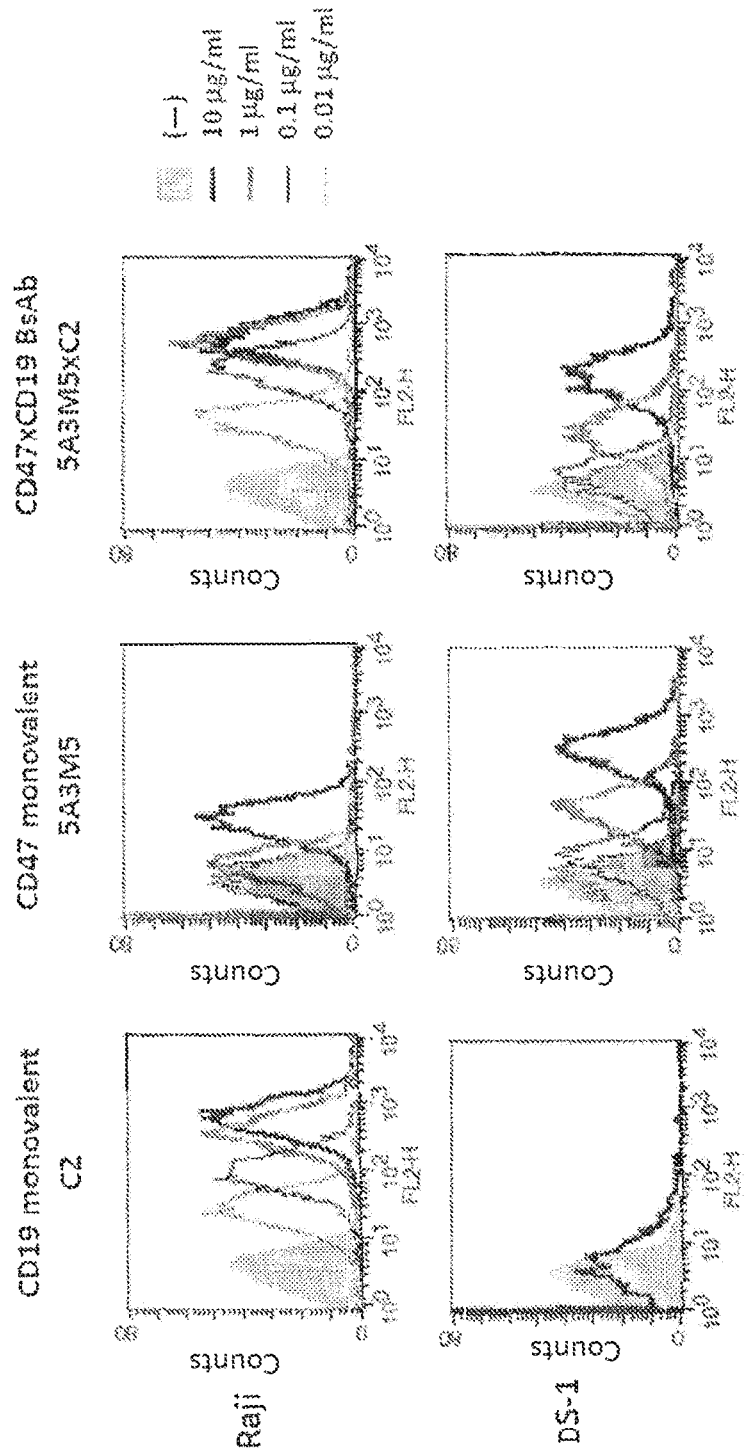
Figure 10A:
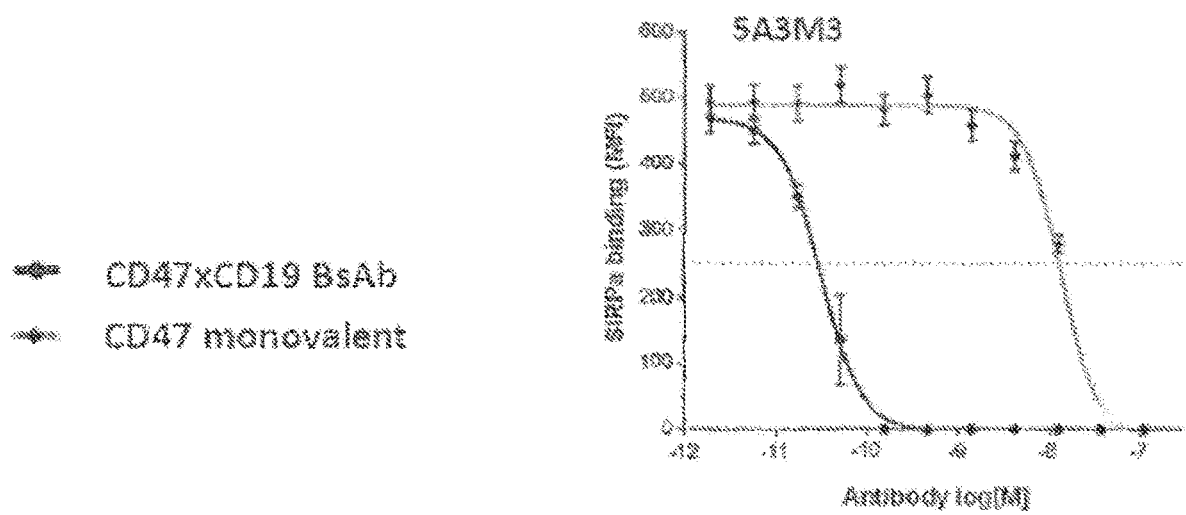
FIG. 10 is a series of graphs depicting the SIRPα Blocking Activity of Monovalent and Bispecific Antibodies.
Figure 10B:
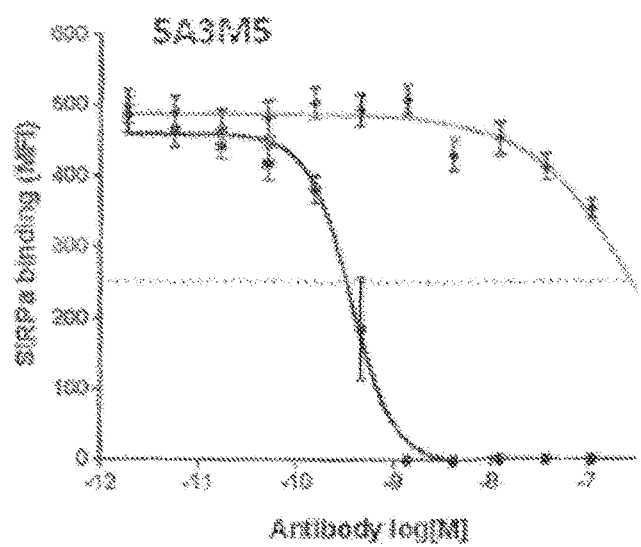
Figure 10C:
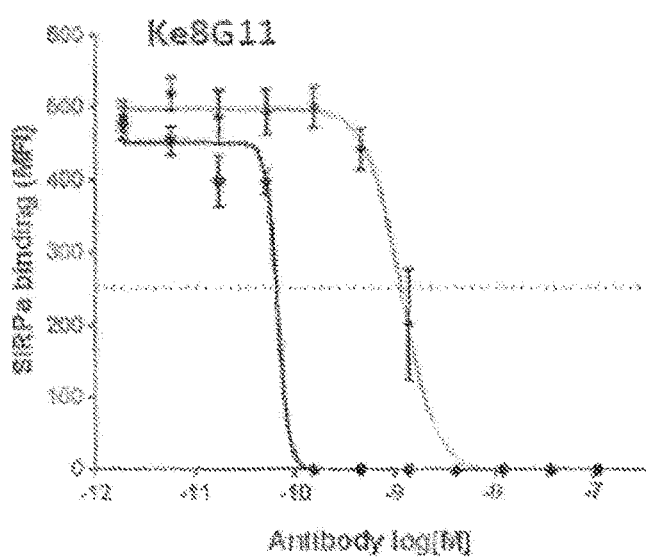
Figure 10D:
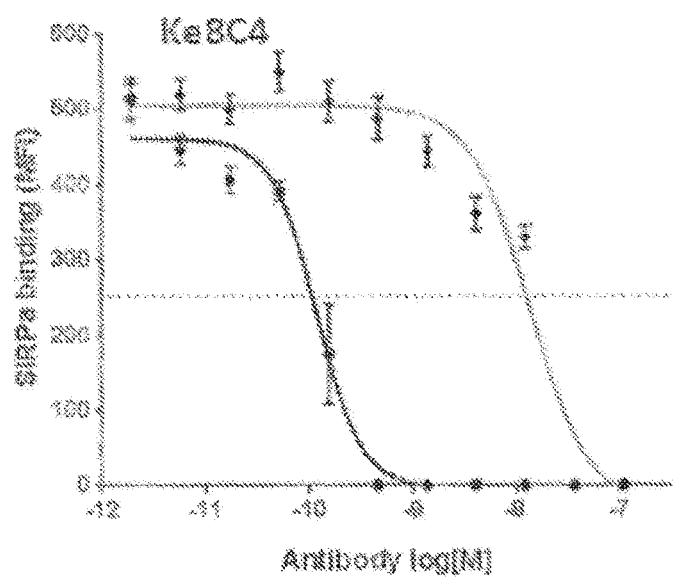
Figure 10E:
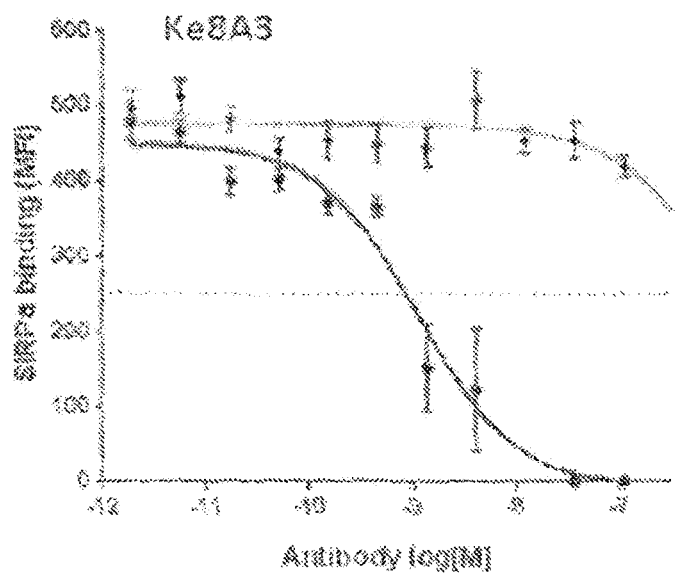
Figure 10F:
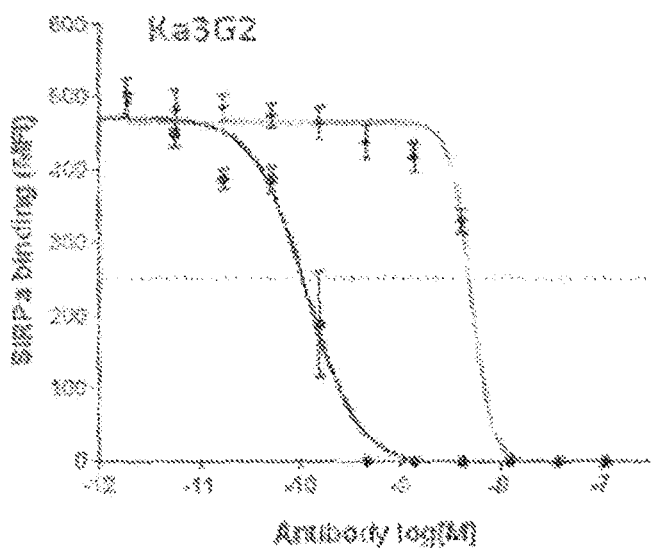
Figure 10G:
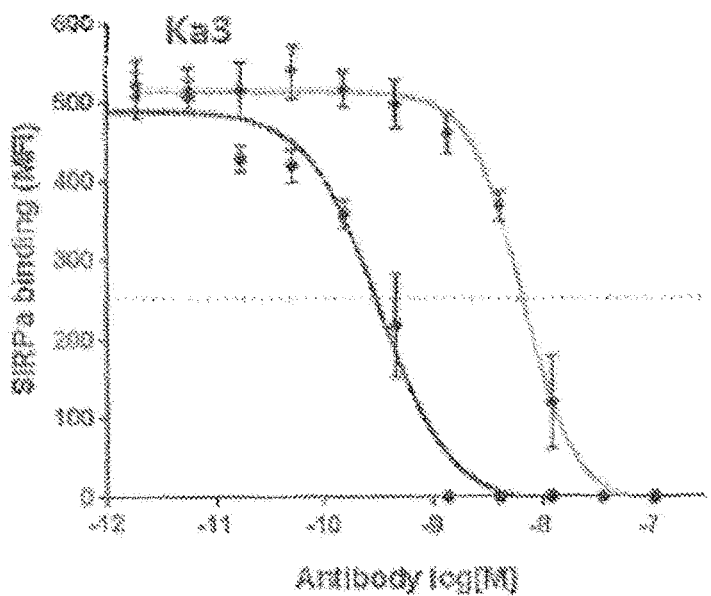
Figure 10H:
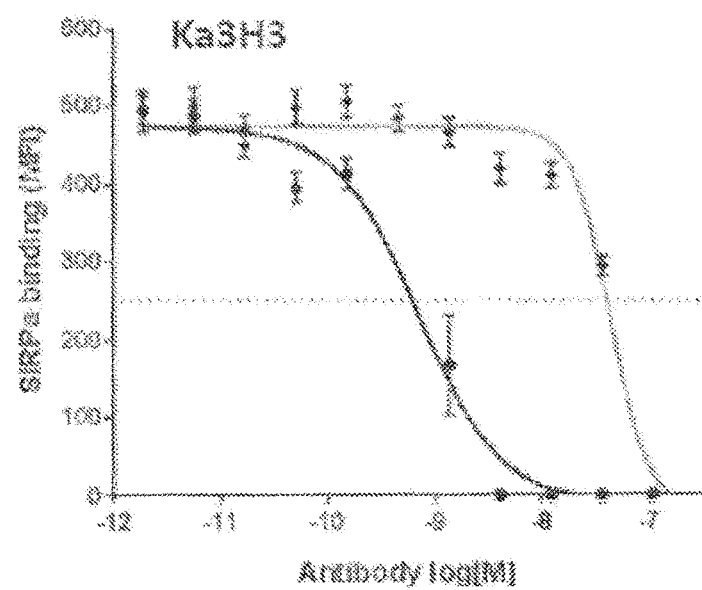

To demonstrate that binding of CD47xCD19 κλ bodies to target cells is CD19 dependent, a series of FACS experiments comparing the binding of CD47xCD19 κλ bodies to their monovalent counterparts were performed. Two types of cells were used, a CD19-positive Burkitt lymphoma cell line Raji (expressing about 65,000 CD47 molecules per cell) and the CD19-negative B-NHL cell line DS-1 (expressing about 150,000 CD47 molecules per cell) as a control. FIGS. 9A-9C demonstrate that a CD47xCD19 κλ body co-engages the two targets at the surface of Raji cells. This is shown by (i) increased affinity to Raji cells as compared to DS-1 cells and (ii) increased affinity of the CD47xCD19 κλ body as compared to the CD47 monovalent antibody, observed with Raji cells—but not with DS-1 cells. A comparison of FACS profiles generated with the binding of CD19 monovalent antibody, the CD47 monovalent antibody, and the CD47xCD19 κλ body to Raji cells clearly demonstrates that binding of the CD47xCD19 κλ to target cells is principally driven by the CD19 arm.

SIRPα Blocking Activity of Monovalent and Bispecific Antibodies

Another series of experiments provides a further proof of co-engagement of CD19 and CD47 on the surface of the target cell by showing that the neutralization of CD47-SIRPα interaction by CD47xCD19 κλ bodies is CD19-dependent. In this experiment, the activity of CD47xCD19 κλ bodies and the corresponding monovalent antibodies was tested in the CD47-SIRPα inhibition assay as described in Example 4. FIG. 10 shows that CD47xCD19 κλ bodies inhibited the CD47-SIRPα interaction in Raji cells with a significantly higher potency than the corresponding CD47 monovalent antibodies. Efficient neutralization of CD47-SIRPα interaction required CD19 co-engagement. IC50 values obtained with CD47xCD19 BsAbs are 20 to 1000× lower than the values obtained with the corresponding CD47 monovalent antibody (see Table 4).

TABLE 4

IC50 values of CD47 monovalent and bispecific antibodies

| CD47 Arm | IC50 CD47-SIRPα Assay (Raji) | | |
|---|---|---|---|
| | CD47Xcd19 BsAb [nM] | CD47 Monovalent [nM] | Monovalent/BsAb ratio |
| 5A3M3 | 0.031 | 13 | 419 |
| 5A3M4 | 0.36 | 400 | 1111 |
| Ke8G11 | 0.066 | 1.2 | 18 |
| Ke8C4 | 0.12 | 13 | 108 |
| Ke8A3 | 1.1 | >500 | >500 |
| Ka3G2 | 0.11 | 5.1 | 46 |
| Ka3 | 0.32 | 6.7 | 21 |
| Ka3H3 | 0.71 | 44 | 62 |

Example 12: ADCC MEDIATED by Bispecific Antibodies is CD19-Dependent

The ability of dual targeting κλ-bodies to co-engage CD47 and CD19 results in a significant increase in the affinity of binding to CD19-positive cells and in CD19-dependent neutralization of the CD47-SIRPα interaction. This, in turn, translates into efficient and selective cancer cell killing mediated by CD47xCD19 κλ body, as demonstrated in ADCC and ADCP experiments described in this and the following example.

Figure 11B:
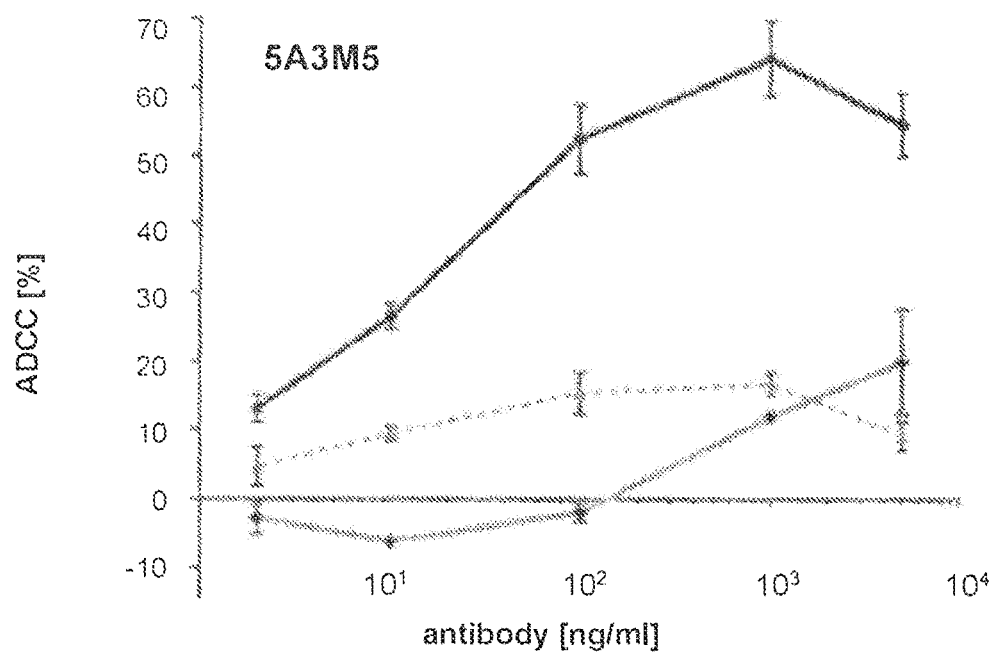
FIGS. 11A-11C show ADCC dose-response curves generated with CD47xCD19 κλ bodies (black) or the corresponding CD47 monovalent antibodies (grey). ADCC with the CD19 Mab C2 is shown for comparison (dashed grey). The ADCC assay was performed with whole human PBMCs as effector cells and Calcein AM-stained Raji (FIG. 11A, 11C) or Ramos (FIG. 11B) as target cells (effector to target ratio: 50). Cytotoxicity was calculated from the degree of calcein release from target cells. The percentage of specific cell killing+/−SD is shown. The experiments were done in duplicates.
Figure 11C:
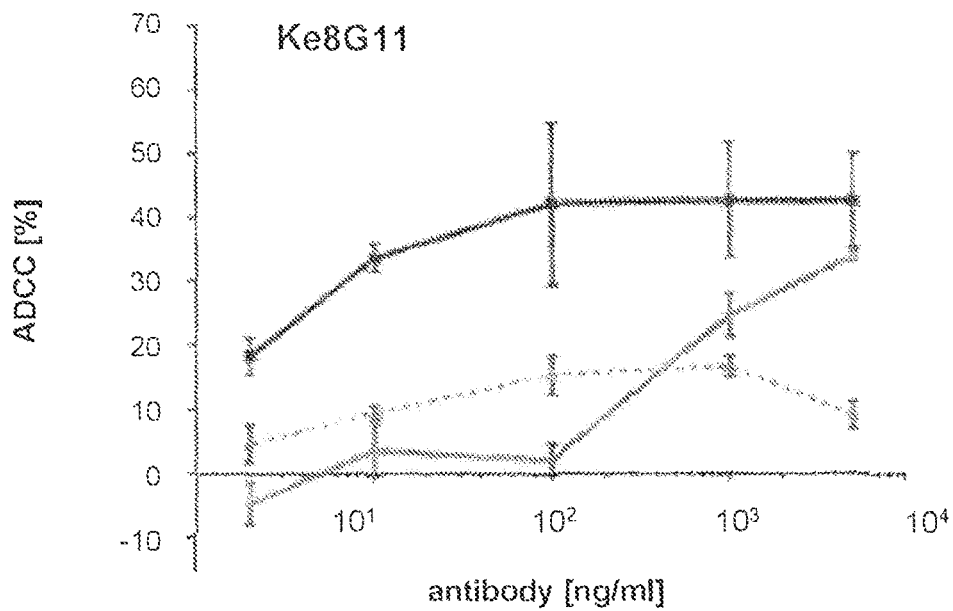
Figure 11D:
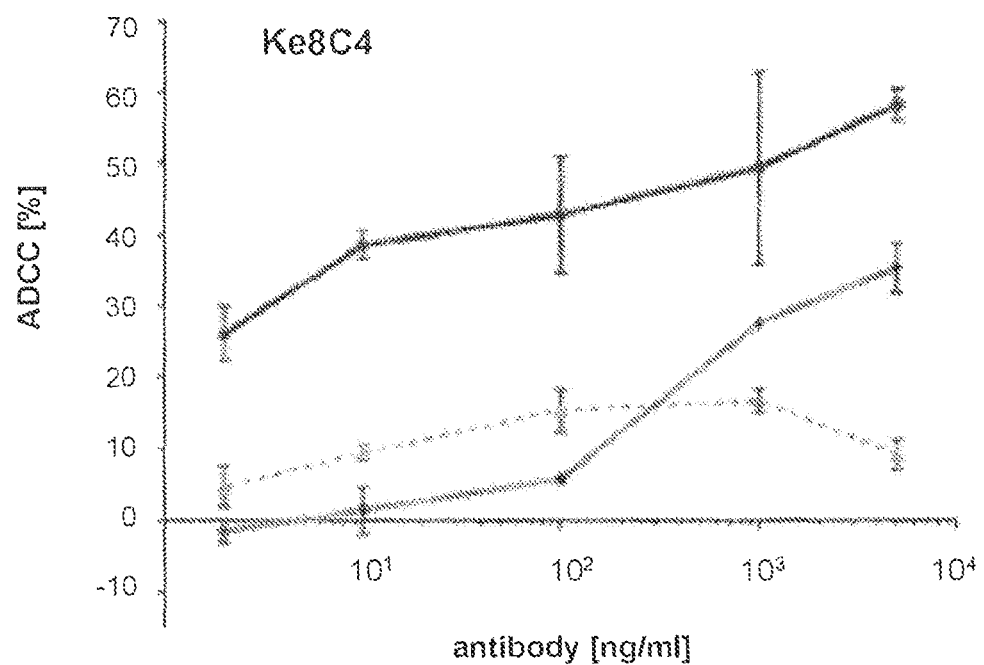
Figure 11E:
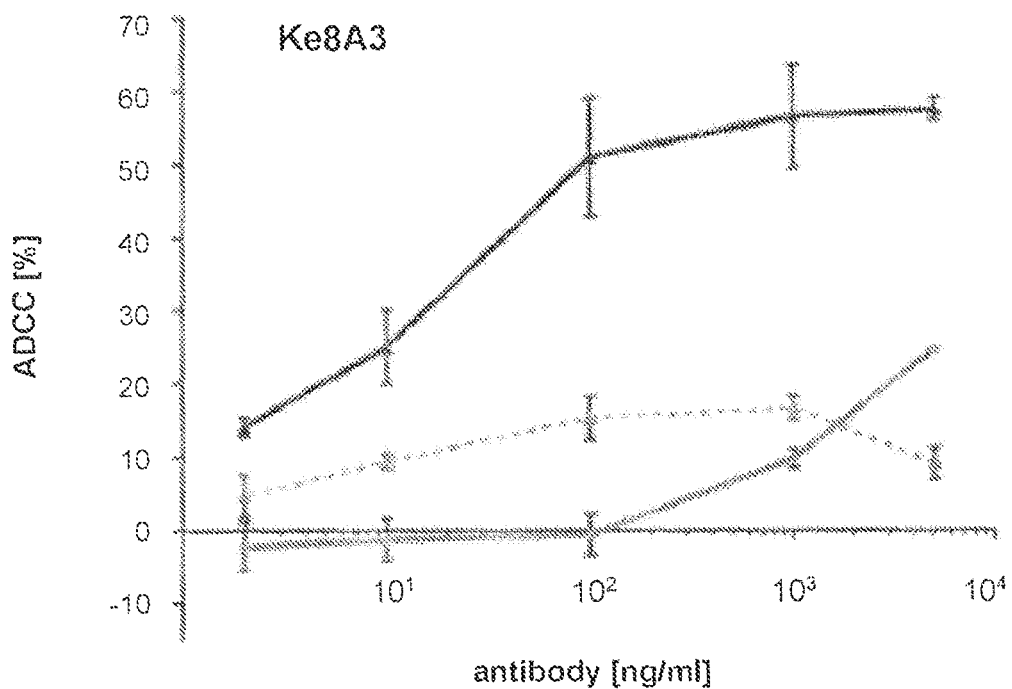
Figure 11F:
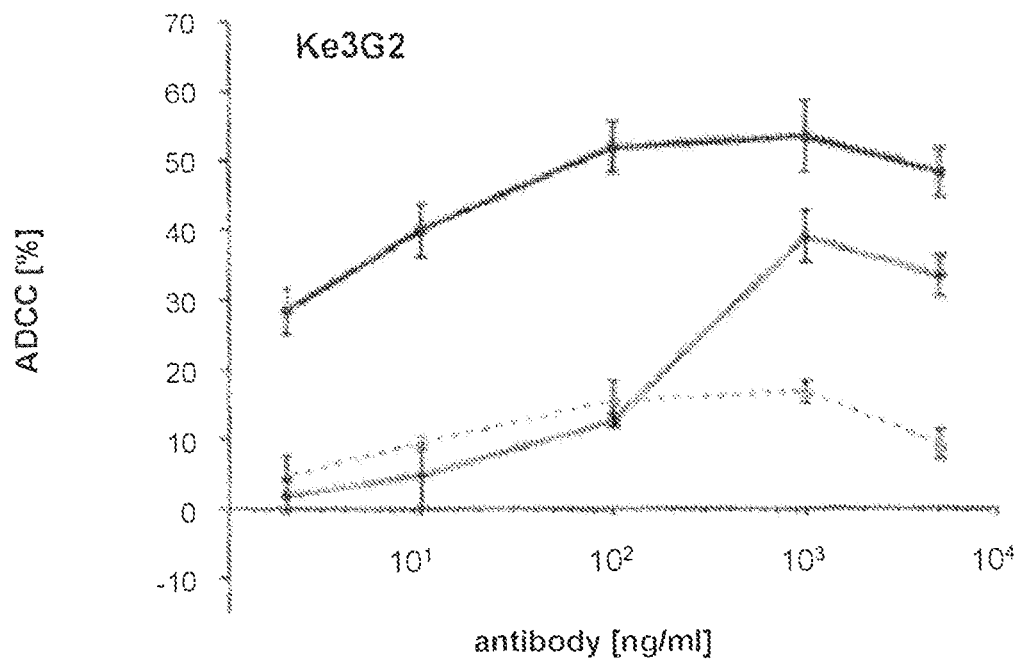
Figure 11G:
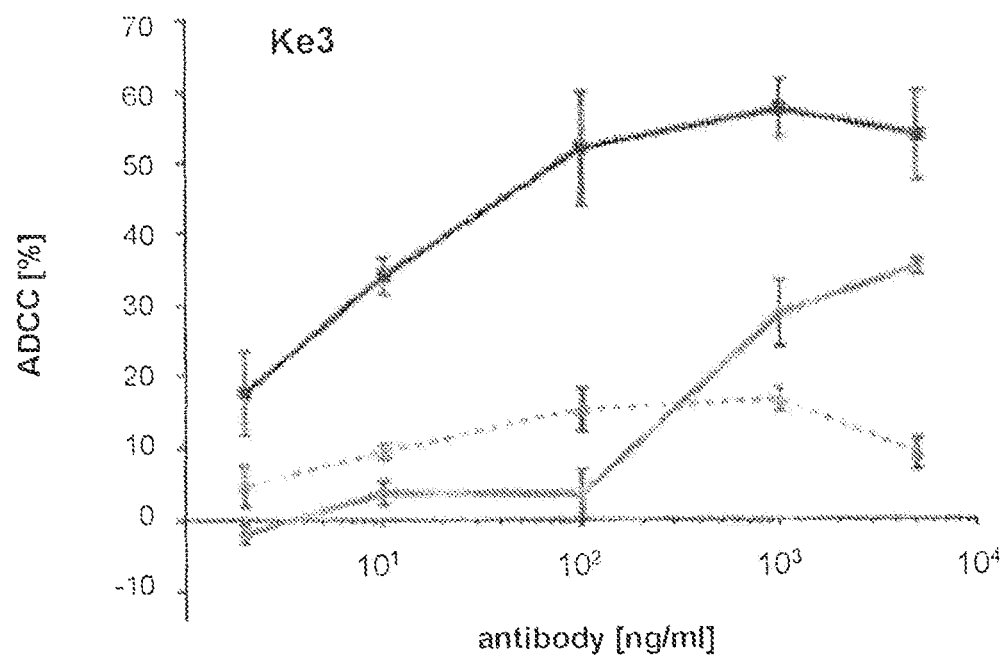
Figure 11J:
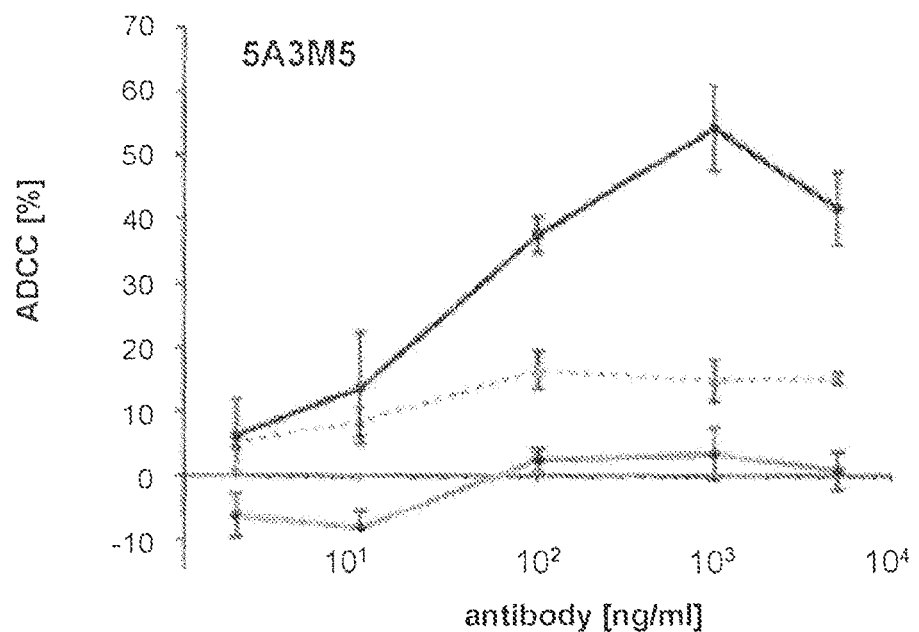
Figure 11K:
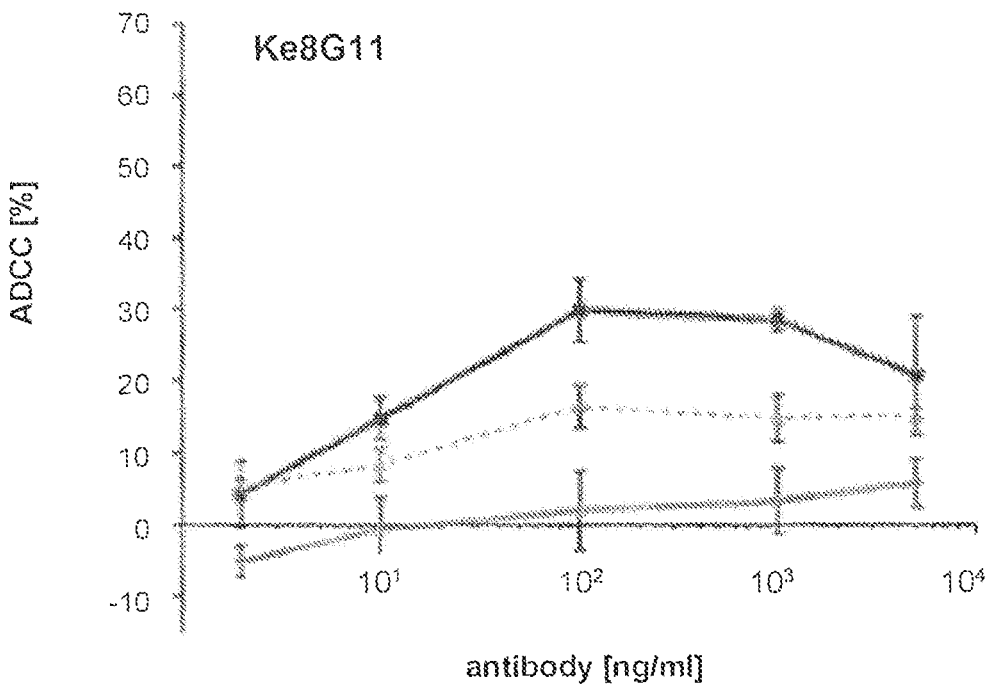
Figure 11L:
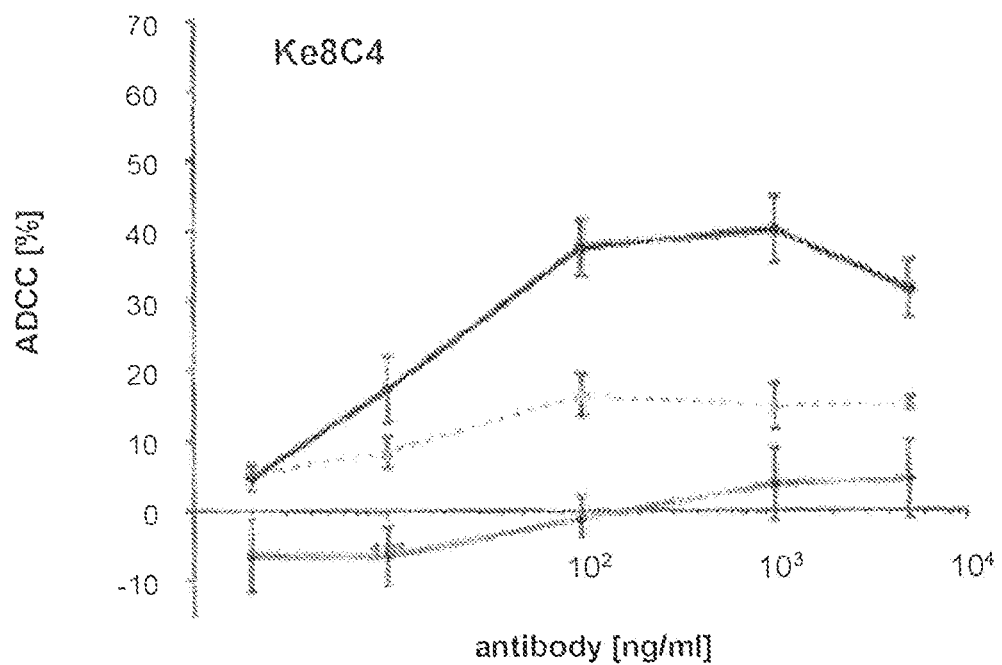
Figure 11M:
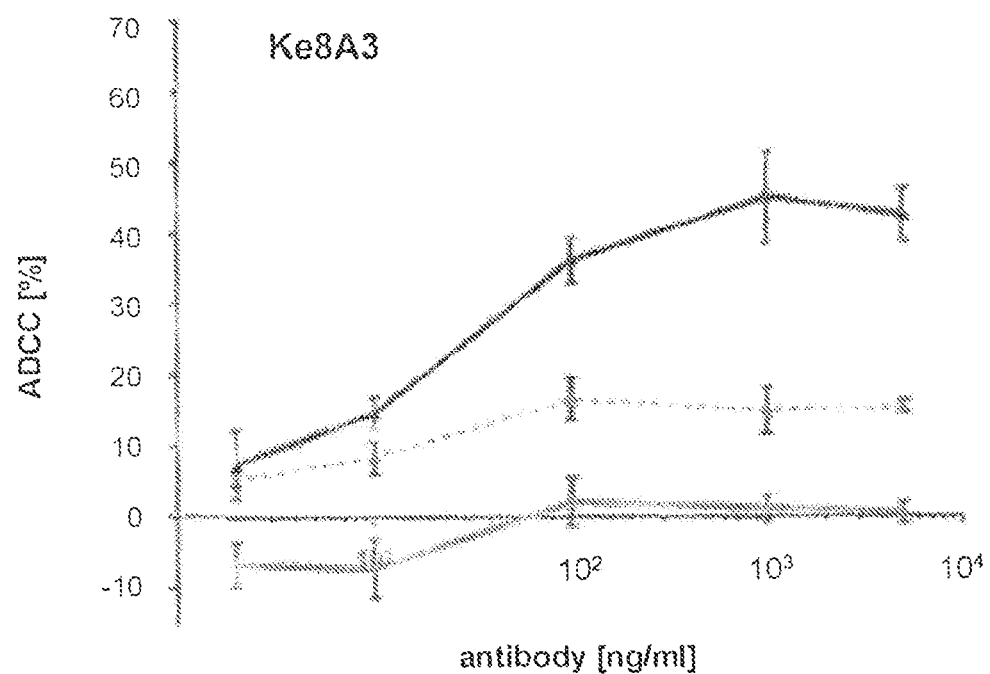
Figure 11N:
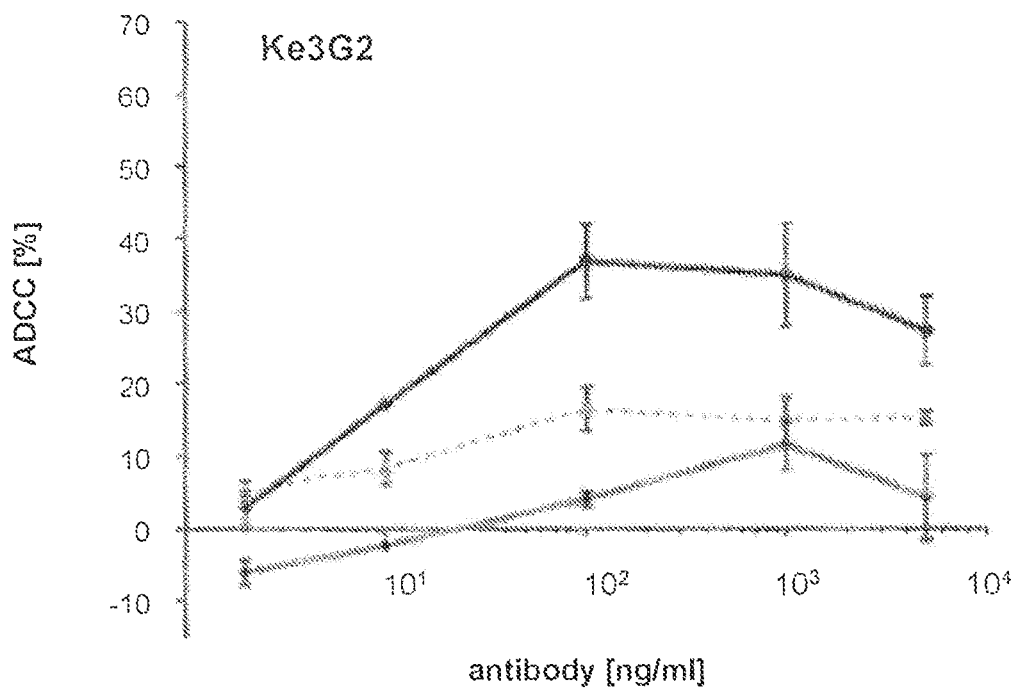
Figure 11O:
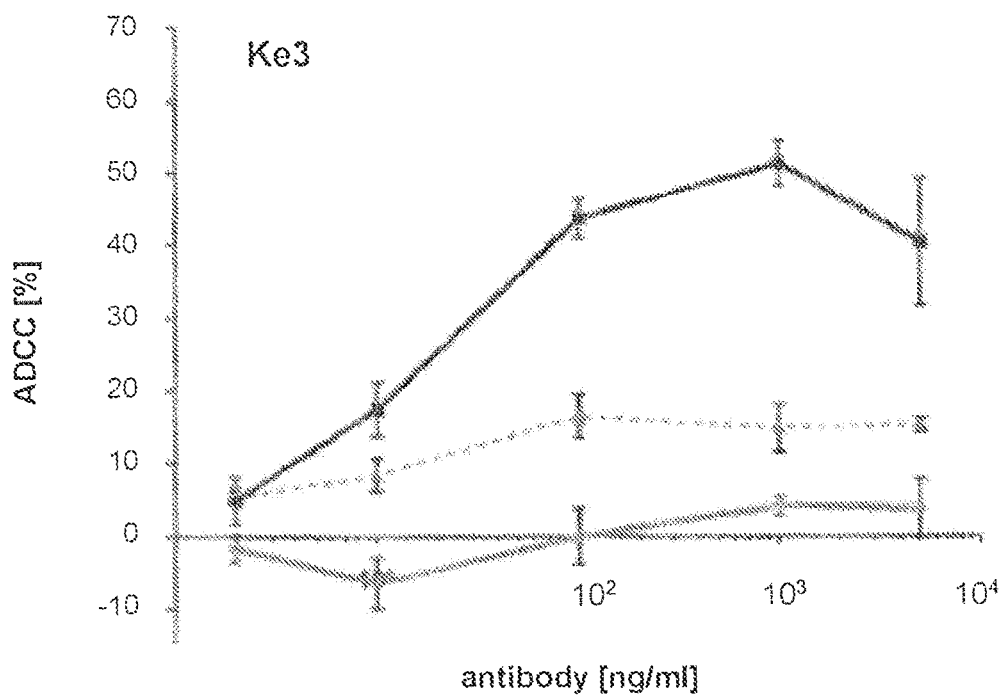
Figure 11P:
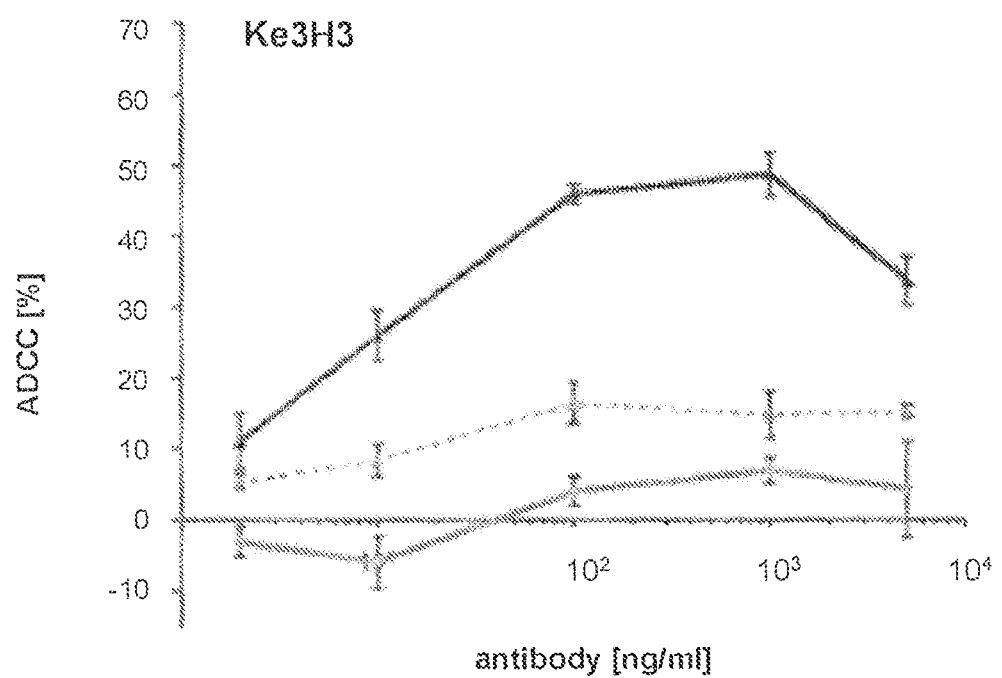

ADCC assays were performed with unfractionated human PBMC and Raji or Ramos B cell lymphoma target cells. Dose-response experiments shown in FIG. 11 demonstrate that CD47xCD19 κλ bodies provided herein kill B cell lymphoma cells in a more efficient way than the corresponding CD47 monovalent antibodies. Efficient ADCC is therefore dependent on CD19 co-engagement. FIG. 11C shows that the efficacy of ADCC with CD47xCD19 κλ bodies is comparable to rituximab and that it is significantly higher than with the CD19 Mab C2.

Example 13: ADCP Mediated by Bispecific Antibodies is CD19-Dependent

Figure 12A:
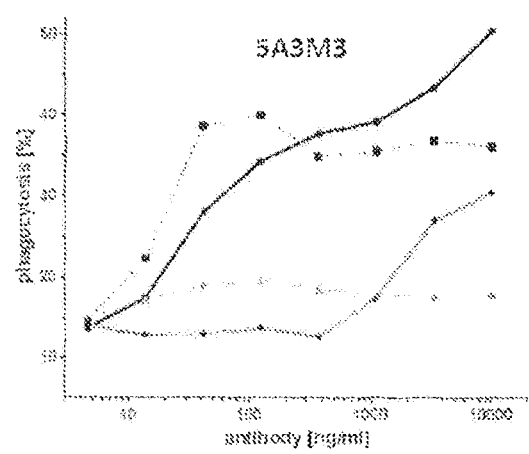
FIG. 12 is a graph depicting the phagocytic activity of three of the CD47xCD19 κλ bodies of the present invention (black lines) compared to the corresponding CD47 monovalent antibodies (grey lines) in dose-response ADCP experiment. Phagocytosis with the CD47 Mab B6H12 (on human IgG1 background, dotted black line) and with the CD19 Mab C2 (dotted grey line) is shown for comparison. The ADCP experiment was performed with human macrophages differentiated from peripheral blood monocytes and Raji as target cells (effector: target ratio 1:5) Phagocytosis was assessed by FACS. The percentage of macrophages having phagocytosed at least one target cells is shown. CD47xCD19 κλ bodies phagocytose CD19-positive cells in a CD19-dependent manner analysis, as the corresponding CD47 monovalent antibodies were much less efficient or not efficient at all.
Figure 12B:
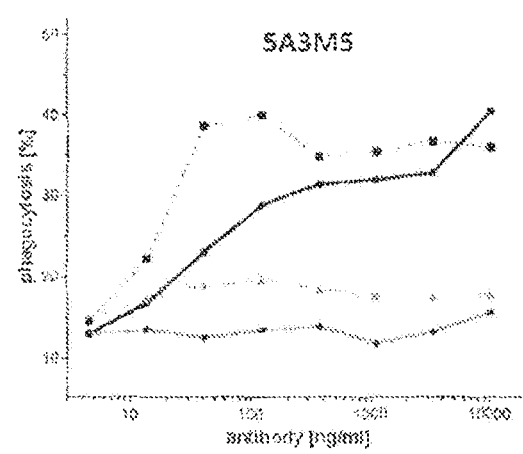
Figure 12C:
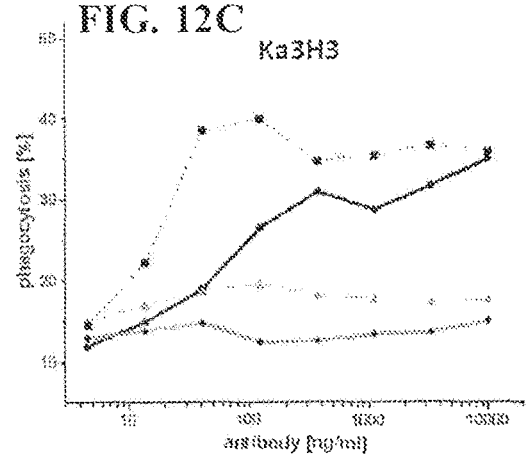

FIG. 12 demonstrates that CD47xCD19 BsAbs provided herein phagocytose CD19-positive cells in a CD19-dependent manner, as the corresponding CD47 monovalent antibodies are much less efficient (if any).

ADCP experiments were performed with human macrophages differentiated from peripheral blood monocytes and Raji as target cells. Macrophages were co-incubated with CFSE-labeled Raji cells (effector: target ratio 1:5) for 2.5 hours at 37° C. in the presence of increasing concentrations of bispecific or monovalent antibody. At the end of the incubation period, biotinylated anti-human CD14 antibody and Strep-Cy5 were added to label the macrophages. The cells were then washed and subjected to FACS analysis. Phagocytosis was evidenced by double-positive events.

Dose-response experiments shown in FIG. 12 demonstrate that CD47xCD19 bodies are more potent than the corresponding CD47 monovalent antibodies. Efficient ADCC is therefore dependent on CD19 co-engagement. CD19 co-engagement by the bispecific antibody drives efficacy. What is more, the experiments shown in FIG. 12 confirm that blocking CD47 is necessary to elicit efficient ADCP, as the CD19 Mab C2, which binds target cells with high affinity, does not induce significant phagocytosis.

Example 14: In Vivo Antitumor Activity of Bispecific Antibodies

The anti-tumor activity of a CD47xCD19 κλ body was evaluated in a Raji model of lymphoma. $2 \cdot 10^6$ Raji cells were implanted subcutaneously in NOD/SCID mice. Tumor volumes were measured 3 times per week. After the tumor graft reached 0.1 cm$^3$, mice were randomized into 5 groups (5 mice per group) and the antibody treatment was initiated. This experiment compared the effect of CD47xCD19 κλ-body Ka3xD11 to the effect of Ka3 monovalent antibody, and two positive control Mabs, the CD47 Mab B6H12 and rituximab. Antibody was injected i.p. three times per week until the end of the experiment (d25). Rituximab was administered at 200 μg per mouse per injection. All the other antibodies were administered at 400 μg per mouse per injection.

Figure 13:
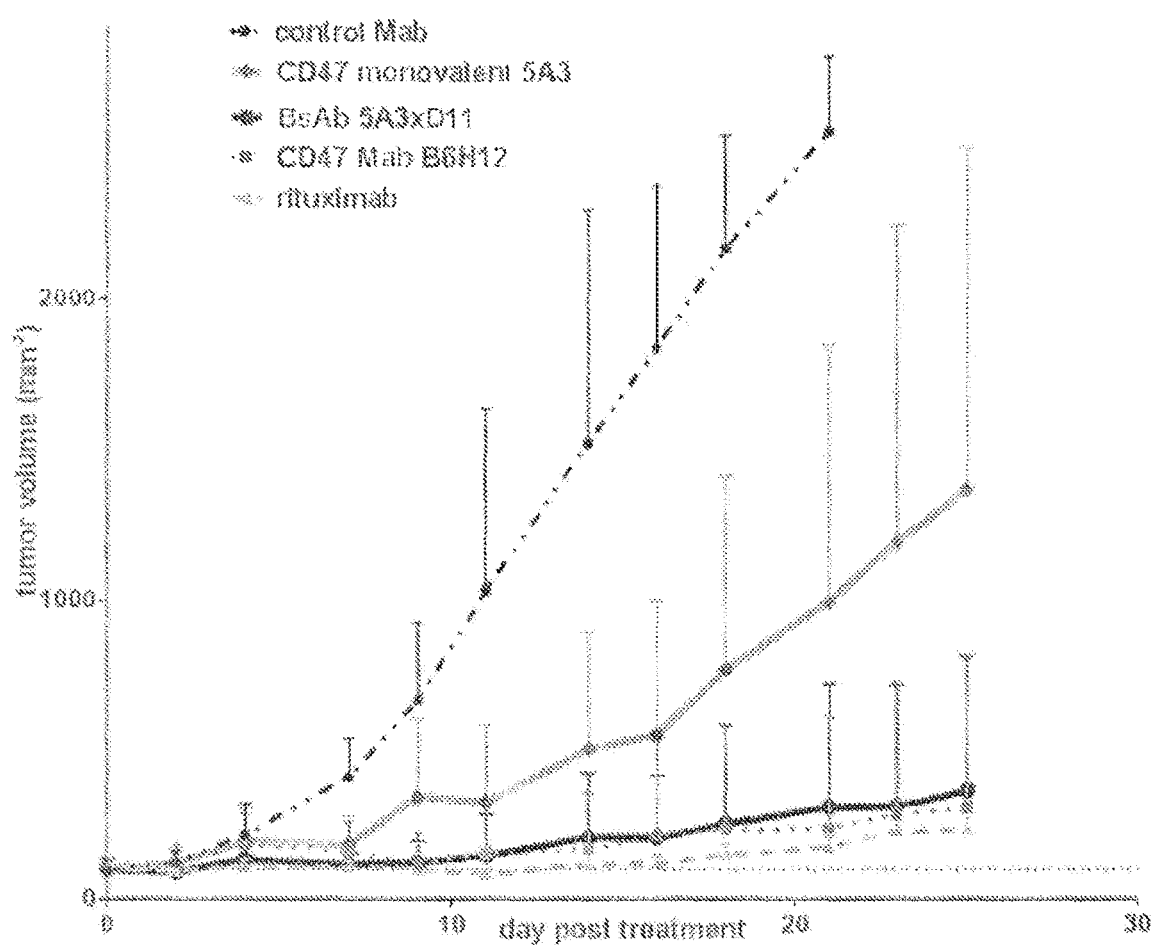
FIG. 13 is a graph depicting the activity of various antibodies in a Raji B cell lymphoma xenograft in NOD/SCID mice. Antibody treatment started after the tumor graft has reached about 0.1 cm³ and ended on D25. Treatment groups (n=5) were as indicated in the inset. Shown is the evolution of average tumor volume per treatment group+/−SD.

As shown in FIG. 13 the efficacy of the CD47xCD19 κλ-body Ka3xD11 is similar to B6H12 known to bind strongly to CD47, block CD47-SIRPα interaction and to suppress tumor growth in this lymphoma model. Of note, the efficacy of the CD47xCD19 κλ-body was also comparable to the efficacy of rituximab. The monovalent CD47 antibody was clearly less efficacious than the CD47xCD19 bispecific κλ-body demonstrating that tumor eradication is CD19-dependent.

Example 15: CD47 Antibody Binding to Erythrocytes

With more than 5 billion cells per ml of blood, and 25,000 CD47 molecules per cell, erythrocytes represent potentially the major antigen sink for CD47-binding antibodies. To assess the effect of erythrocyte adsorption, CD47 antibodies were incubated with whole blood. Following incubation, the fraction of CD47 antibodies remaining in the plasma was determined by ELISA.

In brief, 200 µl of whole blood containing an anti-coagulant was mixed with 20 µl of antibody (110 µl/ml in PBS) and incubated for 30 minutes at 37° C. with shaking. The plasma was then separated from the cells by centrifugation, and the concentration of unbound antibody determined by ELISA. For each antibody tested, the results obtained were compared to the control, that is the same antibody spiked directly into plasma, and normalized against non-binding IgGs tested in parallel.

Figure 14:
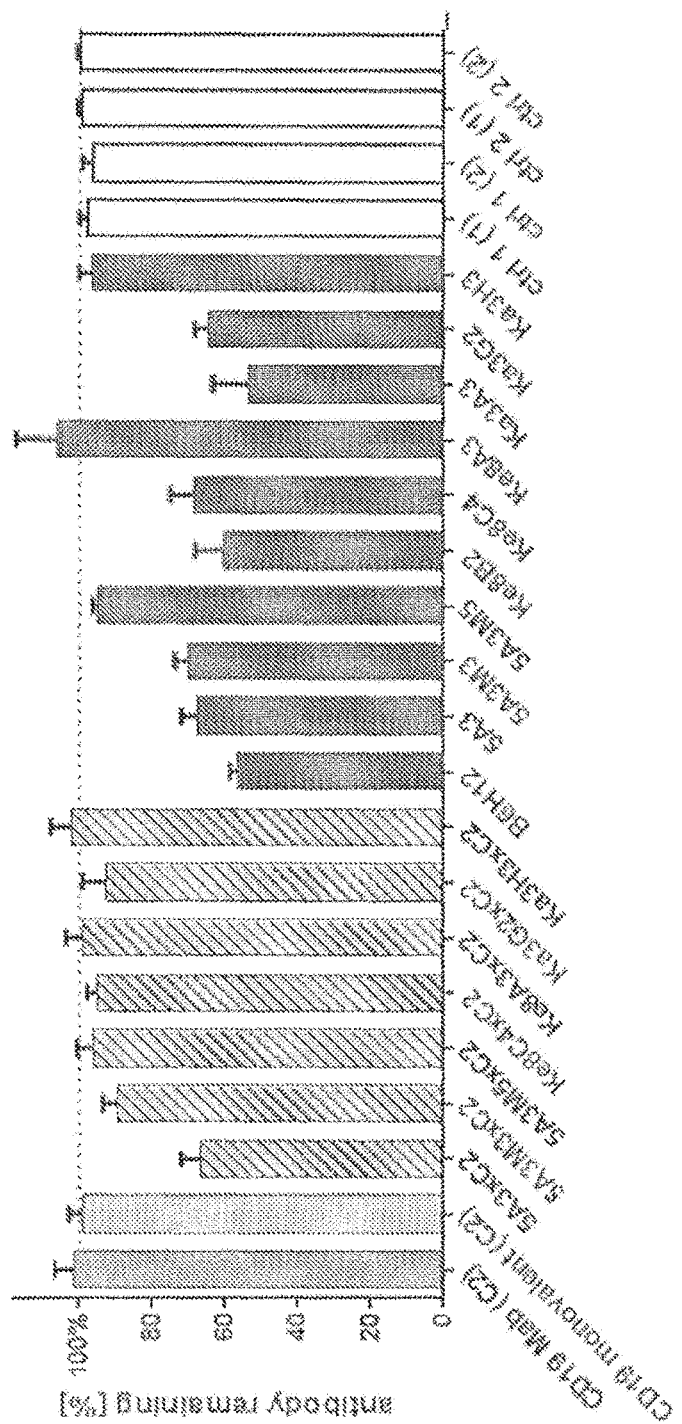
FIG. 14 is a graph depicting that high and moderate affinity CD47 antibodies are efficiently adsorbed on erythrocytes. In the case of BsAbs, this phenomenon is limited to molecules having a high affinity CD47 arms, such as 5A3.

FIG. 14 demonstrates that high and moderate affinity CD47 antibodies are efficiently adsorbed on erythrocytes. However, in the case of BsAbs, this phenomenon is limited to molecules having a high affinity CD47 arms, such as 5A3. This suggests that, in general, BsAbs are less prone to erythrocyte adsorption and TMDD than CD47 Mabs.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An antibody having an Fv fragment that specifically binds CD47, wherein the Fv fragment comprises
   i) a heavy chain variable region comprising a CDRH1 comprising the amino acid sequence of SEQ ID NO: 225; a CDRH2 comprising the amino acid sequence of SEQ ID NO: 226; a CDRH3 comprising the amino acid sequence of SEQ ID NO: 227; and
   ii) a light chain variable region comprising a CDRL1 comprising the amino acid sequence of SEQ ID NO: 240; a CDRL2 comprising the amino acid sequence of SEQ ID NO: 242; and a CDRL3 comprising the amino acid sequence of SEQ ID NO: 254.

2. The antibody of claim 1, wherein the heavy chain variable region comprises the amino acid sequence of SEQ ID NO: 114 and the light chain variable region comprises the amino acid sequence of SEQ ID NO: 168.

* * * * *

UNITED STATES PATENT AND TRADEMARK OFFICE
CERTIFICATE OF CORRECTION

| | | |
|---|---|---|
| PATENT NO. | : 11,840,553 B2 | Page 1 of 1 |
| APPLICATION NO. | : 16/015601 | |
| DATED | : December 12, 2023 | |
| INVENTOR(S) | : Masternak et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 308 days.

Signed and Sealed this
First Day of July, 2025

Coke Morgan Stewart
*Acting Director of the United States Patent and Trademark Office*